(12) United States Patent
Yokoyama et al.

(10) Patent No.: US 10,941,390 B2
(45) Date of Patent: Mar. 9, 2021

(54) PROTEIN DEAMIDASE

(71) Applicant: AJINOMOTO CO., INC., Tokyo (JP)

(72) Inventors: Noriko Yokoyama, Kawasaki (JP); Mayu Nakano, Kawasaki (JP); Shuhei Hashiro, Kawasaki (JP); Masako Hiraga, Kawasaki (JP); Kazutaka Shimbo, Kawasaki (JP); Ayaka Tokunaga, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 16/897,482

(22) Filed: Jun. 10, 2020

(65) Prior Publication Data

US 2020/0318093 A1    Oct. 8, 2020

Related U.S. Application Data

(63) Continuation of application No. 15/252,664, filed on Aug. 31, 2016, now Pat. No. 10,717,971, which is a continuation of application No. PCT/JP2015/056569, filed on Mar. 5, 2015.

(30) Foreign Application Priority Data

Mar. 7, 2014  (JP) ................................. 2014-045531

(51) Int. Cl.
| | |
|---|---|
| C12N 9/82 | (2006.01) |
| A23L 27/60 | (2016.01) |
| A23L 13/00 | (2016.01) |
| A23C 13/16 | (2006.01) |
| C12P 21/00 | (2006.01) |
| A21D 2/26 | (2006.01) |
| A23C 9/12 | (2006.01) |
| A23L 13/40 | (2016.01) |
| A23L 11/00 | (2021.01) |

(52) U.S. Cl.
CPC ............... *C12N 9/82* (2013.01); *A21D 2/267* (2013.01); *A23C 9/1216* (2013.01); *A23C 13/16* (2013.01); *A23L 11/09* (2016.08); *A23L 13/48* (2016.08); *A23L 27/60* (2016.08); *C12P 21/00* (2013.01); *C12Y 305/01001* (2013.01); *A23V 2002/00* (2013.01)

(58) Field of Classification Search
CPC .. A23V 2002/00; A23V 2002/06; C12N 9/82; A23L 27/60; A23L 13/00
See application file for complete search history.

(56) References Cited

U.S. PATENT DOCUMENTS

| | | |
|---|---|---|
| 2004/0091575 A1 | 5/2004 | Matsumura et al. |
| 2004/0166558 A1 | 8/2004 | Yamaguchi et al. |
| 2004/0175799 A1 | 9/2004 | Yamaguchi |
| 2007/0254066 A1 | 11/2007 | Miwa et al. |
| 2009/0075337 A1 | 3/2009 | Yamaguchi |
| 2009/0081763 A1 | 3/2009 | Yamaguchi |
| 2009/0123598 A1 | 5/2009 | Amano et al. |
| 2012/0207878 A1 | 8/2012 | Miwa et al. |
| 2013/0022710 A1 | 1/2013 | Miwa et al. |
| 2013/0236627 A1 | 9/2013 | Miwa |

FOREIGN PATENT DOCUMENTS

| | | |
|---|---|---|
| EP | 1 106 696 A1 | 6/2001 |
| EP | 1 371 734 A1 | 12/2003 |
| EP | 1 914 298 A1 | 4/2008 |
| JP | 2001-218590 A | 8/2001 |
| JP | 2005-052158 A | 3/2005 |
| JP | 2009-219419 A | 10/2009 |
| WO | WO 2006/075771 A1 | 7/2006 |
| WO | WO 2011/024994 A1 | 3/2011 |
| WO | WO 2011/108633 A1 | 9/2011 |

OTHER PUBLICATIONS

International Search Report dated Jun. 9, 2015 in PCT/JP2015/056569 (submitting English translation only).
International Preliminary Report on Patentability and Written Opinion dated Sep. 22, 2016 in PCT/JP2015/056569 (submitting English translation only).
Jamel S. Hamada, "Deamidation of Food Proteins to Improve Functionality", Critical Reviews in Food Science and Nutrition,1994, 34 ( 3), pp. 283-292.
Shotaro Yamaguchi, et al., "Protein-glutaminase from Chryseobacterium proteolyticum, an enzyme that deamidates glutaminyl residues in proteins Purification, characterization and gene cloning", Eur. J. Biochem., 2001,268, pp. 1410-1421.
Akio Kato, et al., "Deamidation of Food Proteins by Protease in Alkaline pH", J. Agric. Food Chem., 1987,35, pp. 224-227.
Akio Kato, et al., "Effects of Deamidation with Chymotrypsin at pH 10 on the Functional Properties of Proteins", J. Agric. Food Chem., 1987, 35, No. 2, pp. 285-288.
Masao Motoki, et al., "Glutamine-specific Deamidation of $\alpha_{s1}$-Casein by Transglutaminase", Agric. Biol. Chem., 1986, 50(12), pp. 3025-3030.
J. S. Hamada, et al., "Preparation and Functional Properties of Enzymatically Deamidated Soy Proteins", Journal of Food Science,1989, vol. 54, No. 3, pp. 598-601, 635.
Jamel S. Hamada, et al., "Enhancement of Peptidoglutaminase Deamidation of Soy Protein by Heat Treatment and/or Proteolysis", Journal of Food Science, 1988, vol. 53, No. 4, pp. 1132-1134 and 1149.
Inthawoot Suppavorasatit, et al., "Optimization of the Enzymatic Deamidation of Soy Protein by Protein-Glutaminase and Its Effect on the Functional Properties of the Protein", J. Agric. Food Chem., 2011, 59' pp. 11621-11628.

(Continued)

*Primary Examiner* — Maryam Monshipouri
(74) *Attorney, Agent, or Firm* — Oblon, McClelland, Maier & Neustadt, L.L.P.

(57) ABSTRACT

A novel protein deamidase having an activity of directly acting on a side chain amide group of an asparagine residue in a protein to form a side chain carboxyl group and release ammonia, a microorganism that produces the same, a gene encoding the same, a method for producing the same, and use of the same are provided. A bacterium classified into the class Actinobacteria is cultured to generate protein deamidase, and the enzyme is collected from culture.

4 Claims, 15 Drawing Sheets

Specification includes a Sequence Listing.

(56) References Cited

OTHER PUBLICATIONS

Yie Hui Yong, et al., "Effects of Enzymatic Deamidation by Protein-Glutaminase on Structure and Functional Properties of Wheat Gluten", J. Agric. Food Chem., 2006, 54, pp. 6034-6040.
Noriko Miwa, et al., "Effect of Enzymatic Deamidation on the Heat-induced Conformational Changes in Whey Protein Isolate and Its Relation to Gel Properties", J. Agric. Food Chem., 2013, 61, pp. 2205-2212.
N. Miwa, et al., "Effect of deamidation by protein-glutaminase on physicochemical and functional properties of skim milk", International Dairy Journal, 2010, 20, pp. 393-399.
The Latest Technology and Application of Food Enzymatic Chemistry—Prospects to Food Proteomics (Food Enzyme Chemistry: its Most Up-to-date Technology and Application and Perspectives to Food Proteomics), 2004, ISBN 978-4-7813-0127-3, Chapter 3, p. 147and its partial English translation.
Albert E. Stewart, et al., "Protein NH$_2$-terminal Asparagine Deamidase Isolation and Characterization of a New Enzyme", The Journal of Biological Chemistry, 1994, vol. 269 No. 38, pp. 23509-23517.
Kikuchi, M. et al., "Peptidoasparaginase. An Enzyme for Deamidation of COOH-Terminal Peptide-Bound Asparagine", Archives of Biochemistry and Biophysics, 1972, 148, pp. 315-317.
Weinstock G., et al., "LPXTG-motif protein cell wall anchor domain protein [Leifsonia aquatica ATCC 14665]", NCBI, 2013, 2 pages [online], [retrieval date May 27, 2015] Internet <URL:http://www.ncbi.nlm.nih.qov/protein/ERK71725.1>.
Extended European Search Report dated Jul. 19, 2017 in Patent Application No. 15758003.6.
Database UniProt [Online] "SubName: Full=LPXTG-Motif Protein Cell Wall Anchor Domain Protein {ECO:0000313 | EMBL:ERK71725. 1}" retrieved from EBI Accession No. UNIPROT: U2R8Y9 Database Accession No. U2R8Y9, XP002771697, Nov. 13, 2013, 1 Page.
Anonymous: "UNIPROT:U2R8Y9" Retrieved from the Internet: URL:http://ibis.internal.epo.org/exam/dbfetch.jsp?id= UNIPROT:U2R8Y9, XP055387594, Nov. 13, 2013, 1 Page.
Shotaro Yamaguchi, et al., "A Novel Protein-Deamidating Enzyme from *Chryseobacterium proteolyticum* sp. nov., a Newly Isolated Bacterium from Soil" Applied and Environmental Microbiology, vol. 66, No. 8, XP002162600, Aug. 1, 2000, pp. 3337-3343.

[Fig. 1]
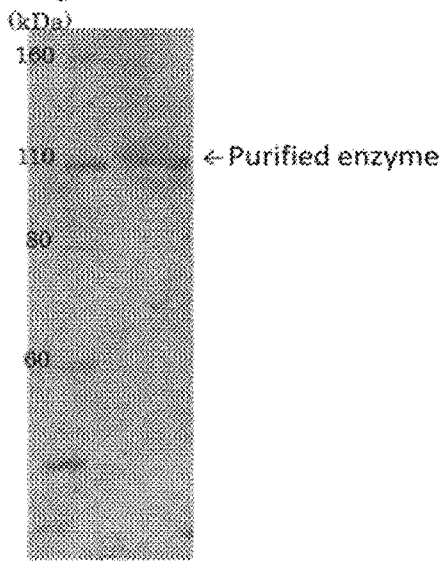
[Fig. 2]
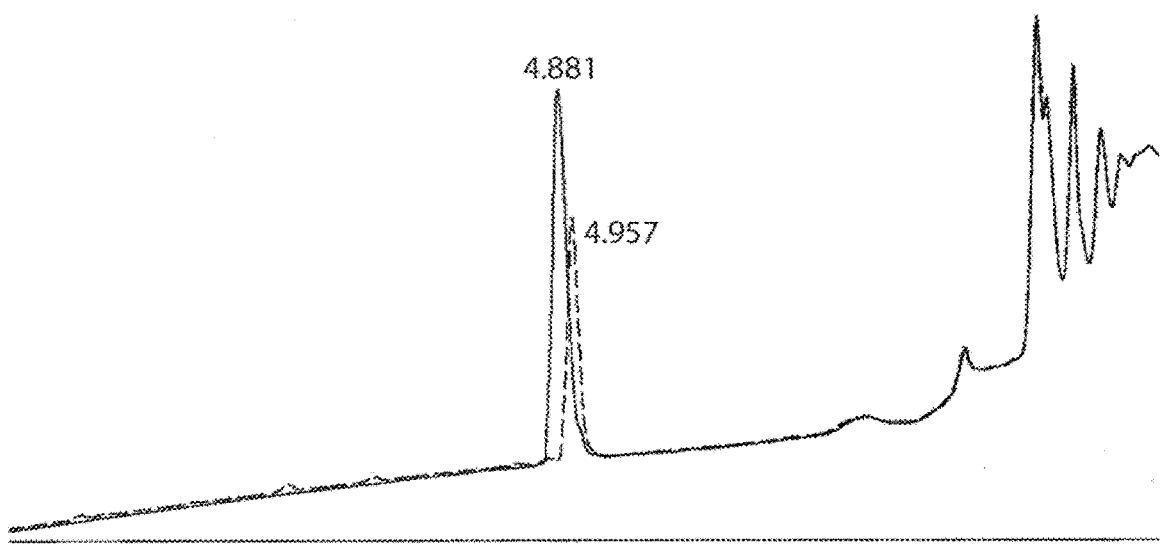

[Fig. 3]
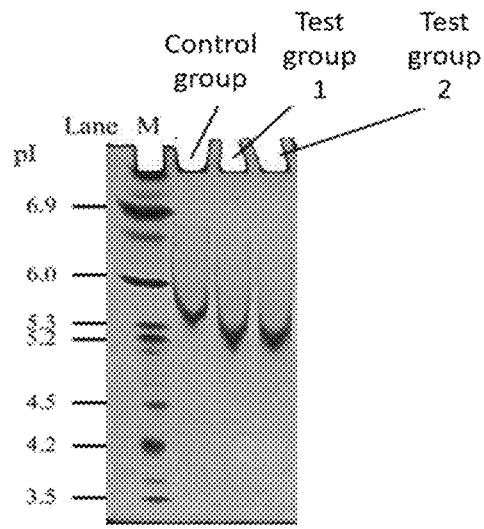
[Fig. 4]
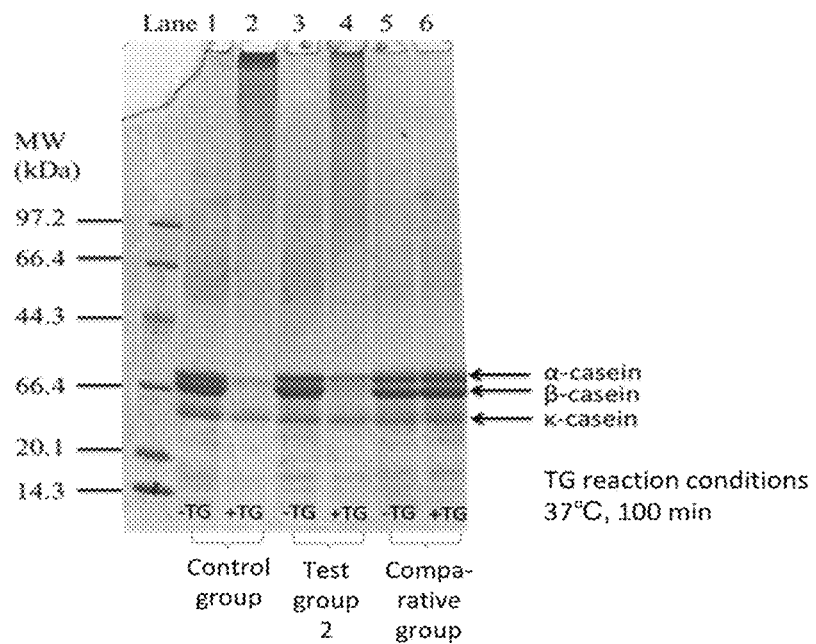

[Fig. 5]
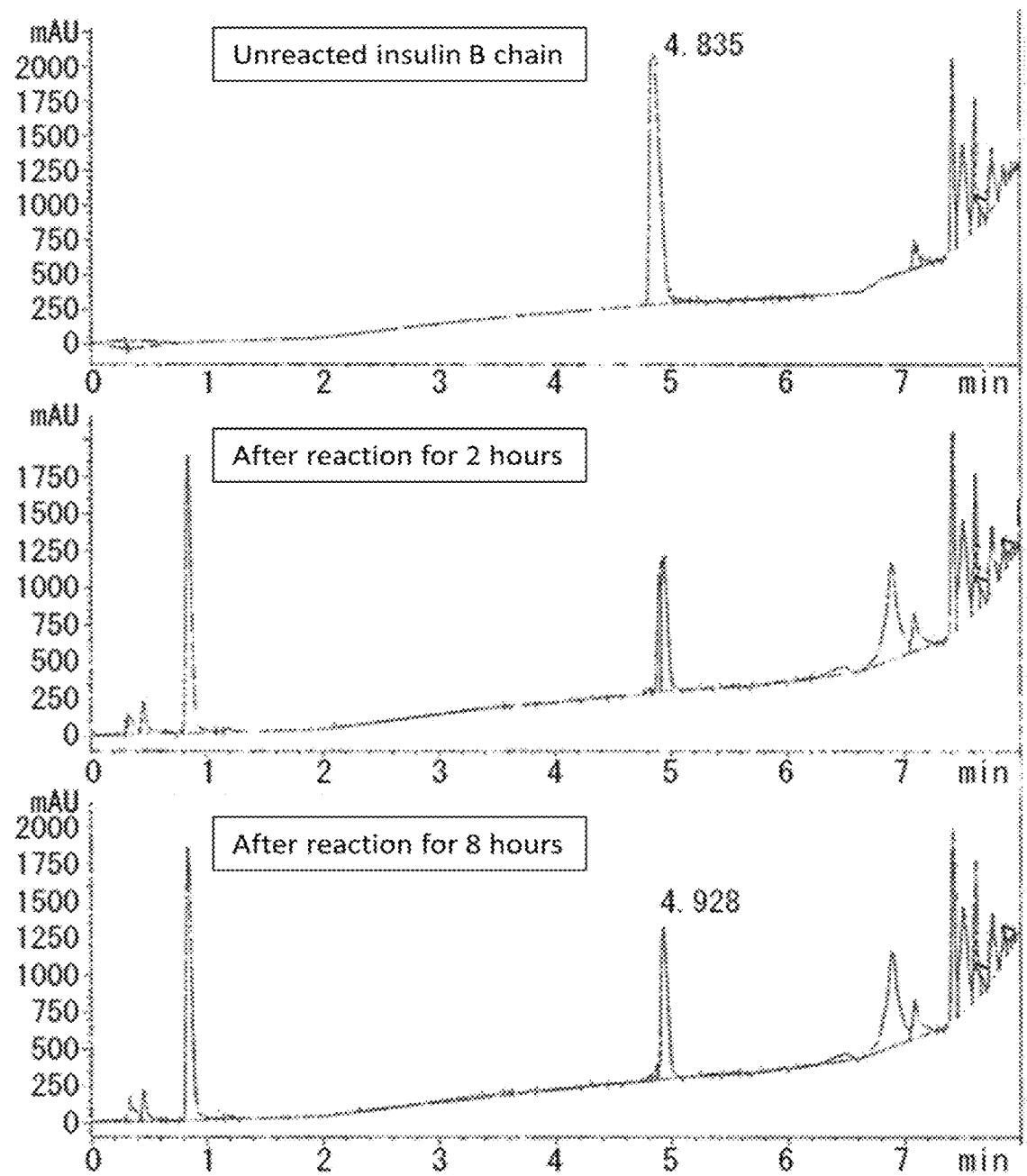

[Fig. 6]
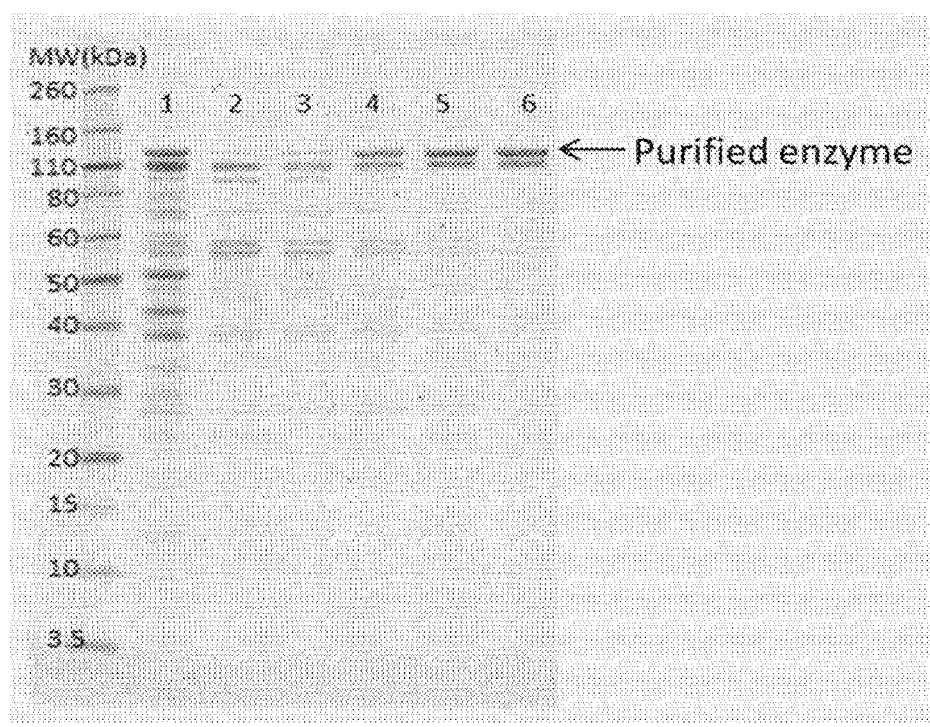

[Fig. 10]
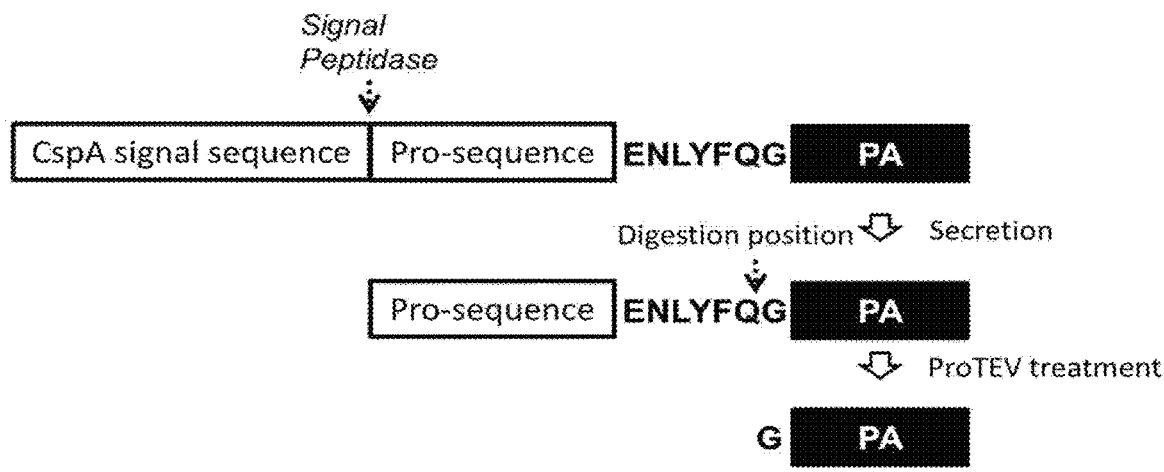
[Fig. 11]
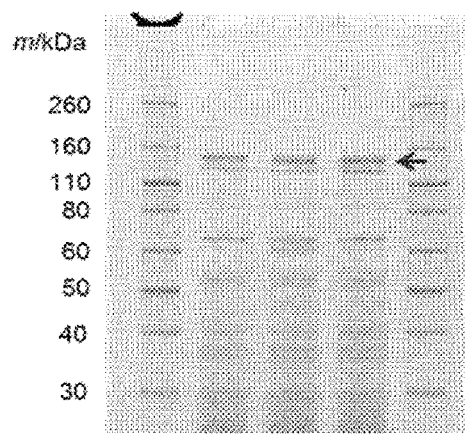

[Fig. 12]
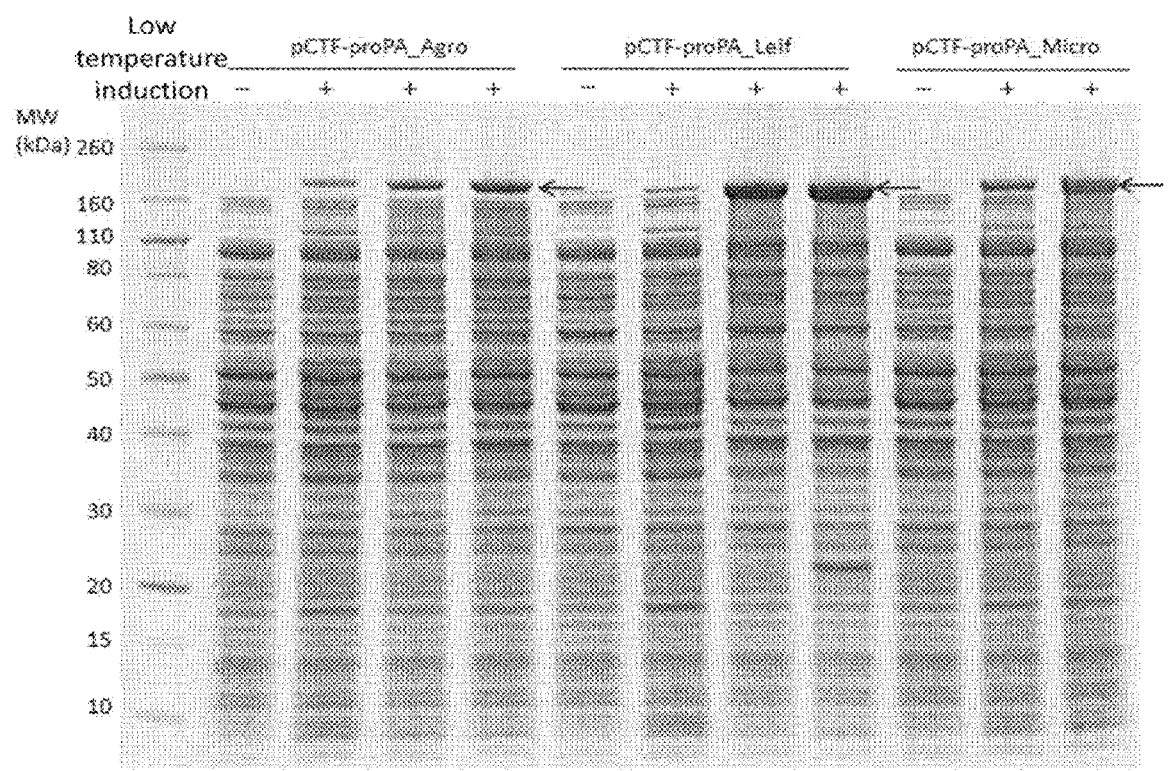

PROTEIN DEAMIDASE

CROSS-REFERENCE TO RELATED APPLICATIONS

This application is a continuation of U.S. patent application Ser. No. 15/252,664, filed Aug. 31, 2016, which is a continuation of International Application No. PCT/JP2015/056569, filed on Mar. 5, 2015, and claims priority to Japanese Patent Application No. 2014-045531, filed on Mar. 7, 2014, all of which are incorporated herein by reference in their entireties.

TECHNICAL FIELD

The present invention relates to a novel protein deamidase, a polynucleotide encoding the enzyme, a recombinant vector containing the polynucleotide, a transformant introduced with the vector, a method for producing the enzyme, and a method for deamidating a protein using the enzyme.

BACKGROUND ART

Deamidation of a protein improves various functional properties of the protein (Non-patent document 1). Therefore, it is expected that deamidation of a protein expands use of the protein. Among the amino acids that constitute proteins, glutamine and asparagine have an amide group. These are converted into glutamic acid and aspartic acid by deamidation, respectively. By deamidation, the negative charge of a protein is increased, and the isoelectric point of the protein is lowered. The solubility and water dispersibility of the protein are thereby markedly increased. Further, along with an increase of the electrostatic repulsive force, the interaction of proteins, i.e., association property of the proteins, is reduced. It is also known that the tertiary structure of a protein is loosen by deamidation to provide a change of the higher-order structure, so that a hydrophobic region that has been buried in the inside of the protein molecule is exposed on the molecular surface, and therefore the deamidated protein comes to have amphipathy, which results in improvement of the emulsification power, emulsification stability, foamability, and foam stability of the protein.

Techniques for deamidation of proteins are classified into chemical techniques and enzymatic techniques. As the chemical deamidation techniques, many methods based on a mild acid or alkaline treatment have been reported. However, all of these have problems, such as problems that they are based on nonspecific reactions, peptide bonds are also cleaved under the acidic or alkaline condition, unexpected by-products are produced. Further, they also have problems that they require facilities for using chemical substances, and impose significant environmental loads. The enzymatic techniques can overcome such problems of the chemical techniques. As the enzymatic deamidation techniques, there have been reported, for example, methods of using protein glutaminase (Patent documents 1 and 2, Non-patent document 2), methods of using protease (Non-patent documents 3 and 4), a method of using transglutaminase (Non-patent document 5), methods of using peptide glutaminase (Non-patent documents 6 and 7), and so forth.

Among these enzymes, protein glutaminase is the only enzyme that can catalyze deamidation reaction of a high molecular protein without accompanying any side reaction. Use of protease, transglutaminase, and peptide glutaminase has problems since the main reaction catalyzed by protease is cleavage of peptide bonds, the main reaction catalyzed by transglutaminase is crosslinking reaction based on formation of isopeptide bonds between glutamine and lysine, and peptide glutaminase is an enzyme that mainly catalyzes deamidation of decomposed low molecular weight peptides. It is considered that protein glutaminase has high practicality as an enzyme having a high deamidation ability for a high molecular weight protein. There have already been reported findings concerning improvement in functions of wheat proteins, milk proteins (casein and whey proteins), and soybean proteins provided by protein glutaminase (Non-patent documents 8 to 11). In patent documents, there have also been reported findings concerning improvement of qualities of actual foods, for example, yogurt, ice cream, coffee whitener, noodles, meat, and so forth provided by protein glutaminase (Patent documents 3 to 7). However, it is definitely described that protein glutaminase uses a glutamine residue in a protein as a substrate, and does not act on asparagine residue at all (Non-patent documents 2 and 12), and hence, effect of the treatment with this enzyme is limited. In fact, amino acids constituting plant and animal proteins contain a large amount of asparagine, and hence, it is preferable to deamidate not only glutamine, but also asparagine, for obtaining further functional reforming effect by deamidation.

Asparaginase (EC 3.5.1.1) is widely known as an enzyme that catalyzes hydrolysis of asparagine to generate aspartic acid. However, asparaginase is an enzyme that specifically acts on asparagine of the free form, and cannot deamidate an asparagine residue in a peptide or high molecular weight protein. There is also known an enzyme that catalyzes the reaction of deamidating an N-terminus asparagine residue having a free α-amino group is known (Non-patent document 13). However, this enzyme cannot deamidate an asparagine residue in a protein other than N-terminus asparagine residue.

As described above, any enzyme that deamidates an asparagine residue in a protein (except for N-terminus asparagine residue having a free α-amino group) is not known.

PRIOR ART REFERENCES

Patent Documents

Patent document 1: Japanese Patent Laid-open (Kokai) No. 2001-218590
Patent document 2: Japanese Patent Laid-open (Kokai) No. 2005-052158
Patent document 3: WO2011/024994
Patent document 4: US2013-22710
Patent document 5: WO2011/108633
Patent document 6: Japanese Patent Laid-open (Kokai) No. 2009-219419
Patent document 7: WO2006/075771

Non-Patent Documents

Non-patent document 1: Hamada J. S., 1994, Critical Reviews in Food Science and Nutrition, 34, 283
Non-patent document 2: Yamaguchi S, Jeenes D J, and Archer D B, 2001, Eur. J. Biochem., 268(5), 1410
Non-patent document 3: Kato A., Tanaka A., Matsudomi N., Kobayashi K., 1987, J. Agric. Food Chem., 35, 224
Non-patent document 4: Kato, A., Tanaka, A., Lee, Y., Matsudomi, N. & Kobayashi, K., 1987, J. Agric. Food Chem. 35, 285

Non-patent document 5: Motoki M., Seguro K., Nio N., Takinami K., 1986, Agric. Biol. Chem., 50, 3025-3030
Non-patent document 6: Hamada J. S., Marshall W. E., 1989, J. Food. Sci., 54, 598-601, 635
Non-patent document 7: Hamada J. S., Marshall W. E., 1988, J. Food. Sci., 53, 1132-1134, 1149
Non-patent document 8: Suppavorasatit I., De Mejia E. G., Cadwallader K. R., 2011, J. Agric. Food Chem., 59, 11621
Non-patent document 9: Yong Y. H., Yamaguchi S., Matsumura Y., 2006, J. Agric. Food Chem., 54, 6034
Non-patent document 10: Miwa, N., Yokoyama, K., Noriki Nio, N., Sonomoto, K., 2013, J. Agric. Food Chem., 61, 2205
Non-patent document 11: Miwa, N., Yokoyama, K., Wakabayashi, H., Nio, N., 2010, Int. Dairy J., 20, 393
Non-patent document 12: The Latest Technology and Application of Food Enzymatic Chemistry—Prospects to Food Proteomics, 2004, ISBN 978-4-7813-0127-3, Chapter 3, p. 147
Non-patent document 13: Stewart A E, Arfin S M, Bradshaw R A, 1994, J. Biol. Chem., 1994 Sep. 23; 269(38): 23509-17

SUMMARY OF THE INVENTION

Object to be Achieved by the Invention

An object of the present invention is to provide a novel protein deamidase (protein asparaginase) that catalyzes the reaction of deamidating an asparagine residue in a protein.

Means for Achieving the Object

The inventors of the present invention conducted various researches in order to achieve the aforementioned object. As a result, they found microorganisms that produce an enzyme that catalyzes the reaction of specifically deamidating an asparagine residue in a protein without causing decomposition and crosslinking of the protein by using a screening system using a peptide having an asparagine residue as a sole nitrogen source, and accomplished the present invention.

That is, the present invention can be embodied, for example, as follows.

[1]
A protein having an activity for catalyzing a reaction of deamidating an asparagine residue in a protein.
[2]
The protein according to [1], which does not substantially have an activity for catalyzing a reaction of hydrolyzing a peptide bond in a protein.
[3]
The protein according to [1] or [2], which is a protein defined in (A), (B), or (C) mentioned below:
(A) a protein comprising the amino acid sequence of SEQ ID NO: 10 or 11, the amino acid sequence of positions 63 to 1260, 245 to 1378, 245 to 1260, or 131 to 1260 of SEQ ID NO: 10, or the amino acid sequence of positions 47 to 1257, 59 to 1258, 96 to 1101, 241 to 1378, 244 to 1258, 244 to 1257, 244 to 1101, 129 to 1258, 120 to 1257, or 120 to 1101 of SEQ ID NO: 11;
(B) a protein comprising the amino acid sequence of SEQ ID NO: 10 or 11, the amino acid sequence of positions 63 to 1260, 245 to 1378, 245 to 1260, or 131 to 1260 of SEQ ID NO: 10, or the amino acid sequence of positions 47 to 1257, 59 to 1258, 96 to 1101, 241 to 1378, 244 to 1258, 244 to 1257, 244 to 1101, 129 to 1258, 120 to 1257, or 120 to 1101 of SEQ ID NO: 11 but including substitution, deletion, insertion, or addition of 1 to 10 amino acid residues, and having an activity for catalyzing a reaction of deamidating an asparagine residue in a protein;
(C) a protein comprising an amino acid sequence showing an identity of 90% or higher to the amino acid sequence of SEQ ID NO: 10 or 11, the amino acid sequence of positions 63 to 1260, 245 to 1378, 245 to 1260, or 131 to 1260 of SEQ ID NO: 10, or the amino acid sequence of positions 47 to 1257, 59 to 1258, 96 to 1101, 241 to 1378, 244 to 1258, 244 to 1257, 244 to 1101, 129 to 1258, 120 to 1257, or 120 to 1101 of SEQ ID NO: 11, and having an activity for catalyzing a reaction of deamidating an asparagine residue in a protein.
[4]
The protein according to any one of [1] to [3], which is a protein defined in (a), (b), or (c) mentioned below:
(a) a protein comprising the amino acid sequence of SEQ ID NO: 2, 5, 7, 8, or 9, the amino acid sequence of positions 240 to 1355 of SEQ ID NO: 2, the amino acid sequence of positions 181 to 1180 or 67 to 1180 of SEQ ID NO: 5, the amino acid sequence of positions 193 to 1172 or 70 to 1172 of SEQ ID NO: 7, or the amino acid sequence of positions 146 to 989 or 21 to 989 of SEQ ID NO: 8;
(b) a protein comprising the amino acid sequence of SEQ ID NO: 2, 5, 7, 8, or 9, the amino acid sequence of positions 240 to 1355 of SEQ ID NO: 2, the amino acid sequence of positions 181 to 1180 or 67 to 1180 of SEQ ID NO: 5, the amino acid sequence of positions 193 to 1172 or 70 to 1172 of SEQ ID NO: 7, or the amino acid sequence of positions 146 to 989 or 21 to 989 of SEQ ID NO: 8 but including substitution, deletion, insertion, or addition of one or several amino acid residues, and having an activity for catalyzing a reaction of deamidating an asparagine residue in a protein;
(c) a protein comprising an amino acid sequence showing an identity of 90% or higher to the amino acid sequence of SEQ ID NO: 2, 5, 7, 8, or 9, the amino acid sequence of positions 240 to 1355 of SEQ ID NO: 2, the amino acid sequence of positions 181 to 1180 or 67 to 1180 of SEQ ID NO: 5, the amino acid sequence of positions 193 to 1172 or 70 to 1172 of SEQ ID NO: 7, or the amino acid sequence of positions 146 to 989 or 21 to 989 of SEQ ID NO: 8, and having an activity for catalyzing a reaction of deamidating an asparagine residue in a protein.
[5]
A polynucleotide encoding the protein according to any one of [1] to [4].
[6]
A recombinant vector containing the polynucleotide according to [5].
[7]
A transformant introduced with the recombinant vector according to [6].
[8]
A method for producing a protein having an activity for catalyzing a reaction of deamidating an asparagine residue in a protein, the method comprising:
culturing the transformant according to [7] in a medium to generate the protein according to any one of [1] to [4]; and collecting the protein from the culture broth.
[9]
A method for producing a protein having an activity for catalyzing a reaction of deamidating an asparagine residue in a protein, the method comprising:

culturing a microorganism having an ability to produce the protein according to any one of [1] to [4] in a medium to generate the protein; and collecting the protein from the culture broth.

[10]

The method according to [9], wherein the microorganism is a bacterium belonging to the class Actinobacteria.

[11]

The method according to [10], wherein the bacterium is a bacterium belonging to the genus *Luteimicrobium*, *Agromyces*, *Microbacterium*, or *Leifsonia*.

[12]

The method according to [11], wherein the bacterium is *Luteimicrobium album*, *Agromyces* sp., *Microbacterium testaceum*, *Leifsonia xyli*, or *Leifsonia aquatica*.

[13]

The method according to any one of [8] to [12], which comprises treating the protein with a processing enzyme.

[14]

The method according to [13], wherein the processing enzyme is protease.

[15]

A method for producing a protein and/or peptide of which an asparagine residue has been deamidated, the method comprising:
allowing the protein according to any one of [1] to [4] to act on a protein and/or peptide.

[16]

The method according to [15], wherein the protein and/or peptide is contained in a food or drink or raw material thereof.

[17]

The method according to [15] or [16], which further comprises allowing transglutaminase and/or protein glutaminase to act on the protein and/or peptide.

[18]

A method for reforming a food or drink or raw material thereof, the method comprising:
allowing the protein according to any one of [1] to [4] to act on a food or drink or raw material thereof containing a protein and/or peptide.

[19]

A method for producing a reformed food or drink or raw material thereof, the method comprising:
allowing the protein according to any one of [1] to [4] to act on a food or drink or raw material thereof containing a protein and/or peptide.

[20]

The method according to [18] or [19], which further comprises allowing transglutaminase and/or protein glutaminase to act on the food or drink or raw material thereof containing a protein and/or peptide.

[21]

The method according to any one of [16] to [20], wherein the food or drink is selected from mayonnaise, dressing, cream, yogurt, meat product, and bread.

[22]

The method according to any one of [15] to [21], wherein 0.001 to 500 U of the protein according to any one of [1] to [4] is used for 1 g of the protein and/or peptide.

BRIEF DESCRIPTION OF THE DRAWINGS

FIG. 1 A photograph showing the result of SDS-PAGE of protein asparaginase derived from *Luteimicrobium album* (Example 2).

FIG. 2 A diagram showing the result of HPLC analysis of the insulin B chain treated with protein asparaginase derived from *Luteimicrobium album* (Example 5).

FIG. 3 A photograph showing the results of isoelectric focusing of casein treated with protein asparaginase derived from *Luteimicrobium album* (Example 6). Control group is a group that used a treatment with water, Test group 1 is a group that used a treatment with protein asparaginase (0.68 U/ml), and Test group 2 is a group that used a treatment with protein asparaginase (2.7 U/ml).

FIG. 4 A photograph showing the results of SDS-PAGE of casein treated with various enzymes (Example 6). Control group is a group that used a treatment with water, Test group 2 is a group that used a treatment with protein asparaginase (2.7 U/ml), and Comparative group is a group that used a treatment with protein glutaminase (10 U/ml). "−TG" means that transglutaminase was not used in combination, and "+TG" means that transglutaminase was used in combination.

FIG. 5 Diagrams showing the results of HPLC analysis of the insulin B chain treated with protein asparaginase derived from *Leifsonia xyli* (Example 7).

FIG. 6 A photograph showing the results of SDS-PAGE of protein asparaginase derived from *Agromyces* sp. (Example 9). Lane 1 is for a chromatography-purified fraction, and lanes 2 to 6 are for anion exchange chromatography-purified fractions.

FIG. 10 A design drawing of a pro-sequence-fused protein asparaginase.

FIG. 11 A photograph showing the results of SDS-PAGE of a pro-sequence-fused protein asparaginase derived from *Agromyces* sp., which was expressed by secretory expression from *Corynebacterium glutamicum* (Example 12, <1>). The arrow indicates the position of the target protein.

FIG. 12 A photograph showing the results of SDS-PAGE of a pro-sequence-fused protein asparaginase, which was intracellularly expressed in *Escherichia coli* (Example 12, <2>). The arrows indicate the positions of the target protein.

MODES FOR CARRYING OUT THE INVENTION

<1> Protein Deamidase

Figure 7A:
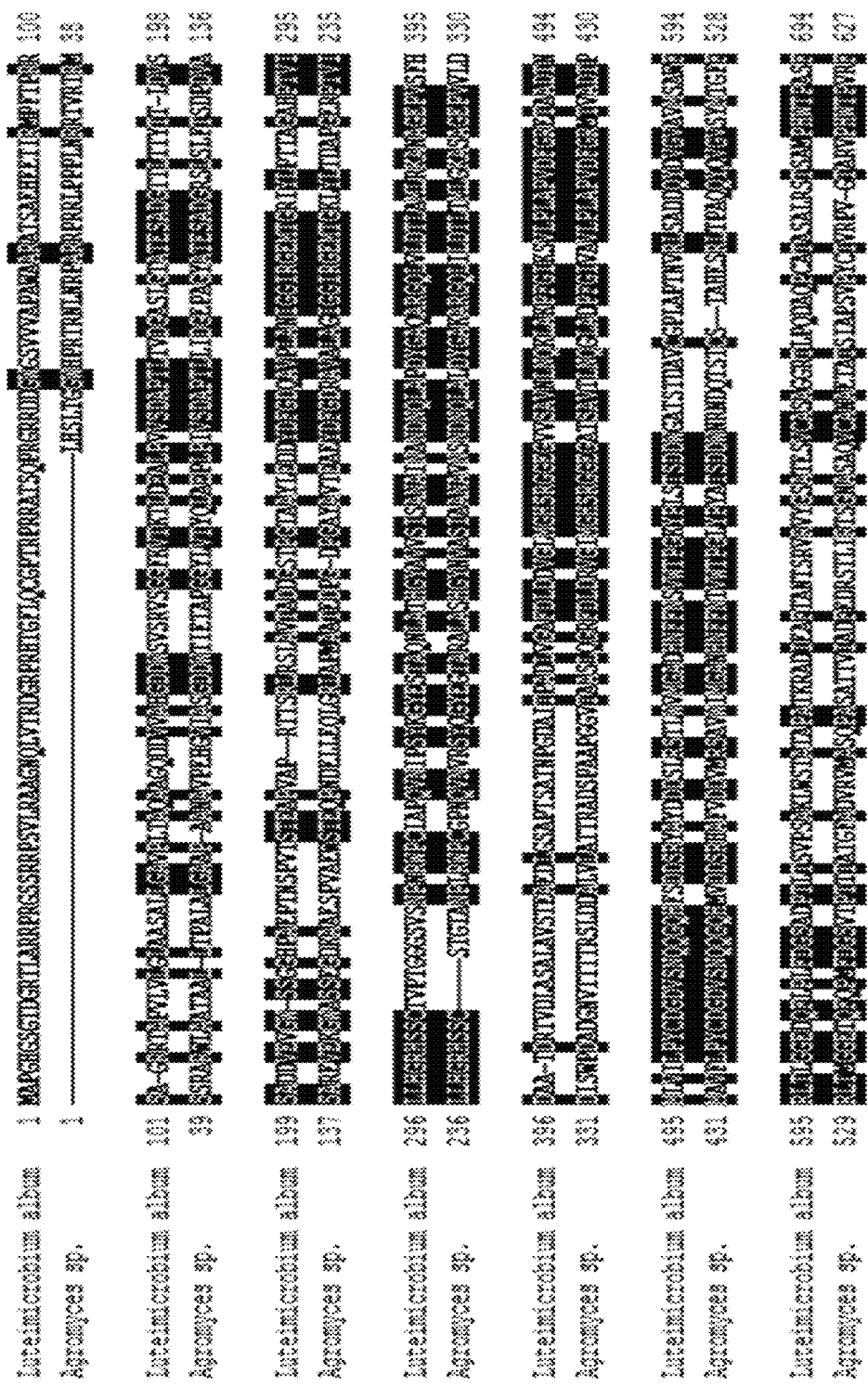
FIGS. 7A and 7B A diagram showing the result of alignment of the sequences of SEQ ID NOS: 2 and 5.

The present invention provides protein deamidase.

In the present invention, the term "protein deamidase" refers to a protein having an activity for catalyzing a reaction of deamidating an asparagine residue in a protein. This activity is also referred to as "protein asparaginase activity". In the present invention, protein deamidase is also referred to as "protein asparaginase".

The term "asparagine residue in a protein" means an asparagine residue existing in a protein, except for N-terminus asparagine residue having a free α-amino group. Protein deamidase may or may not have an activity for catalyzing a reaction of deamidating an N-terminus asparagine residue having a free α-amino group, so long as it has an activity for catalyzing a reaction of deamidating such an "asparagine residue in a protein". Protein deamidase may or may not have an activity for catalyzing a reaction of deamidating monomer asparagine.

In the present invention, a protein to be deamidated by protein deamidase is also referred to as "substrate protein". The length of the substrate protein is not particularly limited so long as the length is 2 residues (dipeptide) or longer. The length of the substrate protein may be, for example, 2 residues (dipeptide) or longer, 3 residues (tripeptide) or longer, 10 residues or longer, 50 residues or longer, or 100 residues or longer. That is, unless otherwise stated, the term "substrate protein" also includes a substance called peptide, such as oligopeptide and polypeptide.

An asparagine residue is hydrolyzed into an aspartic acid residue and ammonia by deamidation. Therefore, the protein asparaginase activity can be measured on the basis of, for example, generation of ammonia accompanying the deamidation of an asparagine residue. For example, protein deamidase can be allowed to act on a peptide having a length of two or more residues, containing asparagine residue, and not containing glutamine residue (such as Cbz-Asn-Gly) as a substrate, and then the protein asparaginase activity can be calculated on the basis of the amount of released ammonia. Specifically, the protein asparaginase activity can be calculated with, for example, the conditions described in the Examples section. That is, the protein asparaginase activity can be measured by adding 25 μL of an enzyme solution of an appropriate concentration to 125 μL of a 0.2 mol/L phosphate buffer (pH 6.5) containing 30 mmol/L of Cbz-Asn-Gly, incubating the mixture at 37° C. for 60 minutes, then adding 150 μL of a 12% trichloroacetic acid solution to terminate the reaction, and measuring the ammonia concentration in the supernatant. In the present invention, the enzymatic activity for generating 1 μmol of ammonia in 1 minute under these conditions is defined as 1 unit (U) of the protein asparaginase activity.

It is preferred that protein deamidase does not substantially have an activity for catalyzing the reaction of deamidating a glutamine residue in a protein. This activity is also referred to as "protein glutaminase activity". A glutamine residue is hydrolyzed into a glutamic acid residue and ammonia by deamidation. Therefore, the protein glutaminase activity can be measured on the basis of, for example, generation of ammonia accompanying deamidation of a glutamine residue. For example, protein deamidase can be allowed to act on a peptide having a length of two or more residues, containing glutamine residue, and not containing asparagine residue (such as Cbz-Gln-Gly) as a substrate, and then the protein glutaminase activity can be calculated on the basis of the amount of released ammonia. Specifically, the protein glutaminase activity can be calculated with, for example, the conditions for measuring the protein asparaginase activity described in the Examples section, provided that the enzymatic reaction is performed by using Cbz-Gln-Gly instead of Cbz-Asn-Gly. That is, the protein glutaminase activity can be measured by adding 25 μL of an enzyme solution of an appropriate concentration to 125 μL of a 0.2 mol/L phosphate buffer (pH 6.5) containing 30 mmol/L of Cbz-Gln-Gly, incubating the mixture at 37° C. for 60 minutes, adding 150 μL of a 12% trichloroacetic acid solution to terminate the reaction, and measuring the ammonia concentration in the supernatant. In the present invention, the enzymatic activity for generating 1 μmol of ammonia in 1 minute under these conditions is defined as 1 unit (U) of the protein glutaminase activity. The expression "protein deamidase does not substantially have the protein glutaminase activity" may mean that, for example, the ratio of the protein glutaminase activity to the protein asparaginase activity (namely, specific activity of the protein glutaminase activity/specific activity of the protein asparaginase activity) of protein deamidase is 1/100 or smaller, 1/1000 or smaller, 1/10000 or smaller, or 0 (zero). The ratio of the specific activities can be calculated by measuring the protein asparaginase activity and protein glutaminase activity.

It is preferred that protein deamidase does not substantially have an activity for catalyzing the reaction of hydrolyzing a peptide bond in a protein. This activity is also referred to as "protease activity". The protease activity can be measured by, for example, a known technique. Specifically, the protease activity can be calculated, for example, by using azocasein as a substrate under the following conditions. That is, 0.5 mL of an enzyme solution of an appropriate concentration is added to 1.0 mL of a 50 mM Tris-hydrochloric acid buffer (pH 8.0) containing 1% azocasein, the mixture is incubated at 37° C. for 30 minutes, and then 2.0 mL of a 12% trichloroacetic acid solution is added to terminate the reaction. The reaction mixture is centrifuged (15,000 rpm, 4° C., 5 minutes), and then $A_{405}$ of the supernatant is measured. As controls, the same procedure is performed for a test group in which 0.5 mL of water is added instead of the enzyme solution, and a test group for compensating influence of color of ingredients that may be contained in the enzyme solution, in which 1.0 mL of a 50 mM Tris-HCl buffer (pH 8.0) not containing azocasein is used instead of the 50 mM Tris-HCl buffer (pH 8.0) containing azocasein, and $A_{405}$ of the supernatant is measured for each of the groups. On the basis of these measured values of $A_{405}$, an increase of $A_{405}$ provided by the enzyme is calculated. In the present invention, the enzymatic activity for increasing $A_{405}$ by 0.01 in 1 minute under these conditions is defined as 1 unit (U) of the protease activity. The expression "protein deamidase does not substantially have the protease activity" may mean that, for example, when a protein is treated with protein deamidase so that deamidation of asparagine residues takes place in a desired degree, the protein is not significantly decomposed into lower molecular weight molecules due to cleavage of peptide bonds by the treatment. Also, the expression "protein deamidase does not substantially have the protease activity" may mean that, for example, the ratio of the protease activity to the protein asparaginase activity (namely, specific activity of the protease activity/specific activity of the protein asparaginase activity) of protein deamidase is 1/100 or smaller, 1/1000 or smaller, 1/10000 or smaller, or 0 (zero). The ratio of the specific activities can be calculated by measuring the protein asparaginase activity and protease activity.

It is preferred that protein deamidase does not substantially have an activity for catalyzing the reaction of crosslinking proteins. This activity is also referred to as "protein crosslinking activity". The protein crosslinking activity can be measured by, for example, a known technique. The expression "protein deamidase does not substantially have the protein crosslinking activity" may mean that, for example, when proteins are treated with protein deamidase so that deamidation of asparagine residues takes place in a desired degree, the proteins are not significantly crosslinked into higher molecular weight molecules due to crosslinking of the proteins caused by the treatment. The expression "protein deamidase does not substantially have the protein crosslinking activity" may specifically mean that, for example, when 25 μL of an enzyme solution adjusted to have 2.7 U/ml of the protein asparaginase activity is added to 500 μL of a 20 mM sodium phosphate buffer (pH 7.0) containing 2% w/v casein sodium, the reaction is performed at 37° C. for 1 hour, and the enzyme is inactivated by a treatment at 100° C. for 5 minutes, the amount of uncrosslinked casein corresponds to 90% or more, or 95% or more of the same of a control group (sample obtained by performing the reaction in the same manner as described above provided that 25 μL of water is added instead of the enzyme solution). The "amount of uncrosslinked casein" can be measured and compared by known techniques. For example, measurement and comparison of the "amount of uncrosslinked casein" may be performed by measuring molecular weight distribution using gel filtration chromatography, or by confirming position and concentration of an objective band in SDS-PAGE.

Examples of protein deamidase include, for example, protein deamidases of bacteria belonging to the class Actinobacteria. Examples of the bacteria belonging to the class Actinobacteria include bacteria belonging to the family Microbacteriaceae such as *Leifsonia* bacteria, *Microbacterium* bacteria, and *Agromyces* bacteria, and bacteria belonging to an unclassified family such as *Luteimicrobium* bacteria. Examples of the *Leifsonia* bacteria include *Leifsonia xyli* and *Leifsonia aquatica*. Examples of the *Microbacterium* bacteria include *Microbacterium testaceum*. Examples of the *Agromyces* bacteria include *Agromyces* sp. obtained in the Examples section mentioned later. Examples of the *Luteimicrobium* bacteria include *Luteimicrobium album*. That is, protein deamidase may be, for example, a protein derived from such bacteria.

The amino acid sequence of protein deamidase of *Luteimicrobium album* AJ111072 (NITE P-01650) and the nucleotide sequence of the gene encoding it are shown as SEQ ID NOS: 2 and 3, respectively. The amino acid sequence of protein deamidase of *Agromyces* sp. AJ111073 (NITE BP-01782) and the nucleotide sequence of the gene encoding it are shown as SEQ ID NOS: 5 and 6, respectively. The amino acid sequence of protein deamidase of *Microbacterium testaceum* is shown as SEQ ID NO: 7. The amino acid sequence of protein deamidase of *Leifsonia xyli* AJ111071 (NITE P-01649) is shown as SEQ ID NO: 8. The amino acid sequence of protein deamidase of *Leifsonia aquatica* is shown as SEQ ID NO: 9. That is, protein deamidase may be, for example, a protein having the amino acid sequence of SEQ ID NO: 2, 5, 7, 8, or 9. Protein deamidase may also be, for example, a protein encoded by a gene having the nucleotide sequence shown as SEQ ID NO: 3 or 6. The expression of "having an (amino acid or nucleotide) sequence" includes both cases of "comprising the (amino acid or nucleotide) sequence" and "consisting of the (amino acid or nucleotide) sequence".

*Luteimicrobium album* AJ111072 (NITE P-01650) was deposited at the independent administrative agency, National Institute of Technology and Evaluation, Patent Microorganisms Depositary (NPMD) (#122, 2-5-8 Kazusakamatari, Kisarazu-shi, Chiba-ken, 292-0818, Japan) on Jul. 5, 2013, and assigned an accession number of NITE P-01650.

*Agromyces* sp. AJ111073 (NITE BP-01782) was deposited at the independent administrative agency, National Institute of Technology and Evaluation, Patent Microorganisms Depositary (NPMD) (#122, 2-5-8 Kazusakamatari, Kisarazu-shi, Chiba-ken, 292-0818, Japan) on Dec. 11, 2013. Then, the deposit was converted to an international deposit under the provisions of the Budapest Treaty on Mar. 4, 2015, and assigned an accession number of NITE BP-01782 (receipt number NITE ABP-01782).

*Leifsonia xyli* AJ111071 (NITE P-01649) was deposited at the independent administrative agency, National Institute of Technology and Evaluation, Patent Microorganisms Depositary (NPMD) (#122, 2-5-8 Kazusakamatari, Kisarazu-shi, Chiba-ken, 292-0818, Japan) on Jul. 5, 2013, and assigned an accession number of NITE P-01649.

The amino acid sequence shown as SEQ ID NO: 2, 5, 7, 8, or 9 may contain a pre-pro-region (pre-sequence and pro-sequence). A protein containing a pre-pro-region is also referred to as "pre-pro-protein". A protein containing a pro-sequence, but not containing pre-sequence is also referred to as "pro-protein". A protein not containing pre-pro-region is also referred to as "mature protein". Protein deamidase may be, for example, a protein having the amino acid sequence of SEQ ID NO: 2, 5, 7, 8, or 9 except for a pre-pro-region (namely, amino acid sequence of mature protein), or a protein having the amino acid sequence of SEQ ID NO: 2, 5, 7, 8, or 9 except for a pre-region (namely, amino acid sequence of pro-protein). The amino acid sequence of the mature protein of protein deamidase of *Luteimicrobium album* corresponds to positions 240 to 1355 of SEQ ID NO: 2. The amino acid sequence of the mature protein of protein deamidase of *Agromyces* sp. corresponds to positions 181 to 1180 of SEQ ID NO: 5. The amino acid sequence of the mature protein of protein deamidase of *Microbacterium testaceum* corresponds to positions 193 to 1172 of SEQ ID NO: 7. The amino acid sequence of the mature protein of protein deamidase of *Leifsonia xyli* corresponds to positions 146 to 989 of SEQ ID NO: 8. The amino acid sequence of the pro-protein of protein deamidase of *Agromyces* sp. corresponds to positions 67 to 1180 of SEQ ID NO: 5. The amino acid sequence of the pro-protein of protein deamidase of *Microbacterium testaceum* corresponds to positions 70 to 1172 of SEQ ID NO: 7. The amino acid sequence of the pro-protein of protein deamidase of *Leifsonia xyli* corresponds to positions 21 to 989 of SEQ ID NO: 8. Protein deamidase may also be, for example, a protein encoded by a gene having a part of the nucleotide sequence of SEQ ID NO: 3 or 6, the part encoding the amino acid sequence other than the pre-pro-region (namely, nucleotide sequence encoding the amino acid sequence of the mature protein), or a protein encoded by a gene having a part of the nucleotide sequence of SEQ ID NO: 3 or 6, the part encoding the amino acid sequence other than the pre-region (namely, nucleotide sequence encoding the amino acid sequence of pro-protein). The nucleotide sequence encoding the amino acid sequence of the mature protein of protein deamidase of *Luteimicrobium album* corresponds to positions 718 to 4068 of SEQ ID NO: 3. The nucleotide sequence encoding the amino acid sequence of the mature protein of protein deamidase of *Agromyces* sp. corresponds to positions 541 to 3543 of SEQ ID NO: 6. The nucleotide sequence encoding the amino acid sequence of the pro-protein of protein deamidase of *Agromyces* sp. corresponds to positions 199 to 3543 of SEQ ID NO: 6. The position of the N-terminus residue of the mature protein may shift forward or backward by several residues depending on various conditions such as type of processing enzyme. The term "several residues" referred to here may be, for example, 1, 2, 3, 4, 5, 6, 7, 8, 9, or 10 residues. That is, for example, the amino acid sequence of the mature protein of protein deamidase of *Agromyces* sp. may correspond to positions 181±several residues to 1180 of SEQ ID NO: 5. In an embodiment, the amino acid sequence of the mature protein of protein deamidase of *Agromyces* sp. may corresponds to positions 177 to 1180 of SEQ ID NO: 5.

Figure 7B:
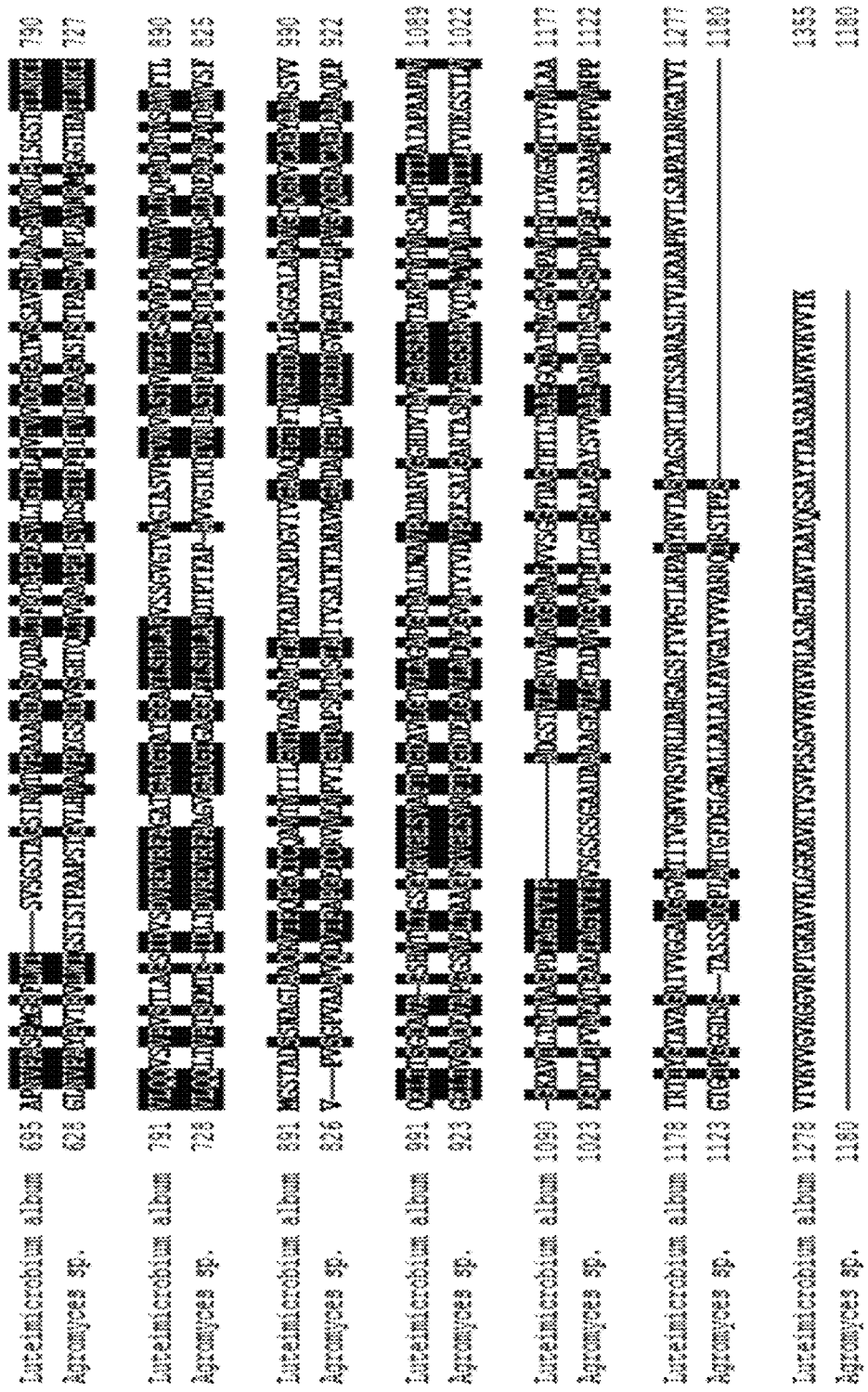
Figure 8A:
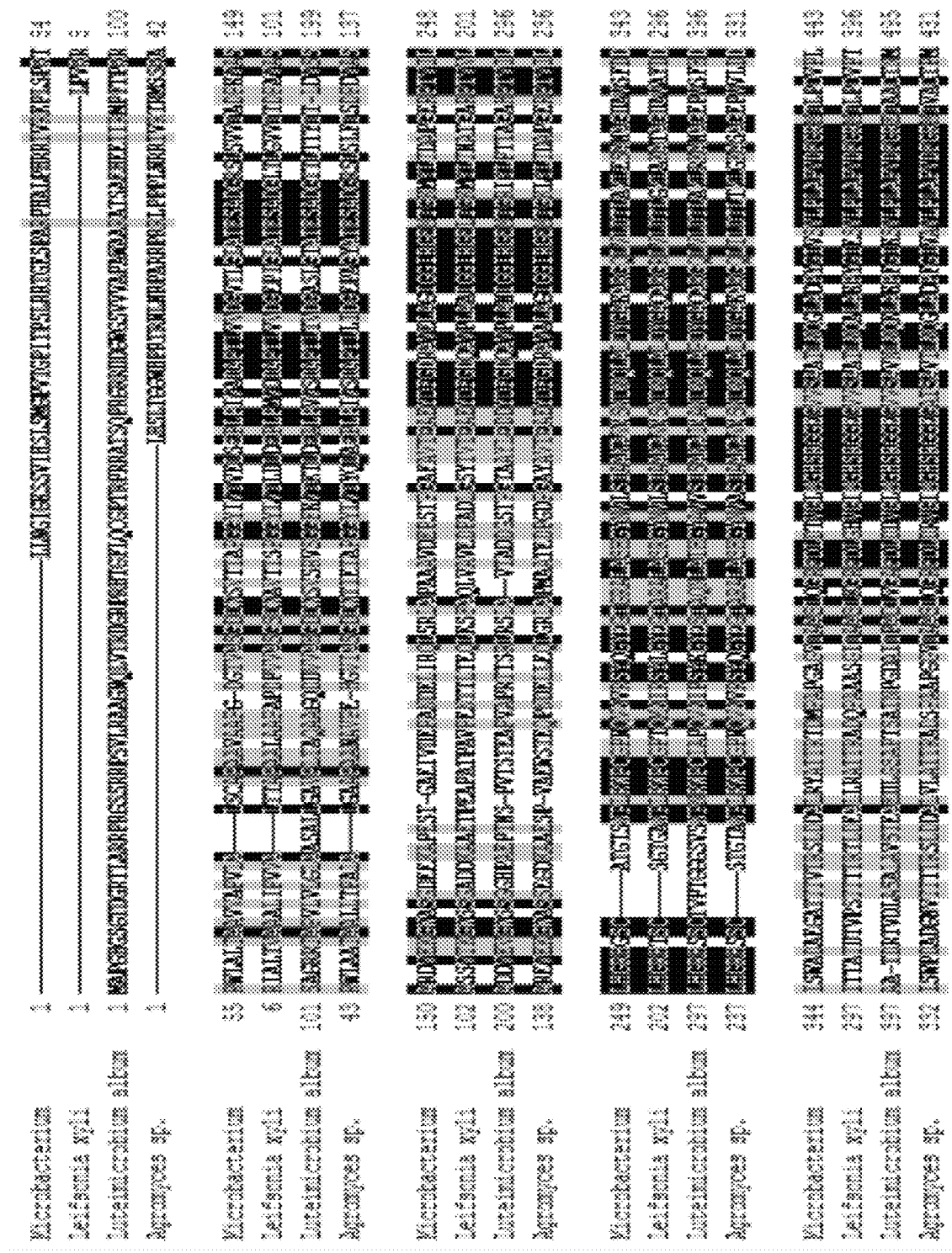
FIGS. 8A to 8C A diagram showing the result of alignment of the sequences of SEQ ID NOS: 2, 5, 7, and 8.
Figure 8B:
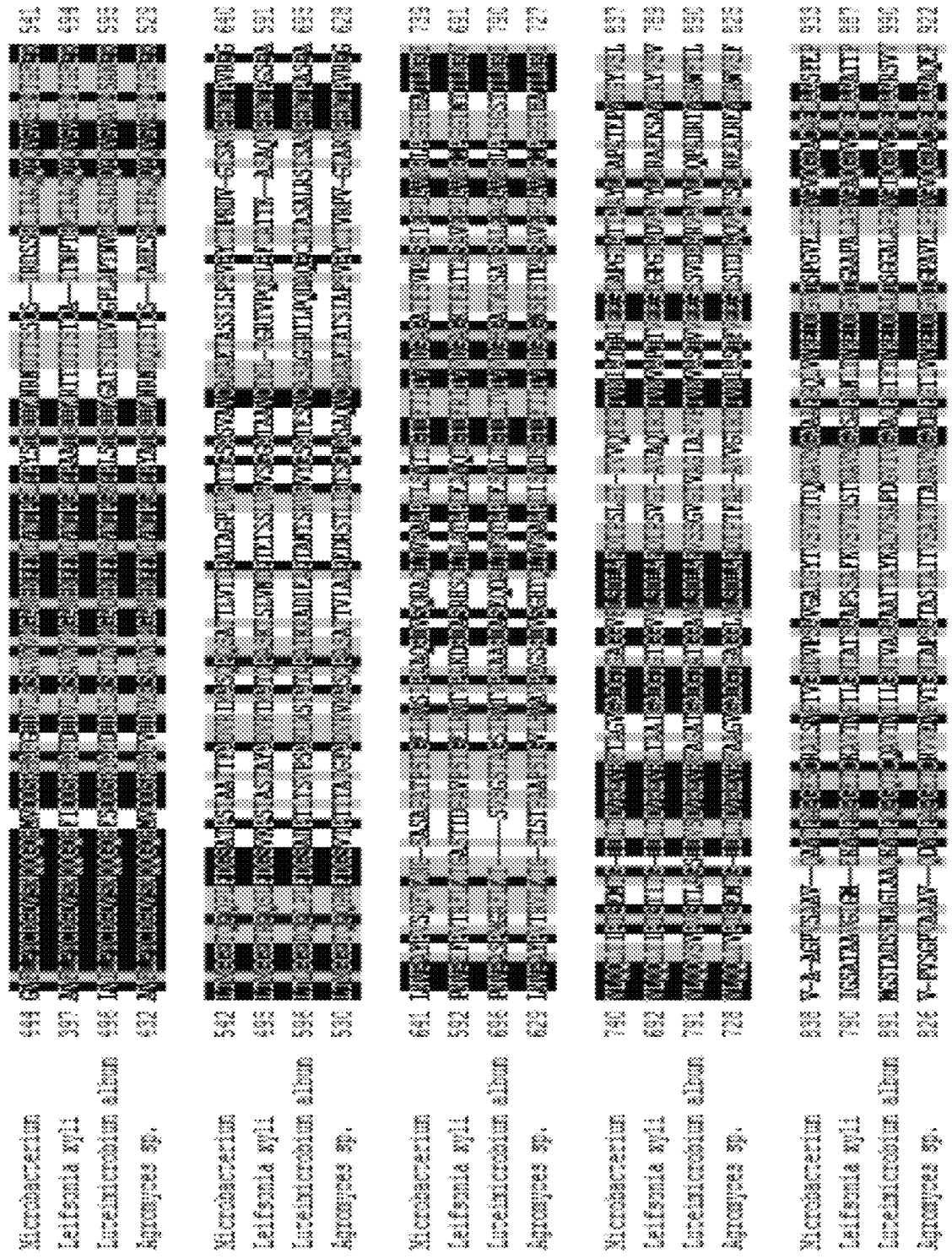
Figure 8C:
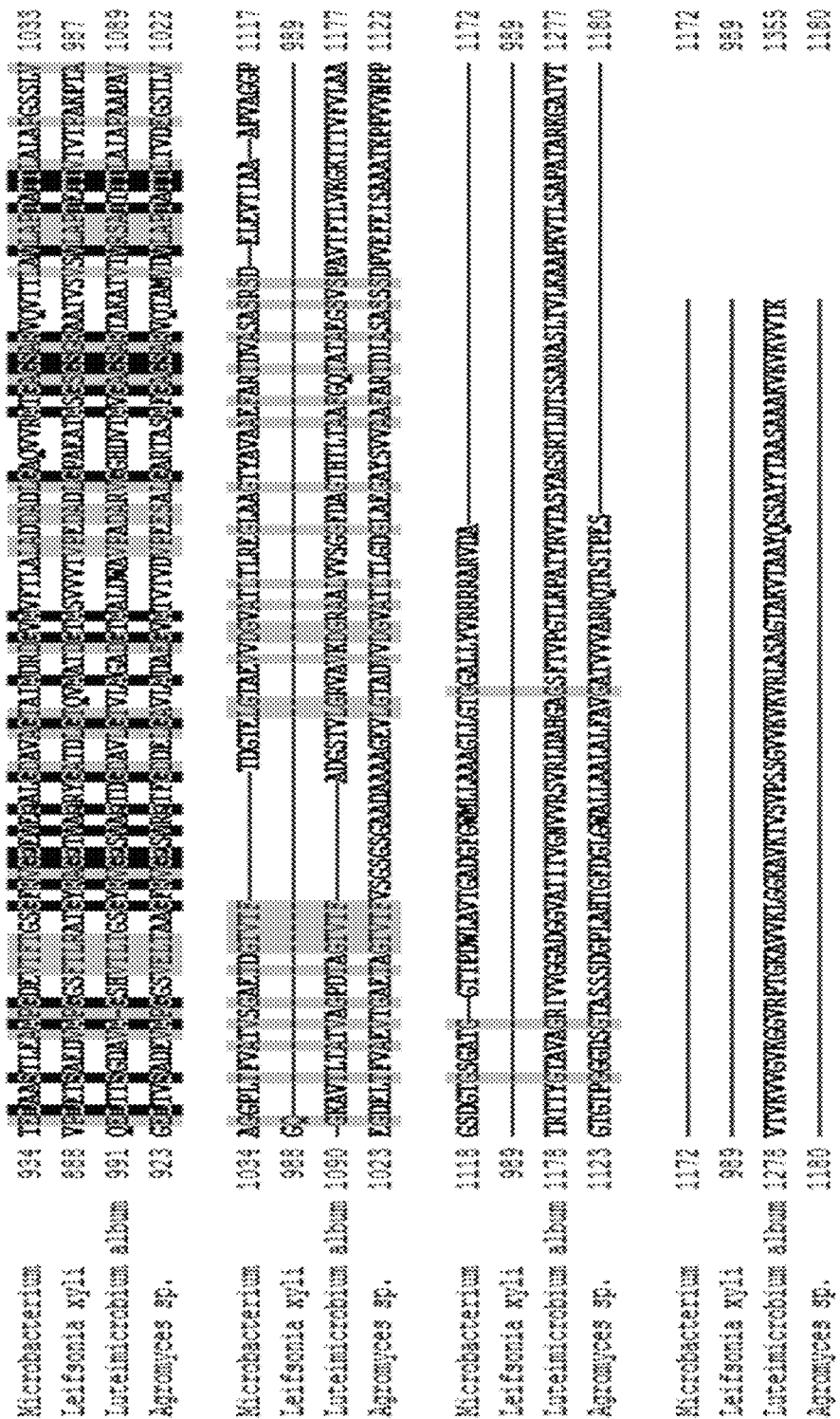
Figure 9A:
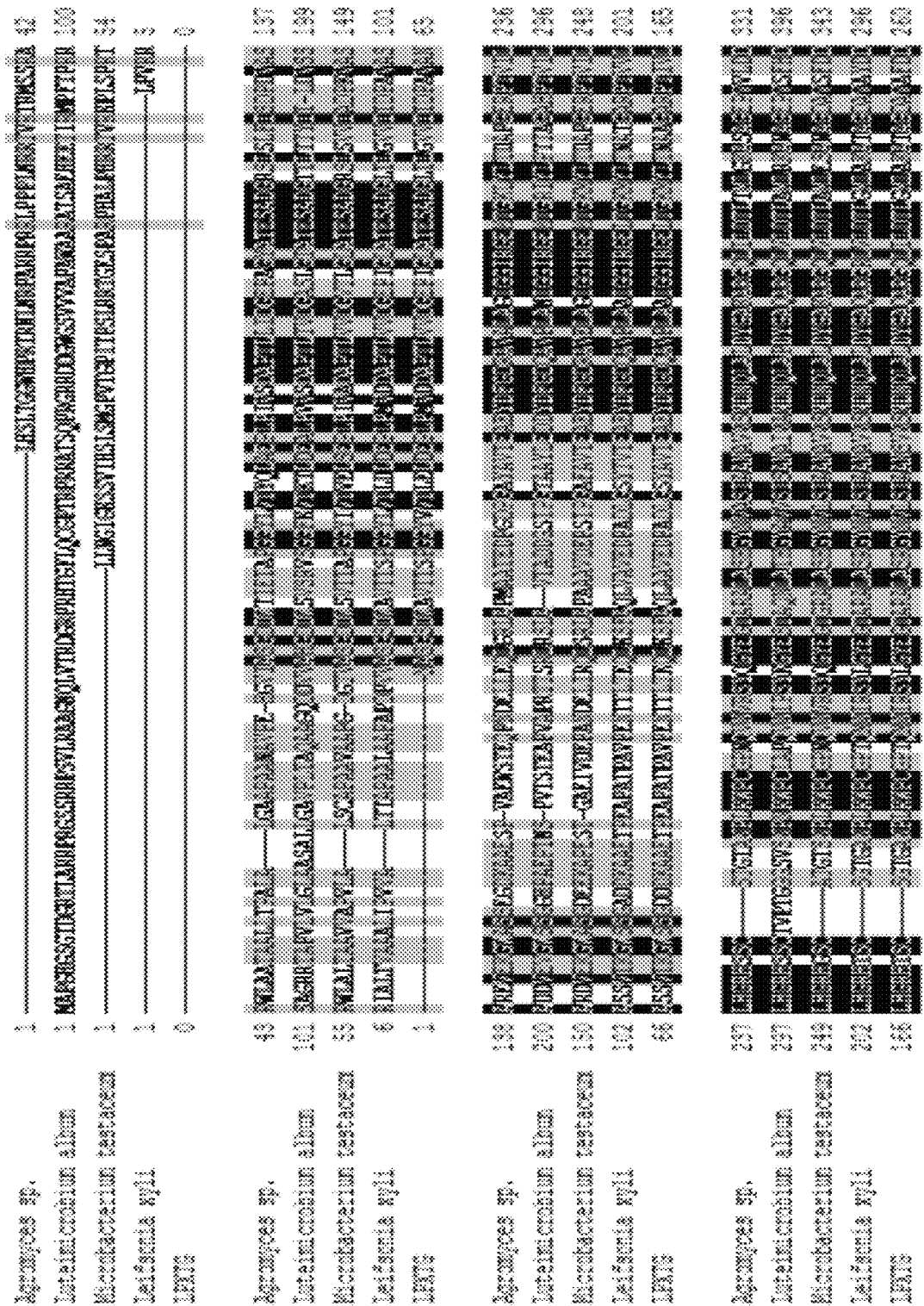
FIGS. 9A to 9D A diagram showing the result of alignment of the sequences of SEQ ID NOS: 2, 5, 7, 8, and 9.
Figure 9B:
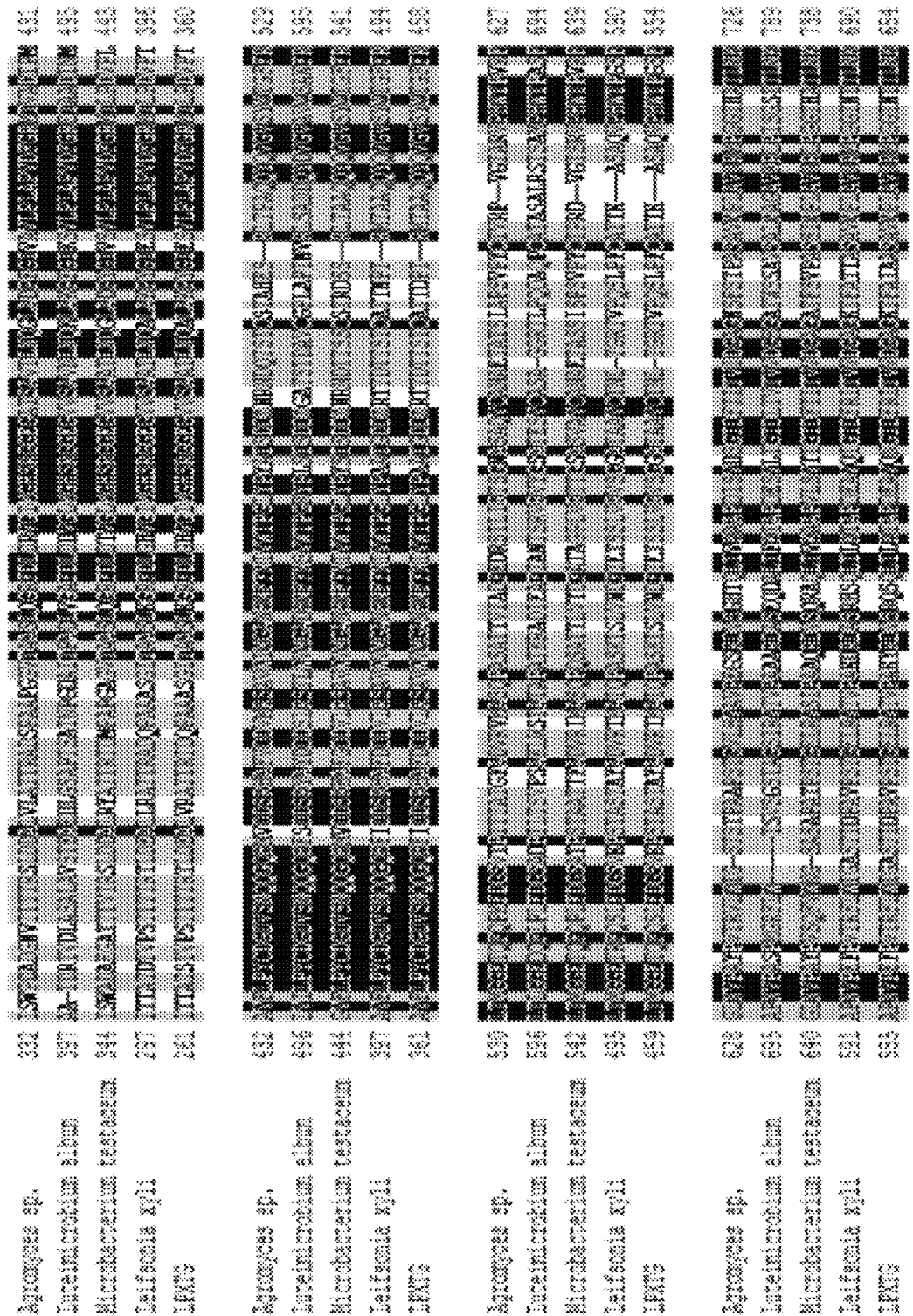
Figure 9C:
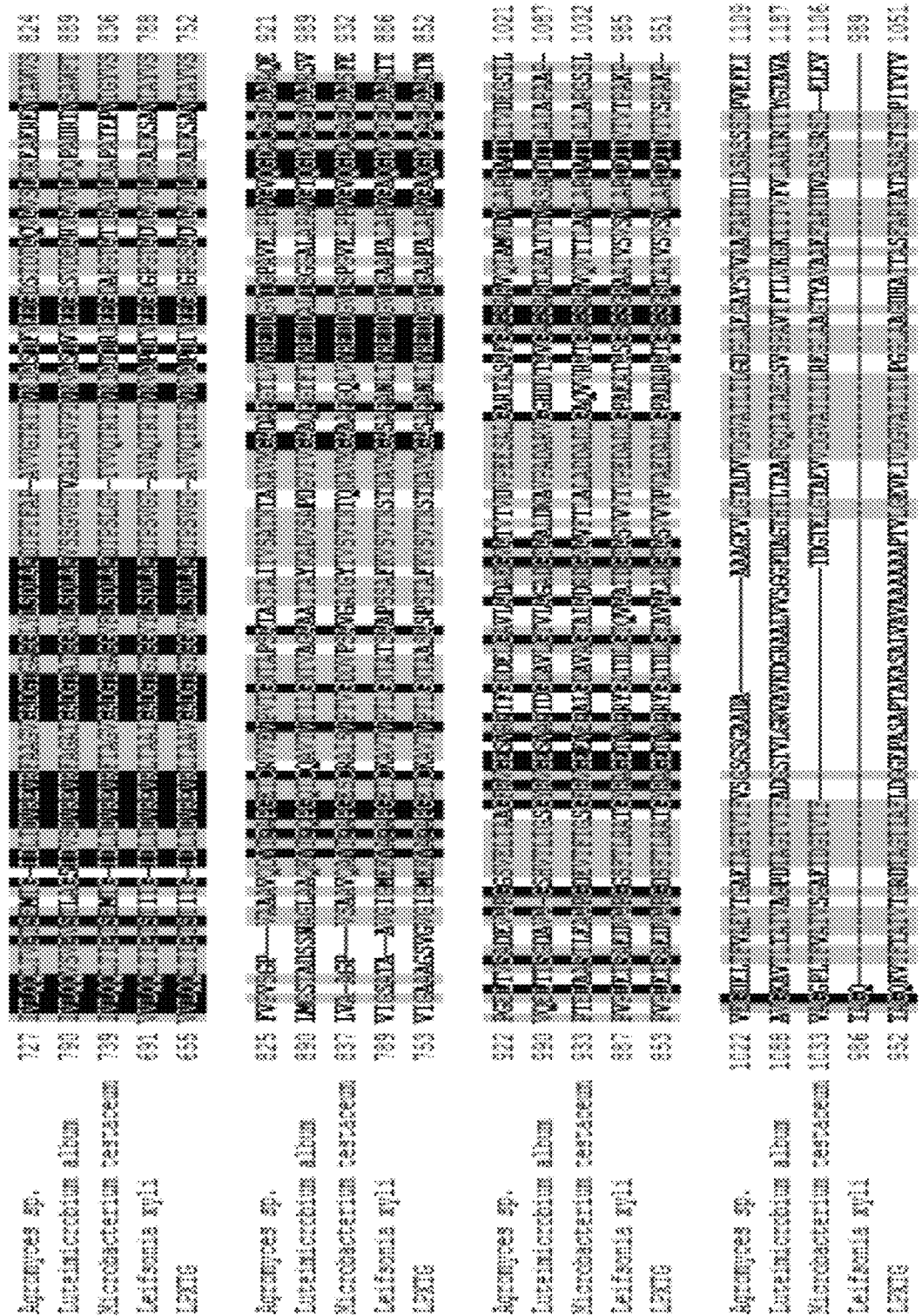
Figure 9D:
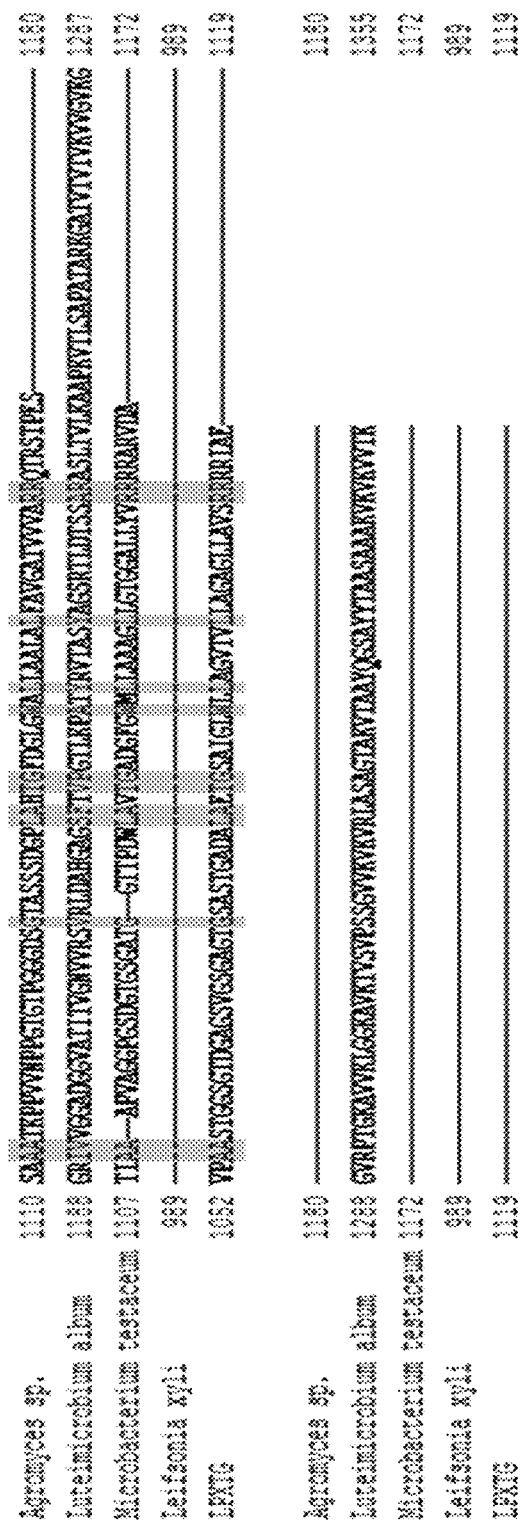

Protein deamidase may be, for example, a protein having an amino acid sequence common to the amino acid sequences of two or more kinds of protein deamidases. The common amino acid sequence can be determined by aligning the amino acid sequences of two or more kinds of protein deamidases. The result of alignment of SEQ ID NOS: 2 and 5 is shown in FIGS. 7A and 7B, and the amino acid sequence common to them is shown as SEQ ID NO: 10. The result of alignment of SEQ ID NOS: 2, 5, 7, and 8 is shown in FIGS. 8A to 8C, and the amino acid sequence common to them is shown as SEQ ID NO: 11. The result of alignment of SEQ ID NOS: 2, 5, 7, 8, and 8 is shown in FIGS. 9A to 9D. That is, protein deamidase may be, for example, a protein having the amino acid sequence shown as SEQ ID NO: 10 or 11. Protein deamidase may also be, for example, a protein having a part of an amino acid sequence common to the amino acid sequences of two or more kinds of protein deamidases, the part corresponding to any of these protein deamidases. Examples of such a part of an amino acid sequence corresponding to protein deamidase include the amino acid sequence of positions 63 to 1260 of SEQ ID NO: 10 (corresponding to protein deamidase of *Agromyces* sp.), the amino acid sequence of positions 47 to 1257 of SEQ ID NO: (corresponding to protein deamidase of *Microbacterium testaceum*), the amino acid sequence of positions 59 to 1258 of SEQ ID NO: 11 (corresponding to protein deamidase of *Agromyces* sp.), and the amino acid sequence of positions 96 to 1101 of SEQ ID NO: 11 (corresponding to protein deamidase of *Leifsonia xyli*). Protein deamidase may also be, for example, a protein having a part of an amino acid sequence common to the amino acid sequences of two or more kinds of protein deamidases, the part corresponding to the mature protein of any of those protein deamidases, or a protein having a part of an amino acid sequence common to the amino acid sequences of two or more kinds of protein deamidases, the part corresponding to the pro-protein of any of those protein deamidases. Examples of such a part of an amino acid sequence corresponding to a mature protein of protein deamidase include the amino acid sequence of positions 245 to 1378 of SEQ ID NO: 10 (corresponding to the mature protein of protein deamidase of *Luteimicrobium album*), the amino acid sequence of positions 245 to 1260 of SEQ ID NO: 10 (corresponding to the mature protein of protein deamidase of *Agromyces* sp.), the amino acid sequence of positions 241 to 1378 of SEQ ID NO: 11 (corresponding to the mature protein of protein deamidase of *Luteimicrobium album*), the amino acid sequence of positions 244 to 1258 of SEQ ID NO: 11 (corresponding to the mature protein of protein deamidase of *Agromyces* sp.), the amino acid sequence of positions 244 to 1257 of SEQ ID NO: 11 (corresponding to the mature protein of protein deamidase of *Microbacterium testaceum*), and the amino acid sequence of positions 244 to 1101 of SEQ ID NO: 11 (corresponding to the mature protein of protein deamidase of *Leifsonia xyli*). Examples of such a part of an amino acid sequence corresponding to a pro-protein of protein deamidase include the amino acid sequence of positions 131 to 1260 of SEQ ID NO: 10 (corresponding to the pro-protein of protein deamidase of *Agromyces* sp.), the amino acid sequence of positions 129 to 1258 of SEQ ID NO: 11 (corresponding to the pro-protein of protein deamidase of *Agromyces* sp.), the amino acid sequence of positions 120 to 1257 of SEQ ID NO: 11 (corresponding to the pro-protein of protein deamidase of *Microbacterium testaceum*), and the amino acid sequence of positions 120 to 1101 of SEQ ID NO: (corresponding to the pro-protein of protein deamidase of *Leifsonia xyli*).

Protein deamidase may be a variant of any of the protein deamidases exemplified above (for example, a protein having the amino acid sequence of SEQ ID NO: 2, 5, 7, 8, 9, 10, or 11, or a protein having a part of any of those amino acid sequences), so long as the original function is maintained. Similarly, the gene encoding protein deamidase (also referred to as "protein deamidase gene") may be a variant of any of the protein deamidase genes exemplified above (for example, a gene having the nucleotide sequence of SEQ ID NO: 3 or 6, or a gene having a part of any of those nucleotide sequences), so long as the original function is maintained. Such a variant that maintains the original function is also referred to as "conservative variant". Examples of the conservative variant include, for example, a homologue and artificially modified version of the protein deamidases exemplified above and genes encoding them.

The expression "the original function is maintained" means that a variant of the gene or protein has a function (activity or property) corresponding to the function (activity or property) of the original gene or protein. That is, the expression "the original function is maintained" means that, in the case of protein deamidase, a variant of the protein has the protein asparaginase activity. Further, the expression "the original function is maintained" may also mean that, in the case of the protein deamidase gene, a variant of the gene encodes a protein that maintains the original function (namely, a protein having the protein asparaginase activity).

Examples of homologues of protein deamidase include, for example, protein deamidases produced by microorganisms obtained by the screening method mentioned later. Examples of homologues of protein deamidase also include, for example, proteins obtained from a public database by BLAST search and FASTA search using any of the aforementioned amino acid sequences as a query sequence. Also, homologues of the aforementioned protein deamidase genes can be obtained by, for example, PCR using a chromosome of any of various microorganisms as the template, and oligonucleotides prepared on the basis of any of those known gene sequences as the primers.

Protein deamidase may be a protein having any of the aforementioned amino acid sequences (for example, the amino acid sequence of SEQ ID NO: 2, 5, 7, 8, 9, 10, or 11, or a part (e.g. part corresponding to mature protein or part corresponding to pro-protein) of any of those amino acid sequences), but including substitution, deletion, insertion, or addition of one or several amino acid residues at one or several positions, so long as it maintains the original function. Although the number meant by the term "one or several" can differ depending on the positions of amino acid residues in the three-dimensional structure of the protein, or the types of amino acid residues, specifically, it is, for example, 1 to 50, 1 to 40, 1 to 30, preferably 1 to 20, more preferably 1 to 10, still more preferably 1 to 5, particularly preferably 1 to 3.

The aforementioned substitution, deletion, insertion, or addition of one or several amino acid residues is a conservative mutation that maintains normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, such substitution, deletion, insertion, addition, inversion, or the like of amino acid residues as mentioned above includes a naturally occurring mutation (mutant or variant), such as those due to a difference of individuals or species of the organism from which the protein is derived.

Protein deamidase may be a protein having an amino acid sequence showing a homology of 80% or higher, preferably 90% or higher, more preferably 95% or higher, still more preferably 97% or higher, particularly preferably 99% or higher, to the whole of any of the aforementioned amino acid sequences, so long as the original function is maintained. In this description, "homology" can mean "identity".

When protein deamidase is a conservative variant of any of the aforementioned common amino acid sequences (for example, the amino acid sequence of SEQ ID NO: 10 or 11, or a part (e.g. part corresponding to mature protein or part corresponding to pro-protein) of any of those amino acid sequences), such a variant may be a protein, wherein a mutation has been introduced into a common portion and/or another portion in the common amino acid sequence, so long as the original function is maintained. It is preferred that such a variant is a protein, wherein the common part in the common amino acid sequence is conserved, and a mutation is introduced into another portion.

Protein deamidase may be a protein encoded by a DNA that hybridizes under stringent conditions with a probe that can be prepared from any of the aforementioned nucleotide sequences (for example, the nucleotide sequence of SEQ ID NO: 3 or 6, or a part (e.g. part encoding mature protein or part encoding pro-protein) of any of those nucleotide sequences), such as a sequence complementary to a part or the whole of any of the aforementioned nucleotide sequences, so long as the original function is maintained. Such a probe can be prepared by PCR using oligonucleotides produced on the basis of any of the aforementioned nucleotide sequences as primers, and a DNA fragment containing any of the aforementioned nucleotide sequences as the template. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 80% homologous, preferably not less than 90% homologous, more preferably not less than 95% homologous, still more preferably not less than 97% homologous, particularly preferably not less than 99% homologous, hybridize to each other, and DNAs less homologous than the above do not hybridize to each other, or conditions of washing of typical Southern hybridization, i.e., conditions of washing once, preferably 2 or 3 times, at a salt concentration and temperature corresponding to 1×SSC, 0.1% SDS at 60° C., preferably 0.1×SSC, 0.1% SDS at 60° C., more preferably 0.1×SSC, 0.1% SDS at 68° C. Further, for example, when a DNA fragment having a length of about 300 bp is used as the probe, the washing conditions of the hybridization can be, for example, 50° C., 2×SSC, and 0.1% SDS.

Such protein deamidase as mentioned above may be, if the amino acid sequence thereof or the nucleotide sequence of the gene encoding it was known at the time of filling of this application, excluded from protein deamidase of the present invention.

Protein deamidase may be a fusion protein with another amino acid sequence. The "another amino acid sequence" is not particularly limited so long as the fusion protein has the protein asparaginase activity. The "another amino acid sequence" can be selected as required depending on various conditions such as purpose of use thereof. Examples of the "another amino acid sequence" include a peptide tag, signal sequence (pre-sequence), pro-sequence, and recognition sequence of a protease. The "another amino acid sequence" may be bound to, for example, either one or both of the N-terminus and C-terminus of protein deamidase. As the "another amino acid sequence", one kind of amino acid sequence may be used, or two or more kinds of amino acid sequences may be used in combination.

A peptide tag can be used for, for example, detection and purification of the expressed protein deamidase. Specific examples of the peptide tag include an His tag, FLAG tag, GST tag, Myc tag, MBP (maltose binding protein), CBP (cellulose binding protein), TRX (thioredoxin), GFP (green fluorescent protein), HRP (horseradish peroxidase), ALP (alkaline phosphatase), and Fc region of antibody. Examples of the His tag include 6×His tag.

A signal sequence can be used for, for example, secretory production of protein deamidase. Examples of the signal sequence include a signal sequence recognized by the Sec system secretory pathway and a signal sequence recognized by the Tat system secretory pathway. Specific examples of the signal sequence recognized by the Sec system secretory pathway include a signal sequence of a cell surface protein of coryneform bacteria. Examples of the cell surface protein of coryneform bacteria include PS1 (CspA) and PS2 (CspB) of *C. glutamicum* (Japanese Patent Laid-open (Kohyo) No. 6-502548), and SlpA (CspA) of *C. ammoniagenes* (*C. stationis*) (Japanese Patent Laid-open (Kokai) No. 10-108675). Specific examples of the signal sequence recognized by the Tat system secretory pathway include the TorA signal sequence of *E. coli*, the SufI signal sequence of *E. coli*, the PhoD signal sequence of *Bacillus subtilis*, the LipA signal sequence of *Bacillus subtilis*, and the IMD signal sequence of *Arthrobacter globiformis* (WO2013/118544). As the signal sequence, a signal sequence of protein deamidase may be used. A signal sequence can be used by, for example, adding it to the N-terminus of the protein to be produced. Specifically, a signal sequence can be used by, for example, adding it to the N-terminus of a pro-protein or mature protein of protein deamidase. A signal sequence is generally digested with a signal peptidase, when a translation product is secreted out of a microbial cell. Therefore, if secretory production of protein deamidase is performed by using a signal sequence, protein deamidase not having the signal sequence may be secreted out of the microbial cell.

Specific examples of the pro-sequence include a pro-sequence of protein deamidase. Examples of the pro-sequence of protein deamidase include the sequence of positions 67 to 180 of SEQ ID NO: 5. A pro-sequence can be used by, for example, adding it to the N-terminus of the protein to be produced. Specifically, a pro-sequence can be used by, for example, adding it to the N-terminus of a mature protein of protein deamidase. When secretory production of protein deamidase is performed, protein deamidase may be constituted to contain a signal sequence, a pro-sequence, and a sequence of mature protein in this order from the N-terminus, and expressed. Expression of protein deamidase in the form of having a pro-sequence may contribute to structural stabilization of protein deamidase. By contrast, from the viewpoint of the protein asparaginase activity, it is preferred that protein deamidase eventually obtained does not have a pro-sequence.

A recognition sequence for a protease can be used for, for example, cleavage of the expressed protein deamidase. It is preferred that the recognition sequence for a protease is a recognition sequence for a protease showing high substrate specificity. Specific examples of the recognition sequence for a protease showing high substrate specificity include the recognition sequence for the factor Xa protease and the recognition sequence for the ProTEV protease. The factor Xa protease and the ProTEV protease recognize the amino acid sequence of Ile-Glu-Gly-Arg (=IEGR, SEQ ID NO: 14) and the amino acid sequence of Glu-Asn-Leu-Tyr-Phe-Gln (=ENLYFQ, SEQ ID NO: 15) in a protein, respectively, to digest the protein specifically at a position on the C-terminus side of the corresponding recognition sequence. For example, when protein deamidase is expressed as a fusion protein with another amino acid sequence such as a peptide tag or pro-sequence, if a recognition sequence for a protease is introduced between protein deamidase and such another amino acid sequence, such another amino acid sequence can be removed from the expressed protein deamidase by using the protease to obtain protein deamidase not having such another amino acid sequence.

The protein deamidase gene may be one having any of the nucleotide sequences of the protein deamidase genes exemplified above and conservative variants thereof, in which arbitrary codons are replaced with equivalent codons. For example, the protein deamidase gene may be modified so that it has codons optimized for codon usage observed in the host to be used.

In the present invention, the term "gene" is not limited to DNA, but may include an arbitrary polynucleotide, so long as it encodes a target protein. That is, the term "protein deamidase gene" may mean an arbitrary polynucleotide encoding protein deamidase. The protein deamidase gene may be DNA, RNA, or a combination thereof. The protein deamidase gene may be single-stranded or double-stranded. The protein deamidase gene may be a single-stranded DNA or a single-stranded RNA. The protein deamidase gene may be a double-stranded DNA, a double-stranded RNA, or a hybrid strand consisting of a DNA strand and an RNA strand. The protein deamidase gene may contain both a DNA residue and an RNA residue in a single polynucleotide chain. When the protein deamidase gene contains RNA, the aforementioned descriptions concerning DNA, such as those concerning nucleotide sequences exemplified above, may be applied to RNA with appropriately changing wordings to those for RNA as required. The mode of the protein deamidase gene can be chosen according to various conditions such as use thereof.

<2> Production of Protein Deamidase

Protein deamidase can be produced by using a host having an ability to produce the protein deamidase. That is, the present invention provides a method for producing protein deamidase, which method comprises culturing a host having an ability to produce protein deamidase in a medium to generate the protein deamidase, and collecting the protein deamidase from the culture broth. This method is also referred to as "the method for producing protein deamidase of the present invention". Protein deamidase can also be produced by expressing a protein deamidase gene in a cell-free protein synthesis system.

The host having an ability to produce protein deamidase may be one inherently having an ability to produce protein deamidase, or may be one modified so as to have an ability to produce protein deamidase.

Examples of the host having an ability to produce protein deamidase include such bacteria belonging to the class Actinobacteria as mentioned above, such as *Luteimicrobium album* AJ111072 (NITE P-01650), *Agromyces* sp. AJ111073 (NITE BP-01782), *Microbacterium testaceum*, and *Leifsonia xyli* AJ111071 (NITE P-01649).

Examples of the host having an ability to produce protein deamidase also include a microorganism obtained by the following screening technique.

(1) A microorganism supply source such as soil is inoculated into a medium containing Cbz-Asn-Gly as a sole N source, and enrichment culture is performed.

(2) The culture broth obtained in (1) is inoculated on an agar medium containing Cbz-Asn-Gly as a sole N source, and a grown strain is obtained.

(3) The obtained strain is cultured in an appropriate liquid nutrition medium, and the activity for releasing ammonia from Cbz-Asn-Gly and casein contained in the culture broth is determined.

The composition of the medium used for the enrichment culture can be appropriately set according to the microorganism to be cultured, provided that Cbz-Asn-Gly is used as a sole N source. Culture conditions such as culture temperature can also be appropriately set according to the microorganism to be cultured. As for specific medium components and culture conditions, the descriptions concerning the culture of a host having an ability to produce protein deamidase described later can be referred to.

Examples of the host having an ability to produce protein deamidase also include a host introduced with a protein deamidase gene.

The host to be introduced with a protein deamidase gene is not particularly limited so long as it can express a functional protein deamidase. Examples of the host include, for example, bacteria, actinomycetes, yeast, fungi, plant cells, insect cells, and animal cells. Preferred examples of the host include microorganisms such as bacteria and yeast. More preferred examples of the host include bacteria. Examples of the bacteria include gram-negative bacteria and gram-positive bacteria. Examples of the gram-negative bacteria include, for example, bacteria belonging to the family Enterobacteriaceae, such as *Escherichia* bacteria, *Enterobacter* bacteria, and *Pantoea* bacteria. Examples of the gram-positive bacteria include *Bacillus* bacteria, and coryneform bacteria such as *Corynebacterium* bacteria. As the host, *Escherichia coli* can be especially preferably used. Also, when protein deamidase is produced by secretory production out of a microbial cell, particularly, coryneform bacteria such as *Corynebacterium glutamicum* and *Corynebacterium stationis* may preferably be used as the host (WO2013/065869, WO2013/065772, WO2013/118544, WO2013/062029).

A protein deamidase gene can be obtained by cloning from an organism having the protein deamidase gene. For the cloning, a nucleic acid containing the gene, such as a genomic DNA or cDNA, can be used. A protein deamidase gene can also be obtained by chemical synthesis (Gene, 60 (1), 115-127 (1987)).

Specifically, a protein deamidase gene can be cloned from, for example, such a microorganism having an ability to produce protein deamidase as mentioned above (for example, a bacterium belonging to the class Actinobacteria, or a microorganism obtained by the aforementioned screening technique) by such a method as described below.

First, protein deamidase is appropriately isolated and purified from a microorganism having an ability to produce the protein deamidase, and information on a partial amino acid sequence thereof is obtained. For determining the partial amino acid sequence, for example, a purified protein deamidase may be directly subjected to amino acid sequence analysis (protein sequencer PPSQ-21A (Shimadzu) etc.) according to the Edman degradation method [Journal of Biological Chemistry, 256, 7990-7997 (1981)] in a conventional manner, or protein deamidase may be subjected to limited hydrolysis by the action of a proteolytic enzyme, the generated peptide fragments may be isolated and purified, and the obtained purified peptide fragments may be subjected to amino acid sequence analysis. Then, the nucleotide sequence of the genomic DNA extracted from the microorganism is determined with a next-generation sequencer (MiSeq, Illumina, etc.), and the partial amino acid sequence obtained by the aforementioned method is searched for. That is, a contig sequence can be created by using CLC Genomics Workbench (CLC bio Japan) on the basis of the obtained nucleotide sequence of the genomic DNA, and the nucleotide sequence of the gene encoding the enzyme can be determined on the basis of the partial amino acid sequence of protein deamidase obtained beforehand. A protein deamidase gene can be cloned by a general method using PCR on the basis of the determined nucleotide sequence.

When a PCR method is used, such a method as mentioned below can be used. First, PCR is performed by using a genomic DNA of a microorganism having an ability to produce protein deamidase as the template, and synthetic oligonucleotide primers designed on the basis of the information on a partial amino acid sequence thereof to obtain a DNA fragment containing a part of the target protein deamidase gene. The PCR method is performed according to the method described in PCR Technology, Erlich, H. A. Eds., Stockton Press, 1989. Subsequently, if the nucleotide sequence of the amplified DNA fragment is determined by a method usually used such as the dideoxy chain terminator method, a sequence corresponding to the partial amino acid sequence of protein deamidase can be found in the determined sequence in addition to the sequences of the synthetic oligonucleotide primers, and that is, a part of the nucleotide sequence of the target protein deamidase gene can be determined. Further, by performing the hybridization method or the like using the obtained gene fragment as a probe, the protein deamidase gene can be cloned for the full length thereof.

Further, the thus-obtained protein deamidase gene can be modified as required to obtain a variant thereof. Modification of a gene can be performed by a known method. For example, by the site-specific mutagenesis method, an objective mutation can be introduced into a target site of a gene. That is, for example, a coding region of a gene can be modified by the site-specific mutagenesis method so that a specific site of the encoded protein include substitution, deletion, insertion, or addition of amino acid residues. Examples of the site-specific mutagenesis method include a method using PCR (Higuchi, R., 61, in PCR Technology, Erlich, H. A. Eds., Stockton Press, 1989; Carter P., Meth., in Enzymol., 154, 382, 1987), and a method of using a phage (Kramer, W. and Frits, H. J., Meth. in Enzymol., 154, 350, 1987; Kunkel, T. A. et al., Meth. in Enzymol., 154, 367, 1987). Further, a variant of the protein deamidase gene can also be obtained by, for example, a mutagenesis treatment. Examples of the mutagenesis treatment include methods such as treating a gene itself in vitro with hydroxylamine or the like, treating a microorganism such as a bacterium belonging to the class Actinobacteria and having a protein deamidase gene with X-ray, ultraviolet ray, or a mutation agent such as N-methyl-N'-nitro-N-nitrosoguanidine (NTG), ethyl methanesulfonate (EMS), and methyl methanesulfonate (MMS), error prone PCR (Cadwell, R. C., PCR Meth. Appl., 2, 28 (1992)), DNA shuffling (Stemmer, W. P., Nature, 370, 389 (1994)), and StEP-PCR (Zhao, H., Nature Biotechnol., 16, 258 (1998)).

The method for introducing a protein deamidase gene into a host is not particularly limited. In a host, a protein deamidase gene may be harbored in such a manner that it can be expressed under control of a promoter that functions in the host. In the host, the protein deamidase gene may exist on a vector autonomously replicable out of the chromosome such as plasmid, or may be introduced into the chromosome. The host may have only one copy of a protein deamidase gene, or may have two or more copies of a protein deamidase gene. The host may have only one kind of protein deamidase gene, or may have two or more kinds of protein deamidase genes.

The promoter for expressing a protein deamidase gene is not particularly limited so long as it is a promoter that functions in the host. The "promoter that functions in a host" refers to a promoter that shows a promoter activity in the host. The promoter may be a promoter derived from the host, or a heterologous promoter. The promoter may be a native promoter of the protein deamidase gene, or may be a promoter of another gene. The promoter may be a strong promoter so that a high expression amount of the gene can be attained. Specific examples of strong promoters that function in Enterobacteriaceae bacteria, such as *Escherichia coli*, include, for example, T7 promoter, trp promoter, trc promoter, lac promoter, tac promoter, tet promoter, araBAD promoter, rpoH promoter, PR promoter, and PL promoter. Examples of strong promoters that function in coryneform bacteria include the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 December; 71 (12):8587-96), as well as lac promoter, tac promoter, and trc promoter. Further, as the stronger promoter, a highly-active type of an existing promoter may also be obtained by using various reporter genes. For example, by making the −35 and −10 regions in a promoter region closer to the consensus sequence, the activity of the promoter can be enhanced (WO00/18935). Examples of highly active-type promoter include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

Also, a terminator for termination of gene transcription may be located downstream of the protein deamidase gene. The terminator is not particularly limited so long as it functions in the bacterium of the present invention. The terminator may be a terminator derived from the host, or a heterogenous terminator. The terminator may be the native terminator of the protein deamidase gene, or a terminator of another gene. Specific examples of the terminator include, for example, T7 terminator, T4 terminator, fd phage terminator, tet terminator, and trpA terminator.

A protein deamidase gene can be introduced into a host, for example, by using a vector containing the gene. A vector containing a protein deamidase gene is also referred to as expression vector or recombinant vector for a protein deamidase gene. The expression vector for a protein deamidase gene can be constructed by, for example, ligating a DNA fragment containing the protein deamidase gene with a vector that functions in the host. By transforming the host with the expression vector for a protein deamidase gene, a transformant into which the vector has been introduced is obtained, i.e. the gene can be introduced into the host. As the vector, a vector autonomously replicable in the cell of the host can be used. The vector is preferably a multi-copy vector. Further, the vector preferably has a marker such as an antibiotic resistance gene for selection of transformant. Further, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in Enterobacteriaceae bacteria such as Escherichia coli include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pACYC, and the broad host spectrum vector RSF1010. Specific examples of vector autonomously replicable in coryneform bacteria include, for example, pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; and pCG4 and pCG11 described in Japanese Patent Laid-open (Kokai) No. 57-183799. When the expression vector is constructed, for example, a protein deamidase gene having a native promoter region as it is may be incorporated into a vector, a coding region of protein deamidase ligated downstream from such a promoter as mentioned above may be incorporated into a vector, or a coding region of protein deamidase may be incorporated into a vector downstream from a promoter originally existing in the vector.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

A protein deamidase gene can also be introduced into, for example, a chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination include, for example, the Red-driven integration method (WO2005/010175), a transduction method using a phage such as P1 phage, a method of using a conjugative transfer vector, and a method of using a suicide vector without a replication origin that functions in a host. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include, for example, repetitive DNAs, and inverted repeats located at the both ends of a transposon. Further, a gene can also be randomly introduced into a chromosome by a method using a transposon or Mini-Mu (Japanese Patent Laid-open (Kokai) No. 2-109985, U.S. Pat. No. 5,882,888, EP 805867 B1). When the gene is introduced into a chromosome, for example, a protein deamidase gene having a native promoter region as it is may be incorporated into a chromosome, a coding region for protein deamidase ligated downstream from such a promoter as mentioned above may be incorporated into a chromosome, or a coding region for protein deamidase may be incorporated into a chromosome downstream from a promoter originally contained in the chromosome.

Introduction of a gene into a chromosome can be confirmed by, for example, Southern hybridization using a probe having a sequence complementary to a part or the whole of the gene, or PCR using primers prepared on the basis of the nucleotide sequence of the gene.

The method for the transformation is not particularly limited, and conventionally known methods can be used. Examples of transformation method include, for example, a method of treating recipient cells with calcium chloride so as to increase the permeability thereof for DNA, which has been reported for the Escherichia coli K-12 strain (Mandel, M. and Higa, A., J. Mol. Biol., 1970, 53, 159-162), a method of preparing competent cells from cells which are in the growth phase, followed by transformation with DNA, which has been reported for Bacillus subtilis (Duncan, C. H., Wilson, G. A. and Young, F. E., Gene, 1977, 1:153-167), and so forth. Further, as the transformation method, there can also be used a method of making DNA-recipient cells into protoplasts or spheroplasts, which can easily take up recombinant DNA, followed by introducing a recombinant DNA into the DNA-recipient cells, which is known to be applicable to Bacillus subtilis, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Further, as the transformation method, the electric pulse method reported for coryneform bacteria (Japanese Patent Laid-open (Kokai) No. 2-207791) can also be used.

A host inherently having a protein deamidase gene may have been modified so that the expression of the protein deamidase gene is increased. Examples of the means for increasing the expression of a protein deamidase gene include increasing the copy number of the protein deamidase gene, and improving the transcription efficiency of the protein deamidase gene. The copy number of a protein deamidase gene can be increased by introducing the protein deamidase gene into a host. Introduction of a protein deamidase gene can be performed as described above. The protein deamidase gene to be introduced may be a gene derived from the host, or heterogenous gene. The transcription efficiency of a protein deamidase gene can be improved by replacing the promoter of the protein deamidase gene with a stronger promoter. As such stronger promoter, the strong promoters mentioned above can be used.

By culturing such a host having an ability to produce protein deamidase as described above, protein deamidase can be expressed. During the culture, induction of gene expression may be performed, if necessary. Conditions for culture of the host and induction of gene expression may be chosen as required depending on various conditions such as type of marker, type of promoter, and type of the host. The medium used for the culture is not be particularly limited, so long as the host can proliferate in the medium and express a protein deamidase. As the medium, for example, a usual medium that contains a carbon source, nitrogen source, sulfur source, inorganic ions, and other organic components as required can be used.

Examples of the carbon source include saccharides such as glucose, fructose, sucrose, molasses, and starch hydrolysate, alcohols such as glycerol and ethanol, and organic acids such as fumaric acid, citric acid, and succinic acid.

Examples of the nitrogen source include inorganic ammonium salts such as ammonium sulfate, ammonium chloride, and ammonium phosphate, organic nitrogen such as soybean hydrolysate, ammonia gas, and aqueous ammonia.

Examples of the sulfur source include inorganic sulfur compounds, such as sulfates, sulfites, sulfides, hyposulfites, and thiosulfates.

Examples of the inorganic ions include calcium ion, magnesium ion, manganese ion, potassium ion, iron ion, and phosphoric acid ion.

Examples of the other organic components include organic trace amount nutrients. Examples of the organic trace amount nutrients include required substances such as vitamin $B_1$, yeast extract containing such substances, and so forth.

Although the culture may be performed as liquid culture or solid culture, liquid culture is preferred. The culture is preferably performed as aerobic culture. Examples of method for aerobic culture include shaking culture method, and aerobic deep culture method using a jar fermenter. In the aeration culture, oxygen concentration may be adjusted to, for example, 5 to 50%, preferably about 10%, with respect to the saturated concentration. Culture temperature may be, for example, 10 to 50° C., preferably 20 to 45° C., more preferably 25 to 40° C. pH of the medium may be adjusted to 3 to 9, preferably 5 to 8. For adjusting pH, inorganic or organic acidic or alkaline substances such as calcium carbonate, ammonia gas, and aqueous ammonia can be used. Culture period may be, for example, 12 hours to 20 days, preferably 1 to 7 days.

By performing the culture under such conditions as mentioned above, a culture broth containing protein deamidase is obtained. Protein deamidase is accumulated in, for example, microbial cells of the host and/or the medium. The term "microbial cell" may be appropriately read as "cell" depending on type of the host. Depending on the host to be used and design of the protein deamidase gene, it is also possible to accumulate protein deamidase in the periplasm, or to produce protein deamidase out of the cells by secretory production.

Protein deamidase may be used in a state that it is contained in microbial cells or the like, or may be separated and purified from microbial cells or the like to be used as a crude enzyme fraction or a purified enzyme, as required.

That is, for example, when protein deamidase is accumulated in microbial cells of the host, by subjecting the cells to disruption, lysis, extraction, etc. as required, the protein deamidase can be collected. The microbial cells can be collected from the culture broth by centrifugation or the like. Disruption, lysis, extraction, etc. of the cells can be performed by known methods. Examples of such methods include, for example, disruption by ultrasonication, disruption in Dyno-Mill, disruption in bead mill, disruption with French press, and lysozyme treatment. These methods may be independently used, or may be used in an appropriate combination. Also, for example, when protein deamidase is accumulated in the medium, a culture supernatant can be obtained by centrifugation or the like, and the protein deamidase can be collected from the culture supernatant.

Protein deamidase can be purified by known methods used for purification of enzymes. Examples of such methods include, for example, ammonium sulfate fractionation, ion exchange chromatography, hydrophobic chromatography, affinity chromatography, gel filtration chromatography, and isoelectric precipitation. These methods may be independently used, or may be used in an appropriate combination. Protein deamidase may be purified to a desired extent.

The purified protein deamidase can be used as "protein deamidase" used in the method of the present invention. Protein deamidase may be used in a free form, or may be used as an immobilized enzyme immobilized on a solid phase of resin etc.

Not only the purified protein deamidase, but also an arbitrary fraction containing protein deamidase may be used as "protein deamidase" for deamidation of a protein. Such a fraction containing protein deamidase is not particularly limited, so long as it contains a protein deamidase so that the protein deamidase can act on a substrate protein. Examples of such a fraction include, for example, a culture broth of a host having an ability to produce protein deamidase, microbial cells collected from such a culture broth (cultured microbial cells), processed products of such microbial cells such as disruption product of the cells, lysate of the cells, extract of the cells (cell-free extract), and immobilized cells obtained by immobilizing such cells as mentioned above on a carrier such as acrylamide and carrageenan, culture supernatant collected from such a culture broth, partially purified products of these (roughly purified products), and combinations of these. These fractions each may be used alone, or may be used together with a purified protein deamidase.

The collected protein deamidase may be made into a formulation (preparation) as required. The dosage form of the formulation is not particularly limited, and can be appropriately determined according to various conditions such as purpose of use of protein deamidase. Examples of the dosage form include, for example, solution, suspension, powder, tablet, pill, and capsule. For preparing such a formulation, pharmaceutically acceptable additives such as excipients, binders, disintegrating agents, lubricants, stabilizers, corrigents, odor-masking agents, perfumes, diluents, and surfactants can be used.

When protein deamidase has a pro-sequence, the protein asparaginase activity may be improved by removal of the pro-sequence. Therefore, the method for producing protein deamidase of the present invention may further comprise removing a pro-sequence from protein deamidase having the pro-sequence. A pro-sequence can be removed by, for example, treating protein deamidase with a processing enzyme. Examples of the processing enzyme include protease. Specific examples of protease include serine proteases such as subtilisin, chymotrypsin, and trypsin; cysteine proteases such as papain, bromelain, caspase, and calpain; acid proteases such as pepsin and cathepsin; and metalloproteases such as thermolysin. Further, if protein deamidase is expressed with a recognition sequence for a specific protease inserted between sequences of a pro-sequence and a mature protein, the pro-sequence can be specifically removed by using the specific protease. Origin of protease is not particularly limited, and any of those derived from microorganisms, animals, plants, and so forth may be used. As protease, a homologue of a known protease or an artificially modified version of a known protease may be used. As protease, there can be used any of those in the form of, for example, a culture broth of a microorganism that produces protease, culture supernatant separated from such a culture broth, microbial cells separated from such a culture broth, processed product of such cells, agricultural, aquatic, or livestock product containing protease, processed product of such agricultural, aquatic, or livestock product, protease separated from any of these, commercial protease preparation, and so forth. Protease may be purified to a desired degree. Examples of the microorganism that produces protease include *Bacillus* bacteria and *Aspergillus* fungi. Examples of the commercial protease preparation include those mentioned in Table 5.

A specific example of the manufacturing procedure of protein deamidase will be explained below. For example, when *Luteimicrobium album* AJ111072 (NITE P-01650) is used as a host having an ability to produce protein deamidase, glycerol stock of the strain is inoculated in an amount of 1% to the tryptic soy medium (Difco), and shaking culture is performed at 30° C. for 24 hours as preculture. Then, shaking culture is performed at 30° C. for 24 hours in a medium containing Yeast Carbon Base (Difco) and polypeptone as main culture to obtain a culture broth containing protein deamidase. The protein deamidase can be purified by centrifuging the culture broth (12,000 rpm, 4° C., 20 minutes) to obtain a supernatant as a crude enzyme solution, and subjecting the crude enzyme solution to UF concentration (Hydrosart membrane, Sartorius, fractionation molecular weight 10,000), hydrophobic chromatography, ion exchange chromatography, gel filtration chromatography, or the like. Also when other hosts are used, the procedures for the case of using *Luteimicrobium album* AJ111072 (NITE P-01650) can be referred to.

<3> Use of Protein Deamidase

According to the present invention, an asparagine residue in a protein can be deamidated by using protein deamidase. That is, the present invention provides a method for deamidating an asparagine residue in a protein, which method comprises allowing protein deamidase to act on a protein. This method is also referred to as "deamidation method of the present invention". An embodiment of this method is a method for producing a protein containing a deamidated asparagine residue, which method comprises allowing protein deamidase to act on a protein.

The protein to be subjected to deamidation with protein deamidase (substrate protein) is not particularly limited so long as it is a protein containing an asparagine residue. As described above, the length of the substrate protein is not particularly limited so long as the length is 2 residues (dipeptide) or longer, and the term "substrate protein" also includes a substance called peptide, such as oligopeptide and polypeptide, unless otherwise stated. That is, specifically, the term "protein (substrate protein)" may mean a protein and/or a peptide. The substrate protein may be a natural substance or artificial product.

The substrate protein may be a protein itself or a material containing a protein. In other words, the substrate protein itself may be subjected to the deamidation reaction alone (namely, in an isolated state), or the substrate protein in a state of being contained in an arbitrary material may be subjected to the deamidation reaction. Examples of the substrate protein include, for example, agricultural, aquatic, or livestock products containing a protein, processed products thereof, and proteins separated therefrom. Examples of materials containing a vegetable protein include, for example, grains such as soybean, wheat, barley, corn, rice, and processed products thereof. Examples of materials containing an animal protein include, for example, meats such as beef, pork, and chicken, fish meat, milk, eggs, and processed products thereof. Examples of vegetable protein include soybean proteins such as glycinin, wheat proteins such as gluten, glutenin, and gliadin, and corn proteins such as cone gluten meal. Examples of animal protein include milk proteins such as casein, lactalbumin, and β-lactoglobulin, egg proteins such as ovalbumin, meat proteins such as myosin and actin, blood proteins such as serum albumin, and tendon proteins such as gelatin and collagen. Examples of the substrate protein also include proteins partially decomposed chemically with an acid, alkaline, or the like, or enzymatically with protease or the like, proteins chemically modified with various reagents, recombinant proteins produced in appropriate hosts, and synthetic peptides. The substrate protein may be one subjected to such a treatment as heating, steaming, pulverization, freezing, thawing, and drying, as required. The material containing a protein may contain one kind of protein or two or more kinds of proteins. As the substrate protein, one kind of protein may be used, or two or more kinds of proteins may be used.

The substrate protein may be, for example, a food or drink containing a protein, or may be a raw material of a food or drink containing a protein. In other words, the substrate protein may be subjected to the deamidation reaction in a state of being contained in, for example, a food or drink or raw material thereof. The type and form of the food or drink or raw material thereof are not particularly limited, so long as the food or drink or raw material thereof contains a protein. For example, each of such agricultural, aquatic, or livestock products containing a protein, processed products thereof, and proteins separated therefrom as mentioned above may be used as a food or drink or raw material thereof alone, an arbitrary combination of two or more of them may be used as a food or drink or raw material thereof, or an arbitrary combination of any one or more of them and another ingredient may be used as a food or drink or raw material thereof. By subjecting a food or drink or raw material thereof containing a protein to a deamidation with protein deamidase, a food or drink or raw material thereof containing a protein having a deamidated asparagine residue can be obtained. Further, a food or drink containing a protein having a deamidated asparagine residue can be produced by using a raw material of the food or drink containing a protein having a deamidated asparagine residue. That is, an embodiment of the deamidation method of the present invention may be a method for producing a food or drink or raw material thereof containing a protein having a deamidated asparagine residue, which method comprises allowing protein deamidase to act on a food or drink or raw material thereof containing a protein. The food or drink containing a protein having a deamidated asparagine residue obtained by an embodiment of the deamidation method of the present invention is also referred to as "food or drink of the present invention". The food or drink of the present invention can be produced by the same method using the same raw material as those for usual foods or drinks, except that the food or drink is obtained via a treatment with protein deamidase. A food or drink also includes a seasoning. Specific examples of the food or drink include, for example, mayonnaise, dressing, cream, yogurt, meat product, and bread.

The substrate protein may be subjected to the deamidation reaction in a state of, for example, solution, suspension, slurry, paste, or the like. The concentration of the substrate protein in a solution etc. is not particularly limited so long as a desired degree of deamidation is attained. The concentration of the substrate protein in a solution etc. can be appropriately determined according to various conditions, such as type and property of the substrate protein, and desired deamidation ratio. The solution etc. containing the substrate protein is not limited to an aqueous solution, and may be an emulsion in oil or fat. The solution etc. containing the substrate protein may consist of the substrate protein and a solvent, or may contain other ingredients. Examples of the other ingredients include, for example, salts, saccharides, proteins, perfumes, moisturizers, and coloring agents.

Reaction conditions (e.g. amount of enzyme, reaction time, reaction temperature, and reaction pH) are not particularly limited so long as a desired degree of deamidation is attained. The reaction conditions can be appropriately determined according to various conditions, such as type and purity of protein deamidase, type and purity of protein, and desired degree of deamidation. The amount of the enzyme may be, for example, 0.001 to 500 U, preferably 0.01 to 100 U, more preferably 0.1 to 10 U, with respect to 1 g of the substrate protein. Reaction temperature may be, for example, 5 to 80° C., preferably 5 to 40° C. pH of the reaction solution may be, for example, 2 to 10, preferably 4 to 8. Reaction time may be, for example, 10 seconds to 48 hours, preferably 10 minutes to 24 hours.

The deamidation can be carried out to a desired degree. The deamidation ratio ((Number of deamidated asparagine residues in substrate protein)/(Number of asparagine residues in substrate protein before deamidation)) may be, for example, 0.1% or higher, 1% or higher, 5% or higher, 10% or higher, or 20% or higher, or 100% or lower, 70% or lower, or 50% or lower.

The negative charge of a protein is increased by deamidation of the protein. With an increase of the negative charge, there may be provided such effects as a fall of the isoelectric point (pI), an increase of the hydration power, and an increase of the electrostatic repulsive force. Further, the higher-order structure of a protein may be changed by deamidation of the protein, and this change may provide such effects as an increase of the surface hydrophobicity. By these effects, there may be provided effects of improving the functional properties of a protein, such as improvement in the solubility and dispersibility, improvement in the foamability and foam stability, and improvement in the emulsifiability and emulsion stability. Such improvement in the functional properties of a protein provides an expanded use of the protein in the field of, for example, food industry. For example, since many vegetable proteins show poor functional properties such as low solubility, low dispersibility, and low emulsifiability, especially under weakly acidic conditions, which correspond to pH range of usual foods, use of them has been limited in many kinds of foods, for example, coffee whitener, acidic beverages such as fruit juice, dressing, mayonnaise, cream, and so forth. However, if such proteins are deamidated with protein deamidase, and the functional properties thereof such as solubility, dispersibility, and emulsifiability are thereby improved, it becomes possible to preferably use such proteins for many kinds of foods.

By deamidating a protein with protein deamidase, the mineral sensitivity of the protein may also be reduced, and the contained amount of a soluble mineral in a solution containing the protein and a mineral may be increased. It is generally known that the absorbability of calcium contained in foods into human bodies is improved by solubilizing calcium using an organic acid or casein phosphopeptide. Therefore, if the contained amount of a soluble mineral in a food or drink is increased by deamidating a protein with protein deamidase, the absorbability of a mineral such as calcium into human bodies can be improved. That is, protein deamidase can also be used as, for example, an active ingredient of a calcium absorption-promoting agent.

In the production of seasonings produced from proteins as raw materials, such as hydrolysates of animal proteins (HAP), hydrolysates of vegetable proteins (HVP), bean paste (miso), and soy sauce, deamidation of a protein with protein deamidase may provide such effects as a reduction of bitter taste and improvement in the ratio of proteolysis by protease. It is generally known that hydrophobic peptides serve as origins of bitter taste. However, by deamidation, the hydrophilic property of such peptides can be improved, and bitter taste thereof can be reduced. Further, deamidation of a protein may change the higher-order structure of the protein, and thereby increase protease sensitivity of the protein. That is, for example, the low decomposition ratio of a protein, which is one of the problems observed in the enzymatic production of HAP and HVP, can also be improved by deamidation.

As described above, the physical properties and functions of a protein or a material containing a protein can be modified by deamidation. Such modifications of physical properties or functions are also generically referred to as "reforming". That is, the deamidation method of the present invention may be, is other wards, a method for reforming a protein, which method comprises allowing protein deamidase to act on a protein, or may be a method for producing a reformed protein, which method comprises allowing protein deamidase to act on a protein. Also, an embodiment of this method may be, for example, a method for reforming a food or drink or raw material thereof, which method comprises allowing protein deamidase to act on a food or drink or raw material thereof containing a protein, or a method for producing a reformed food or drink or raw material thereof, which method comprises allowing protein deamidase to act on a food or drink or raw material thereof containing a protein.

Protein deamidase may also be used in combination with protein glutaminase. Protein glutaminase is an enzyme that catalyzes a reaction of deamidating a glutamine residue in a protein. If protein deamidase and protein glutaminase are used in combination, both asparagine residues and glutamine residues of a protein can be deamidated without causing decomposition of the protein into lower molecular weight molecules. Namely, since combinatory use of both the enzymes may further increase the deamidation ratio of the protein, and shift the isoelectric point (pI) of the protein to more acidic side, there may be provided further effects of improving the functional properties of the protein, such as improvement in the solubility even in a pH region more acidic than the pH region where proteins are originally easily insolubilized.

Protein deamidase may also be used in combination with transglutaminase. Transglutaminase is an enzyme that catalyzes the reaction of binding a glutamine residue and a lysine residue in proteins to crosslink the proteins. By the crosslinking, the protein can be gelled, or the functional properties of the protein can be improved. Therefore, transglutaminase is industrially used in a wide range of fields including the field of food industry as a protein reforming agent. In cases of performing both crosslinking and deamidation of a protein, if deamidation of the protein is performed with protein glutaminase, a glutamine residue as the substrate of transglutaminase is converted into a glutamate residue, and therefore the crosslinking reaction by transglutaminase is inhibited. By contrast, since the substrate of protein deamidase is an asparagine residue, it does not compete with transglutaminase for the substrate, and both crosslinking and deamidation of a protein can be efficiently performed by combinatory use with transglutaminase.

The type of an enzyme used in combination with protein deamidase can be appropriately chosen according to various conditions such as properties of protein deamidase. When protein deamidase is used in combination with another enzyme, timing or order of addition of the enzymes are not particularly limited. Both enzymes may be simultaneously added, or may be added at different timings. When protein deamidase and another enzyme are used in combination, reaction conditions (e.g. amounts of enzymes, reaction time, reaction temperature, and reaction pH) are not particularly limited so long as the desired effects are obtained. The reaction conditions can be appropriately determined according to various conditions such as type of such another enzyme. For example, when protein deamidase is used in combination with protein glutaminase, the amount of protein glutaminase to be used may be preferably 0.001 to 100 U with respect to 1 g of the substrate protein. Also, for example, when protein deamidase is used in combination with transglutaminase, the amount of transglutaminase to be used may be preferably 0.001 to 100 U with respect to 1 g of the substrate protein.

Protein deamidase can also be used as a reagent for protein engineering for modifying the function of a protein. When the substrate protein is an enzyme, the enzyme-chemical properties and physicochemical properties of the enzyme can be modified. For example, by deamidation of an enzyme protein with protein deamidase, the isoelectric point of the enzyme protein can be reduced, and the pH stability thereof can be thereby modified. Further, by changing the structure and electric environment of an active site of an enzyme protein, the properties of the enzyme protein, such as affinity to substrate, substrate specificity, reaction rate, pH dependency, temperature dependency, and thermal stability, can be modified.

Protein deamidase can also be used as a reagent for analysis or research of a protein, such as a reagent for determining the amide concentration of a protein, and a reagent for solubilizing a protein.

Protein deamidase can also be used for improving extraction efficiency and concentration efficiency for proteins of cereals or legumes. In general, many of proteins of cereals or legumes such as wheat and soybean are water-insoluble, and it is not easy to extract those proteins. However, for example, by treating a suspension of wheat flour or soybean flour with protein deamidase to increase the solubility of proteins, the proteins can be easily extracted, and an isolate having a high protein concentration can be obtained.

Protein deamidase can also be used for improving extraction efficiency of animal proteins. For example, gelatin is industrially produced by using mainly cow bone, oxhide, and pig skin as raw materials. In order to efficiently extract high quality gelatin, a pretreatment with an inorganic acid such as hydrochloric acid and sulfuric acid (acid treatment), or a pretreatment with lime (alkali treatment) is performed, but these pretreatments each impose high environmental impact, and require a long treatment time. However, if protein deamidase is used, proteins can be easily extracted, and since it is an enzymatic technique, environmental impact can be reduced.

A protein obtained as described above and showing improved functional properties exhibits superior effects when it is used in various kinds of foods, such as meat or fish meat products, and noodles, and may enable manufacture of a food having a novel mouthfeel and function.

EXAMPLES

Hereafter, the present invention will be more specifically explained with reference to examples. However, the present invention is not limited by these.

Example 1: Screening for Protein Asparaginase-Producing Bacterium Based on Enrichment Culture A soil sample was inoculated to a medium A (described below) containing Cbz-Asn-Gly (Peptide Institute) as a sole nitrogen source, and culture was performed for 5 days with shaking. The culture broth was applied to an agar plate of tryptic soy medium (Difco), and the grown colonies were chosen and collected. The obtained colonies each were applied to two kinds of agar media (containing 0.3% Cbz-Asn-Gly and not containing Cbz-Asn-Gly) similar to the medium A, and strains that showed significant difference in growth depending on the presence or absence of Cbz-Asn-Gly were chosen. These strains each were again cultured in the medium A, the culture supernatant was analyzed by high speed liquid chromatography (HPLC), and strains for which generation of the deamidation product (Cbz-Asp-Gly) was confirmed were regarded as candidate strains of protein asparaginase-producing bacteria. For these candidate strains, genus and species were identified by homology search based on 16S rDNA sequence analysis. The results are shown in Table 1.

Medium A: Yeast Carbon Base (1.17%, Difco) and Cbz-Asn-Gly (0.3%) were dissolved in distilled water, and the solution was subjected to filtration sterilization. pH of the medium was adjusted to 7.2.

TABLE 1

| Genus or species | Number of strain | Cbz-Asp-Gly (mM) |
| --- | --- | --- |
| Leifsonia xyli | 57 | 7.0 |
| Leifsonia (other than xyli) | 14 | 6.1 |
| Microbacterium | 11 | 4.7 |
| Agromyces sp. | 2 | 3.4 |
| Paenibacillus | 10 | 1.7 |
| Luteimicrobium album | 1 | 1.7 |
| Raoultella ornithinolytica | 1 | 0.7 |
| Agrobacterium tumefaciens | 1 | 0.6 |
| Enterobacter asburiae | 1 | 0.6 |
| Citrobacter freundii | 2 | 0.5 |
| Arthrobacter aurescens | 1 | 0.3 |
| Rahnella sp. | 1 | 0.2 |

Example 2: Purification of Protein Asparaginase Derived from Luteimicrobium album From the microorganisms obtained in Example 1, Luteimicrobium album AJ111072 (NITE P-01650) was chosen, and used to perform the following experiments.

*Luteimicrobium album* AJ111072 (MITE P-01650) was inoculated into a medium B (described below), and shaking culture was carried out at 30° C. for 24 hours to obtain a culture broth.

Medium B: The same volumes of a solution obtained by dissolving 2.34% of Yeast Carbon Base in distilled water and subjecting the solution to filtration sterilization, and a 2% polypeptone (NIHON PHARMACEUTICAL) solution subjected to autoclaving (121° C., 20 minutes) were mixed. pH of the medium was adjusted to 7.2.

The aforementioned culture broth was centrifuged at 4° C. and 8000 rpm for 15 minutes to remove the cells, and the obtained centrifugal supernatant was concentrated about 25 times with an ultrafiltration membrane (Sartorius), and filtered through Stericup 0.22 urn (Millipore). The filtrate was applied to a hydrophobic chromatography column, Hiprep Octyl FF 10/16, equilibrated with a 20 mM sodium phosphate buffer (pH 7.0) containing 1.0 M sodium sulfate (GE Healthcare), and the adsorbed proteins were eluted with a sodium sulfate linear density gradient of 1.0 to 0 M. Active fractions were collected, the buffer was exchanged with a 20 mM sodium phosphate buffer (pH 7.0), the resultant was applied to an anion exchange chromatography column, Hiprep DEAE FF 10/16 (GE Healthcare), equilibrated with the same buffer, and the adsorbed proteins were eluted with a sodium chloride linear density gradient of 0 to 0.5 M. Active fractions were collected again, the buffer was similarly exchanged with a 20 mM sodium phosphate buffer (pH 6.0), the resultant was applied to an anion exchange chromatography column, Hiprep DEAE FF 10/16 (GE Healthcare), equilibrated with the same buffer, and the adsorbed proteins were eluted with a sodium chloride linear density gradient of 0 to 0.5 M. Active fractions were concentrated with an ultrafiltration membrane, applied to a gel filtration chromatography column, Superdex™ 200 10/300, equilibrated with a 20 mM sodium phosphate buffer (pH 7.0) containing 0.1 M sodium chloride, and eluted with the same buffer. A purification table is shown as Table 2. Active fractions were mixed with a sample buffer for SDS-polyacrylamide gel electrophoreses (SDS-PAGE) containing a reducing agent, heat-treated, and subjected to electrophoresis on a 7.5% uniform polyacrylamide gel (e-PAGEL, E-T7.5L, Atto), and the gel after the electrophoresis was stained with Coomassie Brilliant Blue. The results are shown in FIG. 1. Judging from the magnitude of the activity and the density of the band, it became clear that the molecular weight of protein asparaginase of *Luteimicrobium album* AJ111072 (NITE P-01650) is about 110,000. In the active fractions obtained by the final purification process, the asparaginase activity for deamidating free asparagine or the protease activity for decomposing proteins was not detected.

The protein asparaginase activity was measured by the following procedures using Cbz-Asn-Gly as a substrate. Proteins were quantified by the Bradford method using bovine serum albumin as a standard protein.

Activity measurement method: An enzyme solution (25 μL) was added to 125 μL of a 0.2 mol/L phosphate buffer (pH 6.5) containing 30 mmol/L of Cbz-Asn-Gly, the mixture was incubated at 37° C. for 60 minutes, and then 150 μL of a 12% trichloroacetic acid solution was added to terminate the reaction. The reaction mixture was centrifuged (15,000 rpm, 4° C., 5 minutes), then the ammonia concentration in the supernatant was measured by using F-Kit ammonia (Boehringer Mannheim), and the protein asparaginase activity was calculated. The protein asparaginase activity that generates 1 μmol of ammonia in 1 minute was defined as 1 unit (U) of the protein asparaginase activity.

TABLE 2

Purification table

| | Total amount of proteins (mg) | Total activity (U) | Specific activity (U/mg) | Recovery (%) |
|---|---|---|---|---|
| Ultrafiltration concentration (molecular weight cut off, 10,000) | 145.52 | 219.02 | 1.5 | 100 |
| Hiprep Octyl FF 16/10 | 53.5 | 85.58 | 1.6 | 39.1 |
| Hiprep DEAE FF 16/10 (pH 7.0) | 2.59 | 49.26 | 19 | 22.5 |
| Hiprep DEAE FF 16/10 (pH 6.0) | 1.86 | 27.99 | 15 | 12.8 |
| Superdex ™ 200 10/300 | 0.53 | 13.65 | 25.9 | 6.2 |

Example 3: Determination of N-Terminus Amino Acid Sequence of Protein Asparaginase Derived from *Luteimicrobium album*

The purified protein asparaginase obtained in Example 2 was analyzed with a protein sequencer (PPSQ-21A, Shimadzu) to determine the N-terminus amino acid sequence thereof for 5 residues. The N-terminus amino acid sequence of the protein asparaginase of *Luteimicrobium album* AJ111072 (NITE P-01650) was Ala-Val-Thr-Ala-Asp (SEQ ID NO: 1).

Example 4: Determination of Full-Length Amino Acid Sequence of Protein Asparaginase Derived from *Luteimicrobium album*

The full-length amino acid sequence of the protein asparaginase was determined by a technique of identifying a protein from LC-MS/MS data using a genome sequence obtained with a next-generation sequencer as a database. That is, *Luteimicrobium album* AJ111072 (NITE P-01650) was cultured at 30° C. for 24 hours on the tryptic soy agar medium, the genomic DNA was extracted from grown cells, and the nucleotide sequence was obtained with Miseq (Illumina). Then, the purified protein asparaginase obtained in Example 2 was subjected to SDS-PAGE, and the objective band was excised and digested with trypsin. The digested fragments were subjected to LC-MS/MS analysis to obtain partial amino acid sequences of the enzyme. Further, from the genome sequence information, partial amino acid sequences, and N-terminus amino acid sequence (SEQ ID NO: 1), which were obtained by the aforementioned methods, the amino acid sequence of 1355 residues of the protein asparaginase of *Luteimicrobium album* AJ111072 (NITE P-01650) including the pre-pro-region (SEQ ID NO: 2) and the full-length nucleotide sequence of the gene encoding this enzyme (SEQ ID NO: 3) were obtained.

Example 5: Deamidation of Protein with Protein Asparaginase Derived from *Luteimicrobium album*

Insulin B chain (Sigma) was dissolved in a 0.1 M sodium phosphate buffer at a concentration of 2.5 mg/ml to prepare a substrate solution. To 45 μL of the substrate solution, 45 μL of a solution of the protein asparaginase of *Luteimicrobium album* AJ111072 (NITE P-01650) (about 0.3 U/ml) or 45 μL of water as a control was added, the reaction was performed at 37° C. for 1 hour, and then 10 μL of 1 N hydrochloric acid was added to terminate the reaction. Then, the reaction mixture was centrifuged, the supernatant was filtered, and the filtrate was analyzed by HPLC. The results are shown in FIG. 2. Whereas the elution time of the insulin B chain observed for the control group (solid line) was 4.88 minutes, the elution time of the insulin B chain observed for the enzyme addition group (dashed line) was 4.96 minutes. Thus, a small difference of the elution time was observed. Therefore, the solutions after the reaction were analyzed with a protein sequencer (PPSQ-21A, Shimadzu), and it was confirmed that the N-terminus sequence of the insulin B chain of the enzyme addition group was Phe-Val-Asp-Gln-, while the N-terminus sequence of the insulin B chain of the control group was Phe-Val-Asn-Gln-. Therefore, it was verified that asparagine of the third residue from the N-terminus of the insulin B chain was converted into aspartic acid by deamidation by this enzyme. By contrast, glutamine as the fourth residue from the N-terminus did not change.

Then, in order to investigate the reactivity against various proteins, α-casein (Sigma), α-lactalbumin (Sigma), casein sodium ("MIPRODAN", Nippon Shinyaku), milk whey protein ("BiPro", Davisco), porcine-derived acidic gelatin (Sigma), bovine-derived alkaline gelatin (Sigma), fish-derived gelatin (Nippi), cornmeal gluten (Sigma), and ovalbumin (Sigma) were each dissolved in a sodium phosphate buffer (0.02 M, pH 6.5) at a concentration of 2% w/v. A 6% w/v solution of skim milk powder (Yotsuba Milk Products, low heat type) was also dissolved in the same buffer. To 100 μL of each substrate solution, 10 μL of a solution of the protein asparaginase of *Luteimicrobium album* AJ111072 (NITE P-01650) (about 5 U/ml) was added, the reaction was performed at 37° C. for 1 hour, and then 100 μL of 12% trichloroacetic acid was added to terminate the reaction. Then, the reaction mixture was centrifuged, and ammonia contained in the centrifugal supernatant was quantified with F-Kit ammonia (Roche). As shown in Table 3, it was confirmed that this enzyme acts on various proteins. Further, a part of the reaction mixtures after completion of the reaction was subjected to SDS-PAGE, and the results were compared with those of the control. As a result, any increase or decrease of the molecular weight of the protein caused by this enzyme was not observed. That is, any activity for crosslinking proteins or protease activity was not detected for the protein asparaginase of *Luteimicrobium album* AJ111072 (NITE P-01650).

TABLE 3

| Substrate | Amount of generated ammonia (mM) |
|---|---|
| α-Casein | 4.69 |
| α-Lactalbumin | 1.84 |
| Skim milk powder | 1.22 |
| Casein sodium | 2.98 |
| Milk whey protein | 1.17 |
| Acidic gelatin (porcine) | 2.23 |
| Alkaline gelatin (bovine) | 0.73 |
| Fish gelatin | 1.27 |
| Soybean proteins | 0.98 |
| Rice proteins | 0.04 |
| Cornmeal | 0.41 |
| Ovalbumin | 0.01 |

Example 6: Modification of Properties of Protein with Protein Asparaginase Derived from *Luteimicrobium album*

Casein sodium (Nippon Shinyaku, trade name: MIPRODAN) was dissolved in a 20 mM sodium phosphate buffer (pH 7.0) at a concentration of 2% w/v to prepare a substrate solution. To 500 μL of the substrate solution, 25 μL of a solution of the protein asparaginase of *Luteimicrobium album* AJ111072 (NITE P-01650) (0.68 U/ml or 2.7 U/ml) was added, the reaction was performed at 37° C. for 1 hour, and then the enzyme was inactivated by a treatment at 100° C. for 5 minutes. The 0.68 U/ml enzyme addition group is referred to as test group 1, and the 2.7 U/ml enzyme addition group is referred to as test group 2. As a control, 25 μL of water was added instead of the enzyme solution, and the mixture was treated in the same manner (control group). The ammonia concentrations of the reaction mixtures were quantified, and the value of the control group was subtracted from those of the experimental groups. As a result, the released ammonia amounts obtained with addition of 0.68 U/ml and 2.7 U/ml of the enzyme solution were 1.0 mM and 1.3 mM, respectively. The results of isoelectric focusing (IEF) performed for these samples are shown in FIG. 3. In the samples added with the enzyme (test groups 1 and 2), the isoelectric point (pI) shifted to more acidic side compared with the control group, and thus a fall of pI of the protein due to deamidation was confirmed.

The solubility was investigated for the samples of the control group and the test group 2 by the following method. To 5 μL of each of the samples, 200 μL of each of buffers of various pH values (mentioned below) was added, the mixture was left standing at room temperature for 5 minute, and then centrifuged at 15,000 rpm for 5 minutes, and the protein concentration in the supernatant was determined by the Bradford method. The solubility was calculated as a relative value based on the protein concentration at pH 9.0 of the control group, which was taken as 100%. In the test group 2, in which the enzyme was added, the solubility was increased compared with the control group, especially around pH 5.0, and thus improvement in the solubility of proteins provided by deamidation was confirmed.

The pH buffers: acetate buffer (pH 4 to 6.0), phosphate buffer (pH 6.0 to 7.5), and Tris-hydrochloric acid buffer (pH 7.5 to 9.0), of which the concentrations were 0.2 M.

<Effect of Combinatory Use with Transglutaminase>

Transglutaminase is an enzyme that forms an isopeptide bond between a glutamine residue and lysine residue in proteins to crosslink the proteins. Transglutaminase and protein glutaminase have a problem that since they both use glutamine in a protein as a substrate, if these are used together, the reactions conflict to each other. By contrast, since protein asparaginase of the present invention uses asparagine in a protein as a substrate, it does not compete with transglutaminase, and therefore combinatory use of them provides both the effect of deamidation and the effect of crosslinking. Therefore, in this example, effects of combinatory use of transglutaminase with protein asparaginase and transglutaminase with protein glutaminase were compared. As transglutaminase, a product purified from Activa (registered trademark) TG bulk powder was used. As protein glutaminase, a purified product prepared by the method described in WO2006/075771 was used. For comparison, to 500 μL of 2% v/v solution of casein sodium, 25 μL of the protein glutaminase (10 U/ml) was added, the reaction was performed at 37° C. for 1 hour, and then the enzyme was inactivated with a treatment at 100° C. for 5 minutes (comparative group). To the casein solutions of the control group, test group 2, and the comparative group, 6.5 U of the transglutaminase was added per 1 g of casein, the reaction was performed at 37° C. for 100 minutes, and then the enzyme was inactivated by a treatment at 95° C. for 5 minutes. The reaction mixtures each were subjected to SDS-PAGE, and molecular weight change of casein was investigated. The results are shown in FIG. 4. Whereas crosslinking by transglutaminase was suppressed in the comparative group (protein glutaminase-treated casein), formation of crosslinking products was confirmed in the test group 2 (protein asparaginase-treated casein) almost similarly to the control group. Therefore, it was suggested that enhancement of physical properties due to crosslinking and improvement in functions such as solubility due to deamidation are expected to be simultaneously provided by combinatory use of transglutaminase and protein asparaginase.

Example 7: Analysis of Protein Asparaginase Derived from *Leifsonia xyli*

From the microorganisms obtained in Example 1, *Leifsonia xyli* AJ111071 (NITE P-01649) was chosen, and used to perform the following experiments.

*Leifsonia xyli* AJ111071 (NITE P-01649) was inoculated into a medium C (described below), and shaking culture was carried out at 30° C. for 24 hours to obtain a culture broth.

Medium C: The same volumes of a solution obtained by dissolving 1.17% of Yeast Carbon Base in distilled water and subjecting the solution to filtration sterilization, and a 1% solution of casein sodium (Wako Pure Chemical Industries) subjected to autoclaving (121° C., 20 minutes) were mixed. pH of the medium was adjusted to 7.2.

The culture broth was centrifuged at 15000 rpm for 15 minutes, and the protease activity in the obtained supernatant was measured. As a result, the protease activity was not detected. By contrast, the protein asparaginase activity in the supernatant was 0.029 U/ml.

A 2% casein sodium solution (100 μL) as a substrate was reacted with 100 μl of the supernatant for 3 hours, and then 200 μl of 12% TCA was added to terminate the reaction. As a control group, a mixture was also prepared by adding 12% TCA, and then adding the supernatant. Ammonia in each of the reaction mixtures was quantified, and from the ammonia amount of the reaction mixture observed after the reaction for 3 hours, the corresponding value of the control group was subtracted. As a result, 0.289 mM of ammonia was released, and it was confirmed that the enzyme produced by this bacterium deamidates casein.

In the same manner as that described in Example 5, the insulin B chain was used as the substrate, and reacted with the culture supernatant. The results of HPLC analysis of the reaction mixtures obtained after the reaction at 37° C. for 2 hours and 8 hours are shown in FIG. 5. Peaks of both the unreacted substrate and the reaction product were observed for the reaction mixture obtained after the reaction for 2 hours, while the substrate was totally converted into the reaction product in the reaction mixture obtained after the reaction for 8 hours. When the reaction mixture obtained after the reaction for 8 hours was analyzed with a protein sequencer, it was confirmed that asparagine of the third residue from the N-terminus of the insulin B chain was converted into aspartic acid by deamidation. By contrast, glutamine of the fourth residue from the N-terminus did not change.

Example 8: Analysis of Protein Asparaginase Derived from *Agromyces* sp. (1)

From the microorganisms obtained in Example 1, *Agromyces* sp. AJ111073 (NITE BP-01782) was chosen, and used to perform experiments similar to those of Examples 2 to 4. That is, protein asparaginase was purified from a culture broth of *Agromyces* sp. AJ111073 (NITE BP-01782), and subjected to SDS-PAGE. The objective band was excised, and digested with trypsin, and peptides were isolated from the trypsin digestion product of the objective enzyme, and analyzed with a protein sequencer (PPSQ-21A, Shimadzu). As a result, an internal amino acid sequence of 12 residues shown as SEQ ID NO: 4 (Ala-Arg-Gly-Gln-Leu-Ile-Leu-Asp-Thr-Leu-Thr-Met) was determined. A gene encoding the amino acid of SEQ ID NO: 4 was searched for by using the total genome sequence of *Agromyces* sp. AJ111073 (NITE BP-01782) obtained beforehand with a next-generation sequencer as a database. As a result, the amino acid sequence of 1180 residues of the protein asparaginase of *Agromyces* sp. AJ111073 (NITE BP-01782) including a pre-pro-region (SEQ ID NO: 5), and the full-length nucleotide sequence of the gene encoding this enzyme (SEQ ID NO: 6) were obtained.

Example 9: Analysis of Protein Asparaginase Derived from *Agromyces* sp. (2)

<1> Purification of Protein Asparaginase Derived from *Agromyces* sp.

From the microorganisms obtained in Example 1, *Agromyces* sp. AJ111073 (NITE BP-01782) was chosen, and used to perform the following experiments.

<1-1> Cultivation

*Agromyces* sp. AJ111073 (NITE BP-01782) was inoculated into the medium C (described below), and shaking culture was carried out at 37° C. for 24 hours to obtain a culture broth.

Medium C: The same volumes of a solution obtained by dissolving 1.17% of Yeast Carbon Base in distilled water and subjecting the solution to filtration sterilization, and a 1% solution of casein sodium (Wako Pure Chemical Industries) subjected to autoclaving (121° C., 20 minutes) were mixed. pH of the medium was adjusted to 7.2.

<1-2> Treatment for Activation of Protein Asparaginase

The obtained culture broth was mixed with 1/10 volume of a culture supernatant of *Bacillus subtilis* (described below), and the mixture was left standing overnight. By this operation, the protein asparaginase activity of the culture supernatant was improved from 0.005 U/ml to 1.06 U/ml.

Culture supernatant of *Bacillus subtilis*: *Bacillus subtilis* subsp. *subtilis*$^T$ JCM1465 was inoculated into the aforementioned medium C, and shaking culture was carried out at 37° C. for 24 hours to obtain a culture broth. The obtained culture broth was centrifuged at 4° C. and 8,000 rpm for 15 minutes to remove the cells, and the supernatant was filtered with Stericup 0.22 μm (Millipore) to obtain a culture supernatant.

<1-3> Purification and Molecular Weight Determination of Protein Asparaginase

The culture broth after the activation treatment was centrifuged at 4° C. and 40,000 rpm for 1 hour to remove the cells, and the obtained centrifugal supernatant was filtered with Stericup 0.22 μm (Millipore). NaCl was dissolved to the filtrate at a final concentration of 2.0 M, and the mixture was applied to a hydrophobic chromatography column, Hiprep Phenyl FF 10/16 (GE Healthcare), equilibrated with a 20 mM sodium phosphate buffer (pH 6.0) containing 2.0 M NaCl. The adsorbed proteins were eluted with a NaCl linear density gradient of 2.0 to 0 M to collect active fractions, and the buffer thereof was exchanged with a 20 mM sodium phosphate buffer (pH 6.0). The sample was applied to an anion exchange chromatography column, Hiprep DEAE FF 10/16 (GE Healthcare), equilibrated with the same buffer, and the adsorbed proteins were eluted with a sodium chloride linear density gradient of 0 to 0.5 M. A purification table is shown as Table 4. Active fractions were mixed with a sample buffer for SDS-polyacrylamide gel electrophoreses (SDS-PAGE) containing a reducing agent, heat-treated, and subjected to electrophoresis on a 4-12% Bis-Tris Gel (NuPAGE, Invitrogen), and the gel after the electrophoresis was stained with SimplyBlue SafeStain (Invitrogen). The results are shown in FIG. 6. Judging from the magnitude of the activity and the density of the band, it became clear that the molecular weight of protein asparaginase of *Agromyces* sp. AJ111073 (NITE BP-01782) is about 120,000. In the active fractions obtained by the final purification process, the asparaginase activity that acts on free asparagine or the protease activity for decomposing proteins was not detected.

TABLE 4

Purification table of protein asparaginase

|  | Total activity (U) | Recovery (%) |
|---|---|---|
| Culture supernatant | 819.75 | 100 |
| Hiprep Phenyl FF 16/10 | 415.56 | 50.7 |
| Hiprep DEAE FF 16/10 (pH 6.0) | 195.79 | 23.9 |

<2> Determination of Internal Amino Acid Sequence and N-Terminus Amino Acid Sequence of Protein Asparaginase Derived from *Agromyces* sp.

The band corresponding to the protein asparaginase was excised from the gel after the electrophoresis, and digestion was performed in the gel. That is, the excised gel piece was washed, and treated with a Tris-hydrochloric acid buffer (pH 8.5) containing lysyl endopeptidase at 35° C. for 20 hours. Then, the treated sample was subjected to reverse phase HPLC to separate fragmented peptides. Analyzable peptide peaks were isolated, and analyzed with a protein sequencer (Procise 494 HT Protein Sequencing System). As a result, a sequence containing Ala-Arg-Gly-Gln-Leu-Ile-Leu-Asp-Thr-Leu-Thr-Met (SEQ ID NO: 4) was confirmed. The purified protein asparaginase obtained above was also analyzed with a protein sequencer (PPSQ-21A, Shimadzu) to determine the N-terminus amino acid sequence for 5 residues. The N-terminus amino acid sequence of the protein asparaginase (mature protein) of *Agromyces* sp. AJ111073 (NITE BP-01782) was Ala-Ala-Thr-Glu-Asp (SEQ ID NO: 12).

Example 10: Activation of Protein Asparaginase Precursor by Processing

From the microorganisms obtained in Example 1, *Agromyces* sp. AJ111073 (NITE BP-01782) was chosen, and used to perform investigation of processing enzymes for converting a protein asparaginase precursor in a culture broth into a mature enzyme.

Aqueous solutions of various commercial proteases at concentrations of 1% (100-fold diluted solutions in cases of liquid enzymes) were prepared, and each added in an amount of 5% v/v to the culture broth of *Agromyces* sp. AJ111073 (NITE BP-01782), and the mixtures each were left standing at room temperature for 30 minutes. The protein asparaginase activities of the culture broths treated with the proteases are shown in Table 5. In the table, "PA act." means the protein asparaginase activity. The protein asparaginase activity of the culture broth was 0.21 U/mL before the activation (before the protease treatment), but it was improved even to 4.6 to 5.7 U/mL by the protease treatment. Also, when a culture supernatant of *Bacillus subtilis* (described below) was added in a volume of 10% v/v to the culture broth of *Agromyces* sp. AJ111073 (NITE BP-01782), and the mixture was left standing at room temperature for 30 minutes, the same activation effect was obtained (Table 5).

Culture supernatant of *Bacillus subtilis: Bacillus subtilis* subsp. *subtilis*$^T$ JCM1465 was inoculated into the aforementioned medium C, and shaking culture was carried out at 37° C. for 24 hours to obtain a culture broth. The obtained culture broth was centrifuged at 4° C. and 8,000 rpm for 15 minutes to remove the cells, and the supernatant was filtered with Stericup 0.22 μm (Millipore) to obtain a culture supernatant.

TABLE 5

Protein asparaginase activation effect of various proteases

| Product | Manufacturer | PA act. (U/mL) | Origin |
|---|---|---|---|
| Protin SD-NY10 | Amano Enzyme | 5.62 | *Bacillus amyloliquefaciens* |
| Sumizyme ACP-G | Shinnihon Chemicals | 5.69 | *Aspergillus oryzae* |
| Protease P "Amano" 3SD | Amano Enzyme | 5.45 | *Aspergillus melleus* |
| Protease S "Amano" G | Amano Enzyme | 5.18 | *Bacillus stearothermophilus* |
| Corolase N | Higuchi Inc. | 5.31 | *Bacillus subtilis* |
| Purified papain for foods | Nagase ChemteX | 4.56 | Papaya |
| Papain W-40 | Amano Enzyme | 5.28 | *Carica papaya* L. |
| Actinase AS | Kaken Pharmaceutical | 5.45 | *Streptomyces griseus* |
| Sumizyme LP | Shinnihon Chemicals | 5.22 | *Aspergillus oryzae.* |
| Pancreatic Trypsin Novo | Novozymes | 5.36 | Porcine pancreatic trypsin |
| Nucleicin | HBI Enzymes | 5.59 | *Bacillus subtilis* |
| Protin SD-AC10F | Amano Enzyme | 5.65 | *Bacillus licheniformis* |
| Protin SD-AY10 | Amano Enzyme | 5.50 | *Bacillus licheniformis* |
| DELVOLASE | DSM | 5.58 | *Bacillus licheniformis* |
| Alcalase | Novozymes | 5.56 | *Bacillus licheniformis* |
| Enzylon ALK-4 | Rakuto Kasei Industrial | 4.75 | *Bacillus licheniformis* |
| Protease M "Amano" SD | Amano Enzyme | 5.56 | *Aspergillus oryzae* |
| Culture supernatant of *Bacillus subtilis* | — | 5.26 | — |
| Before activation | — | 0.21 | — |

The N-terminus amino acid sequence of the protein asparaginase precursor of *Agromyces* sp. AJ111073 (NITE BP-01782) was determined to be VPEHGVIASGD (SEQ ID NO: 13), and it was found that it located upstream from the N-terminus amino acid sequence of the mature enzyme (SEQ ID NO: 12) by 114 residues.

Example 11: Reforming of Gelatin with Protein Asparaginase Derived from *Agromyces* sp.

An aqueous solution of porcine acidic gelatin (Nitta Gelatin) at a concentration of 5% wt (adjusted to pH 7.0) was prepared. To the aqueous solution, the protein asparaginase of *Agromyces* sp. AJ111073 (NITE BP-01782) was added in an amount of 1, 2, or 10 U per 1 g of the raw material gelatin, and an enzymatic treatment was performed at 37° C. for 2 hours. For comparison, a sample was prepared by adding water instead of the enzyme, and treated in the same manner. The samples after completion of the reaction each were diluted 50 times with water, and the isoelectric point (pI) thereof was determined with a zeta potential meter (Zetasizer Nano ZS, Malvern) equipped with an automatic titrator (MPT-2). The results are shown in Table 6. With an increase in the amount of the added enzyme, the isoelectric point of gelatin was reduced, and thereby gelatins having different surface charges were prepared. As described above, use of protein asparaginase of the present invention enables control of the surface charge of a gelatin protein, which is important for functional expression of the gelatin protein.

TABLE 6

Change of isoelectric point of gelatin provided by protein asparaginase treatment

| Enzyme (U/g (protein raw material)) | Isoelectric point (PI) |
|---|---|
| 0 | 8.96 |
| 1 | 7.41 |
| 2 | 6.65 |
| 10 | 6.05 |

<Effect of Combinatory Use with Protein Glutaminase (1)>

Aqueous solutions of porcine acidic gelatin and bovine alkaline gelatin (both are products of Nitta Gelatin) at concentrations of 5% wt (adjusted to pH 7.0) were prepared. To each of the aqueous solutions, the protein asparaginase of *Agromyces* sp. AJ111073 (NITE BP-01782) was first added in an amount of 15 U per 1 g of the raw material gelatin. Immediately thereafter, protein glutaminase prepared by the method described in WO2006/075771 (purified enzyme) was added in an amount of 50 U per 1 g of the raw material gelatin, and the enzymatic treatment was performed at 37° C. for 2 hours. The groups in which the acidic gelatin and alkaline gelatin were treated with the enzymes are referred to as test groups A and B, respectively. As controls, the above procedure was repeated with adding water instead of the enzymes, and these groups are referred to as control groups A and B, respectively. After completion of the reaction, the samples were diluted 50 times with water, and the isoelectric points (pI) thereof were determined in the same manner as described above. As a result, the pI values of the control groups A and B were 8.98 and 5.03, respectively, while pI values of the test groups A and B were 4.85 and 4.81, respectively, and thus it was confirmed that pI values shifted to more acidic side in both of the test groups. In particular, pI of the enzyme-treated acidic gelatin (test group A) markedly changed, and thus it was demonstrated that the treatment markedly changes the electric properties of the gelatin. A further fall of pI was also observed for the enzyme-treated alkaline gelatin (test group B).

<Effect of Combinatory Use with Protein Glutaminase (2)>

Aqueous solutions of fish acidic gelatin (Nippi) and bovine alkaline gelatin (Sigma) at concentrations of 1% wt were prepared with a 20 mM sodium phosphate buffer (pH 6.5), respectively. To each of the aqueous solutions, the protein asparaginase of *Agromyces* sp. AJ111073 (NITE BP-01782) was first added in an amount of 50 U per 1 g of the raw material gelatin, and the enzymatic treatment was performed at 37° C. for 1 hour. Then, protein glutaminase prepared by the method described in WO2006/075771 (purified enzyme) was added in an amount of 80 U per 1 g of the raw material gelatin, and the enzymatic treatment was performed at 55° C. for 1 hour. Then, the enzymes were inactivated by a treatment at 100° C. for 5 minutes. The groups in which the acidic gelatin and alkaline gelatin were treated with the enzymes are referred to as test groups A and B, respectively. As controls, the above procedure was repeated with adding water instead of the enzymes, and these groups are referred to as control groups A and B, respectively. The isoelectric points (pI) of these samples were determined with a zeta potential meter (Zetasizer Nano ZS, Malvern). As a result, the pI values of the control groups A and B were 8.63 and 5.25, respectively, while pI values of the test groups A and B were 4.59 and 4.61, respectively, and thus it was confirmed that pI values shifted to more acidic side in both of the test groups. In particular, pI of the enzyme-treated acidic gelatin (test group A) markedly changed, and thus it was demonstrated that the treatment markedly changes the electric properties of the gelatin. A further fall of pI was also observed for the enzyme-treated alkaline gelatin (test group B).

It can be expected that gelatin, which is broadly utilized for food, medical, industrial uses etc., can be made to have higher quality and higher added value by use of protein asparaginase as described above.

Example 12: Heterogeneous Expression of Protein Asparaginase

<1> Secretory Expression of Protein Asparaginase Derived from *Agromyces* sp. in *Corynebacterium glutamicum*
<1-1> Construction of Plasmid for Secretory Expression of Protein Asparaginase When protein asparaginase is heterogeneously expressed, expression of the protein asparaginase in the form of having the original pro-sequence on the N-terminus side may contribute to stabilization of the structure of the protein asparaginase. For expressing an objective protein in the form of a fusion protein with an amino acid sequence other than the objective protein, there is widely known a method of providing a recognition sequence for a specific protease showing high substrate specificity between the amino acid sequence of the objective protein and the fused amino acid sequence, so that the expressed fusion protein is cleaved with the specific protease to easily obtain the objective protein. Further, as the protease showing high substrate specificity, for example, there are known the factor Xa protease and the ProTEV protease, and they recognize the sequence of Ile-Glu-Gly-Arg (=IEGR) (SEQ ID NO: 14) and Glu-Asn-Leu-Tyr-Phe-Gln (=ENLYFQ) (SEQ ID NO: 15) in a protein, respectively, to specifically cleave the protein on the C-terminus side of the respective sequences. Therefore, for example, concerning a pro-sequence-fused protein asparaginase, if a pro-sequence-fused protein asparaginase gene is constructed so that a nucleotide sequence encoding the recognition sequence for the factor Xa protease (IEGR) or the recognition sequence for the ProTEV protease (ENLYFQ) is inserted between the nucleotide sequence encoding the pro-sequence amino acid residues of protein asparaginase and the nucleotide sequence encoding a mature protein asparaginase, and the pro-sequence-fused protein asparaginase is expressed from the gene, it becomes possible to easily remove the pro-sequence from the pro-sequence-fused protein asparaginase to obtain the mature protein asparaginase by using any of these proteases.

In consideration of the codon usage of *C. glutamicum*, there was designed a DNA sequence (SEQ ID NO: 16) encoding a fusion protein (SEQ ID NO: 17) in which, from the N-terminus, the signal sequence of the CspA protein derived from *C. ammoniagenes* (WO2013/06029), the pro-sequence of the protein asparaginase derived from *Agromyces* sp. AJ111073 (NITE BP-01782), the recognition sequence for the ProTEV protease (ENLYFQG), and the sequence of the mature protein asparaginase derived from *Agromyces* sp. AJ111073 (NITE BP-01782) were ligated in this order (FIG. 10). Further, a DNA sequence (SEQ ID NO: 18) comprising the above DNA sequence (SEQ ID NO: 16), the CspB promoter region provided immediately upstream of the above DNA sequence, and the recognition sequences for the restriction enzymes KpnI and BamHI on the 5' side and 3' side thereof, respectively, was synthesized by an artificial gene synthesis method, and cloned into the plasmid vector pPK4 (*Corynebacterium-E. coli* shuttle vector carrying the kanamycin resistance gene, Japanese Patent Laid-open (Kokai) No. 9-322774). Specifically, the synthesized DNA sequence (SEQ ID NO: 18) and pPK4 were simultaneously digested at two sites with the restriction enzymes KpnI and BamHI, then both DNA fragments were ligated, and used to transform competent cells of the *Escherichia coli* JM109 strain (TaKaRa), and the transformed cells were applied to the LB agar medium containing 50 µg/ml of kanamycin, and cultured overnight at 37° C. Then, single colonies were separated from the colonies that appeared to obtain transformants. Plasmid DNAs were extracted from the obtained transformants in a conventional manner, the objective plasmid was confirmed by DNA sequencing, and this plasmid was designated as pPK4-Pro-TEV-PA.

<1-2> Secretory Expression of Protein Asparaginase in *C. glutamicum*

Then, the *C. glutamicum* YDK010 strain (WO2004/029254) was transformed with pPK4-Pro-TEV-PA in a conventional manner to obtain YDK010/pPK4-Pro-TEV-PA strain. The *C. glutamicum* YDK010 strain is a strain deficient in the cell surface protein PS2 (CspB), of *C. glutamicum* AJ12036 (FERM BP-734) (WO2004/029254). The AJ12036 strain was originally deposited at the Agency of Industrial Science and Technology, Fermentation Research Institute (presently, the independent administrative agency, National Institute of Technology and Evaluation, International Patent Organism Depositary, #120, 2-5-8 Kazusakamatari, Kisarazu-shi, Chiba-ken, 292-0818, Japan) on Mar. 26, 1984 as an international deposit, and given with an accession number of FERM BP-734. The YDK010/pPK4-Pro-TEV-PA strain was cultured at 30° C. for 72 hours in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate tetrahydrate, 0.45 mg of thiamine hydrochloride, 0.45 mg of biotin, 0.15 g of DL-methionine, and 50 g of calcium carbonate in a volume of 1 L made with water, adjusted to pH 7.0) containing 25 mg/L of kanamycin. After the culture for 72 hours, the culture broth was centrifuged (13,800×g, 2 minutes), 4 µL of the supernatant was subjected to reducing SDS-PAGE, and staining was performed with SimplyBlue SafeStain (Novex), to analyze the proteins secreted in the culture broth. As a result, a band was confirmed at position around 115 kDa, which is the expected molecular weight size of the pro-sequence-fused protein asparaginase (FIG. 11). Since the amino acid composition of the protein asparaginase contains many acidic amino acids, it was estimated that the molecular weight slightly shifted to the higher molecular weight side from 115 kDa.

Since this fusion protein has the recognition sequence for ProTEV in the connection part between the pro-sequence and the mature protein asparaginase, the mature protein asparaginase can be obtained by digesting this fusion protein with ProTEV. Therefore, this fusion protein contained in the crude enzyme solution (culture supernatant) was processed into the mature protein asparaginase by digestion with ProTEV, and it was investigated whether the protein asparaginase activity was observed for the resultant. The crude enzyme solution (culture supernatant) obtained as described above was concentrated about 9 times by using Vivaspin 10,000 MWCO (GE Healthcare), and subjected to the processing with ProTEV. The processing was performed by adding 4 µL of ProTEV Plus (Promega), 10 µL of 10× buffer (1 M NaCl, 500 mM Tris-HCl, 50 mM $CaCl_2$, pH 8.0), and 46 µL of Mili-Q water to 40 µL of the concentrated crude enzyme solution, and incubating the mixture at 25° C. for 2 hours. The protein asparaginase activity of the concentrated crude enzyme solution treated with ProTEV was measured, and found to be 0.37 U/ml. As seen from the above result, secretory expression of protein asparaginase derived from *Agromyces* sp. was attained in *C. glutamicum*.

<2> Intracellular Expression of Protein Asparaginase in *E. coli*

<2-1> Expression of Protein Asparaginase Derived from *Agromyces* sp.

In consideration of the codon usage of *E. coli*, a DNA sequence (SEQ ID NO: 19) encoding a fusion protein (SEQ ID NO: 20) in which, from the N-terminus, the pro-sequence of the protein asparaginase derived from *Agromyces* sp. AJ111073 (NITE BP-01782), the recognition sequence for the ProTEV protease (ENLYFQG), and the sequence of the mature protein asparaginase (mature PA) derived from *Agromyces* sp. AJ111073 (NITE BP-01782) were ligated in this order was synthesized by an artificial gene synthesis method, and cloned into a plasmid vector pCold TF DNA (TaKaRa). pCold TF DNA is a cold shock expression vector, with which transcription for the objective protein is induced at a low temperature, designed so that an objective gene is expressed to provide the objective protein in the form of being fused with the trigger factors (TF), which is a kind of chaperon, as a soluble tag. The cloning was carried out according to the following procedures by using In-Fusion HD Cloning Kit (Clontech). A pCold TF DNA fragment was amplified by PCR using the pCold TF DNA as the template and the primers of SEQ ID NOS: 21 and 22. A DNA fragment for cloning encoding the fusion protein was amplified by PCR using the synthesized DNA sequence (SEQ ID NO: 19) as the template and the primers of SEQ ID NOS: 23 and 24. As the polymerase, Prime STAR GXL (TOYOBO) was used. In PCR, a cycle of reactions at 98° C. for 10 seconds, 60° C. for 15 seconds, and 68° C. for 60 seconds was repeated 30 times. The amplified fragments were ligated by the In-Fusion reaction, and the *E. coli* JM109 strain was transformed with the reaction product, applied on the LB agar medium containing 50 µg/ml of ampicillin, and cultured overnight at 37° C. Then, single colonies were separated from the colonies that appeared to obtain transformants. From the obtained transformants, there was obtained a strain having an expression plasmid for the pro-sequence-fused protein asparaginase derived from *Agromyces* sp. (proPA_Agro), in which plasmid the DNA encoding the fusion protein of the pro-sequence, the recognition sequence for ProTEV, and the mature PA sequence was correctly ligated downstream from the DNA encoding TF, which plasmid was designated as pCTF-proPA_Agro.

pCTF-proPA_Agro was extracted from the obtained strain by using a plasmid extraction kit, QIAprep Spin Miniprep Kit (QIAGEN). The *E. coli* Rosetta 2 strain (Novagen) was transformed with pCTF-proPA_Agro to construct a proPA_Agro-expression strain, E. coli Rosetta2/pCTF-proPA_Agro. This expression strain was cultured overnight at 37° C. on the LB agar medium (Difco) containing ampicillin at a final concentration of 100 μg/ml as seed culture. The cells were inoculated to fresh LB medium containing ampicillin at a final concentration of 100 μg/ml with a 1 μl inoculation loop, and shaking culture was performed at 37° C. for about 3 hours. Then, isopropyl-β-D-thiogalactopyranoside (IPTG) was added at a final concentration of 1 mM, and the culture temperature was lowered to 15° C. to induce transcription from the cspA promoter of pCTF-proPA_Agro (low temperature induction). Culture was performed at 15° C. for 24 hours, and then the cells were collected by centrifugation. As a control, the cells immediately before the low temperature induction were also collected in a similar manner. Then, the cells from 1 ml of the culture broth were suspended in 350 μl of 20 mM Tris-HCl (pH 8.0), and disrupted by repeating a cycle of sonication of being "ON for 30 seconds, and OFF for 30 seconds" 10 times under cooling conditions by using an ultrasonicator UCD-250 (Cosmobio). The obtained disrupted cell suspension was centrifuged (21,600×g, 4° C., 10 minutes) to remove the insoluble fraction, and the supernatant fraction was regarded as a crude extract. Then, 5 μl of the NuPAGE LDS sample buffer (Novex) and 2 μl of the NuPAGE sample reducing reagent (Novex) were added to 13 μL of the crude extract, and the mixture was heat-treated at 70° C. for 10 minutes, and then subjected to electrophoresis using NuPAGE 4-12% Bis-Tris Gel (Novex). As a result, as shown in FIG. 12, a band of a protein at position around the objective molecular weight of 176 kDa was more distinctly observed for the sample subjected to the low temperature induction of the expression plasmid, compared with that before the low temperature induction. Since the theoretical molecular weights of TF and proPA_Agro are 52 kDa and 124 kDa, respectively, the molecular weight of the objective protein of this expression experiment, TF-proPA_Agro fusion protein, is estimated to be about 176 kDa.

Since this fusion protein has the digestion recognition site (Glu-Asn-Leu-Tyr-Phe-Gln) for the ProTEV protease in the connection part between the pro-sequence and the mature PA, the mature PA can be obtained by digesting this fusion protein with ProTEV (Novagen). Therefore, PA contained in the crude extract obtained after the low temperature induction was processed into the mature PA by digestion with ProTEV, and it was investigated whether the PA activity was observed for the resultant. The crude enzyme solution obtained as described above was concentrated about 20 times by using Vivaspin 10,000 MWCO (GE Healthcare), and subjected to the processing with ProTEV. The PA activity of the concentrated crude enzyme solution treated with ProTEV was measured, and found to be 0.069 U/ml. As seen from the above result, intracellular expression of protein asparaginase derived from *Agromyces* sp. was attained in *E. coli*.

<2-2> Expression of Protein Asparaginase Derived from *Leifsonia xyli*

In consideration of the codon usage of *E. coli*, a DNA sequence (SEQ ID NO: 25) encoding a fusion protein (SEQ ID NO: 26) in which, from the N-terminus, the pro-sequence of the protein asparaginase derived from *Leifsonia xyli* AJ111071 (NITEP-01649), the recognition sequence for the ProTEV protease (ENLYFQG), and the sequence of the mature protein asparaginase (mature PA) derived from *Leifsonia xyli* AJ111071 (NITEP-01649) were ligated in this order was synthesized by an artificial gene synthesis method, and cloned into the plasmid vector pCold TF DNA (TaKaRa). The procedures of the following experiments were the same as those of Example 12, <2-1>, unless otherwise stated. A pCold TF DNA fragment was amplified by PCR using the pCold TF DNA as the template and the primers of SEQ ID NOS: 21 and 22. A DNA fragment for cloning encoding the fusion protein was amplified by PCR using the synthesized DNA sequence (SEQ ID NO: 25) as the template and the primers of SEQ ID NOS: 27 and 28. The amplified fragments were ligated by the In-Fusion reaction, and the *E. coli* JM109 strain was transformed with the reaction product. From the obtained transformants, there was obtained a strain having an expression plasmid for the pro-sequence-fused protein asparaginase derived from *Leifsonia xyli* (proPA_Leif), in which plasmid the DNA encoding the fusion protein of the pro-sequence, the recognition sequence for ProTEV, and the mature PA sequence was correctly ligated downstream from the DNA encoding TF, which plasmid was designated as pCTF-proPA_Leif.

The plasmid was extracted from the obtained strain, and transformation of the *E. coli* Rosetta 2 strain (Novagen), culture of a proPA_Leif-expression strain, and preparation of a crude extract were performed. The crude extract was subjected to electrophoresis. As a result, as shown in FIG. 12, a band of a protein at position around the objective molecular weight of 159 kDa was more distinctly observed for the sample subjected to the low temperature induction of the expression plasmid, compared with that before the low temperature induction. Since the theoretical molecular weights of TF and proPA_Leif are 52 kDa and 107 kDa, respectively, the molecular weight of the objective protein of this expression experiment, TF-proPA_Leif fusion protein, is estimated to be about 159 kDa.

Since this fusion protein has the digestion recognition site for the ProTEV protease (Glu-Asn-Leu-Tyr-Phe-Gln) in the connection part between the pro-sequence and the mature PA, the mature PA can be obtained by digesting this fusion protein with ProTEV (Novagen). Therefore, PA contained in the crude extract obtained after the low temperature induction was processed into the mature PA by digestion with ProTEV, and it was investigated whether the PA activity was observed for the resultant. The crude enzyme solution was concentrated about 20 times by using Vivaspin 10,000 MWCO (GE Healthcare), and the pro-sequence was cleaved by a treatment with ProTEV for 2 hours. The PA activity of the concentrated crude enzyme solution treated with ProTEV was measured, and found to be 0.047 U/ml. As seen from the above result, intracellular expression of protein asparaginase derived from *Leifsonia xyli* was attained in *E. coli*.

<2-3> Expression of Protein Asparaginase Derived from *Microbacterium testaceum*

In consideration of the codon usage of *E. coli*, a DNA sequence (SEQ ID NO: 29) encoding a fusion protein (SEQ ID NO: 30) in which, from the N-terminus, the pro-sequence of the protein asparaginase derived from *Microbacterium testaceum*, the recognition sequence for the ProTEV protease (ENLYFQG), and the sequence of the mature protein asparaginase (mature PA) derived from *Microbacterium testaceum* were ligated in this order was synthesized by an artificial gene synthesis method, and cloned into the plasmid vector pCold TF DNA (TaKaRa). The procedures of the following experiments were the same as those of Example 12, <2-1>, unless otherwise stated. A pCold TF DNA fragment was amplified by PCR using the pCold TF DNA as the template and the primers of SEQ ID NOS: 21 and 22. A DNA fragment encoding the fusion protein was amplified by PCR using the synthesized DNA sequence (SEQ ID NO: 29) as the template and the primers of SEQ ID NOS: 31 and 32. The amplified fragments were ligated by the In-Fusion reaction, and the E. coli JM109 strain was transformed with the reaction product. From the obtained transformants, there was obtained a strain having an expression plasmid for the pro-sequence-fused protein asparaginase derived from *Microbacterium testaceum* (proPA_Micro), in which plasmid the DNA encoding the fusion protein of the pro-sequence, the recognition sequence for ProTEV, and the mature PA sequence was correctly ligated downstream from DNA encoding TF, which plasmid was designated as pCTF-proPA_Micro.

The plasmid was extracted from the obtained strain, and transformation of E. coli Rosetta 2 strain (Novagen), culture of a proPA_Micro-expression strain, and preparation of a crude extract were performed. The crude extract was subjected to electrophoresis. As a result, as shown in FIG. 12, a band of a protein at position around the objective molecular weight of 174 kDa was more distinctly observed for the sample subjected to the low temperature induction of the expression plasmid, compared with that before the low temperature induction. Since the theoretical molecular weights of TF and proPA_Micro are 52 kDa and 122 kDa, respectively, the molecular weight of the objective protein of this expression experiment, TF-proPA_Micro fusion protein, is estimated to be about 174 kDa.

Since this fusion protein has the digestion recognition site for the ProTEV protease (Glu-Asn-Leu-Tyr-Phe-Gln) in the connection part between the pro-sequence and the mature PA, the mature PA can be obtained by digesting this fusion protein with ProTEV (Novagen). Therefore, PA contained in the crude extract obtained after the low temperature induction was processed into the mature PA by digestion with ProTEV, and it was investigated whether the PA activity was observed for the resultant. The crude enzyme solution was concentrated about 20 times by using Vivaspin 10,000 MWCO (GE Healthcare), and the pro-sequence was cleaved by a treatment with ProTEV for 2 hours. The PA activity of the concentrated crude enzyme solution treated with Pro-TEV was measured, and found to be 0.022 U/ml. As seen from the above result, intracellular expression of protein asparaginase derived from *Microbacterium testaceum* was attained in E. coli.

INDUSTRIAL APPLICABILITY

According to the present invention, a novel protein deamidase (protein asparaginase) that catalyzes a reaction of deamidating an asparagine residue in a protein is provided. According to an embodiment thereof, by using this enzyme, an asparagine residue in a protein can be deamidated to improve the functional properties of the protein.

EXPLANATION OF SEQUENCE LISTING

SEQ ID NO: 1, N-Terminus amino acid sequence of protein asparaginase derived from *Luteimicrobium album* (5 residues)

SEQ ID NO: 2, Amino acid sequence of protein asparaginase derived from *Luteimicrobium album* (including pre-pro-region)

SEQ ID NO: 3, Full-length nucleotide sequence of protein asparaginase gene derived from *Luteimicrobium album*

SEQ ID NO: 4, Internal amino acid sequence of protein asparaginase derived from *Agromyces* sp. (12 residues)

SEQ ID NO: 5, Amino acid sequence of protein asparaginase derived from *Agromyces* sp. (including pre-pro-region)

SEQ ID NO: 6, Full-length nucleotide sequence of protein asparaginase gene derived from *Agromyces* sp.

SEQ ID NO: 7, Amino acid sequence of protein asparaginase derived from *Microbacterium testaceum*

SEQ ID NO: 8, Amino acid sequence of protein asparaginase derived from *Leifsonia xyli*

SEQ ID NO: 9, Amino acid sequence of protein asparaginase derived from *Leifsonia aquatica*

SEQ ID NO: 10, Common amino acid sequence for sequences of SEQ ID NOS: 2 and 5

SEQ ID NO: 11, Common amino acid sequence for sequences of SEQ ID NOS: 2, 5, 7, and 8

SEQ ID NO: 12, N-Terminus amino acid sequence of mature protein of protein asparaginase derived from *Agromyces* sp. (5 residues)

SEQ ID NO: 13, N-Terminus amino acid sequence of precursor (pro-protein) of protein asparaginase derived from *Agromyces* sp. (11 residues)

SEQ ID NO: 14, Recognition sequence for factor Xa protease

SEQ ID NO: 15, Recognition sequence for ProTEV protease

SEQ ID NO: 16, Nucleotide sequence of gene encoding pro-sequence-fused protein asparaginase derived from *Agromyces* sp. for secretory expression in *C. glutamicum*

SEQ ID NO: 17, Amino acid sequence of pro-sequence-fused protein asparaginase derived from *Agromyces* sp. for secretory expression in *C. glutamicum*

SEQ ID NO: 18, Nucleotide sequence of insertion fragment containing gene encoding pro-sequence-fused protein asparaginase derived from *Agromyces* sp. for secretory expression in *C. glutamicum*

SEQ ID NO: 19, Nucleotide sequence of gene encoding pro-sequence-fused protein asparaginase derived from *Agromyces* sp. for intracellular expression in *E. coli*

SEQ ID NO: 20: Amino acid sequence of pro-sequence-fused protein asparaginase derived from *Agromyces* sp. for intracellular expression in *E. coli* SEQ ID NOS: 21 to 24, Primers SEQ ID NO: 25, Nucleotide sequence of gene encoding pro-sequence-fused protein asparaginase derived from *Leifsonia xyli* for intracellular expression in *E. coli*

SEQ ID NO: 26, Amino acid sequence of pro-sequence-fused protein asparaginase derived from *Leifsonia xyli* for intracellular expression in *E. coli* SEQ ID NOS: 27 and 28, Primers SEQ ID NO: 29, Nucleotide sequence of gene encoding pro-sequence-fused protein asparaginase derived from *Microbacterium testaceum* for intracellular expression in *E. coli*

SEQ ID NO: 30, Amino acid sequence of pro-sequence-fused protein asparaginase derived from *Microbacterium testaceum* for intracellular expression in *E. coli*

SEQ ID NOS: 31 and 32, Primers

The invention claimed is:

1. A method for reforming a food or drink or raw material thereof, the method comprising:
   allowing a protein having an activity for catalyzing a reaction of deamidating an asparagine residue in a protein to act on a food or drink or raw material thereof containing a protein and/or peptide,
   wherein the protein having the activity is selected from the group consisting of (a), (b), and (c):
   (a) a protein comprising the amino acid sequence of SEQ ID NO: 2, 5, 7, 8, or 9, the amino acid sequence of positions 240 to 1355 of SEQ ID NO: 2, the amino acid sequence of positions 181 to 1180 or 67 to 1180 of SEQ ID NO: 5, the amino acid sequence of positions 193 to 1172 or 70 to 1172 of SEQ ID NO: 7, or the amino acid sequence of positions 146 to 989 or 21 to 989 of SEQ ID NO: 8;
   (b) a protein comprising the amino acid sequence of SEQ ID NO: 2, 5, 7, 8, or 9, the amino acid sequence of positions 240 to 1355 of SEQ ID NO: 2, the amino acid sequence of positions 181 to 1180 or 67 to 1180 of SEQ ID NO: 5, the amino acid sequence of positions 193 to 1172 or 70 to 1172 of SEQ ID NO: 7, or the amino acid sequence of positions 146 to 989 or 21 to 989 of SEQ ID NO: 8 but including substitution, deletion, insertion, or addition of one to fifty amino acid residues; and
   (c) a protein comprising an amino acid sequence showing an identity of 90% or higher to the amino acid sequence of SEQ ID NO: 2, 5, 7, 8, or 9, the amino acid sequence of positions 240 to 1355 of SEQ ID NO: 2, the amino acid sequence of positions 181 to 1180 or 67 to 1180 of SEQ ID NO: 5, the amino acid sequence of positions 193 to 1172 or 70 to 1172 of SEQ ID NO: 7, or the amino acid sequence of positions 146 to 989 or 21 to 989 of SEQ ID NO: 8.

2. A method for producing a reformed food or drink or raw material thereof, the method comprising:
   allowing a protein having an activity for catalyzing a reaction of deamidating an asparagine residue in a protein to act on a food or drink or raw material thereof containing a protein and/or peptide,
   wherein the protein having the activity is selected from the group consisting of (a), (b), and (c):
   (a) a protein comprising the amino acid sequence of SEQ ID NO: 2, 5, 7, 8, or 9, the amino acid sequence of positions 240 to 1355 of SEQ ID NO: 2, the amino acid sequence of positions 181 to 1180 or 67 to 1180 of SEQ ID NO: 5, the amino acid sequence of positions 193 to 1172 or 70 to 1172 of SEQ ID NO: 7, or the amino acid sequence of positions 146 to 989 or 21 to 989 of SEQ ID NO: 8;
   (b) a protein comprising the amino acid sequence of SEQ ID NO: 2, 5, 7, 8, or 9, the amino acid sequence of positions 240 to 1355 of SEQ ID NO: 2, the amino acid sequence of positions 181 to 1180 or 67 to 1180 of SEQ ID NO: 5, the amino acid sequence of positions 193 to 1172 or 70 to 1172 of SEQ ID NO: 7, or the amino acid sequence of positions 146 to 989 or 21 to 989 of SEQ ID NO: 8 but including substitution, deletion, insertion, or addition of one to fifty amino acid residues; and
   (c) a protein comprising an amino acid sequence showing an identity of 90% or higher to the amino acid sequence of SEQ ID NO: 2, 5, 7, 8, or 9, the amino acid sequence of positions 240 to 1355 of SEQ ID NO: 2, the amino acid sequence of positions 181 to 1180 or 67 to 1180 of SEQ ID NO: 5, the amino acid sequence of positions 193 to 1172 or 70 to 1172 of SEQ ID NO: 7, or the amino acid sequence of positions 146 to 989 or 21 to 989 of SEQ ID NO: 8.

3. The method according to claim 1, which further comprises allowing a transglutaminase and/or a protein glutaminase to act on the food or drink or raw material thereof containing a protein and/or peptide.

4. The method according to claim 1, wherein the food or drink is selected from mayonnaise, dressing, cream, yogurt, meat product, and bread.

* * * * *

SEQUENCE LISTING

<160> NUMBER OF SEQ ID NOS: 32

<210> SEQ ID NO 1
<211> LENGTH: 5
<212> TYPE: PRT
<213> ORGANISM: Luteimicrobium album

<400> SEQUENCE: 1

Ala Val Thr Ala Asp
1               5

<210> SEQ ID NO 2
<211> LENGTH: 1355
<212> TYPE: PRT
<213> ORGANISM: Luteimicrobium album

<400> SEQUENCE: 2

Met Ala Pro Gly His Gly Ser Gly Thr Asp Gly Arg Thr Leu Ala Arg
1               5                   10                  15

Arg Pro Arg Gly Ser Ser Arg Pro Ser Val Leu Arg Ala Ala Gly
            20                  25                  30

Asn Gln Leu Val Thr Arg Asp Gly Arg Pro Arg His Thr Gly Phe Leu
        35                  40                  45

Gln Cys Gly Pro Thr Arg Pro Arg Arg Ala Thr Ser Gln Pro Arg Gly
    50                  55                  60

Arg Arg Asp Asp Gly Trp Gly Ser Val Val Ala Pro Ala Trp Ala
65                  70                  75                  80

Ala Arg Ala Thr Ser Ala Glu His Glu Glu Thr Ile Arg Met Pro Phe
                85                  90                  95

Thr Pro Arg Arg Ser Ala Gly Arg Arg Thr Ala Pro Val Leu Val Leu
            100                 105                 110

Gly Leu Ala Ala Ser Ala Leu Leu Gly Ala Val Pro Leu Thr Ala Gln
        115                 120                 125

Ala Ala Gly Gln Asp Asp Val Val Ala His Gly Asp Asp Trp Ser Val
    130                 135                 140

Ser Arg Val Ser Gly Gly Phe Lys Val Thr Lys Thr Leu Asp Glu Ala
145                 150                 155                 160

Leu Pro Val Val Ser Asp Ala Pro Thr Leu Thr Val Asp Gly Ala Ser
                165                 170                 175

Leu Gly Thr Ala Thr Glu Ser Ala Asp Gly Thr Thr Leu Thr Thr Tyr
            180                 185                 190

Thr Thr Leu Asp Val Ser Ser Ala Asp Asp Val Glu Val Gly Trp Ser
        195                 200                 205

Ser Gly Gly His Pro Ala Glu Pro Thr Asn Ser Pro Val Thr Ser Thr
    210                 215                 220

Glu Ala Pro Val Ala Pro Arg Thr Thr Ser Arg Leu Arg Ser Leu Ala
225                 230                 235                 240

Val Thr Ala Asp Asp Gly Ser Thr Pro Gly Thr Ala Ala Tyr Leu Glu
                245                 250                 255

Asp Asp Tyr Asp Phe Gly Asp Gln Ala Val Pro Leu Ala Asn Ile Gly
            260                 265                 270

Gly Ile Arg Gly Glu Met Thr Gly Arg Ile Tyr Leu Pro Thr Thr Ala
        275                 280                 285

Gly Ala His Pro Thr Val Ile Leu Leu His Gly Arg His Ser Ser Cys
    290                 295                 300

Thr Val Pro Thr Gly Gly Gly Ser Val Ser Asn Pro Asn Arg Trp Pro

```
305                 310                 315                 320

Cys Ile Ala Pro Gln Val Asn Ile Pro Ser Tyr Lys Gly Tyr Glu Ser
            325                 330                 335

Thr Ala Gln Asn Leu Ala Thr His Gly Tyr Ala Val Ser Ile Ser
            340                 345                 350

Ala Asn Ala Ile Asn Ala Asn Asp Asn Gln Leu Ala Pro Asp Tyr Gly
            355                 360                 365

Ala Gln Ala Arg Gly Gln Leu Val Leu Asp Thr Leu Ala Met Leu Arg
        370                 375                 380

Lys Ala Asn Ala Gly Glu Pro Val Ser Phe His Asp Ala Ala Thr Asp
385                 390                 395                 400

Arg Thr Val Asp Leu Ala Ser Ala Leu Ala Val Ser Thr Glu Ala Glu
                405                 410                 415

Asp Leu Gly Ser Ala Pro Thr Ser Ala Thr Asn Pro Gly Asp Ala Ile
            420                 425                 430

Thr Pro Ala Asp Leu Val Gly Ala Phe Asp Leu Asp Asp Val Gly Leu
            435                 440                 445

Met Gly His Ser Arg Gly Gly Glu Gly Val Val Ser Ala Val Asn Leu
        450                 455                 460

Asn Gln Lys Leu Ala Lys Pro Phe Gly Ile Lys Ser Val Leu Pro Leu
465                 470                 475                 480

Ala Pro Val Asp Phe Gly Arg Glu Thr Ala Ala Asp Thr Asn Met Leu
                485                 490                 495

Val Ile Leu Pro Tyr Cys Asp Gly Asp Val Ser Asn Gln Gln Gly Gln
            500                 505                 510

His Phe Ser Asp Asp Ser Arg Tyr Ala Tyr Asp Asp Ser Leu Arg
            515                 520                 525

Ser Thr Leu Trp Val Met Gly Ala Asp His Asn Phe Phe Asn Ser Val
        530                 535                 540

Trp Thr Pro Gly Lys Tyr Pro Leu Ser Thr Ser Asp Asp Trp Gly Ala
545                 550                 555                 560

Thr Ser Thr Asp Ala Val Cys Gly Pro Leu Ala Pro Thr Asn Val Arg
                565                 570                 575

Leu Ser Ala Asp Asp Gln Tyr Asp Val Gly Val Ala Val Met Ser Ala
            580                 585                 590

Trp Phe Arg Leu Thr Leu Gly Gly Glu Asp Gln Phe Leu Pro Leu Phe
        595                 600                 605

Asp Gly Ser Ala Asp Pro Thr Leu Thr Ser Val Pro Ser Ala Lys Leu
    610                 615                 620

Trp Ser Thr Ala Thr Ala Pro Ala Thr Lys Arg Ala Asp Ile Glu Ala
625                 630                 635                 640

Phe Thr Ala Asn Thr Ser Arg Val Arg Val Tyr Gly Ser Ala Thr Glu
                645                 650                 655

Ser Val Cys Ala Ser Ala Gly Gly Arg Thr Leu Pro Gln Asp Ala Gln
            660                 665                 670

Pro Cys Ala Thr Ala Ser Ala Leu Arg Ser Thr Ser Ala Met Pro His
            675                 680                 685

Trp Thr Pro Ala Ser Phe Ala Pro Asn Val Pro Ala Ser Pro Met Gly
        690                 695                 700

Arg Phe Leu Trp Thr Ser Val Ser Gly Ser Thr Ala Gly Ser Ile Arg
705                 710                 715                 720

Val Thr Val Pro Ala Ala Ala Arg Asp Ala Ser Glu Gln Asp Ala Leu
                725                 730                 735
```

```
Thr Phe Lys Thr Ala Pro Asp Glu Ser Val Leu Thr Gly Thr Asp Leu
            740                 745                 750

Thr Val Thr Val Val Asp Gly His Gly Ala Thr Trp Ser Ser Ala Val
            755                 760                 765

Ser Ala Leu Asn Ala Gly Ala Val Lys Arg Leu Pro Ile Ser Gly Ser
            770                 775                 780

Thr Thr Leu Asn Lys Ile Val Leu Gln Gln Val Ser Val Pro Val Ser
785                 790                 795                 800

Thr Leu Ala Gly Ser Ile Asp Val Ser Asp Val Arg Glu Val Arg Phe
            805                 810                 815

Ala Gly Ala Thr Gly Ala Asp Gly Thr Ala Thr Gly Ala Tyr Leu
            820                 825                 830

Ser Asp Leu Ala Phe Val Ser Ser Gly Val Gly Thr Val Ala Gly Ile
            835                 840                 845

Ala Ser Val Pro Thr Val Asn Val Ala Ser Thr Val Val Glu Glu Gly
            850                 855                 860

Ser Ser Val Asp Glu Ala Arg Val Ala Val Val Leu Asp Gln Pro Ala
865                 870                 875                 880

Asp Arg Thr Val Ser Ala Trp Phe Thr Leu Met Gly Ser Thr Ala Asp
            885                 890                 895

Ser Ser Asn Ala Gly Leu Ala Ala Gln Lys Val Thr Phe Gln Pro Gly
            900                 905                 910

Gln Thr Cys Gln Ala Val Thr Val Thr Ile Leu Gly Asn Thr Val Ala
            915                 920                 925

Gly Ala Ala Thr Thr Ala Tyr Lys Ala Asp Val Ser Ala Pro Asp
            930                 935                 940

Gly Val Ile Val Gly Ala Ala Gln Phe Gly Thr Phe Thr Val Arg Glu
945                 950                 955                 960

Asp Asp Ala Leu Thr Ser Gly Gly Ala Leu Ala Pro Ala Val Gly Thr
            965                 970                 975

Gln Gly Asp Val Cys Ala Glu Tyr Ala Ala Arg Ser Val Val Gln Glu
            980                 985                 990

Leu Thr Thr Ser Gly Asp Ala Val Ala Gly Ser His Val Thr Leu Thr
            995                 1000                1005

Gly Ser Gly Tyr Arg Val Gly Glu Ser Val Ala Phe Thr Asp Gly
            1010                1015                1020

Asp Ala Val Leu Gly Thr Val Leu Ala Gly Ala Asp Gly Thr Ala
            1025                1030                1035

Ala Leu Asp Trp Ala Val Pro Ala Asp Ala Arg Val Gly Gly His
            1040                1045                1050

Asp Val Thr Ala Val Gly Ala Gly Ser Ala Arg Thr Ala Lys Ala
            1055                1060                1065

Thr Val Thr Val Arg Ser Ala Thr Thr Thr Thr Leu Ala Ile Ala
            1070                1075                1080

Pro Ala Ala Pro Ala Val Gly Lys Ala Val Thr Leu Thr Ala Thr
            1085                1090                1095

Val Ala Gly Pro Asp Thr Ala Gly Thr Val Thr Phe Ala Asp Gly
            1100                1105                1110

Ser Thr Val Leu Gly Arg Val Ala Val Lys Asp Gly Arg Ala Ala
            1115                1120                1125

Leu Val Val Ser Gly Gly Phe Asp Ala Gly Thr His Thr Leu Thr
            1130                1135                1140
```

| | | | | | | | | | | | |
|---|---|---|---|---|---|---|---|---|---|---|---|
|Ala|Ala|Phe|Gly|Gln|Thr|Ala|Thr|Ala|Glu|Gly|Ser|Val|Ser|Pro|
| |1145| | | |1150| | | |1155| | | | | |

Ala Val Thr Phe Thr Leu Val Lys Gly Lys Thr Thr Val Phe
    1160            1165            1170

Val Leu Ala Ala Thr Arg Thr Thr Tyr Gly Thr Ala Val Ala Gly
    1175            1180            1185

Arg Ile Val Val Gly Gly Ala Asp Gly Gly Val Ala Thr Ile Thr
    1190            1195            1200

Val Gly Asn Val Val Arg Ser Val Arg Leu Asp Ala His Gly Ala
    1205            1210            1215

Gly Ser Phe Thr Val Pro Gly Thr Leu Lys Pro Ala Thr Tyr Arg
    1220            1225            1230

Val Thr Ala Ser Tyr Ala Gly Ser Arg Thr Leu Asp Thr Ser Ser
    1235            1240            1245

Ala Arg Ala Ser Leu Thr Val Leu Lys Ala Ala Pro Lys Val Thr
    1250            1255            1260

Leu Ser Ala Pro Ala Thr Ala Arg Lys Gly Ala Thr Val Thr Val
    1265            1270            1275

Thr Val Lys Val Val Gly Val Lys Gly Gly Val Arg Pro Thr Gly
    1280            1285            1290

Lys Ala Val Val Lys Leu Gly Gly Lys Ala Val Lys Thr Val Ser
    1295            1300            1305

Val Pro Ser Ser Gly Val Val Lys Val Lys Val Arg Leu Ala Ser
    1310            1315            1320

Ala Gly Thr Ala Lys Val Thr Ala Ala Tyr Gln Gly Ser Ala Tyr
    1325            1330            1335

Tyr Thr Ala Ala Ser Ala Ala Ala Lys Val Lys Val Lys Val Val
    1340            1345            1350

Thr Lys
    1355

<210> SEQ ID NO 3
<211> LENGTH: 4068
<212> TYPE: DNA
<213> ORGANISM: Luteimicrobium album

<400> SEQUENCE: 3

```
atggcaccgg gtcacggtag cgggacggac ggtcgcacgc tcgcccggcg tccgcgcggc    60
tcctcccggc ggccgtcggt gctgcgtgcc gcgggaaacc aactcgtaac gcgggacggc   120
cgtcctcgac acacaggctt cctacagtgc ggaccaaccc ggcctcgccg gccacgtcg    180 cagccccgtg ggcgccgcga cgacgggtgg gggtccgtgg tcgtggcgcc cgcgtgggcc   240
gctcgtgcga cgtccgcaga gcacgaggag accatccgca tgcccttcac ccacgacgg    300 tccgcaggac gacgcaccgc cccggtgctc gtcctcggcc tcgccgcgag cgccctgctc   360
ggggccgtac ccctgacggc gcaggccgcc ggtcaggacg acgtcgtcgc gcacggagac   420
gactggtccg tctcacgcgt ctccggcggc ttcaaggtca ccaagaccct cgacgaggcg   480
cttcccgtcg tctcggacgc ccccacgctg acggtcgacg gcgcgagcct cggcacggcc   540
acggagtccg cggacgggac caccctcacc acgtacacga ccctcgacgt gtcgtcggcg   600
gacgacgtcg aggtcggctg gagcagcggc ggccacccgg ccgagccgac gaactcgccc   660
gtgacgtcca ccgaggcgcc ggtcgccccg cgcacgacgt cccgcctgcg gtccctcgcg   720
gtcacggccg acgacggctc cacgcccggc acggccgcc acctggagga cgactacgac   780
```

-continued

```
ttcggcgacc aggcggtccc gctcgcgaac atcggcggca tccgcggtga gatgacggga    840
cggatctacc tgccgacgac ggccggcgcg cacccgaccg tgatcctgct gcacggtcgg    900
cactcgtcct gcaccgtgcc gacgggcggc ggcagcgtct cgaacccgaa ccggtggccg    960
tgcatcgcgc cgcaggtgaa catcccgagc tacaagggct acgagtcgac cgcgcagaac   1020
ctcgcgacgc acggctacgc cgtcgtgtcg atctccgcga acgcgatcaa cgccaacgac   1080
aaccagctcg cgcccgacta cggcgcgcag gcgcgcgggc agctcgtgct cgacacgctc   1140
gcgatgctgc gcaaggcgaa cgcgggcgag cccgtgtcct ccacgacgc cgcgacggac    1200 cggacggtcg acctcgcgtc cgcgctcgcc gtgagcacgg aggccgagga cctgggctcc   1260
gccccgacgt cggccacgaa ccccggcgac gcgatcacgc cggcggacct cgtgggcgcg   1320
ttcgacctcg acgacgtcgg cctcatgggc cactcgcgcg gcggggaggg cgtcgtctcg   1380
gcggtcaacc tcaaccagaa gctcgcgaag ccgttcggga tcaagagcgt gctgccgctc   1440
gcgcccgtcg acttcggccg cgagacagcc gcggacacga acatgctcgt gatcctgccc   1500
tactgcgacg gcgacgtgtc gaaccagcag gggcagcact tcagcgacga ctcccgctac   1560
gcctacgacg acgactccct gcgctcgacg ctgtgggtca tgggcgccga ccacaacttc   1620
ttcaactcgg tgtggacgcc cgggaagtac ccgctctcga cgtcggacga ctggggcgcc   1680
acgagcacgg acgcggtctg cggcccgctc gcgcccacga acgtgcgcct gagcgcggac   1740
gaccagtacg acgtcggggt cgccgtcatg agcgcgtggt tccggctcac gctcggcggc   1800
gaggaccagt tcctgccgct gttcgacggg agcgccgacc cgacgctcac gtcggtcccg   1860
tcggcgaagc tctggtcgac ggccaccgct ccggcgacga agcgcgccga catcgaggcg   1920
ttcacggcca acacgagccg tgtgcgcgtc tacgggtcgg cgaccgagag cgtctgcgcg   1980
agcgcgggcg gccgcaccct gccgcaggac gcgcagccct gcgccacggc gagcgccctg   2040
cgctcgacga gcgccatgcc gcactggacc ccggcgtcgt tcgcgccgaa cgtcccggcg   2100
tcgccgatgg gccgcttcct gtggacgtcg gtgagcggct cgaccgccgg gtcgatccgg   2160
gtcaccgtgc ccgccgccgc gcgcgacgcg agcgagcagg acgccctgac gttcaagacg   2220
gcgcccgacg agtcggttct cacgggcacc gacctgacgg tgacggtcgt ggacggccac   2280
ggggccacct ggagctccgc ggtctcggcg ctcaacgcgg gtgccgtgaa gcggctcccg   2340
atcagcggct cgacgacgct caacaagatc gtcctgcagc aggtctcggt cccggtctcc   2400
acgctcgcgg gctcgatcga cgtgagcgac gtccgtgagg tccgtttcgc gggcgcgacc   2460
ggcgccgacg gcacggccac gggcggggcg tacctgtccg acctggcgtt cgtcagctcc   2520
ggcgtcggca ccgtcgcggg catcgcgtcc gtcccgacgg tcaacgtcgc gagcacggtc   2580
gtcgaggagg gctcgtcggt cgacgaggcc cgcgtggccg tggtcctcga ccagcccgcc   2640
gaccggacgg tctcggcgtg gttcacgctc atgggctcga ccgcggacag cagcaacgcc   2700
gggctggccg cgcagaaggt cacgttccag ccgggccaga cgtgccaggc cgtgaccgtg   2760
acgatcctcg ggaacacggt ggcgggcgcg ccgcgacga cggcctacaa ggccgacgtc    2820
agcgcgcccg acggcgtgat cgtgggcgcg gcccagttcg ggacgttcac ggtccgcgag   2880
gacgacgccc tcacgtccgg cggggcgctc gctcccgccg tcggcacgca gggcgacgtc   2940
tgcgccgagt acgcggcacg gtccgtcgtg caggagctga cgacgtcggg cgacgcggtc   3000
gccgggtcgc acgtcacgct caccggcagc gggtaccggg tcggcgagtc ggtcgcgttc   3060
accgacggtg acgccgtcct cggtaccgtg ctcgcgggcg ccgacgggac cgcggccctc   3120
gactgggccg tccccgcgga cgcgcgcgtc ggcggtcatg acgtgaccgc cgtcggggcg   3180
```

```
ggctcggccc ggaccgcgaa ggccaccgtg accgtgcggt cggccaccac gacgaccctc    3240
gcgatcgcgc ccgcggcccc ggccgtgggc aaggccgtga ccctcacggc gaccgtcgcc    3300
gggcccgaca ccgcgggcac cgtgacgttc gccgacggct cgacggtcct cggccgggtc    3360
gcggtcaagg acgccgggc ggccctcgtc gtctccggcg gcttcgacgc cgggacgcac    3420
accctgaccg cggcgttcgg gcagaccgcc acggccgagg gctccgtgtc cccggccgtg    3480
acgttcaccc tggtcaaggg caagacgacc acggtgttcg tgctcgccgc gacccgcacg    3540
acgtacggca cggcggtcgc cgggcggatc gtcgtcggcg gcgccgacgg cggggtcgcg    3600
acgatcaccg tcgggaacgt cgtccggtcg gtccggctcg acgcccacgg cgccgggtcg    3660
ttcaccgtcc ccggcacgct gaagcccgcg acctaccggg tgacggcgtc gtacgcgggg    3720
tcccggaccc tcgacacgag cagcgcgcgg gcctccctga cggtcctcaa ggccgcgccg    3780
aaggtcacgc tgtccgcccc ggccacggcc aggaagggtg cgaccgtcac ggtgaccgtg    3840
aaggtcgtcg gcgtgaaggg cggcgtccgg ccgaccggca aggccgtcgt caagctcggc    3900
gggaaggccg tgaagacggt ctccgtcccg tcgtcgggcg tggtgaaggt caaggtccgg    3960
ctcgcctcgg ccgggaccgc gaaggtcacg gcggcctacc agggcagcgc ctactacacg    4020
gcggcgtccg cggcggccaa ggtcaaggtc aaggtcgtca cgaagtag             4068
```

<210> SEQ ID NO 4
<211> LENGTH: 12
<212> TYPE: PRT
<213> ORGANISM: Agromyces sp.

<400> SEQUENCE: 4

Ala Arg Gly Gln Leu Ile Leu Asp Thr Leu Thr Met
1               5                   10

<210> SEQ ID NO 5
<211> LENGTH: 1180
<212> TYPE: PRT
<213> ORGANISM: Agromyces sp.

<400> SEQUENCE: 5

Leu His Ser Leu Thr Gly Gly Trp His Pro Arg Thr Arg Asn Leu Asn
1               5                   10                  15

Arg Pro Ala Arg Pro Arg Arg Leu Pro Pro Leu Asn Arg Arg
            20                  25                  30

Thr Val Arg Thr Arg Met Ser Ser Arg Ala Arg Trp Leu Ala Ala Thr
        35                  40                  45

Ala Ala Leu Leu Thr Pro Ala Leu Ala Leu Gly Ala Ala Pro Ala Ala
    50                  55                  60

Asn Ala Val Pro Glu His Gly Val Ile Ala Ser Gly Asp Asp Trp Thr
65                  70                  75                  80

Ile Glu Thr Ala Pro Gly Gly Tyr Leu Val Thr Tyr Gln Leu Ala Glu
                85                  90                  95

Pro Leu Pro Ile Val Ser Asp Ala Pro Thr Leu Leu Ile Asp Gly Glu
            100                 105                 110

Pro Ala Gly Tyr Ala Thr Glu Ser Ala Asp Gly Arg Ser Leu Ser Leu
        115                 120                 125

Phe Thr Ser Asp Pro Asp Val Ala Ser Ala Arg Glu Val Glu Lys Gly
    130                 135                 140

Trp Ala Ser Ser Glu Gly Asp Lys Ala Ala Glu Ser Pro Val Ala Glu
145                 150                 155                 160

```
Trp Ser Thr Glu Gln Pro Asn Asp Glu Leu Leu Glu Gln Leu Gly Arg
                165                 170                 175

Leu Ala Pro Met Ala Ala Thr Glu Asp Pro Gly Asp Pro Gly Ala Tyr
            180                 185                 190

Ala Val Thr Glu Ala Glu Tyr Asp Phe Gly Asp Arg Ala Val Ala Leu
        195                 200                 205

Ala Gly Ile Gly Gly Ile Arg Gly Glu Met Thr Gly Lys Leu Tyr Leu
    210                 215                 220

Thr Asp Ala Pro Gly Glu Arg Pro Thr Val Ile Leu Leu His Gly Arg
225                 230                 235                 240

His Ser Ser Cys Ser Thr Gly Thr Ala Asn Pro Leu Arg Trp Pro Cys
                245                 250                 255

Gly Pro Asn Gln Val Asn Val Arg Ser Tyr Gln Gly Tyr Glu Gly Thr
                260                 265                 270

Ala Arg Ala Leu Ala Ser His Gly Tyr Asn Val Ala Ser Ile Ala Ala
            275                 280                 285

Asn Ala Val Asn Ser Asn Asp Asn Gln Leu Ala Leu Asp Tyr Gly Ala
        290                 295                 300

Lys Ala Arg Gly Gln Leu Ile Leu Asp Thr Leu Thr Met Leu Gly Lys
305                 310                 315                 320

Ala Ser Ala Gly Glu Pro Val Val Leu Asp Asp Ile Ser Trp Pro Asp
                325                 330                 335

Ala Asp Gly Asn Val Thr Thr Thr Arg Ser Leu Asp Asp Ala Leu
                340                 345                 350

Val Leu Ala Thr Thr Arg Ala Asp Ser Pro Ala Ala Pro Gly Gly Val
            355                 360                 365

Thr Ala Ala Ser Leu Gln Gly Arg Phe Asp Leu Asp Arg Val Gly Ile
        370                 375                 380

Met Gly His Ser Arg Gly Gly Glu Gly Ala Thr Ser Ala Val Thr Leu
385                 390                 395                 400

Asn Gln Gly Leu Ala Asp Pro Phe Gly Ile Val Ala Val Leu Pro Leu
                405                 410                 415

Ala Pro Val Asp Phe Gly Arg Met Thr Val Ala Asp Thr Pro Met Ala
                420                 425                 430

Val Phe Leu Pro Tyr Cys Asp Gly Asp Val Ser Asn Gln Gln Gly Gln
            435                 440                 445

His Met Val Asp Asp Ser Arg His Ala Phe Val Asp Asp Val Met Arg
        450                 455                 460

Ser Ala Val Trp Ile Met Gly Ala Asn His Asn Phe Phe Asn Thr Val
465                 470                 475                 480

Trp Thr Pro Gly Leu Tyr Pro Tyr Ala Thr Ser Asp Asp Trp Asn Arg
                485                 490                 495

Asn Asp Gln Thr Ser Thr Cys Ser Thr Ala His Glu Ser Arg Leu Thr
                500                 505                 510

Pro Ala Gln Gln Tyr Gln Val Gly Val Ser Tyr Met Thr Gly Phe Phe
            515                 520                 525

Arg Leu Thr Met Gly Gly Glu Thr Gln Phe Gln Pro Met Phe Asp Gly
        530                 535                 540

Ser Val Thr Pro Thr Thr Thr Ala Thr Gly Phe Ala Asp Val Arg Val
545                 550                 555                 560

Met Ala Ser Gln Pro Ala Ser Ala Thr Thr Val Ile Ala Asp Phe Glu
                565                 570                 575
```

```
Asp Arg Ser Thr Leu Ile Arg Thr Ser Gly Asn Ala Ser Ala Gln Val
            580                 585                 590

Cys Ala Asn Ala Glu Thr Ala Thr Ser Ile Ala Pro Ser Val Pro Tyr
        595                 600                 605

Cys Thr Val Arg Pro Val Gly Thr Ala Arg Val Pro His Trp Thr Pro
    610                 615                 620

Val Arg Phe Gly Leu Asn Val Pro Ala Tyr Pro Val Thr Arg Val Leu
625                 630                 635                 640

Trp Thr Gly Ser Thr Ser Thr Pro Ala Ala Pro Ser Thr Gly Val Leu
                645                 650                 655

His Val Ala Val Pro Glu Gly Ser Arg Asp Val Ser Gly His Thr Gln
            660                 665                 670

Leu Thr Val Lys Ala Ala Pro Asp Ile Ser Val Asp Ser Gly Thr Asp
        675                 680                 685

Phe Thr Ile Thr Val Ile Asp Gly Ala Gly Asn Ser Phe Ser Thr Pro
    690                 695                 700

Ala Ser Ala Val Asn Pro Leu Ala Val Asn Arg Met Pro Gly Gly Thr
705                 710                 715                 720

His Ala Thr Leu Asn Lys Ile Val Leu Gln Gln Leu Thr Val Pro Thr
                725                 730                 735

Ser Glu Met Thr Gly Ile Asp Leu Thr Asp Val Arg Glu Val Arg Phe
            740                 745                 750

Ala Ala Gly Val Gly Ala Asp Gly Thr Gly Ala Gly Leu Tyr Leu
        755                 760                 765

Ser Asp Leu Ala Phe Asp Thr Pro Thr Phe Ala Pro Ala Val Val Gly
770                 775                 780

Thr Arg Thr Thr Val Asn Ile Ala Ser Thr Phe Val Glu Glu Gly Asp
785                 790                 795                 800

Ser Thr Asp Thr Ala Gln Val Ala Val Ser Leu Asp Arg Glu Ala Glu
            805                 810                 815

Arg Glu Val Thr Ala Trp Val Ser Phe Val Pro Val Ser Gly Pro Val
        820                 825                 830

Ala Ala Ala Val Gln Asp Val Thr Phe Ala Pro Gly Glu Thr Cys Arg
    835                 840                 845

Val Val Glu Val Pro Val Thr Gly Asn Thr Ala Pro Ser Ala Thr Ala
850                 855                 860

Ser Thr Ala Ile Thr Val Ser Ala Thr Asn Thr Ala Asn Ala Val Met
865                 870                 875                 880

Gly Ala Asp Ala Phe Gly Thr Leu Val Arg Glu Asp Asp Gly Val
            885                 890                 895

Thr Gly Pro Ala Val Glu Leu Pro Pro Val Gly Val Gln Gly Asp Ala
        900                 905                 910

Cys Ala Glu Leu Ala Ala Ala Gln Glu Pro Gly Glu Leu Thr Val Ser
    915                 920                 925

Ala Asp Glu Val Ala Pro Gly Gly Ser Val Glu Leu Thr Ala Ala Gly
930                 935                 940

Phe Arg Val Gly Glu Ser Val Arg Phe Thr Phe Gly Asp Asp Glu Leu
945                 950                 955                 960

Gly Ala Val Leu Ala Asp Ala Glu Gly Val Ala Thr Val Thr Val Asp
                965                 970                 975

Val Pro Glu Glu Ser Ala Leu Gly Ala Arg Thr Ala Ser Ala Phe Gly
            980                 985                 990

Ala Gly Ser Ala Arg Val Gln Thr  Ala Met Val Asp Val Leu Ala Pro
```

-continued

```
                  995                1000               1005
Thr Ala Thr Thr Leu Thr Val Asp Glu Gly Ser Thr Leu Val Glu
        1010               1015               1020

Gly Asp Glu Leu Thr Phe Val Ala Glu Val Thr Gly Ala Glu Thr
        1025               1030               1035

Ala Gly Thr Val Thr Phe Val Ser Gly Ser Gly Ser Gly Ala Ala
        1040               1045               1050

Asp Ala Ala Ala Gly Glu Val Leu Gly Thr Ala Asp Val Val
        1055               1060               1065

Asp Gly Val Ala Thr Leu Thr Leu Gly Asp Gly Leu Ala Glu Gly
        1070               1075               1080

Ala Tyr Ser Val Val Ala Ala Phe Ala Arg Thr Asp Ile Ala Ser
        1085               1090               1095

Ala Ser Ser Ser Asp Pro Val Glu Phe Glu Ile Ser Ala Ala Ala
        1100               1105               1110

Thr Lys Pro Pro Val Val Asn Pro Pro Gly Thr Gly Thr Pro Gly
        1115               1120               1125

Gly Gly Asp Ser Gly Thr Ala Ser Ser Ser Asp Gly Pro Leu Ala
        1130               1135               1140

His Thr Gly Phe Asp Gly Leu Gly Trp Ala Leu Leu Ala Ala Leu
        1145               1150               1155

Ala Leu Phe Ala Val Gly Ala Thr Val Val Val Ala Arg Arg Gln
        1160               1165               1170

Thr Arg Ser Thr Pro Glu Ser
        1175               1180
```

<210> SEQ ID NO 6
<211> LENGTH: 3543
<212> TYPE: DNA
<213> ORGANISM: Agromyces sp.

<400> SEQUENCE: 6

| | | | | | |
|---|---|---|---|---|---|
| ctgcatagtc | tcaccggtgg | gtggcacccc | cgcacccgga | atctcaaccg | gcccgcgcga | 60 |
| cgtccgcgcc | ggcttccccc | tccctgaat | cggagaaccg | tgagaacacg | tatgtcctcg | 120 |
| cgggcgcggt | ggctcgccgc | caccgcagcc | ctgctcacgc | ccgccctcgc | cctcggcgcc | 180 |
| gcacccgcag | ccaacgccgt | gccggagcac | ggcgtcatcg | cctcgggcga | cgactggacg | 240 |
| atcgagaccg | caccaggcgg | atacctcgtc | acctaccagc | tcgccgagcc | gctgccgatc | 300 |
| gtcagcgacg | caccgacgct | gctcatcgac | ggcgagcccg | cgggctacgc | caccgagtcg | 360 |
| gcggacggcc | ggtcgctgtc | gctgttcacg | agcgaccccg | acgtcgcctc | ggcgcgcgag | 420 |
| gtcgagaagg | gctgggcctc | gagcgagggc | gacaaggccg | ccgagtcgcc | cgtggcggag | 480 |
| tggagcaccg | agcagccgaa | cgacgagctc | ctcgagcagc | tcggccggct | cgcgccgatg | 540 |
| gccgcgaccg | aggacccggg | cgaccccggg | cgtacgcgg | tcaccgaggc | cgagtacgac | 600 |
| ttcggcgacc | gggcggtcgc | actcgccggc | atcggcggga | tccgcggcga | gatgaccggc | 660 |
| aagctctacc | tcacggatgc | tccgggcgag | cggccgaccg | tcatcctgct | gcacggtcgc | 720 |
| cactcttcct | gttcgacggg | gaccgcgaac | ccgctgcgct | ggccctgcgg | ccccaaccag | 780 |
| gtgaacgtcc | gcagctacca | gggctacgag | ggcacggcgc | gcgcgctcgc | gtcgcacggc | 840 |
| tacaacgtgg | cgtcgatcgc | cgcgaacgcc | gtcaactcga | acgacaacca | gctcgcgctc | 900 |
| gactacggtg | ccaaggcgcg | cggccagctc | atcctcgaca | ccctcacgat | gctcgggaag | 960 |
| gcctcggcgg | gcgagccggt | cgtgctcgac | gacatctctt | ggccggacgc | agacggcaac | 1020 |

```
gtcacgacga cgacgcgctc gctcgacgac gccctcgtgc tcgccacgac gcgtgcggac   1080
tccccggccg ccccgggcgg cgtcaccgcg gcgtcgctgc aggggcgctt cgacctcgac   1140
cgggtcggca tcatggggca ctcccgcggt ggtgagggcg cgacctcggc ggtcaccctg   1200
aaccaaggcc tggccgaccc gttcggcatc gtggcggtgc tgccgctcgc gccggtcgac   1260
ttcggccgga tgaccgtggc cgacacgccc atggcggtgt tcctcccgta ctgcgacggc   1320
gacgtcagca accagcaggg ccagcacatg gtcgacgact cgcggcacgc gttcgtcgac   1380
gacgtgatgc gctcggcggt gtggatcatg ggcgccaacc acaacttctt caacacggtg   1440
tggacgccgg gtctgtaccc ctatgcgacg agtgacgact ggaaccgcaa cgaccagacg   1500
tccacctgca gcacggccca cgagagccgc ctcactccgg cgcagcagta ccaggtcggc   1560
gtgtcgtaca tgacgggctt cttccgtctg accatgggcg gggagacgca gttccagcct   1620
atgttcgacg gttcggtcac gcccaccacg accgcgacgg gcttcgccga cgtccgcgtg   1680
atggcctccc agcccgcgag cgcgacgacc gtgatcgccg acttcgagga ccgcagcacg   1740
ctgatccgca cgagcggcaa cgcctcggcg caggtgtgcg cgaacgccga cggcgacg    1800 tcgatcgctc cgagcgtgcc gtactgcacc gtgcggccgg tcggcacggc gcgcgtgccg   1860
cactggaccc ccgtccgctt cggcctgaac gtgccggcgt accccgtgac ccgggtcctg   1920
tggaccggtt cgacgagcac ccccgccgca cccagcaccg gtgtgctcca cgtcgcggtg   1980
cctgaggggt cacgggatgt ctcgggccac acgcagctca ccgtcaaggc ggcgccggac   2040
atctcggtcg actcgggcac ggacttcacc atcacggtga tcgacggcgc cggcaactcg   2100
ttcagcacgc ccgcctcggc ggtcaacccg ctcgcggtca accggatgcc gggtggcacg   2160
cacgcgacgc tgaacaagat cgtgctgcag cagctgaccg ttccgacgtc cgagatgacg   2220
ggcatcgacc tcaccgacgt gcgcgaggtg cgcttcgcgg cgggcgtcgg cgcggacggc   2280
accggcgcgg gtggtctata cctgtccgac ctggccttcg acacgccgac gttcgcgccg   2340
gctgtcgtcg gcacccgcac cacggtcaac atcgcatcga ccttcgtgga ggagggcgac   2400
tcgaccgaca cggctcaggt cgcggtctcc ctcgaccgcg aagccgagcg tgaggtcacg   2460
gcctgggtga gcttcgtccc ggtctcgggt ccggtcgccg cggcggtgca ggatgtcacg   2520
ttcgcacccg gtgagacctg ccgggtcgtc gaggtgccgg tgacggggaa caccgccccg   2580
tcggcgacgg cctcgaccgc gatcacggtg agcgcgacga acaccgccaa tgccgtcatg   2640
ggcgcggacg cgttcggcac gctggtcgtc cgcgaggacg acggggtcac cggtcccgcc   2700
gtcgagctgc cgccggtcgg cgtgcagggc gacgcgtgcg ccgagctggc cgcggctcag   2760
gagccgggcg agctcaccgt gtcggccgac gaggtcgccc cgggcggcag cgtcgagctg   2820
accgccgccg cgttccgcgt cggcgagtcg gtgcgcttca ccttcggcga cgacgagctc   2880
ggtgcggtcc tggccgacgc cgagggcgtc gcgacggtca cggtcgacgt gcccgaggag   2940
agcgcgctcg gtgcacggac ggcctcggcg ttcggtgccg ggtcggcacg cgtgcagacg   3000
gccatggtgg acgtcctcgc cccgaccgcg acgacgctca cggtggacga gggatcgacc   3060
ctcgtcgagg gcgacgagct cacgttcgtg gccgaggtca cgggtgctga gaccgcgggc   3120
acggtgacgt tcgtgagtgg atccggctcg ggcgctgcgg atgccgcggc ggccggcgag   3180
gtgctcggca ccgccgacgt cgtcgacggc gtcgcgacgc tgacgctggg cgatgggctc   3240
gccgagggcg cgtactcggt ggtggcggca ttcgcgagga ccgacatcgc gtccgcctcg   3300
agctcggatc ccgtcgagtt cgagatctcg gcagcggcca ccaagccgcc ggtcgtcaac   3360
```

```
ccgcccggga ccggcactcc cggtggaggt gactccggca ccgcctcgtc gtcggacggt    3420
ccgctcgcgc acaccggctt cgacggcctc ggctgggcgc tgctcgccgc gctcgcgctg    3480
ttcgccgtcg gtgccacggt ggtggtcgcg cggcgccaga cgcggtccac gcccgaatcc    3540
tga                                                                  3543
```

<210> SEQ ID NO 7
<211> LENGTH: 1172
<212> TYPE: PRT
<213> ORGANISM: Microbacterium testaceum

<400> SEQUENCE: 7

```
Leu Leu Asn Gly Ile Gly Lys Ser Ser Val Ile His Ser Leu Ser Met
1               5                   10                  15

Gly Pro Val Thr Gly Pro Ile Thr Pro Ser Leu Arg Arg Thr Gly Glu
            20                  25                  30

Ser Pro Ala Arg Pro His Ala Leu Pro His Arg Arg Thr Val Arg Lys
        35                  40                  45

Pro Leu Ser Pro Arg Thr Arg Trp Leu Ala Leu Thr Ala Ala Val Val
50                  55                  60

Ala Pro Val Leu Ala Leu Ser Cys Ala Pro Ala Ala Val Ala Ala Pro
65                  70                  75                  80

Gly Asp Gly Thr Val Ala Ser Gly Asp Asp Trp Ser Val Thr Thr Ala
                85                  90                  95

Pro Gly Gly Tyr Ile Val Thr Val Glu Leu Ser Glu Pro Leu Pro Ile
            100                 105                 110

Val Ala Asp Ala Pro Thr Leu Val Asp Gly Val Thr Leu Gly Leu
        115                 120                 125

Ala Thr Glu Ser Ala Asp Gly Arg Ser Leu Ser Val Val Thr Ala Asp
130                 135                 140

Pro Lys Val Ala Ser Ala Arg Asp Val Glu Lys Gly Trp Ala Ser Gly
145                 150                 155                 160

Asp Glu Glu Lys Ala Pro Glu Ser Thr Gly Ala Glu Ile Val Asp Glu
                165                 170                 175

Pro Ala Asn Asp Glu Leu Ile Arg Gln Leu Ser Arg Leu Ala Pro Ala
            180                 185                 190

Ala Ala Val Asp Glu Pro Ser Thr Pro Gly Ala Phe Ala Val Thr Glu
        195                 200                 205

Ala Glu Tyr Asp Phe Gly Asp Arg Ala Val Glu Leu Ala Gly Ile Gly
210                 215                 220

Gly Ile Arg Gly Glu Met Thr Gly Lys Met Tyr Leu Thr Asp Ala Pro
225                 230                 235                 240

Gly Glu Arg Pro Thr Val Ile Leu Leu His Gly Arg His Gly Ser Cys
                245                 250                 255

Ala Thr Gly Thr Ser Asn Pro Leu Arg Trp Pro Cys Gly Pro Asn Gln
            260                 265                 270

Val Asn Val Arg Ser Tyr Gln Gly Tyr Glu Gly Thr Gly Arg Ala Leu
        275                 280                 285

Ala Ser His Gly Tyr Asn Val Leu Ser Ile Ala Ala Asn Ala Val Asn
290                 295                 300

Ser Asn Asp Asn Gln Leu Ala Leu Asp Tyr Gly Ala Lys Ala Arg Gly
305                 310                 315                 320

Gln Leu Val Leu Asp Thr Leu Ala Met Leu Glu Ser Ala Asn Ala Gly
                325                 330                 335
```

```
Asp Ala Val Ser Phe Asp Asp Ile Ser Trp Ala Asp Ala Glu Gly Ala
            340                 345                 350
Thr Thr Thr Val Thr Arg Ser Leu Asp Asp Ala Leu Arg Tyr Ala Thr
        355                 360                 365
Thr Arg Thr Asp Met Pro Ala Pro Gly Ala Gly Val Thr Ala Ala Ser
    370                 375                 380
Leu Gln Gly Arg Phe Asp Leu Asp Thr Val Gly Leu Met Gly His Ser
385                 390                 395                 400
Arg Gly Gly Glu Gly Val Val Ser Ala Ala Thr Leu Asn Gln Gly Leu
                405                 410                 415
Ala Asp Pro Tyr Gly Ile Val Ser Val Leu Pro Leu Ala Pro Val Asp
            420                 425                 430
Phe Gly Arg Met Thr Leu Pro Asp Val Pro Leu Gly Val Phe Leu Pro
        435                 440                 445
Tyr Cys Asp Gly Asp Val Ser Asn Gln Gln Gly Gln His Met Val Asp
    450                 455                 460
Asp Ser Arg His Ala Phe Gly Asp Val Leu Arg Ser Ala Val Trp
465                 470                 475                 480
Val Met Gly Ala Asn His Asn Phe Phe Asn Thr Val Trp Thr Pro Gly
                485                 490                 495
Leu Tyr Pro Tyr Ser Thr Ser Asp Asp Trp Asn Arg Asn Asp Thr Thr
            500                 505                 510
Ser Ser Cys Ser Thr Arg Asp Ser Ser Arg Leu Thr Ala Ala Gln Gln
        515                 520                 525
Tyr Gln Val Gly Val Ser Tyr Met Thr Gly Phe Phe Arg Leu Thr Met
    530                 535                 540
Gly Gly Glu Thr Gln Phe Gln Pro Leu Phe Asp Gly Ser Ala Thr Pro
545                 550                 555                 560
Ser Thr Ala Ala Thr Thr Phe Ala Asp Val Arg Ile Met Ala Ser Gln
                565                 570                 575
Pro Gln Ser Ala Thr Thr Leu Val Thr Asp Phe Ala Thr Ala Gly Pro
            580                 585                 590
Leu Val Arg Thr Thr Gly Ser Ala Ser Val Ala Val Cys Ala Asn Ala
        595                 600                 605
Glu Thr Ala Ser Ser Ile Ser Pro Ser Val Pro Tyr Cys Thr Pro Arg
    610                 615                 620
Asp Val Gly Thr Ser Arg Val Pro His Trp Thr Pro Val Arg Phe Gly
625                 630                 635                 640
Leu Asn Val Pro Ala Tyr Pro Val Ser Gln Phe Val Trp Asn Gly Ser
                645                 650                 655
Ala Ser Ala Pro Ala Thr Pro Ser Thr Gly Glu Leu Arg Val Ser Ile
            660                 665                 670
Pro Ala Ala Gln Arg Asp Val Ser Gln Arg Ala Gln Leu Thr Val Lys
        675                 680                 685
Ala Ala Pro Val Leu Ser Val Thr Thr Gly Thr Asp Phe Thr Ile Thr
    690                 695                 700
Val Val Asp Gly Ala Gly Ala Thr Phe Ser Val Pro Ala Ser Ser Ile
705                 710                 715                 720
Asn Pro Leu Ala Val Asn Arg Leu Pro Gly Gly Thr His Ala Thr Leu
                725                 730                 735
Asn Lys Ile Val Leu Gln Gln Leu Thr Ile Pro Thr Ser Glu Met Thr
            740                 745                 750
Gly Ile Asp Leu Thr Asp Val Arg Glu Val Arg Phe Thr Ala Gly Val
```

```
            755           760           765
Gly Ala Asp Gly Thr Gly Ala Gly Gly Val Phe Leu Ser Asp Leu Ala
            770           775           780

Phe Asp Thr Pro Ser Leu Gly Thr Thr Val Val Gln Thr Arg Thr Thr
785               790               795               800

Val Asn Ile Ala Thr Thr Arg Ile Glu Glu Gly Asp Ala Pro Gly Thr
                805               810               815

Ala Thr Ile Ala Ala Tyr Leu Asp Ala Pro Ala Thr Glu Pro Val Thr
                820               825               830

Gly Tyr Val Ser Leu Val Ala Ala Gly Pro Val Ser Ala Ala Val Gln
                835               840               845

Ala Val Thr Phe Ala Pro Gly Glu Ser Cys Arg Ala Ile Ser Val Pro
850               855               860

Thr Val Gly Asp Asp Val Pro Ser Ala Val Gly Ala Thr Gly Tyr Thr
865               870               875               880

Val Ser Val Thr Asn Thr Gln Asn Ala Val Met Gly Ala Ala Ala Phe
                885               890               895

Gly Gln Leu Val Val Arg Glu Asp Asp Gly Val Thr Ser Pro Gly Val
                900               905               910

Glu Leu Pro Pro Val Gly Val Gln Gly Asp Ala Cys Ala Glu Leu Ala
                915               920               925

Ala Ser Phe Glu Pro Thr Glu Leu Ala Ala Ser Thr Leu Glu Ala Ala
                930               935               940

Pro Gly Asp Glu Val Thr Phe Thr Gly Ser Gly Phe Arg Val Gly Glu
945               950               955               960

Glu Val Glu Phe Ala Leu Gly Asp Ala Val Ala Gly Thr Ala Ile Ala
                965               970               975

Asp Arg Asp Gly Val Ala Val Phe Thr Leu Ala Leu Ala Asp Asp Ala
                980               985               990

Asp Leu Gly Ala Gln Val Val Arg Ala Thr Gly Ala Gly Ser Ala Arg
                995              1000              1005

Val Gln Val Thr Thr Leu Ala Val Leu Ala Pro Thr Ala Thr Thr
        1010              1015              1020

Leu Ala Leu Ala Pro Gly Ser Ser Leu Val Ala Gly Gly Pro Leu
        1025              1030              1035

Thr Phe Val Ala Thr Val Ser Gly Ala Glu Thr Asp Gly Thr Val
        1040              1045              1050

Thr Phe Thr Asp Gly Thr Glu Leu Gly Thr Ala Glu Val Val Asp
        1055              1060              1065

Gly Val Ala Thr Leu Thr Leu Arg Glu Gly Leu Ala Ala Gly Thr
        1070              1075              1080

Tyr Ala Val Ala Ala Glu Phe Ala Arg Thr Asp Val Ala Ser Ala
        1085              1090              1095

Ser Arg Ser Asp Glu Leu Glu Val Thr Ile Ala Ala Ala Pro Val
        1100              1105              1110

Ala Gly Gly Pro Gly Ser Asp Gly Thr Gly Ser Gly Ala Thr Gly
        1115              1120              1125

Gly Thr Thr Pro Asp Trp Leu Ala Val Thr Gly Ala Asp Gly Phe
        1130              1135              1140

Gly Trp Met Leu Leu Ala Ala Gly Leu Leu Gly Thr Gly Gly
        1145              1150              1155

Ala Leu Leu Tyr Val Arg Arg Arg Arg Ala Arg Val Asp Ala
        1160              1165              1170
```

<210> SEQ ID NO 8
<211> LENGTH: 989
<212> TYPE: PRT
<213> ORGANISM: Leifsonia xyli

<400> SEQUENCE: 8

```
Leu Pro Val Arg Arg Ile Ala Leu Thr Val Ala Ala Ala Leu Ile
1               5                   10                  15

Pro Val Val Ala Leu Thr Thr Ala Pro Ala Ala Leu Ala Ala Pro Ala
            20                  25                  30

Pro Asp Pro Val Val Ala Ser Gly Ser Asp Trp Ala Val Thr Thr Ser
        35                  40                  45

Pro Gly Gly Tyr Leu Val Thr Leu Asp Leu Asp Glu Pro Leu Pro Met
    50                  55                  60

Val Asp Asp Ala Pro Thr Leu Val Val Asp Gly Glu Pro Ile Gly Leu
65                  70                  75                  80

Ala Thr Glu Ser Ala Asp Gly Leu Thr Leu Gly Val Val Thr Thr Asp
                85                  90                  95

Pro Ala Val Ala Ser Ala Ser Ser Val Thr Lys Gly Trp Ser Ser Gly
            100                 105                 110

Ala Asp Asp Lys Ala Ala Glu Thr Pro Glu Ala Pro Ala Thr Pro Ala
        115                 120                 125

Val Pro Glu Asn Thr Thr Leu Thr Glu Gln Leu Lys Ser Phe Ala Gln
    130                 135                 140

Leu Val Ala Val Glu Asp Pro Ala Asp Leu Gly Ser Tyr Thr Val Thr
145                 150                 155                 160

Glu Ala Glu Tyr Asp Phe Gly Asp Gln Ala Val Pro Leu Ala Ala Ile
                165                 170                 175

Gly Gly Ile Arg Gly Glu Leu Thr Gly Lys Met Tyr Leu Thr Asn Ala
            180                 185                 190

Thr Gly Ala Arg Pro Thr Val Val Leu Leu His Gly Arg His Thr Ser
        195                 200                 205

Cys Ser Gly Thr Gly Ala Asn Pro Leu Arg Trp Pro Cys Gly Pro Thr
    210                 215                 220

Gln Met Asn Ile Arg Ser Tyr Leu Gly Tyr Glu Gly Thr Ala Arg Ala
225                 230                 235                 240

Leu Ala Ser Arg Gly Tyr Asn Val Leu Ser Ile Ala Ala Asn Ala Val
                245                 250                 255

Asn Ser Asn Asp Asn Gln Leu Ala Leu Asp Tyr Gly Ala Gln Ala Arg
            260                 265                 270

Gly Arg Leu Val Leu Asp Thr Leu Gly Met Leu Ala Lys Ala Thr Ala
        275                 280                 285

Gly Asp Ala Val Ala Tyr Asp Asp Ile Thr Thr Ala Thr Asp Thr Val
    290                 295                 300

Pro Ser Thr Thr Thr Arg Thr Leu Asp Glu Ala Leu Leu Arg Ala
305                 310                 315                 320

Thr Thr Arg Ala Asp Gln Pro Ala Ala Ala Ser Gly Ile Thr Ala Ala
                325                 330                 335

Ser Leu Lys Gly Arg Phe Asp Leu Gly His Val Gly Ile Met Gly His
            340                 345                 350

Ser Arg Gly Gly Glu Gly Val Val Ser Ala Ala Thr Leu Asn Gln Ala
        355                 360                 365

Leu Ala Lys Pro Tyr Gly Ile Glu Ser Val Leu Pro Leu Ala Pro Val
```

```
                    370                 375                 380
Asp Phe Gly Arg Met Thr Leu Pro Asp Val Pro Thr Ala Val Phe Leu
385                 390                 395                 400

Pro Tyr Cys Asp Gly Asp Val Ser Asn Gln Gln Gly Gln His Phe Ile
                405                 410                 415

Asp Asp Ser Arg His Ala Phe Asp Asp Val Leu Arg Ser Ala Val
                420                 425                 430

Trp Val Met Gly Ala Asn His Asn Phe Phe Asn Thr Val Trp Thr Pro
                435                 440                 445

Gly Leu Tyr Pro Ala Ala Thr Gly Asp Trp Arg Thr Thr Asp Thr
            450                 455                 460

Thr Ser Thr Cys Ala Thr Thr Asn Pro Thr Arg Met Thr Ala Ala Gln
465                 470                 475                 480

Gln Tyr Gln Val Gly Val Ser Tyr Met Thr Gly Phe Phe Arg Leu Thr
                    485                 490                 495

Met Gly Gly Glu Thr Arg Phe Gln Ser Leu Phe Asp Gly Ser Val Lys
                500                 505                 510

Pro Ser Thr Ala Ser Thr Ala Tyr Ala Asp Val Arg Thr Met Ala Thr
                515                 520                 525

Gln Pro Ala Ser Lys Thr Ser Leu Val Asn Asp Phe Thr Glu Thr Ser
            530                 535                 540

Ser Leu Val Arg Val Ser Gly Gly Ala Thr Ala Ala Val Cys Thr Asn
545                 550                 555                 560

Leu Thr Gly Arg Thr Val Pro Gln Ser Leu Pro Phe Cys Ala Thr Thr
                565                 570                 575

Lys Ala Ser Ala Gln Val Pro His Trp Thr Pro Gly Ser Phe Ala Pro
                580                 585                 590

Asn Val Pro Glu Phe Pro Val Thr Arg Phe Leu Trp Thr Gly Ala Ser
                595                 600                 605

Thr Thr Asp Pro Ala Val Pro Ser Thr Gly Glu Leu Arg Val Thr Val
            610                 615                 620

Pro Ala Lys Asp Arg Asp Ala Ser Arg His Ser Gln Leu Thr Leu Lys
625                 630                 635                 640

Thr Ala Pro Asp Glu Ala Val Gln Thr Gly Thr Asp Phe Arg Ile Thr
                645                 650                 655

Val Val Asp Gly Ala Gly Lys Thr Phe Ala Thr Thr Ala Ser Ala Val
                660                 665                 670

Asn Pro Leu Ala Val Asn Arg Met Pro Gly Gly Thr Asn Thr Thr Leu
                675                 680                 685

Asn Lys Val Val Leu Gln Gln Leu Thr Ile Pro Thr Ser Thr Ile Thr
            690                 695                 700

Gly Ile Asp Leu Thr Asp Val Arg Glu Val Arg Leu Thr Ala Ala Ile
705                 710                 715                 720

Gly Ala Asp Gly Thr Gly Thr Gly Val Tyr Leu Ser Asp Leu Ala
                    725                 730                 735

Phe Asp Thr Pro Ser Val Gly Thr Ala Val Ala Gln Thr Arg Thr Thr
                740                 745                 750

Val Asn Val Ala Pro Thr Thr Val Glu Glu Gly Asp Gly Pro Gly Thr
            755                 760                 765

Ala Asp Val Ala Val Tyr Leu Asn Arg Ala Glu Lys Ser Ala Val Thr
            770                 775                 780

Ala Tyr Val Ser Val Ile Gly Ser Ala Thr Ala Ala Val Gly Ile Gly
785                 790                 795                 800
```

```
Met Glu Lys Val Ala Phe Ala Pro Gly Glu Thr Cys Lys Ala Val Thr
                805                 810                 815

Val Pro Thr Leu Gly Asn Thr Ala Thr Ser Ala Ala Pro Ser Ser Ala
            820                 825                 830

Phe Lys Val Ser Val Thr Asn Ser Thr Asn Ala Val Met Gly Ala Ser
        835                 840                 845

Ala Phe Ala Asn Leu Thr Val Arg Glu Asp Asp Gly Val Thr Gly Ala
850                 855                 860

Ala Pro Ala Leu Ala Pro Val Gly Ala Gln Gly Asp Val Cys Thr Glu
865                 870                 875                 880

Leu Ala Ala Ala Thr Thr Pro Val Pro Leu Gly Thr Ser Ala Glu Asp
                885                 890                 895

Val Ala Pro Gly Gly Ser Phe Thr Leu Arg Ala Thr Gly Tyr Arg Ala
            900                 905                 910

Gly Glu Thr Val Ala Phe Arg Tyr Gly Ala Thr Asp Leu Gly Thr Gln
        915                 920                 925

Val Ala Ala Thr Asp Gly Thr Ala Ser Val Val Thr Val Pro Glu
930                 935                 940

Asp Ala Asp Leu Gly Pro Ala Glu Ala Thr Ala Ser Gly Ser Gly Ser
945                 950                 955                 960

Gly Arg Ala Ala Thr Val Ser Val Ser Val Leu Ala Pro Thr Glu Thr
                965                 970                 975

Thr Val Thr Val Thr Pro Ala Lys Pro Thr Ala Gly Gln
            980                 985

<210> SEQ ID NO 9
<211> LENGTH: 1119
<212> TYPE: PRT
<213> ORGANISM: Leifsonia aquatica

<400> SEQUENCE: 9

Met Ala Ser Gly Ser Asp Trp Ala Val Thr Thr Ser Pro Gly Gly Tyr
1               5                   10                  15

Val Val Thr Leu Glu Leu Asp Glu Pro Leu Pro Met Val Asp Asp Ala
                20                  25                  30

Pro Thr Leu Val Val Asp Gly Glu Pro Ile Gly Leu Ala Thr Glu Ser
            35                  40                  45

Ala Asp Gly Leu Thr Leu Gly Val Val Thr Thr Asp Pro Ala Val Ala
        50                  55                  60

Asn Ala Ser Ser Val Thr Lys Gly Trp Ser Ser Gly Asp Asp Asp Lys
65                  70                  75                  80

Ala Ala Glu Thr Pro Glu Ala Pro Ala Thr Pro Ala Val Pro Glu Asn
                85                  90                  95

Thr Thr Leu Thr Lys Gln Leu Lys Ser Phe Ala Gln Leu Ala Ala Val
            100                 105                 110

Glu Asp Pro Ala Asp Leu Gly Ser Tyr Ala Val Thr Glu Ala Glu Tyr
        115                 120                 125

Asp Phe Gly Asp Gln Ala Val Pro Leu Ala Ala Ile Gly Gly Ile Arg
130                 135                 140

Gly Glu Leu Thr Gly Lys Met Tyr Leu Thr Asn Ala Ala Gly Ala Arg
145                 150                 155                 160

Pro Thr Ile Val Leu Leu His Gly Arg His Thr Ser Cys Ser Gly Thr
                165                 170                 175

Gly Ala Asn Pro Leu Arg Trp Pro Cys Gly Pro Thr Gln Met Asn Ile
```

```
            180                 185                 190
Arg Ser Tyr Leu Gly Tyr Glu Gly Thr Ala Arg Ala Leu Ala Ser Arg
            195                 200                 205
Gly Tyr Asn Val Leu Ser Ile Ala Ala Asn Ser Val Asn Ser Asn Asp
            210                 215                 220
Asn Gln Leu Ala Leu Asp Tyr Gly Ala Gln Ala Arg Gly Gln Leu Ile
225                 230                 235                 240
Leu Asp Thr Leu Gly Met Leu Ala Lys Ala Thr Ala Gly Asp Ala Val
                    245                 250                 255
Ala Phe Asp Asp Ile Thr Thr Ala Thr Ser Thr Val Pro Ser Thr Thr
                    260                 265                 270
Thr Thr Arg Thr Leu Asp Glu Ala Leu Val Arg Ala Thr Thr Arg Thr
            275                 280                 285
Asp Gln Pro Ala Ala Ser Gly Ile Thr Ala Ala Ser Leu Lys Gly
            290                 295                 300
Arg Phe Asp Leu Gly His Val Gly Ile Met Gly His Ser Arg Gly Gly
305                 310                 315                 320
Glu Gly Val Val Ser Ala Ala Thr Leu Asn Gln Ala Leu Ala Lys Pro
                    325                 330                 335
Tyr Gly Ile Glu Ser Val Leu Pro Leu Ala Pro Val Asp Phe Gly Arg
                    340                 345                 350
Met Thr Leu Pro Asp Val Pro Thr Ala Val Phe Leu Pro Tyr Cys Asp
                    355                 360                 365
Gly Asp Val Ser Asn Gln Gln Gly Gln His Phe Ile Asp Asp Ser Arg
            370                 375                 380
His Ala Phe Asp Asp Val Leu Arg Ser Ala Val Trp Val Met Gly
385                 390                 395                 400
Ala Asn His Asn Phe Phe Asn Thr Val Trp Thr Pro Gly Leu Tyr Pro
                    405                 410                 415
Ala Ala Thr Gly Asp Asp Trp Arg Thr Thr Asp Thr Thr Ser Thr Cys
            420                 425                 430
Ala Thr Thr Asp Pro Thr Arg Met Thr Ala Ala Gln Gln Tyr Gln Val
            435                 440                 445
Gly Val Ser Tyr Met Thr Gly Phe Phe Arg Leu Thr Met Gly Gly Glu
            450                 455                 460
Thr Gln Phe Gln Ser Leu Phe Asp Gly Ser Val Lys Pro Ser Thr Ala
465                 470                 475                 480
Ser Thr Ala Tyr Ala Asp Val Arg Thr Met Ala Thr Gln Pro Ala Ser
                    485                 490                 495
Lys Thr Ser Leu Val Asn Asp Phe Thr Glu Thr Ser Ser Leu Val Arg
            500                 505                 510
Val Ser Gly Gly Ala Thr Ala Ala Val Cys Thr Asn Leu Thr Gly Arg
            515                 520                 525
Thr Val Pro Gln Ser Leu Pro Phe Cys Ala Thr Lys Ala Ser Ala
            530                 535                 540
Gln Val Pro His Trp Thr Pro Gly Ser Phe Ala Pro Asn Val Pro Glu
545                 550                 555                 560
Phe Pro Val Thr Arg Phe Leu Trp Thr Gly Ala Ser Thr Thr Asp Pro
                    565                 570                 575
Ala Val Pro Ser Thr Gly Glu Leu Arg Val Thr Val Pro Ala Lys Tyr
                    580                 585                 590
Arg Asp Val Ser Arg Gln Ser Gln Leu Thr Leu Lys Thr Ala Pro Asp
            595                 600                 605
```

Glu Ala Val Gln Asn Gly Thr Asp Phe Arg Ile Thr Val Val Asp Gly
          610                 615                 620

Ala Gly Lys Thr Phe Ala Ile Ala Ala Ser Ala Val Asn Pro Leu Ala
625                 630                 635                 640

Val Asn Arg Met Pro Gly Gly Thr Asn Thr Thr Leu Asn Lys Val Val
              645                 650                 655

Leu Gln Gln Leu Thr Ile Pro Thr Ser Thr Ile Thr Gly Ile Asp Leu
              660                 665                 670

Thr Asp Val Arg Glu Val Arg Leu Thr Ala Ala Val Gly Ala Asp Gly
          675                 680                 685

Thr Gly Thr Gly Gly Val Tyr Leu Ser Asp Leu Ala Phe Asp Thr Pro
      690                 695                 700

Ser Val Gly Thr Ala Val Val Gln Thr Arg Thr Ser Val Asn Val Ala
705                 710                 715                 720

Pro Thr Ile Val Glu Glu Gly Asn Gly Pro Gly Ser Ala Asp Val Ala
              725                 730                 735

Val Tyr Leu Asn Arg Ala Glu Lys Ser Ala Val Thr Ala Tyr Val Ser
              740                 745                 750

Val Ile Gly Ala Ala Gly Ser Val Gly Val Gly Ile Gly Met Glu
          755                 760                 765

Lys Val Ala Phe Ala Pro Gly Glu Thr Cys Lys Ala Val Thr Val Pro
770                 775                 780

Thr Leu Gly Asn Thr Ala Ala Ser Ala Ser Pro Ser Thr Ala Phe Lys
785                 790                 795                 800

Val Ser Val Thr Asn Ser Thr Asn Ala Val Met Gly Ala Ser Ala Phe
              805                 810                 815

Ala Asn Leu Thr Val Arg Glu Asp Asp Gly Val Thr Gly Ala Ala Pro
              820                 825                 830

Ala Leu Ala Pro Val Gly Ala Gln Gly Asp Val Cys Ala Glu Leu Ala
          835                 840                 845

Ala Ala Thr Asn Pro Val Pro Leu Glu Thr Ser Ala Glu Asp Val Ala
850                 855                 860

Pro Gly Asp Ser Phe Thr Leu Arg Ala Thr Gly Tyr Arg Ala Gly Glu
865                 870                 875                 880

Thr Val Ala Phe Arg Tyr Gly Ala Thr Asp Leu Gly Thr Ala Val Ala
              885                 890                 895

Glu Ala Asp Gly Thr Ala Ser Val Val Pro Val Ala Glu Asp Ala
              900                 905                 910

Asp Leu Gly Pro Ala Asp Ala Arg Ala Thr Gly Ser Gly Ser Gly Arg
          915                 920                 925

Thr Ala Thr Val Ser Val Ser Val Leu Ala Pro Thr Glu Thr Thr Val
      930                 935                 940

Thr Val Ser Pro Ala Lys Pro Thr Ala Gly Gln Lys Val Thr Phe Thr
945                 950                 955                 960

Ala Thr Val Thr Gly Arg Asp Thr Ala Gly Thr Ile Ala Phe Leu Asp
              965                 970                 975

Gly Gly Glu Pro Ala Ser Ala Pro Thr Ala Lys Ala Ser Ala Leu Val
              980                 985                 990

Ala Val Ala Ala Ala Ala Ala Pro Thr Val Leu Gly Glu Val Glu
          995                 1000                1005

Ile Val Asp Gly Val Ala Thr Leu Thr Leu Pro Gly Gly Leu Ala
      1010                1015                1020

Ala Gly Asp His Ala Ile Thr Ala Ser Phe Ala Arg Thr Ala Thr
1025                1030                1035

Ala Ser Ala Ser Thr Ser Asp Pro Ile Thr Val Thr Val Val Pro
1040                1045                1050

Ala Ala Ser Thr Gly Gly Ser Gly Thr Asp Gly Ala Gly Ser Val
1055                1060                1065

Gly Ser Gly Ala Gly Thr Gly Ser Ala Ser Thr Gly Ala Asp Ala
1070                1075                1080

Leu Ala Glu Thr Gly Ser Ala Ile Gly Leu Trp Leu Leu Ala Gly
1085                1090                1095

Val Thr Val Leu Leu Ala Gly Ala Gly Leu Leu Ala Val Ser Arg
1100                1105                1110

Arg Arg Arg Ile Ala Glu
    1115

<210> SEQ ID NO 10
<211> LENGTH: 1378
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(62)
<223> OTHER INFORMATION: The amino acid(s) can either be present or
      absent
<220> FEATURE:
<221> NAME/KEY: misc_feature
<222> LOCATION: (63)..(68)
<223> OTHER INFORMATION: Xaa can be any naturally occurring amino acid
<220> FEATURE:
<221> NAME/KEY: misc_feature
<222> LOCATION: (71)..(80)
<223> OTHER INFORMATION: Xaa can be any naturally occurring amino acid
<220> FEATURE:
<221> NAME/KEY: misc_feature
<222> LOCATION: (83)..(92)
<223> OTHER INFORMATION: Xaa can be any naturally occurring amino acid
<220> FEATURE:
<221> NAME/KEY: misc_feature
<222> LOCATION: (94)..(98)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: MISC_FEATURE
<222> LOCATION: (103)..(103)
<223> OTHER INFORMATION: The amino acid(s) can either be present or
      absent
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(107)
<223> OTHER INFORMATION: Xaa can be any naturally occurring amino acid
<220> FEATURE:
<221> NAME/KEY: misc_feature
<222> LOCATION: (109)..(112)
<223> OTHER INFORMATION: Xaa can be any naturally occurring amino acid
<220> FEATURE:
<221> NAME/KEY: MISC_FEATURE
<222> LOCATION: (114)..(114)
<223> OTHER INFORMATION: The amino acid(s) can either be present or
      absent

```
<220> FEATURE:
<221> NAME/KEY: misc_feature
<222> LOCATION: (116)..(120)
<223> OTHER INFORMATION: Xaa can be any naturally occurring amino acid
<220> FEATURE:
<221> NAME/KEY: misc_feature
<222> LOCATION: (124)..(124)
<223> OTHER INFORMATION: Xaa can be any naturally occurring amino acid
<220> FEATURE:
<221> NAME/KEY: MISC_FEATURE
<222> LOCATION: (126)..(126)
<223> OTHER INFORMATION: The amino acid(s) can either be present or
      absent
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (131)..(135)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: misc_feature
<222> LOCATION: (144)..(149)
<223> OTHER INFORMATION: Xaa can be any naturally occurring amino acid
<220> FEATURE:
<221> NAME/KEY: misc_feature
<222> LOCATION: (152)..(153)
<223> OTHER INFORMATION: Xaa can be any naturally occurring amino acid
<220> FEATURE:
<221> NAME/KEY: misc_feature
<222> LOCATION: (156)..(157)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (172)..(173)
<223> OTHER INFORMATION: Xaa can be any naturally occurring amino acid
<220> FEATURE:
<221> NAME/KEY: misc_feature
<222> LOCATION: (176)..(178)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid
<220> FEATURE:
<221> NAME/KEY: misc_feature
<222> LOCATION: (188)..(189)
<223> OTHER INFORMATION: Xaa can be any naturally occurring amino acid
<220> FEATURE:
<221> NAME/KEY: misc_feature
<222> LOCATION: (191)..(193)
<223> OTHER INFORMATION: Xaa can be any naturally occurring amino acid
<220> FEATURE:
<221> NAME/KEY: misc_feature
```

```
<222> LOCATION: (195)..(195)
<223> OTHER INFORMATION: Xaa can be any naturally occurring amino acid
<220> FEATURE:
<221> NAME/KEY: MISC_FEATURE
<222> LOCATION: (196)..(196)
<223> OTHER INFORMATION: The amino acid(s) can either be present or
      absent
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (203)..(204)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: MISC_FEATURE
<222> LOCATION: (210)..(210)
<223> OTHER INFORMATION: The amino acid(s) can either be present or
      absent
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (215)..(216)
<223> OTHER INFORMATION: Xaa can be any naturally occurring amino acid
<220> FEATURE:
<221> NAME/KEY: misc_feature
<222> LOCATION: (218)..(225)
<223> OTHER INFORMATION: Xaa can be any naturally occurring amino acid
<220> FEATURE:
<221> NAME/KEY: misc_feature
<222> LOCATION: (229)..(229)
<223> OTHER INFORMATION: Xaa can be any naturally occurring amino acid
<220> FEATURE:
<221> NAME/KEY: misc_feature
<222> LOCATION: (231)..(233)
<223> OTHER INFORMATION: Xaa can be any naturally occurring amino acid
<220> FEATURE:
<221> NAME/KEY: MISC_FEATURE
<222> LOCATION: (234)..(235)
<223> OTHER INFORMATION: The amino acid(s) can either be present or
      absent
<220> FEATURE:
<221> NAME/KEY: misc_feature
<222> LOCATION: (236)..(239)
<223> OTHER INFORMATION: Xaa can be any naturally occurring amino acid
<220> FEATURE:
<221> NAME/KEY: misc_feature
<222> LOCATION: (242)..(244)
<223> OTHER INFORMATION: Xaa can be any naturally occurring amino acid
<220> FEATURE:
<221> NAME/KEY: misc_feature
<222> LOCATION: (246)..(246)
<223> OTHER INFORMATION: Xaa can be any naturally occurring amino acid
<220> FEATURE:
<221> NAME/KEY: misc_feature
<222> LOCATION: (248)..(248)
<223> OTHER INFORMATION: Xaa can be any naturally occurring amino acid
<220> FEATURE:
<221> NAME/KEY: misc_feature
<222> LOCATION: (250)..(250)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid
<220> FEATURE:
<221> NAME/KEY: misc_feature
```

```
<222> LOCATION: (256)..(257)
<223> OTHER INFORMATION: Xaa can be any naturally occurring amino acid
<220> FEATURE:
<221> NAME/KEY: misc_feature
<222> LOCATION: (259)..(260)
<223> OTHER INFORMATION: Xaa can be any naturally occurring amino acid
<220> FEATURE:
<221> NAME/KEY: misc_feature
<222> LOCATION: (262)..(263)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (272)..(272)
<223> OTHER INFORMATION: Xaa can be any naturally occurring amino acid
<220> FEATURE:
<221> NAME/KEY: misc_feature
<222> LOCATION: (275)..(275)
<223> OTHER INFORMATION: Xaa can be any naturally occurring amino acid
<220> FEATURE:
<221> NAME/KEY: misc_feature
<222> LOCATION: (286)..(287)
<223> OTHER INFORMATION: Xaa can be any naturally occurring amino acid
<220> FEATURE:
<221> NAME/KEY: misc_feature
<222> LOCATION: (290)..(293)
<223> OTHER INFORMATION: Xaa can be any naturally occurring amino acid
<220> FEATURE:
<221> NAME/KEY: misc_feature
<222> LOCATION: (295)..(296)
<223> OTHER INFORMATION: Xaa can be any naturally occurring amino acid
<220> FEATURE:
<221> NAME/KEY: MISC_FEATURE
<222> LOCATION: (310)..(314)
<223> OTHER INFORMATION: The amino acid(s) can either be present or
      absent
<220> FEATURE:
<221> NAME/KEY: misc_feature
<222> LOCATION: (315)..(319)
<223> OTHER INFORMATION: Xaa can be any naturally occurring amino acid
<220> FEATURE:
<221> NAME/KEY: misc_feature
<222> LOCATION: (322)..(322)
<223> OTHER INFORMATION: Xaa can be any naturally occurring amino acid
<220> FEATURE:
<221> NAME/KEY: misc_feature
<222> LOCATION: (327)..(329)
<223> OTHER INFORMATION: Xaa can be any naturally occurring amino acid
<220> FEATURE:
<221> NAME/KEY: misc_feature
<222> LOCATION: (333)..(334)
<223> OTHER INFORMATION: Xaa can be any naturally occurring amino acid
<220> FEATURE:
<221> NAME/KEY: misc_feature
<222> LOCATION: (337)..(337)
<223> OTHER INFORMATION: Xaa can be any naturally occurring amino acid
<220> FEATURE:
<221> NAME/KEY: misc_feature
<222> LOCATION: (341)..(341)
<223> OTHER INFORMATION: Xaa can be any naturally occurring amino acid
<220> FEATURE:
<221> NAME/KEY: misc_feature
<222> LOCATION: (344)..(345)
<223> OTHER INFORMATION: Xaa can be any naturally occurring amino acid
<220> FEATURE:
<221> NAME/KEY: misc_feature
<222> LOCATION: (348)..(348)
<223> OTHER INFORMATION: Xaa can be any naturally occurring amino acid
<220> FEATURE:
<221> NAME/KEY: misc_feature
<222> LOCATION: (352)..(352)
<223> OTHER INFORMATION: Xaa can be any naturally occurring amino acid
<220> FEATURE:
<221> NAME/KEY: misc_feature
<222> LOCATION: (354)..(354)
<223> OTHER INFORMATION: Xaa can be any naturally occurring amino acid
```

```
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (361)..(361)
<223> OTHER INFORMATION: Xaa can be any naturally occurring amino acid
<220> FEATURE:
<221> NAME/KEY: misc_feature
<222> LOCATION: (363)..(363)
<223> OTHER INFORMATION: Xaa can be any naturally occurring amino acid
<220> FEATURE:
<221> NAME/KEY: misc_feature
<222> LOCATION: (370)..(370)
<223> OTHER INFORMATION: Xaa can be any naturally occurring amino acid
<220> FEATURE:
<221> NAME/KEY: misc_feature
<222> LOCATION: (375)..(375)
<223> OTHER INFORMATION: Xaa can be any naturally occurring amino acid
<220> FEATURE:
<221> NAME/KEY: misc_feature
<222> LOCATION: (381)..(381)
<223> OTHER INFORMATION: Xaa can be any naturally occurring amino acid
<220> FEATURE:
<221> NAME/KEY: misc_feature
<222> LOCATION: (386)..(386)
<223> OTHER INFORMATION: Xaa can be any naturally occurring amino acid
<220> FEATURE:
<221> NAME/KEY: misc_feature
<222> LOCATION: (389)..(389)
<223> OTHER INFORMATION: Xaa can be any naturally occurring amino acid
<220> FEATURE:
<221> NAME/KEY: misc_feature
<222> LOCATION: (392)..(392)
<223> OTHER INFORMATION: Xaa can be any naturally occurring amino acid
<220> FEATURE:
<221> NAME/KEY: misc_feature
<222> LOCATION: (398)..(400)
<223> OTHER INFORMATION: Xaa can be any naturally occurring amino acid
<220> FEATURE:
<221> NAME/KEY: misc_feature
<222> LOCATION: (402)..(403)
<223> OTHER INFORMATION: Xaa can be any naturally occurring amino acid
<220> FEATURE:
<221> NAME/KEY: MISC_FEATURE
<222> LOCATION: (404)..(404)
<223> OTHER INFORMATION: The amino acid(s) can either be present or
     absent
<220> FEATURE:
<221> NAME/KEY: misc_feature
<222> LOCATION: (405)..(405)
<223> OTHER INFORMATION: Xaa can be any naturally occurring amino acid
<220> FEATURE:
<221> NAME/KEY: misc_feature
<222> LOCATION: (407)..(420)
<223> OTHER INFORMATION: Xaa can be any naturally occurring amino acid
<220> FEATURE:
<221> NAME/KEY: misc_feature
<222> LOCATION: (422)..(423)
<223> OTHER INFORMATION: Xaa can be any naturally occurring amino acid
<220> FEATURE:
<221> NAME/KEY: misc_feature
<222> LOCATION: (425)..(438)
<223> OTHER INFORMATION: Xaa can be any naturally occurring amino acid
<220> FEATURE:
<221> NAME/KEY: misc_feature
<222> LOCATION: (440)..(440)
<223> OTHER INFORMATION: Xaa can be any naturally occurring amino acid
<220> FEATURE:
<221> NAME/KEY: misc_feature
<222> LOCATION: (442)..(442)
<223> OTHER INFORMATION: Xaa can be any naturally occurring amino acid
<220> FEATURE:
<221> NAME/KEY: misc_feature
<222> LOCATION: (444)..(444)
<223> OTHER INFORMATION: Xaa can be any naturally occurring amino acid
<220> FEATURE:
<221> NAME/KEY: misc_feature
```

```
<222> LOCATION: (446)..(446)
<223> OTHER INFORMATION: Xaa can be any naturally occurring amino acid
<220> FEATURE:
<221> NAME/KEY: misc_feature
<222> LOCATION: (451)..(451)
<223> OTHER INFORMATION: Xaa can be any naturally occurring amino acid
<220> FEATURE:
<221> NAME/KEY: misc_feature
<222> LOCATION: (454)..(454)
<223> OTHER INFORMATION: Xaa can be any naturally occurring amino acid
<220> FEATURE:
<221> NAME/KEY: misc_feature
<222> LOCATION: (464)..(465)
<223> OTHER INFORMATION: Xaa can be any naturally occurring amino acid
<220> FEATURE:
<221> NAME/KEY: misc_feature
<222> LOCATION: (469)..(469)
<223> OTHER INFORMATION: Xaa can be any naturally occurring amino acid
<220> FEATURE:
<221> NAME/KEY: misc_feature
<222> LOCATION: (473)..(473)
<223> OTHER INFORMATION: Xaa can be any naturally occurring amino acid
<220> FEATURE:
<221> NAME/KEY: misc_feature
<222> LOCATION: (476)..(476)
<223> OTHER INFORMATION: Xaa can be any naturally occurring amino acid
<220> FEATURE:
<221> NAME/KEY: misc_feature
<222> LOCATION: (481)..(482)
<223> OTHER INFORMATION: Xaa can be any naturally occurring amino acid
<220> FEATURE:
<221> NAME/KEY: misc_feature
<222> LOCATION: (494)..(494)
<223> OTHER INFORMATION: Xaa can be any naturally occurring amino acid
<220> FEATURE:
<221> NAME/KEY: misc_feature
<222> LOCATION: (496)..(496)
<223> OTHER INFORMATION: Xaa can be any naturally occurring amino acid
<220> FEATURE:
<221> NAME/KEY: misc_feature
<222> LOCATION: (500)..(500)
<223> OTHER INFORMATION: Xaa can be any naturally occurring amino acid
<220> FEATURE:
<221> NAME/KEY: misc_feature
<222> LOCATION: (502)..(502)
<223> OTHER INFORMATION: Xaa can be any naturally occurring amino acid
<220> FEATURE:
<221> NAME/KEY: misc_feature
<222> LOCATION: (504)..(504)
<223> OTHER INFORMATION: Xaa can be any naturally occurring amino acid
<220> FEATURE:
<221> NAME/KEY: misc_feature
<222> LOCATION: (520)..(521)
<223> OTHER INFORMATION: Xaa can be any naturally occurring amino acid
<220> FEATURE:
<221> NAME/KEY: misc_feature
<222> LOCATION: (526)..(526)
<223> OTHER INFORMATION: Xaa can be any naturally occurring amino acid
<220> FEATURE:
<221> NAME/KEY: misc_feature
<222> LOCATION: (528)..(529)
<223> OTHER INFORMATION: Xaa can be any naturally occurring amino acid
<220> FEATURE:
<221> NAME/KEY: misc_feature
<222> LOCATION: (532)..(533)
<223> OTHER INFORMATION: Xaa can be any naturally occurring amino acid
<220> FEATURE:
<221> NAME/KEY: misc_feature
<222> LOCATION: (536)..(537)
<223> OTHER INFORMATION: Xaa can be any naturally occurring amino acid
<220> FEATURE:
<221> NAME/KEY: misc_feature
<222> LOCATION: (539)..(539)
<223> OTHER INFORMATION: Xaa can be any naturally occurring amino acid
<220> FEATURE:
<221> NAME/KEY: misc_feature
<222> LOCATION: (543)..(543)
<223> OTHER INFORMATION: Xaa can be any naturally occurring amino acid
<220> FEATURE:
```

```
<221> NAME/KEY: misc_feature
<222> LOCATION: (549)..(549)
<223> OTHER INFORMATION: Xaa can be any naturally occurring amino acid
<220> FEATURE:
<221> NAME/KEY: misc_feature
<222> LOCATION: (555)..(555)
<223> OTHER INFORMATION: Xaa can be any naturally occurring amino acid
<220> FEATURE:
<221> NAME/KEY: misc_feature
<222> LOCATION: (558)..(559)
<223> OTHER INFORMATION: Xaa can be any naturally occurring amino acid
<220> FEATURE:
<221> NAME/KEY: misc_feature
<222> LOCATION: (565)..(572)
<223> OTHER INFORMATION: Xaa can be any naturally occurring amino acid
<220> FEATURE:
<221> NAME/KEY: misc_feature
<222> LOCATION: (574)..(574)
<223> OTHER INFORMATION: Xaa can be any naturally occurring amino acid
<220> FEATURE:
<221> NAME/KEY: MISC_FEATURE
<222> LOCATION: (575)..(576)
<223> OTHER INFORMATION: The amino acid(s) can either be present or
      absent
<220> FEATURE:
<221> NAME/KEY: misc_feature
<222> LOCATION: (577)..(581)
<223> OTHER INFORMATION: Xaa can be any naturally occurring amino acid
<220> FEATURE:
<221> NAME/KEY: misc_feature
<222> LOCATION: (584)..(587)
<223> OTHER INFORMATION: Xaa can be any naturally occurring amino acid
<220> FEATURE:
<221> NAME/KEY: misc_feature
<222> LOCATION: (590)..(590)
<223> OTHER INFORMATION: Xaa can be any naturally occurring amino acid
<220> FEATURE:
<221> NAME/KEY: misc_feature
<222> LOCATION: (594)..(595)
<223> OTHER INFORMATION: Xaa can be any naturally occurring amino acid
<220> FEATURE:
<221> NAME/KEY: misc_feature
<222> LOCATION: (597)..(599)
<223> OTHER INFORMATION: Xaa can be any naturally occurring amino acid
<220> FEATURE:
<221> NAME/KEY: misc_feature
<222> LOCATION: (604)..(604)
<223> OTHER INFORMATION: Xaa can be any naturally occurring amino acid
<220> FEATURE:
<221> NAME/KEY: misc_feature
<222> LOCATION: (608)..(608)
<223> OTHER INFORMATION: Xaa can be any naturally occurring amino acid
<220> FEATURE:
<221> NAME/KEY: misc_feature
<222> LOCATION: (611)..(611)
<223> OTHER INFORMATION: Xaa can be any naturally occurring amino acid
<220> FEATURE:
<221> NAME/KEY: misc_feature
<222> LOCATION: (613)..(613)
<223> OTHER INFORMATION: Xaa can be any naturally occurring amino acid
<220> FEATURE:
<221> NAME/KEY: misc_feature
<222> LOCATION: (618)..(619)
<223> OTHER INFORMATION: Xaa can be any naturally occurring amino acid
<220> FEATURE:
<221> NAME/KEY: misc_feature
<222> LOCATION: (622)..(622)
<223> OTHER INFORMATION: Xaa can be any naturally occurring amino acid
<220> FEATURE:
<221> NAME/KEY: misc_feature
<222> LOCATION: (624)..(627)
<223> OTHER INFORMATION: Xaa can be any naturally occurring amino acid
<220> FEATURE:
<221> NAME/KEY: misc_feature
<222> LOCATION: (629)..(633)
<223> OTHER INFORMATION: Xaa can be any naturally occurring amino acid
<220> FEATURE:
<221> NAME/KEY: misc_feature
<222> LOCATION: (635)..(636)
```

```
<223> OTHER INFORMATION: Xaa can be any naturally occurring amino acid
<220> FEATURE:
<221> NAME/KEY: misc_feature
<222> LOCATION: (639)..(643)
<223> OTHER INFORMATION: Xaa can be any naturally occurring amino acid
<220> FEATURE:
<221> NAME/KEY: misc_feature
<222> LOCATION: (645)..(646)
<223> OTHER INFORMATION: Xaa can be any naturally occurring amino acid
<220> FEATURE:
<221> NAME/KEY: misc_feature
<222> LOCATION: (648)..(654)
<223> OTHER INFORMATION: Xaa can be any naturally occurring amino acid
<220> FEATURE:
<221> NAME/KEY: misc_feature
<222> LOCATION: (656)..(657)
<223> OTHER INFORMATION: Xaa can be any naturally occurring amino acid
<220> FEATURE:
<221> NAME/KEY: misc_feature
<222> LOCATION: (659)..(659)
<223> OTHER INFORMATION: Xaa can be any naturally occurring amino acid
<220> FEATURE:
<221> NAME/KEY: misc_feature
<222> LOCATION: (661)..(663)
<223> OTHER INFORMATION: Xaa can be any naturally occurring amino acid
<220> FEATURE:
<221> NAME/KEY: misc_feature
<222> LOCATION: (667)..(667)
<223> OTHER INFORMATION: Xaa can be any naturally occurring amino acid
<220> FEATURE:
<221> NAME/KEY: misc_feature
<222> LOCATION: (669)..(671)
<223> OTHER INFORMATION: Xaa can be any naturally occurring amino acid
<220> FEATURE:
<221> NAME/KEY: misc_feature
<222> LOCATION: (673)..(678)
<223> OTHER INFORMATION: Xaa can be any naturally occurring amino acid
<220> FEATURE:
<221> NAME/KEY: misc_feature
<222> LOCATION: (680)..(681)
<223> OTHER INFORMATION: Xaa can be any naturally occurring amino acid
<220> FEATURE:
<221> NAME/KEY: misc_feature
<222> LOCATION: (683)..(686)
<223> OTHER INFORMATION: Xaa can be any naturally occurring amino acid
<220> FEATURE:
<221> NAME/KEY: MISC_FEATURE
<222> LOCATION: (687)..(687)
<223> OTHER INFORMATION: The amino acid(s) can either be present or
      absent
<220> FEATURE:
<221> NAME/KEY: misc_feature
<222> LOCATION: (688)..(688)
<223> OTHER INFORMATION: Xaa can be any naturally occurring amino acid
<220> FEATURE:
<221> NAME/KEY: misc_feature
<222> LOCATION: (690)..(692)
<223> OTHER INFORMATION: Xaa can be any naturally occurring amino acid
<220> FEATURE:
<221> NAME/KEY: misc_feature
<222> LOCATION: (698)..(699)
<223> OTHER INFORMATION: Xaa can be any naturally occurring amino acid
<220> FEATURE:
<221> NAME/KEY: misc_feature
<222> LOCATION: (701)..(702)
<223> OTHER INFORMATION: Xaa can be any naturally occurring amino acid
<220> FEATURE:
<221> NAME/KEY: misc_feature
<222> LOCATION: (707)..(707)
<223> OTHER INFORMATION: Xaa can be any naturally occurring amino acid
<220> FEATURE:
<221> NAME/KEY: misc_feature
<222> LOCATION: (709)..(710)
<223> OTHER INFORMATION: Xaa can be any naturally occurring amino acid
<220> FEATURE:
<221> NAME/KEY: misc_feature
<222> LOCATION: (712)..(712)
<223> OTHER INFORMATION: Xaa can be any naturally occurring amino acid
<220> FEATURE:
```

```
<221> NAME/KEY: MISC_FEATURE
<222> LOCATION: (716)..(719)
<223> OTHER INFORMATION: The amino acid(s) can either be present or
      absent
<220> FEATURE:
<221> NAME/KEY: misc_feature
<222> LOCATION: (720)..(726)
<223> OTHER INFORMATION: Xaa can be any naturally occurring amino acid
<220> FEATURE:
<221> NAME/KEY: misc_feature
<222> LOCATION: (728)..(730)
<223> OTHER INFORMATION: Xaa can be any naturally occurring amino acid
<220> FEATURE:
<221> NAME/KEY: misc_feature
<222> LOCATION: (732)..(732)
<223> OTHER INFORMATION: Xaa can be any naturally occurring amino acid
<220> FEATURE:
<221> NAME/KEY: misc_feature
<222> LOCATION: (735)..(737)
<223> OTHER INFORMATION: Xaa can be any naturally occurring amino acid
<220> FEATURE:
<221> NAME/KEY: misc_feature
<222> LOCATION: (740)..(740)
<223> OTHER INFORMATION: Xaa can be any naturally occurring amino acid
<220> FEATURE:
<221> NAME/KEY: misc_feature
<222> LOCATION: (742)..(745)
<223> OTHER INFORMATION: Xaa can be any naturally occurring amino acid
<220> FEATURE:
<221> NAME/KEY: misc_feature
<222> LOCATION: (748)..(748)
<223> OTHER INFORMATION: Xaa can be any naturally occurring amino acid
<220> FEATURE:
<221> NAME/KEY: misc_feature
<222> LOCATION: (750)..(750)
<223> OTHER INFORMATION: Xaa can be any naturally occurring amino acid
<220> FEATURE:
<221> NAME/KEY: misc_feature
<222> LOCATION: (754)..(754)
<223> OTHER INFORMATION: Xaa can be any naturally occurring amino acid
<220> FEATURE:
<221> NAME/KEY: misc_feature
<222> LOCATION: (757)..(758)
<223> OTHER INFORMATION: Xaa can be any naturally occurring amino acid
<220> FEATURE:
<221> NAME/KEY: misc_feature
<222> LOCATION: (762)..(762)
<223> OTHER INFORMATION: Xaa can be any naturally occurring amino acid
<220> FEATURE:
<221> NAME/KEY: misc_feature
<222> LOCATION: (764)..(764)
<223> OTHER INFORMATION: Xaa can be any naturally occurring amino acid
<220> FEATURE:
<221> NAME/KEY: misc_feature
<222> LOCATION: (767)..(767)
<223> OTHER INFORMATION: Xaa can be any naturally occurring amino acid
<220> FEATURE:
<221> NAME/KEY: misc_feature
<222> LOCATION: (770)..(770)
<223> OTHER INFORMATION: Xaa can be any naturally occurring amino acid
<220> FEATURE:
<221> NAME/KEY: misc_feature
<222> LOCATION: (772)..(774)
<223> OTHER INFORMATION: Xaa can be any naturally occurring amino acid
<220> FEATURE:
<221> NAME/KEY: misc_feature
<222> LOCATION: (776)..(778)
<223> OTHER INFORMATION: Xaa can be any naturally occurring amino acid
<220> FEATURE:
<221> NAME/KEY: misc_feature
<222> LOCATION: (781)..(781)
<223> OTHER INFORMATION: Xaa can be any naturally occurring amino acid
<220> FEATURE:
<221> NAME/KEY: misc_feature
<222> LOCATION: (783)..(784)
<223> OTHER INFORMATION: Xaa can be any naturally occurring amino acid
<220> FEATURE:
<221> NAME/KEY: misc_feature
<222> LOCATION: (787)..(787)
```

```
<223> OTHER INFORMATION: Xaa can be any naturally occurring amino acid
<220> FEATURE:
<221> NAME/KEY: misc_feature
<222> LOCATION: (789)..(789)
<223> OTHER INFORMATION: Xaa can be any naturally occurring amino acid
<220> FEATURE:
<221> NAME/KEY: misc_feature
<222> LOCATION: (791)..(795)
<223> OTHER INFORMATION: Xaa can be any naturally occurring amino acid
<220> FEATURE:
<221> NAME/KEY: misc_feature
<222> LOCATION: (805)..(806)
<223> OTHER INFORMATION: Xaa can be any naturally occurring amino acid
<220> FEATURE:
<221> NAME/KEY: misc_feature
<222> LOCATION: (809)..(809)
<223> OTHER INFORMATION: Xaa can be any naturally occurring amino acid
<220> FEATURE:
<221> NAME/KEY: misc_feature
<222> LOCATION: (811)..(813)
<223> OTHER INFORMATION: Xaa can be any naturally occurring amino acid
<220> FEATURE:
<221> NAME/KEY: MISC_FEATURE
<222> LOCATION: (815)..(815)
<223> OTHER INFORMATION: The amino acid(s) can either be present or
      absent
<220> FEATURE:
<221> NAME/KEY: misc_feature
<222> LOCATION: (818)..(819)
<223> OTHER INFORMATION: Xaa can be any naturally occurring amino acid
<220> FEATURE:
<221> NAME/KEY: misc_feature
<222> LOCATION: (828)..(830)
<223> OTHER INFORMATION: Xaa can be any naturally occurring amino acid
<220> FEATURE:
<221> NAME/KEY: misc_feature
<222> LOCATION: (836)..(837)
<223> OTHER INFORMATION: Xaa can be any naturally occurring amino acid
<220> FEATURE:
<221> NAME/KEY: misc_feature
<222> LOCATION: (840)..(840)
<223> OTHER INFORMATION: Xaa can be any naturally occurring amino acid
<220> FEATURE:
<221> NAME/KEY: misc_feature
<222> LOCATION: (848)..(854)
<223> OTHER INFORMATION: Xaa can be any naturally occurring amino acid
<220> FEATURE:
<221> NAME/KEY: MISC_FEATURE
<222> LOCATION: (855)..(855)
<223> OTHER INFORMATION: The amino acid(s) can either be present or
      absent
<220> FEATURE:
<221> NAME/KEY: misc_feature
<222> LOCATION: (857)..(862)
<223> OTHER INFORMATION: Xaa can be any naturally occurring amino acid
<220> FEATURE:
<221> NAME/KEY: misc_feature
<222> LOCATION: (866)..(866)
<223> OTHER INFORMATION: Xaa can be any naturally occurring amino acid
<220> FEATURE:
<221> NAME/KEY: misc_feature
<222> LOCATION: (870)..(870)
<223> OTHER INFORMATION: Xaa can be any naturally occurring amino acid
<220> FEATURE:
<221> NAME/KEY: misc_feature
<222> LOCATION: (875)..(875)
<223> OTHER INFORMATION: Xaa can be any naturally occurring amino acid
<220> FEATURE:
<221> NAME/KEY: misc_feature
<222> LOCATION: (877)..(877)
<223> OTHER INFORMATION: Xaa can be any naturally occurring amino acid
<220> FEATURE:
<221> NAME/KEY: misc_feature
<222> LOCATION: (879)..(879)
<223> OTHER INFORMATION: Xaa can be any naturally occurring amino acid
<220> FEATURE:
<221> NAME/KEY: misc_feature
<222> LOCATION: (881)..(881)
<223> OTHER INFORMATION: Xaa can be any naturally occurring amino acid
```

```
<220> FEATURE:
<221> NAME/KEY: misc_feature
<222> LOCATION: (885)..(885)
<223> OTHER INFORMATION: Xaa can be any naturally occurring amino acid
<220> FEATURE:
<221> NAME/KEY: misc_feature
<222> LOCATION: (888)..(889)
<223> OTHER INFORMATION: Xaa can be any naturally occurring amino acid
<220> FEATURE:
<221> NAME/KEY: misc_feature
<222> LOCATION: (891)..(891)
<223> OTHER INFORMATION: Xaa can be any naturally occurring amino acid
<220> FEATURE:
<221> NAME/KEY: misc_feature
<222> LOCATION: (893)..(893)
<223> OTHER INFORMATION: Xaa can be any naturally occurring amino acid
<220> FEATURE:
<221> NAME/KEY: misc_feature
<222> LOCATION: (895)..(895)
<223> OTHER INFORMATION: Xaa can be any naturally occurring amino acid
<220> FEATURE:
<221> NAME/KEY: misc_feature
<222> LOCATION: (898)..(901)
<223> OTHER INFORMATION: Xaa can be any naturally occurring amino acid
<220> FEATURE:
<221> NAME/KEY: MISC_FEATURE
<222> LOCATION: (902)..(904)
<223> OTHER INFORMATION: The amino acid(s) can either be present or
      absent
<220> FEATURE:
<221> NAME/KEY: misc_feature
<222> LOCATION: (905)..(906)
<223> OTHER INFORMATION: Xaa can be any naturally occurring amino acid
<220> FEATURE:
<221> NAME/KEY: misc_feature
<222> LOCATION: (908)..(912)
<223> OTHER INFORMATION: Xaa can be any naturally occurring amino acid
<220> FEATURE:
<221> NAME/KEY: misc_feature
<222> LOCATION: (914)..(914)
<223> OTHER INFORMATION: Xaa can be any naturally occurring amino acid
<220> FEATURE:
<221> NAME/KEY: misc_feature
<222> LOCATION: (916)..(916)
<223> OTHER INFORMATION: Xaa can be any naturally occurring amino acid
<220> FEATURE:
<221> NAME/KEY: misc_feature
<222> LOCATION: (920)..(920)
<223> OTHER INFORMATION: Xaa can be any naturally occurring amino acid
<220> FEATURE:
<221> NAME/KEY: misc_feature
<222> LOCATION: (923)..(923)
<223> OTHER INFORMATION: Xaa can be any naturally occurring amino acid
<220> FEATURE:
<221> NAME/KEY: misc_feature
<222> LOCATION: (926)..(927)
<223> OTHER INFORMATION: Xaa can be any naturally occurring amino acid
<220> FEATURE:
<221> NAME/KEY: misc_feature
<222> LOCATION: (929)..(929)
<223> OTHER INFORMATION: Xaa can be any naturally occurring amino acid
<220> FEATURE:
<221> NAME/KEY: misc_feature
<222> LOCATION: (931)..(933)
<223> OTHER INFORMATION: Xaa can be any naturally occurring amino acid
<220> FEATURE:
<221> NAME/KEY: misc_feature
<222> LOCATION: (937)..(939)
<223> OTHER INFORMATION: Xaa can be any naturally occurring amino acid
<220> FEATURE:
<221> NAME/KEY: misc_feature
<222> LOCATION: (941)..(941)
<223> OTHER INFORMATION: Xaa can be any naturally occurring amino acid
<220> FEATURE:
<221> NAME/KEY: misc_feature
<222> LOCATION: (943)..(943)
<223> OTHER INFORMATION: Xaa can be any naturally occurring amino acid
<220> FEATURE:
<221> NAME/KEY: misc_feature
```

```
<222> LOCATION: (946)..(958)
<223> OTHER INFORMATION: Xaa can be any naturally occurring amino acid
<220> FEATURE:
<221> NAME/KEY: misc_feature
<222> LOCATION: (961)..(962)
<223> OTHER INFORMATION: Xaa can be any naturally occurring amino acid
<220> FEATURE:
<221> NAME/KEY: misc_feature
<222> LOCATION: (966)..(967)
<223> OTHER INFORMATION: Xaa can be any naturally occurring amino acid
<220> FEATURE:
<221> NAME/KEY: misc_feature
<222> LOCATION: (973)..(974)
<223> OTHER INFORMATION: Xaa can be any naturally occurring amino acid
<220> FEATURE:
<221> NAME/KEY: misc_feature
<222> LOCATION: (976)..(981)
<223> OTHER INFORMATION: Xaa can be any naturally occurring amino acid
<220> FEATURE:
<221> NAME/KEY: misc_feature
<222> LOCATION: (983)..(983)
<223> OTHER INFORMATION: Xaa can be any naturally occurring amino acid
<220> FEATURE:
<221> NAME/KEY: misc_feature
<222> LOCATION: (986)..(986)
<223> OTHER INFORMATION: Xaa can be any naturally occurring amino acid
<220> FEATURE:
<221> NAME/KEY: misc_feature
<222> LOCATION: (990)..(990)
<223> OTHER INFORMATION: Xaa can be any naturally occurring amino acid
<220> FEATURE:
<221> NAME/KEY: misc_feature
<222> LOCATION: (994)..(994)
<223> OTHER INFORMATION: Xaa can be any naturally occurring amino acid
<220> FEATURE:
<221> NAME/KEY: misc_feature
<222> LOCATION: (997)..(1001)
<223> OTHER INFORMATION: Xaa can be any naturally occurring amino acid
<220> FEATURE:
<221> NAME/KEY: misc_feature
<222> LOCATION: (1005)..(1005)
<223> OTHER INFORMATION: Xaa can be any naturally occurring amino acid
<220> FEATURE:
<221> NAME/KEY: misc_feature
<222> LOCATION: (1007)..(1007)
<223> OTHER INFORMATION: Xaa can be any naturally occurring amino acid
<220> FEATURE:
<221> NAME/KEY: misc_feature
<222> LOCATION: (1009)..(1009)
<223> OTHER INFORMATION: Xaa can be any naturally occurring amino acid
<220> FEATURE:
<221> NAME/KEY: MISC_FEATURE
<222> LOCATION: (1012)..(1012)
<223> OTHER INFORMATION: The amino acid(s) can either be present or
      absent
<220> FEATURE:
<221> NAME/KEY: misc_feature
<222> LOCATION: (1014)..(1015)
<223> OTHER INFORMATION: Xaa can be any naturally occurring amino acid
<220> FEATURE:
<221> NAME/KEY: misc_feature
<222> LOCATION: (1017)..(1017)
<223> OTHER INFORMATION: Xaa can be any naturally occurring amino acid
<220> FEATURE:
<221> NAME/KEY: misc_feature
<222> LOCATION: (1020)..(1021)
<223> OTHER INFORMATION: Xaa can be any naturally occurring amino acid
<220> FEATURE:
<221> NAME/KEY: misc_feature
<222> LOCATION: (1023)..(1023)
<223> OTHER INFORMATION: Xaa can be any naturally occurring amino acid
<220> FEATURE:
<221> NAME/KEY: misc_feature
<222> LOCATION: (1030)..(1030)
<223> OTHER INFORMATION: Xaa can be any naturally occurring amino acid
<220> FEATURE:
<221> NAME/KEY: misc_feature
<222> LOCATION: (1033)..(1033)
<223> OTHER INFORMATION: Xaa can be any naturally occurring amino acid
```

```
<220> FEATURE:
<221> NAME/KEY: misc_feature
<222> LOCATION: (1036)..(1037)
<223> OTHER INFORMATION: Xaa can be any naturally occurring amino acid
<220> FEATURE:
<221> NAME/KEY: misc_feature
<222> LOCATION: (1040)..(1040)
<223> OTHER INFORMATION: Xaa can be any naturally occurring amino acid
<220> FEATURE:
<221> NAME/KEY: misc_feature
<222> LOCATION: (1044)..(1044)
<223> OTHER INFORMATION: Xaa can be any naturally occurring amino acid
<220> FEATURE:
<221> NAME/KEY: misc_feature
<222> LOCATION: (1046)..(1046)
<223> OTHER INFORMATION: Xaa can be any naturally occurring amino acid
<220> FEATURE:
<221> NAME/KEY: misc_feature
<222> LOCATION: (1048)..(1048)
<223> OTHER INFORMATION: Xaa can be any naturally occurring amino acid
<220> FEATURE:
<221> NAME/KEY: misc_feature
<222> LOCATION: (1050)..(1054)
<223> OTHER INFORMATION: Xaa can be any naturally occurring amino acid
<220> FEATURE:
<221> NAME/KEY: misc_feature
<222> LOCATION: (1057)..(1061)
<223> OTHER INFORMATION: Xaa can be any naturally occurring amino acid
<220> FEATURE:
<221> NAME/KEY: misc_feature
<222> LOCATION: (1063)..(1067)
<223> OTHER INFORMATION: Xaa can be any naturally occurring amino acid
<220> FEATURE:
<221> NAME/KEY: misc_feature
<222> LOCATION: (1069)..(1069)
<223> OTHER INFORMATION: Xaa can be any naturally occurring amino acid
<220> FEATURE:
<221> NAME/KEY: misc_feature
<222> LOCATION: (1076)..(1078)
<223> OTHER INFORMATION: Xaa can be any naturally occurring amino acid
<220> FEATURE:
<221> NAME/KEY: misc_feature
<222> LOCATION: (1080)..(1080)
<223> OTHER INFORMATION: Xaa can be any naturally occurring amino acid
<220> FEATURE:
<221> NAME/KEY: misc_feature
<222> LOCATION: (1082)..(1082)
<223> OTHER INFORMATION: Xaa can be any naturally occurring amino acid
<220> FEATURE:
<221> NAME/KEY: misc_feature
<222> LOCATION: (1084)..(1086)
<223> OTHER INFORMATION: Xaa can be any naturally occurring amino acid
<220> FEATURE:
<221> NAME/KEY: misc_feature
<222> LOCATION: (1088)..(1088)
<223> OTHER INFORMATION: Xaa can be any naturally occurring amino acid
<220> FEATURE:
<221> NAME/KEY: misc_feature
<222> LOCATION: (1092)..(1099)
<223> OTHER INFORMATION: Xaa can be any naturally occurring amino acid
<220> FEATURE:
<221> NAME/KEY: MISC_FEATURE
<222> LOCATION: (1101)..(1101)
<223> OTHER INFORMATION: The amino acid(s) can either be present or
      absent
<220> FEATURE:
<221> NAME/KEY: misc_feature
<222> LOCATION: (1103)..(1105)
<223> OTHER INFORMATION: Xaa can be any naturally occurring amino acid
<220> FEATURE:
<221> NAME/KEY: misc_feature
<222> LOCATION: (1107)..(1108)
<223> OTHER INFORMATION: Xaa can be any naturally occurring amino acid
<220> FEATURE:
<221> NAME/KEY: misc_feature
<222> LOCATION: (1110)..(1110)
<223> OTHER INFORMATION: Xaa can be any naturally occurring amino acid
<220> FEATURE:
<221> NAME/KEY: misc_feature
```

```
<222> LOCATION: (1112)..(1112)
<223> OTHER INFORMATION: Xaa can be any naturally occurring amino acid
<220> FEATURE:
<221> NAME/KEY: misc_feature
<222> LOCATION: (1114)..(1115)
<223> OTHER INFORMATION: Xaa can be any naturally occurring amino acid
<220> FEATURE:
<221> NAME/KEY: MISC_FEATURE
<222> LOCATION: (1123)..(1133)
<223> OTHER INFORMATION: The amino acid(s) can either be present or
      absent
<220> FEATURE:
<221> NAME/KEY: misc_feature
<222> LOCATION: (1135)..(1138)
<223> OTHER INFORMATION: Xaa can be any naturally occurring amino acid
<220> FEATURE:
<221> NAME/KEY: misc_feature
<222> LOCATION: (1142)..(1144)
<223> OTHER INFORMATION: Xaa can be any naturally occurring amino acid
<220> FEATURE:
<221> NAME/KEY: misc_feature
<222> LOCATION: (1146)..(1146)
<223> OTHER INFORMATION: Xaa can be any naturally occurring amino acid
<220> FEATURE:
<221> NAME/KEY: misc_feature
<222> LOCATION: (1149)..(1149)
<223> OTHER INFORMATION: Xaa can be any naturally occurring amino acid
<220> FEATURE:
<221> NAME/KEY: misc_feature
<222> LOCATION: (1151)..(1151)
<223> OTHER INFORMATION: Xaa can be any naturally occurring amino acid
<220> FEATURE:
<221> NAME/KEY: misc_feature
<222> LOCATION: (1153)..(1156)
<223> OTHER INFORMATION: Xaa can be any naturally occurring amino acid
<220> FEATURE:
<221> NAME/KEY: misc_feature
<222> LOCATION: (1158)..(1160)
<223> OTHER INFORMATION: Xaa can be any naturally occurring amino acid
<220> FEATURE:
<221> NAME/KEY: misc_feature
<222> LOCATION: (1162)..(1166)
<223> OTHER INFORMATION: Xaa can be any naturally occurring amino acid
<220> FEATURE:
<221> NAME/KEY: misc_feature
<222> LOCATION: (1170)..(1171)
<223> OTHER INFORMATION: Xaa can be any naturally occurring amino acid
<220> FEATURE:
<221> NAME/KEY: misc_feature
<222> LOCATION: (1173)..(1174)
<223> OTHER INFORMATION: Xaa can be any naturally occurring amino acid
<220> FEATURE:
<221> NAME/KEY: misc_feature
<222> LOCATION: (1176)..(1177)
<223> OTHER INFORMATION: Xaa can be any naturally occurring amino acid
<220> FEATURE:
<221> NAME/KEY: misc_feature
<222> LOCATION: (1179)..(1179)
<223> OTHER INFORMATION: Xaa can be any naturally occurring amino acid
<220> FEATURE:
<221> NAME/KEY: misc_feature
<222> LOCATION: (1181)..(1182)
<223> OTHER INFORMATION: Xaa can be any naturally occurring amino acid
<220> FEATURE:
<221> NAME/KEY: misc_feature
<222> LOCATION: (1184)..(1184)
<223> OTHER INFORMATION: Xaa can be any naturally occurring amino acid
<220> FEATURE:
<221> NAME/KEY: misc_feature
<222> LOCATION: (1186)..(1191)
<223> OTHER INFORMATION: Xaa can be any naturally occurring amino acid
<220> FEATURE:
<221> NAME/KEY: misc_feature
<222> LOCATION: (1193)..(1196)
<223> OTHER INFORMATION: Xaa can be any naturally occurring amino acid
<220> FEATURE:
<221> NAME/KEY: misc_feature
<222> LOCATION: (1198)..(1203)
<223> OTHER INFORMATION: Xaa can be any naturally occurring amino acid
```

```
-continued

<220> FEATURE:
<221> NAME/KEY: misc_feature
<222> LOCATION: (1205)..(1205)
<223> OTHER INFORMATION: Xaa can be any naturally occurring amino acid
<220> FEATURE:
<221> NAME/KEY: misc_feature
<222> LOCATION: (1207)..(1210)
<223> OTHER INFORMATION: Xaa can be any naturally occurring amino acid
<220> FEATURE:
<221> NAME/KEY: MISC_FEATURE
<222> LOCATION: (1212)..(1213)
<223> OTHER INFORMATION: The amino acid(s) can either be present or
      absent
<220> FEATURE:
<221> NAME/KEY: misc_feature
<222> LOCATION: (1214)..(1218)
<223> OTHER INFORMATION: Xaa can be any naturally occurring amino acid
<220> FEATURE:
<221> NAME/KEY: misc_feature
<222> LOCATION: (1221)..(1222)
<223> OTHER INFORMATION: Xaa can be any naturally occurring amino acid
<220> FEATURE:
<221> NAME/KEY: misc_feature
<222> LOCATION: (1224)..(1253)
<223> OTHER INFORMATION: Xaa can be any naturally occurring amino acid
<220> FEATURE:
<221> NAME/KEY: misc_feature
<222> LOCATION: (1255)..(1259)
<223> OTHER INFORMATION: Xaa can be any naturally occurring amino acid
<220> FEATURE:
<221> NAME/KEY: MISC_FEATURE
<222> LOCATION: (1261)..(1378)
<223> OTHER INFORMATION: The amino acid(s) can either be present or
      absent

<400> SEQUENCE: 10

Met Ala Pro Gly His Gly Ser Gly Thr Asp Gly Arg Thr Leu Ala Arg
1               5                   10                  15

Arg Pro Arg Gly Ser Ser Arg Arg Pro Ser Val Leu Arg Ala Ala Gly
            20                  25                  30

Asn Gln Leu Val Thr Arg Asp Gly Arg Pro Arg His Thr Gly Phe Leu
        35                  40                  45

Gln Cys Gly Pro Thr Arg Pro Arg Arg Ala Thr Ser Gln Pro Xaa Xaa
    50                  55                  60

Xaa Xaa Xaa Xaa Gly Trp Xaa Xaa Xaa Xaa Xaa Xaa Xaa Xaa Xaa Xaa
65                  70                  75                  80

Ala Arg Xaa Xaa Xaa Xaa Xaa Xaa Xaa Xaa Xaa Arg Xaa Xaa Xaa
                85                  90                  95

Xaa Xaa Arg Xaa Ser Xaa Arg Xaa Arg Xaa Xaa Ala Xaa Xaa Xaa Xaa
            100                 105                 110

Leu Gly Leu Xaa Xaa Xaa Xaa Xaa Leu Gly Ala Xaa Pro Leu Xaa Ala
            115                 120                 125

Xaa Ala Xaa Xaa Xaa Xaa Xaa Val Xaa Ala Xaa Gly Asp Asp Trp Xaa
            130                 135                 140

Xaa Xaa Xaa Xaa Xaa Gly Gly Xaa Xaa Val Thr Xaa Xaa Leu Xaa Glu
145                 150                 155                 160

Xaa Leu Pro Xaa Val Ser Asp Ala Pro Thr Leu Xaa Xaa Asp Gly Xaa
                165                 170                 175

Xaa Xaa Gly Xaa Ala Thr Glu Ser Ala Asp Gly Xaa Xaa Leu Xaa Xaa
            180                 185                 190

Xaa Thr Xaa Asp Xaa Asp Val Xaa Ser Ala Xaa Xaa Val Glu Xaa Gly
            195                 200                 205

Trp Ala Ser Ser Xaa Gly Xaa Xaa Ala Xaa Xaa Xaa Xaa Xaa Xaa Xaa
            210                 215                 220
```

-continued

```
Xaa Ser Thr Glu Xaa Pro Xaa Xaa Xaa Leu Leu Xaa Xaa Xaa Xaa Arg
225                 230                 235                 240

Leu Xaa Xaa Xaa Ala Xaa Thr Xaa Asp Xaa Gly Ser Xaa Pro Gly Xaa
            245                 250                 255

Xaa Ala Xaa Xaa Glu Xaa Xaa Tyr Asp Phe Gly Asp Xaa Ala Val Xaa
        260                 265                 270

Leu Ala Xaa Ile Gly Gly Ile Arg Gly Glu Met Thr Gly Xaa Xaa Tyr
        275                 280                 285

Leu Xaa Xaa Xaa Gly Xaa Xaa Pro Thr Val Ile Leu Leu His Gly
    290                 295                 300

Arg His Ser Ser Cys Thr Val Pro Thr Gly Xaa Xaa Xaa Xaa Asn
305             310              315                  320

Pro Xaa Arg Trp Pro Cys Xaa Xaa Xaa Gln Val Asn Xaa Xaa Ser Tyr
            325                 330                 335

Xaa Gly Tyr Glu Xaa Thr Ala Xaa Xaa Leu Ala Xaa His Gly Tyr Xaa
            340                 345                 350

Val Xaa Ser Ile Xaa Ala Asn Ala Xaa Asn Xaa Asn Asp Asn Gln Leu
        355                 360                 365

Ala Xaa Asp Tyr Gly Ala Xaa Ala Arg Gly Gln Leu Xaa Leu Asp Thr
    370                 375                 380

Leu Xaa Met Leu Xaa Lys Ala Xaa Ala Gly Glu Pro Val Xaa Xaa Xaa
385                 390                 395                 400

Asp Xaa Xaa Trp Xaa Asp Xaa Xaa Xaa Xaa Xaa Xaa Xaa Xaa Xaa Xaa
            405                 410                 415

Xaa Xaa Xaa Xaa Ala Xaa Xaa Leu Xaa Xaa Xaa Xaa Xaa Xaa Xaa Xaa
            420                 425                 430

Xaa Xaa Xaa Xaa Xaa Xaa Thr Xaa Ala Xaa Leu Xaa Gly Xaa Phe Asp
            435                 440                 445

Leu Asp Xaa Val Gly Xaa Met Gly His Ser Arg Gly Gly Glu Gly Xaa
    450                 455                 460

Xaa Ser Ala Val Xaa Leu Asn Gln Xaa Leu Ala Xaa Pro Phe Gly Ile
465                 470                 475                 480

Xaa Xaa Val Leu Pro Leu Ala Pro Val Asp Phe Gly Arg Xaa Thr Xaa
            485                 490                 495

Ala Asp Thr Xaa Met Xaa Val Xaa Leu Pro Tyr Cys Asp Gly Asp Val
            500                 505                 510

Ser Asn Gln Gln Gly Gln His Xaa Xaa Asp Asp Ser Arg Xaa Ala Xaa
            515                 520                 525

Xaa Asp Asp Xaa Xaa Arg Ser Xaa Xaa Trp Xaa Met Gly Ala Xaa His
    530                 535                 540

Asn Phe Phe Asn Xaa Val Trp Thr Pro Gly Xaa Tyr Pro Xaa Xaa Thr
545                 550                 555                 560

Ser Asp Asp Trp Xaa Xaa Xaa Xaa Xaa Xaa Xaa Cys Xaa Pro Leu
            565                 570                 575

Xaa Xaa Xaa Xaa Xaa Arg Leu Xaa Xaa Xaa Gln Tyr Xaa Val Gly
            580                 585                 590

Val Xaa Xaa Met Xaa Xaa Xaa Phe Arg Leu Thr Xaa Gly Gly Glu Xaa
        595                 600                 605

Gln Phe Xaa Pro Xaa Phe Asp Gly Ser Xaa Xaa Pro Thr Xaa Thr Xaa
        610                 615                 620

Xaa Xaa Xaa Ala Xaa Xaa Xaa Xaa Xaa Ala Xaa Xaa Pro Ala Xaa Xaa
625                 630                 635                 640

Xaa Xaa Xaa Ile Xaa Xaa Phe Xaa Xaa Xaa Xaa Xaa Xaa Xaa Arg Xaa
```

645                 650                 655
Xaa Gly Xaa Ala Xaa Xaa Xaa Val Cys Ala Xaa Ala Xaa Xaa Xaa Thr
                660                 665                 670

Xaa Xaa Xaa Xaa Xaa Pro Xaa Xaa Thr Xaa Xaa Xaa Xaa Arg Xaa
            675                 680                 685

Thr Xaa Xaa Xaa Pro His Trp Thr Pro Xaa Xaa Phe Xaa Xaa Asn Val
690                 695                 700

Pro Ala Xaa Pro Xaa Xaa Arg Xaa Leu Trp Thr Gly Ser Thr Ser Xaa
705                 710                 715                 720

Xaa Xaa Xaa Xaa Xaa Xaa Gly Xaa Xaa Xaa Val Xaa Val Pro Xaa Xaa
                725                 730                 735

Xaa Arg Asp Xaa Ser Xaa Xaa Xaa Xaa Leu Thr Xaa Lys Xaa Ala Pro
                740                 745                 750

Asp Xaa Ser Val Xaa Xaa Gly Thr Asp Xaa Thr Xaa Thr Val Xaa Asp
            755                 760                 765

Gly Xaa Gly Xaa Xaa Xaa Ser Xaa Xaa Xaa Ser Ala Xaa Asn Xaa Xaa
770                 775                 780

Ala Val Xaa Arg Xaa Pro Xaa Xaa Xaa Xaa Thr Leu Asn Lys Ile
785                 790                 795                 800

Val Leu Gln Gln Xaa Xaa Val Pro Xaa Ser Xaa Xaa Xaa Gly Ser Ile
                805                 810                 815

Asp Xaa Xaa Asp Val Arg Glu Val Arg Phe Ala Xaa Xaa Xaa Gly Ala
            820                 825                 830

Asp Gly Thr Xaa Xaa Gly Gly Xaa Tyr Leu Ser Asp Leu Ala Phe Xaa
            835                 840                 845

Xaa Xaa Xaa Xaa Xaa Xaa Val Ala Xaa Xaa Xaa Xaa Xaa Xaa Thr Val
850                 855                 860

Asn Xaa Ala Ser Thr Xaa Val Glu Glu Gly Xaa Ser Xaa Asp Xaa Ala
865                 870                 875                 880

Xaa Val Ala Val Xaa Leu Asp Xaa Xaa Ala Xaa Arg Xaa Val Xaa Ala
            885                 890                 895

Trp Xaa Xaa Xaa Xaa Gly Ser Thr Xaa Xaa Ser Xaa Xaa Xaa Xaa Xaa
                900                 905                 910

Ala Xaa Gln Xaa Val Thr Phe Xaa Pro Gly Xaa Thr Cys Xaa Xaa Val
            915                 920                 925

Xaa Val Xaa Xaa Xaa Gly Asn Thr Xaa Xaa Xaa Ala Xaa Ala Xaa Thr
        930                 935                 940

Ala Xaa Xaa Xaa Xaa Xaa Xaa Xaa Xaa Xaa Xaa Xaa Xaa Xaa Gly Ala
945                 950                 955                 960

Xaa Xaa Phe Gly Thr Xaa Xaa Val Arg Glu Asp Asp Xaa Xaa Thr Xaa
            965                 970                 975

Xaa Xaa Xaa Xaa Xaa Pro Xaa Val Gly Xaa Gln Gly Asp Xaa Cys Ala
            980                 985                 990

Glu Xaa Ala Ala Xaa Xaa Xaa Xaa Xaa Glu Leu Thr Xaa Ser Xaa Asp
        995                 1000                1005

Xaa Val Ala Pro Gly Xaa Xaa Val Xaa Leu Thr Xaa Xaa Gly Xaa
    1010                1015                1020

Arg Val Gly Glu Ser Val Xaa Phe Thr Xaa Gly Asp Xaa Xaa Leu
    1025                1030                1035

Gly Xaa Val Leu Ala Xaa Ala Xaa Gly Xaa Ala Xaa Xaa Xaa Xaa
    1040                1045                1050

Xaa Val Pro Xaa Xaa Xaa Xaa Gly Xaa Xaa Xaa Xaa Xaa Ala
    1055                1060                1065

Xaa Gly Ala Gly Ser Ala Arg Xaa Xaa Xaa Ala Xaa Val Xaa Val
    1070                1075                1080

Xaa Xaa Xaa Thr Xaa Thr Thr Leu Xaa Xaa Xaa Xaa Xaa Xaa
    1085                1090                1095

Xaa Val Glu Gly Xaa Xaa Xaa Thr Xaa Xaa Ala Xaa Val Xaa Gly
    1100                1105                1110

Xaa Xaa Thr Ala Gly Thr Val Thr Phe Val Ser Gly Ser Gly Ser
    1115                1120                1125

Gly Ala Ala Asp Ala Ala Xaa Xaa Xaa Xaa Val Leu Gly Xaa Xaa
    1130                1135                1140

Xaa Val Xaa Asp Gly Xaa Ala Xaa Leu Xaa Xaa Xaa Xaa Gly Xaa
    1145                1150                1155

Xaa Xaa Gly Xaa Xaa Xaa Xaa Xaa Ala Ala Phe Xaa Xaa Thr Xaa
    1160                1165                1170

Xaa Ala Xaa Xaa Ser Xaa Ser Xaa Xaa Val Xaa Phe Xaa Xaa Xaa
    1175                1180                1185

Xaa Xaa Xaa Thr Xaa Xaa Xaa Xaa Val Xaa Xaa Xaa Xaa Xaa Xaa
    1190                1195                1200

Thr Xaa Gly Xaa Xaa Xaa Xaa Gly Arg Ile Xaa Xaa Xaa Xaa Xaa
    1205                1210                1215

Asp Gly Xaa Xaa Ala Xaa Xaa Xaa Xaa Xaa Xaa Xaa Xaa Xaa Xaa
    1220                1225                1230

Xaa Xaa Xaa Xaa Xaa Xaa Xaa Xaa Xaa Xaa Xaa Xaa Xaa Xaa Xaa
    1235                1240                1245

Xaa Xaa Xaa Xaa Thr Xaa Xaa Xaa Xaa Xaa Ser Tyr Ala Gly
    1250                1255                1260

Ser Arg Thr Leu Asp Thr Ser Ser Ala Arg Ala Ser Leu Thr Val
    1265                1270                1275

Leu Lys Ala Ala Pro Lys Val Thr Leu Ser Ala Pro Ala Thr Ala
    1280                1285                1290

Arg Lys Gly Ala Thr Val Thr Val Thr Val Lys Val Val Gly Val
    1295                1300                1305

Lys Gly Gly Val Arg Pro Thr Gly Lys Ala Val Val Lys Leu Gly
    1310                1315                1320

Gly Lys Ala Val Lys Thr Val Ser Val Pro Ser Ser Gly Val Val
    1325                1330                1335

Lys Val Lys Val Arg Leu Ala Ser Ala Gly Thr Ala Lys Val Thr
    1340                1345                1350

Ala Ala Tyr Gln Gly Ser Ala Tyr Tyr Thr Ala Ala Ser Ala Ala
    1355                1360                1365

Ala Lys Val Lys Val Lys Val Val Thr Lys
    1370                1375

<210> SEQ ID NO 11
<211> LENGTH: 1378
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(46)
<223> OTHER INFORMATION: The amino acid(s) can either be present or
      absent
<220> FEATURE:
<221> NAME/KEY: MISC_FEATURE
<222> LOCATION: (47)..(95)

```
<223> OTHER INFORMATION: The amino acid(s) can either be present or
      absent.  Xaa can be any naturally occurring amino acid
<220> FEATURE:
<221> NAME/KEY: misc_feature
<222> LOCATION: (96)..(98)
<223> OTHER INFORMATION: Xaa can be any naturally occurring amino acid
<220> FEATURE:
<221> NAME/KEY: misc_feature
<222> LOCATION: (100)..(106)
<223> OTHER INFORMATION: Xaa can be any naturally occurring amino acid
<220> FEATURE:
<221> NAME/KEY: misc_feature
<222> LOCATION: (108)..(114)
<223> OTHER INFORMATION: Xaa can be any naturally occurring amino acid
<220> FEATURE:
<221> NAME/KEY: MISC_FEATURE
<222> LOCATION: (116)..(119)
<223> OTHER INFORMATION: The amino acid(s) can either be present or
      absent
<220> FEATURE:
<221> NAME/KEY: misc_feature
<222> LOCATION: (121)..(123)
<223> OTHER INFORMATION: Xaa can be any naturally occurring amino acid
<220> FEATURE:
<221> NAME/KEY: misc_feature
<222> LOCATION: (125)..(131)
<223> OTHER INFORMATION: Xaa can be any naturally occurring amino acid
<220> FEATURE:
<221> NAME/KEY: MISC_FEATURE
<222> LOCATION: (132)..(132)
<223> OTHER INFORMATION: The amino acid(s) can either be present or
      absent.  Xaa can be any naturally occurring amino acid
<220> FEATURE:
<221> NAME/KEY: misc_feature
<222> LOCATION: (133)..(136)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (143)..(148)
<223> OTHER INFORMATION: Xaa can be any naturally occurring amino acid
<220> FEATURE:
<221> NAME/KEY: misc_feature
<222> LOCATION: (151)..(152)
<223> OTHER INFORMATION: Xaa can be any naturally occurring amino acid
<220> FEATURE:
<221> NAME/KEY: misc_feature
<222> LOCATION: (155)..(156)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (165)..(165)
<223> OTHER INFORMATION: Xaa can be any naturally occurring amino acid
<220> FEATURE:
<221> NAME/KEY: misc_feature
<222> LOCATION: (171)..(172)
<223> OTHER INFORMATION: Xaa can be any naturally occurring amino acid
<220> FEATURE:
<221> NAME/KEY: misc_feature
<222> LOCATION: (175)..(177)
```

```
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (187)..(188)
<223> OTHER INFORMATION: Xaa can be any naturally occurring amino acid
<220> FEATURE:
<221> NAME/KEY: misc_feature
<222> LOCATION: (190)..(192)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: MISC_FEATURE
<222> LOCATION: (195)..(195)
<223> OTHER INFORMATION: The amino acid(s) can either be present or
      absent
<220> FEATURE:
<221> NAME/KEY: misc_feature
<222> LOCATION: (196)..(197)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
<222> LOCATION: (202)..(203)
<223> OTHER INFORMATION: Xaa can be any naturally occurring amino acid
<220> FEATURE:
<221> NAME/KEY: misc_feature
<222> LOCATION: (205)..(206)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (211)..(220)
<223> OTHER INFORMATION: Xaa can be any naturally occurring amino acid
<220> FEATURE:
<221> NAME/KEY: MISC_FEATURE
<222> LOCATION: (221)..(221)
<223> OTHER INFORMATION: The amino acid(s) can either be present or
      absent.  Xaa can be any naturally occurring amino acid
<220> FEATURE:
<221> NAME/KEY: misc_feature
<222> LOCATION: (222)..(236)
<223> OTHER INFORMATION: Xaa can be any naturally occurring amino acid
<220> FEATURE:
<221> NAME/KEY: misc_feature
<222> LOCATION: (238)..(240)
<223> OTHER INFORMATION: Xaa can be any naturally occurring amino acid
<220> FEATURE:
<221> NAME/KEY: MISC_FEATURE
<222> LOCATION: (242)..(243)
<223> OTHER INFORMATION: The amino acid(s) can either be present or
      absent.  Xaa can be any naturally occurring amino acid
<220> FEATURE:
<221> NAME/KEY: misc_feature
<222> LOCATION: (244)..(252)
<223> OTHER INFORMATION: Xaa can be any naturally occurring amino acid
<220> FEATURE:
<221> NAME/KEY: misc_feature
<222> LOCATION: (254)..(258)
<223> OTHER INFORMATION: Xaa can be any naturally occurring amino acid
<220> FEATURE:
<221> NAME/KEY: misc_feature
<222> LOCATION: (260)..(261)
<223> OTHER INFORMATION: Xaa can be any naturally occurring amino acid
<220> FEATURE:
<221> NAME/KEY: misc_feature
<222> LOCATION: (267)..(267)
```

```
<223> OTHER INFORMATION: Xaa can be any naturally occurring amino acid
<220> FEATURE:
<221> NAME/KEY: misc_feature
<222> LOCATION: (270)..(270)
<223> OTHER INFORMATION: Xaa can be any naturally occurring amino acid
<220> FEATURE:
<221> NAME/KEY: misc_feature
<222> LOCATION: (273)..(273)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (284)..(285)
<223> OTHER INFORMATION: Xaa can be any naturally occurring amino acid
<220> FEATURE:
<221> NAME/KEY: misc_feature
<222> LOCATION: (288)..(291)
<223> OTHER INFORMATION: Xaa can be any naturally occurring amino acid
<220> FEATURE:
<221> NAME/KEY: misc_feature
<222> LOCATION: (293)..(294)
<223> OTHER INFORMATION: Xaa can be any naturally occurring amino acid
<220> FEATURE:
<221> NAME/KEY: misc_feature
<222> LOCATION: (298)..(298)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: MISC_FEATURE
<222> LOCATION: (308)..(312)
<223> OTHER INFORMATION: The amino acid(s) can either be present or
      absent
<220> FEATURE:
<221> NAME/KEY: misc_feature
<222> LOCATION: (313)..(317)
<223> OTHER INFORMATION: Xaa can be any naturally occurring amino acid
<220> FEATURE:
<221> NAME/KEY: misc_feature
<222> LOCATION: (320)..(320)
<223> OTHER INFORMATION: Xaa can be any naturally occurring amino acid
<220> FEATURE:
<221> NAME/KEY: misc_feature
<222> LOCATION: (325)..(327)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (331)..(332)
<223> OTHER INFORMATION: Xaa can be any naturally occurring amino acid
<220> FEATURE:
<221> NAME/KEY: misc_feature
<222> LOCATION: (335)..(335)
<223> OTHER INFORMATION: Xaa can be any naturally occurring amino acid
<220> FEATURE:
<221> NAME/KEY: misc_feature
<222> LOCATION: (339)..(339)
<223> OTHER INFORMATION: Xaa can be any naturally occurring amino acid
<220> FEATURE:
<221> NAME/KEY: misc_feature
<222> LOCATION: (341)..(343)
<223> OTHER INFORMATION: Xaa can be any naturally occurring amino acid
<220> FEATURE:
<221> NAME/KEY: misc_feature
<222> LOCATION: (346)..(347)
<223> OTHER INFORMATION: Xaa can be any naturally occurring amino acid
<220> FEATURE:
<221> NAME/KEY: misc_feature
<222> LOCATION: (350)..(350)
<223> OTHER INFORMATION: Xaa can be any naturally occurring amino acid
<220> FEATURE:
```

```
<221> NAME/KEY: misc_feature
<222> LOCATION: (352)..(352)
<223> OTHER INFORMATION: Xaa can be any naturally occurring amino acid
<220> FEATURE:
<221> NAME/KEY: misc_feature
<222> LOCATION: (355)..(355)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (361)..(361)
<223> OTHER INFORMATION: Xaa can be any naturally occurring amino acid
<220> FEATURE:
<221> NAME/KEY: misc_feature
<222> LOCATION: (368)..(368)
<223> OTHER INFORMATION: Xaa can be any naturally occurring amino acid
<220> FEATURE:
<221> NAME/KEY: misc_feature
<222> LOCATION: (373)..(373)
<223> OTHER INFORMATION: Xaa can be any naturally occurring amino acid
<220> FEATURE:
<221> NAME/KEY: misc_feature
<222> LOCATION: (377)..(377)
<223> OTHER INFORMATION: Xaa can be any naturally occurring amino acid
<220> FEATURE:
<221> NAME/KEY: misc_feature
<222> LOCATION: (379)..(379)
<223> OTHER INFORMATION: Xaa can be any naturally occurring amino acid
<220> FEATURE:
<221> NAME/KEY: misc_feature
<222> LOCATION: (384)..(384)
<223> OTHER INFORMATION: Xaa can be any naturally occurring amino acid
<220> FEATURE:
<221> NAME/KEY: misc_feature
<222> LOCATION: (387)..(388)
<223> OTHER INFORMATION: Xaa can be any naturally occurring amino acid
<220> FEATURE:
<221> NAME/KEY: misc_feature
<222> LOCATION: (390)..(390)
<223> OTHER INFORMATION: Xaa can be any naturally occurring amino acid
<220> FEATURE:
<221> NAME/KEY: misc_feature
<222> LOCATION: (393)..(394)
<223> OTHER INFORMATION: Xaa can be any naturally occurring amino acid
<220> FEATURE:
<221> NAME/KEY: misc_feature
<222> LOCATION: (396)..(398)
<223> OTHER INFORMATION: Xaa can be any naturally occurring amino acid
<220> FEATURE:
<221> NAME/KEY: misc_feature
<222> LOCATION: (400)..(401)
<223> OTHER INFORMATION: Xaa can be any naturally occurring amino acid
<220> FEATURE:
<221> NAME/KEY: MISC_FEATURE
<222> LOCATION: (402)..(402)
<223> OTHER INFORMATION: The amino acid(s) can either be present or
      absent.  Xaa can be any naturally occurring amino acid
<220> FEATURE:
<221> NAME/KEY: misc_feature
<222> LOCATION: (403)..(418)
<223> OTHER INFORMATION: Xaa can be any naturally occurring amino acid
<220> FEATURE:
<221> NAME/KEY: misc_feature
<222> LOCATION: (420)..(436)
<223> OTHER INFORMATION: Xaa can be any naturally occurring amino acid
<220> FEATURE:
<221> NAME/KEY: misc_feature
<222> LOCATION: (438)..(438)
<223> OTHER INFORMATION: Xaa can be any naturally occurring amino acid
<220> FEATURE:
<221> NAME/KEY: misc_feature
<222> LOCATION: (440)..(440)
<223> OTHER INFORMATION: Xaa can be any naturally occurring amino acid
<220> FEATURE:
<221> NAME/KEY: misc_feature
<222> LOCATION: (442)..(442)
```

```
<223> OTHER INFORMATION: Xaa can be any naturally occurring amino acid
<220> FEATURE:
<221> NAME/KEY: misc_feature
<222> LOCATION: (444)..(444)
<223> OTHER INFORMATION: Xaa can be any naturally occurring amino acid
<220> FEATURE:
<221> NAME/KEY: misc_feature
<222> LOCATION: (448)..(449)
<223> OTHER INFORMATION: Xaa can be any naturally occurring amino acid
<220> FEATURE:
<221> NAME/KEY: misc_feature
<222> LOCATION: (452)..(452)
<223> OTHER INFORMATION: Xaa can be any naturally occurring amino acid
<220> FEATURE:
<221> NAME/KEY: misc_feature
<222> LOCATION: (462)..(463)
<223> OTHER INFORMATION: Xaa can be any naturally occurring amino acid
<220> FEATURE:
<221> NAME/KEY: misc_feature
<222> LOCATION: (466)..(467)
<223> OTHER INFORMATION: Xaa can be any naturally occurring amino acid
<220> FEATURE:
<221> NAME/KEY: misc_feature
<222> LOCATION: (471)..(471)
<223> OTHER INFORMATION: Xaa can be any naturally occurring amino acid
<220> FEATURE:
<221> NAME/KEY: misc_feature
<222> LOCATION: (474)..(474)
<223> OTHER INFORMATION: Xaa can be any naturally occurring amino acid
<220> FEATURE:
<221> NAME/KEY: misc_feature
<222> LOCATION: (476)..(476)
<223> OTHER INFORMATION: Xaa can be any naturally occurring amino acid
<220> FEATURE:
<221> NAME/KEY: misc_feature
<222> LOCATION: (479)..(480)
<223> OTHER INFORMATION: Xaa can be any naturally occurring amino acid
<220> FEATURE:
<221> NAME/KEY: misc_feature
<222> LOCATION: (492)..(492)
<223> OTHER INFORMATION: Xaa can be any naturally occurring amino acid
<220> FEATURE:
<221> NAME/KEY: misc_feature
<222> LOCATION: (494)..(495)
<223> OTHER INFORMATION: Xaa can be any naturally occurring amino acid
<220> FEATURE:
<221> NAME/KEY: misc_feature
<222> LOCATION: (497)..(500)
<223> OTHER INFORMATION: Xaa can be any naturally occurring amino acid
<220> FEATURE:
<221> NAME/KEY: misc_feature
<222> LOCATION: (502)..(502)
<223> OTHER INFORMATION: Xaa can be any naturally occurring amino acid
<220> FEATURE:
<221> NAME/KEY: misc_feature
<222> LOCATION: (518)..(519)
<223> OTHER INFORMATION: Xaa can be any naturally occurring amino acid
<220> FEATURE:
<221> NAME/KEY: misc_feature
<222> LOCATION: (524)..(524)
<223> OTHER INFORMATION: Xaa can be any naturally occurring amino acid
<220> FEATURE:
<221> NAME/KEY: misc_feature
<222> LOCATION: (526)..(527)
<223> OTHER INFORMATION: Xaa can be any naturally occurring amino acid
<220> FEATURE:
<221> NAME/KEY: misc_feature
<222> LOCATION: (530)..(531)
<223> OTHER INFORMATION: Xaa can be any naturally occurring amino acid
<220> FEATURE:
<221> NAME/KEY: misc_feature
<222> LOCATION: (534)..(535)
<223> OTHER INFORMATION: Xaa can be any naturally occurring amino acid
<220> FEATURE:
<221> NAME/KEY: misc_feature
<222> LOCATION: (537)..(537)
<223> OTHER INFORMATION: Xaa can be any naturally occurring amino acid
<220> FEATURE:
<221> NAME/KEY: misc_feature
```

```
<222> LOCATION: (541)..(541)
<223> OTHER INFORMATION: Xaa can be any naturally occurring amino acid
<220> FEATURE:
<221> NAME/KEY: misc_feature
<222> LOCATION: (547)..(547)
<223> OTHER INFORMATION: Xaa can be any naturally occurring amino acid
<220> FEATURE:
<221> NAME/KEY: misc_feature
<222> LOCATION: (553)..(553)
<223> OTHER INFORMATION: Xaa can be any naturally occurring amino acid
<220> FEATURE:
<221> NAME/KEY: misc_feature
<222> LOCATION: (556)..(557)
<223> OTHER INFORMATION: Xaa can be any naturally occurring amino acid
<220> FEATURE:
<221> NAME/KEY: misc_feature
<222> LOCATION: (559)..(559)
<223> OTHER INFORMATION: Xaa can be any naturally occurring amino acid
<220> FEATURE:
<221> NAME/KEY: misc_feature
<222> LOCATION: (563)..(570)
<223> OTHER INFORMATION: Xaa can be any naturally occurring amino acid
<220> FEATURE:
<221> NAME/KEY: misc_feature
<222> LOCATION: (572)..(572)
<223> OTHER INFORMATION: Xaa can be any naturally occurring amino acid
<220> FEATURE:
<221> NAME/KEY: MISC_FEATURE
<222> LOCATION: (573)..(574)
<223> OTHER INFORMATION: The amino acid(s) can either be present or
      absent
<220> FEATURE:
<221> NAME/KEY: misc_feature
<222> LOCATION: (575)..(579)
<223> OTHER INFORMATION: Xaa can be any naturally occurring amino acid
<220> FEATURE:
<221> NAME/KEY: misc_feature
<222> LOCATION: (581)..(585)
<223> OTHER INFORMATION: Xaa can be any naturally occurring amino acid
<220> FEATURE:
<221> NAME/KEY: misc_feature
<222> LOCATION: (588)..(588)
<223> OTHER INFORMATION: Xaa can be any naturally occurring amino acid
<220> FEATURE:
<221> NAME/KEY: misc_feature
<222> LOCATION: (592)..(593)
<223> OTHER INFORMATION: Xaa can be any naturally occurring amino acid
<220> FEATURE:
<221> NAME/KEY: misc_feature
<222> LOCATION: (595)..(597)
<223> OTHER INFORMATION: Xaa can be any naturally occurring amino acid
<220> FEATURE:
<221> NAME/KEY: misc_feature
<222> LOCATION: (602)..(602)
<223> OTHER INFORMATION: Xaa can be any naturally occurring amino acid
<220> FEATURE:
<221> NAME/KEY: misc_feature
<222> LOCATION: (606)..(607)
<223> OTHER INFORMATION: Xaa can be any naturally occurring amino acid
<220> FEATURE:
<221> NAME/KEY: misc_feature
<222> LOCATION: (609)..(611)
<223> OTHER INFORMATION: Xaa can be any naturally occurring amino acid
<220> FEATURE:
<221> NAME/KEY: misc_feature
<222> LOCATION: (616)..(617)
<223> OTHER INFORMATION: Xaa can be any naturally occurring amino acid
<220> FEATURE:
<221> NAME/KEY: misc_feature
<222> LOCATION: (619)..(625)
<223> OTHER INFORMATION: Xaa can be any naturally occurring amino acid
<220> FEATURE:
<221> NAME/KEY: misc_feature
<222> LOCATION: (627)..(631)
<223> OTHER INFORMATION: Xaa can be any naturally occurring amino acid
<220> FEATURE:
<221> NAME/KEY: misc_feature
<222> LOCATION: (633)..(634)
<223> OTHER INFORMATION: Xaa can be any naturally occurring amino acid
```

```
<220> FEATURE:
<221> NAME/KEY: misc_feature
<222> LOCATION: (636)..(644)
<223> OTHER INFORMATION: Xaa can be any naturally occurring amino acid
<220> FEATURE:
<221> NAME/KEY: misc_feature
<222> LOCATION: (646)..(652)
<223> OTHER INFORMATION: Xaa can be any naturally occurring amino acid
<220> FEATURE:
<221> NAME/KEY: misc_feature
<222> LOCATION: (654)..(655)
<223> OTHER INFORMATION: Xaa can be any naturally occurring amino acid
<220> FEATURE:
<221> NAME/KEY: misc_feature
<222> LOCATION: (657)..(657)
<223> OTHER INFORMATION: Xaa can be any naturally occurring amino acid
<220> FEATURE:
<221> NAME/KEY: misc_feature
<222> LOCATION: (659)..(661)
<223> OTHER INFORMATION: Xaa can be any naturally occurring amino acid
<220> FEATURE:
<221> NAME/KEY: misc_feature
<222> LOCATION: (664)..(666)
<223> OTHER INFORMATION: Xaa can be any naturally occurring amino acid
<220> FEATURE:
<221> NAME/KEY: MISC_FEATURE
<222> LOCATION: (667)..(667)
<223> OTHER INFORMATION: The amino acid(s) can either be present or
      absent.  Xaa can be any naturally occurring amino acid
<220> FEATURE:
<221> NAME/KEY: misc_feature
<222> LOCATION: (668)..(676)
<223> OTHER INFORMATION: Xaa can be any naturally occurring amino acid
<220> FEATURE:
<221> NAME/KEY: misc_feature
<222> LOCATION: (678)..(683)
<223> OTHER INFORMATION: Xaa can be any naturally occurring amino acid
<220> FEATURE:
<221> NAME/KEY: MISC_FEATURE
<222> LOCATION: (684)..(684)
<223> OTHER INFORMATION: The amino acid(s) can either be present or
      absent.  Xaa can be any naturally occurring amino acid
<220> FEATURE:
<221> NAME/KEY: MISC_FEATURE
<222> LOCATION: (685)..(685)
<223> OTHER INFORMATION: The amino acid(s) can either be present or
      absent
<220> FEATURE:
<221> NAME/KEY: misc_feature
<222> LOCATION: (686)..(690)
<223> OTHER INFORMATION: Xaa can be any naturally occurring amino acid
<220> FEATURE:
<221> NAME/KEY: misc_feature
<222> LOCATION: (696)..(697)
<223> OTHER INFORMATION: Xaa can be any naturally occurring amino acid
<220> FEATURE:
<221> NAME/KEY: misc_feature
<222> LOCATION: (699)..(700)
<223> OTHER INFORMATION: Xaa can be any naturally occurring amino acid
<220> FEATURE:
<221> NAME/KEY: misc_feature
<222> LOCATION: (704)..(705)
<223> OTHER INFORMATION: Xaa can be any naturally occurring amino acid
<220> FEATURE:
<221> NAME/KEY: misc_feature
<222> LOCATION: (707)..(711)
<223> OTHER INFORMATION: Xaa can be any naturally occurring amino acid
<220> FEATURE:
<221> NAME/KEY: misc_feature
<222> LOCATION: (713)..(713)
<223> OTHER INFORMATION: Xaa can be any naturally occurring amino acid
<220> FEATURE:
<221> NAME/KEY: MISC_FEATURE
<222> LOCATION: (714)..(714)
<223> OTHER INFORMATION: The amino acid(s) can either be present or
      absent
<220> FEATURE:
<221> NAME/KEY: MISC_FEATURE
<222> LOCATION: (715)..(715)
```

-continued

```
<223> OTHER INFORMATION: The amino acid(s) can either be present or
      absent
<220> FEATURE:
<221> NAME/KEY: MISC_FEATURE
<222> LOCATION: (716)..(716)
<223> OTHER INFORMATION: The amino acid(s) can either be present or
      absent
<220> FEATURE:
<221> NAME/KEY: MISC_FEATURE
<222> LOCATION: (717)..(718)
<223> OTHER INFORMATION: The amino acid(s) can either be present or
      absent.  Xaa can be any naturally occurring amino acid
<220> FEATURE:
<221> NAME/KEY: misc_feature
<222> LOCATION: (719)..(725)
<223> OTHER INFORMATION: Xaa can be any naturally occurring amino acid
<220> FEATURE:
<221> NAME/KEY: misc_feature
<222> LOCATION: (727)..(729)
<223> OTHER INFORMATION: Xaa can be any naturally occurring amino acid
<220> FEATURE:
<221> NAME/KEY: misc_feature
<222> LOCATION: (731)..(732)
<223> OTHER INFORMATION: Xaa can be any naturally occurring amino acid
<220> FEATURE:
<221> NAME/KEY: misc_feature
<222> LOCATION: (734)..(736)
<223> OTHER INFORMATION: Xaa can be any naturally occurring amino acid
<220> FEATURE:
<221> NAME/KEY: misc_feature
<222> LOCATION: (739)..(739)
<223> OTHER INFORMATION: Xaa can be any naturally occurring amino acid
<220> FEATURE:
<221> NAME/KEY: misc_feature
<222> LOCATION: (741)..(744)
<223> OTHER INFORMATION: Xaa can be any naturally occurring amino acid
<220> FEATURE:
<221> NAME/KEY: misc_feature
<222> LOCATION: (747)..(747)
<223> OTHER INFORMATION: Xaa can be any naturally occurring amino acid
<220> FEATURE:
<221> NAME/KEY: misc_feature
<222> LOCATION: (749)..(749)
<223> OTHER INFORMATION: Xaa can be any naturally occurring amino acid
<220> FEATURE:
<221> NAME/KEY: misc_feature
<222> LOCATION: (752)..(754)
<223> OTHER INFORMATION: Xaa can be any naturally occurring amino acid
<220> FEATURE:
<221> NAME/KEY: misc_feature
<222> LOCATION: (756)..(757)
<223> OTHER INFORMATION: Xaa can be any naturally occurring amino acid
<220> FEATURE:
<221> NAME/KEY: misc_feature
<222> LOCATION: (761)..(763)
<223> OTHER INFORMATION: Xaa can be any naturally occurring amino acid
<220> FEATURE:
<221> NAME/KEY: misc_feature
<222> LOCATION: (766)..(766)
<223> OTHER INFORMATION: Xaa can be any naturally occurring amino acid
<220> FEATURE:
<221> NAME/KEY: misc_feature
<222> LOCATION: (769)..(769)
<223> OTHER INFORMATION: Xaa can be any naturally occurring amino acid
<220> FEATURE:
<221> NAME/KEY: misc_feature
<222> LOCATION: (771)..(777)
<223> OTHER INFORMATION: Xaa can be any naturally occurring amino acid
<220> FEATURE:
<221> NAME/KEY: misc_feature
<222> LOCATION: (779)..(780)
<223> OTHER INFORMATION: Xaa can be any naturally occurring amino acid
<220> FEATURE:
<221> NAME/KEY: misc_feature
<222> LOCATION: (782)..(783)
<223> OTHER INFORMATION: Xaa can be any naturally occurring amino acid
<220> FEATURE:
<221> NAME/KEY: misc_feature
<222> LOCATION: (786)..(786)
```

```
<223> OTHER INFORMATION: Xaa can be any naturally occurring amino acid
<220> FEATURE:
<221> NAME/KEY: misc_feature
<222> LOCATION: (788)..(788)
<223> OTHER INFORMATION: Xaa can be any naturally occurring amino acid
<220> FEATURE:
<221> NAME/KEY: misc_feature
<222> LOCATION: (790)..(794)
<223> OTHER INFORMATION: Xaa can be any naturally occurring amino acid
<220> FEATURE:
<221> NAME/KEY: misc_feature
<222> LOCATION: (799)..(799)
<223> OTHER INFORMATION: Xaa can be any naturally occurring amino acid
<220> FEATURE:
<221> NAME/KEY: misc_feature
<222> LOCATION: (804)..(806)
<223> OTHER INFORMATION: Xaa can be any naturally occurring amino acid
<220> FEATURE:
<221> NAME/KEY: misc_feature
<222> LOCATION: (808)..(808)
<223> OTHER INFORMATION: Xaa can be any naturally occurring amino acid
<220> FEATURE:
<221> NAME/KEY: misc_feature
<222> LOCATION: (810)..(812)
<223> OTHER INFORMATION: Xaa can be any naturally occurring amino acid
<220> FEATURE:
<221> NAME/KEY: MISC_FEATURE
<222> LOCATION: (814)..(814)
<223> OTHER INFORMATION: The amino acid(s) can either be present or
      absent
<220> FEATURE:
<221> NAME/KEY: misc_feature
<222> LOCATION: (817)..(818)
<223> OTHER INFORMATION: Xaa can be any naturally occurring amino acid
<220> FEATURE:
<221> NAME/KEY: misc_feature
<222> LOCATION: (825)..(829)
<223> OTHER INFORMATION: Xaa can be any naturally occurring amino acid
<220> FEATURE:
<221> NAME/KEY: misc_feature
<222> LOCATION: (835)..(836)
<223> OTHER INFORMATION: Xaa can be any naturally occurring amino acid
<220> FEATURE:
<221> NAME/KEY: misc_feature
<222> LOCATION: (839)..(840)
<223> OTHER INFORMATION: Xaa can be any naturally occurring amino acid
<220> FEATURE:
<221> NAME/KEY: misc_feature
<222> LOCATION: (847)..(853)
<223> OTHER INFORMATION: Xaa can be any naturally occurring amino acid
<220> FEATURE:
<221> NAME/KEY: MISC_FEATURE
<222> LOCATION: (854)..(854)
<223> OTHER INFORMATION: The amino acid(s) can either be present or
      absent
<220> FEATURE:
<221> NAME/KEY: misc_feature
<222> LOCATION: (855)..(861)
<223> OTHER INFORMATION: Xaa can be any naturally occurring amino acid
<220> FEATURE:
<221> NAME/KEY: misc_feature
<222> LOCATION: (865)..(865)
<223> OTHER INFORMATION: Xaa can be any naturally occurring amino acid
<220> FEATURE:
<221> NAME/KEY: misc_feature
<222> LOCATION: (867)..(867)
<223> OTHER INFORMATION: Xaa can be any naturally occurring amino acid
<220> FEATURE:
<221> NAME/KEY: misc_feature
<222> LOCATION: (869)..(870)
<223> OTHER INFORMATION: Xaa can be any naturally occurring amino acid
<220> FEATURE:
<221> NAME/KEY: misc_feature
<222> LOCATION: (874)..(878)
<223> OTHER INFORMATION: Xaa can be any naturally occurring amino acid
<220> FEATURE:
<221> NAME/KEY: misc_feature
<222> LOCATION: (880)..(881)
<223> OTHER INFORMATION: Xaa can be any naturally occurring amino acid
```

-continued

```
<220> FEATURE:
<221> NAME/KEY: misc_feature
<222> LOCATION: (883)..(884)
<223> OTHER INFORMATION: Xaa can be any naturally occurring amino acid
<220> FEATURE:
<221> NAME/KEY: misc_feature
<222> LOCATION: (886)..(892)
<223> OTHER INFORMATION: Xaa can be any naturally occurring amino acid
<220> FEATURE:
<221> NAME/KEY: misc_feature
<222> LOCATION: (894)..(900)
<223> OTHER INFORMATION: Xaa can be any naturally occurring amino acid
<220> FEATURE:
<221> NAME/KEY: MISC_FEATURE
<222> LOCATION: (901)..(901)
<223> OTHER INFORMATION: The amino acid(s) can either be present or
      absent
<220> FEATURE:
<221> NAME/KEY: misc_feature
<222> LOCATION: (902)..(902)
<223> OTHER INFORMATION: Xaa can be any naturally occurring amino acid
<220> FEATURE:
<221> NAME/KEY: MISC_FEATURE
<222> LOCATION: (903)..(903)
<223> OTHER INFORMATION: The amino acid(s) can either be present or
      absent.  Xaa can be any naturally occurring amino acid
<220> FEATURE:
<221> NAME/KEY: misc_feature
<222> LOCATION: (904)..(911)
<223> OTHER INFORMATION: Xaa can be any naturally occurring amino acid
<220> FEATURE:
<221> NAME/KEY: MISC_FEATURE
<222> LOCATION: (912)..(913)
<223> OTHER INFORMATION: The amino acid(s) can either be present or
      absent
<220> FEATURE:
<221> NAME/KEY: misc_feature
<222> LOCATION: (914)..(915)
<223> OTHER INFORMATION: Xaa can be any naturally occurring amino acid
<220> FEATURE:
<221> NAME/KEY: misc_feature
<222> LOCATION: (917)..(917)
<223> OTHER INFORMATION: Xaa can be any naturally occurring amino acid
<220> FEATURE:
<221> NAME/KEY: misc_feature
<222> LOCATION: (919)..(919)
<223> OTHER INFORMATION: Xaa can be any naturally occurring amino acid
<220> FEATURE:
<221> NAME/KEY: misc_feature
<222> LOCATION: (922)..(923)
<223> OTHER INFORMATION: Xaa can be any naturally occurring amino acid
<220> FEATURE:
<221> NAME/KEY: misc_feature
<222> LOCATION: (925)..(928)
<223> OTHER INFORMATION: Xaa can be any naturally occurring amino acid
<220> FEATURE:
<221> NAME/KEY: misc_feature
<222> LOCATION: (930)..(932)
<223> OTHER INFORMATION: Xaa can be any naturally occurring amino acid
<220> FEATURE:
<221> NAME/KEY: misc_feature
<222> LOCATION: (934)..(938)
<223> OTHER INFORMATION: Xaa can be any naturally occurring amino acid
<220> FEATURE:
<221> NAME/KEY: misc_feature
<222> LOCATION: (940)..(957)
<223> OTHER INFORMATION: Xaa can be any naturally occurring amino acid
<220> FEATURE:
<221> NAME/KEY: misc_feature
<222> LOCATION: (960)..(961)
<223> OTHER INFORMATION: Xaa can be any naturally occurring amino acid
<220> FEATURE:
<221> NAME/KEY: misc_feature
<222> LOCATION: (963)..(966)
<223> OTHER INFORMATION: Xaa can be any naturally occurring amino acid
<220> FEATURE:
<221> NAME/KEY: misc_feature
<222> LOCATION: (972)..(973)
<223> OTHER INFORMATION: Xaa can be any naturally occurring amino acid
```

```
<220> FEATURE:
<221> NAME/KEY: misc_feature
<222> LOCATION: (975)..(982)
<223> OTHER INFORMATION: Xaa can be any naturally occurring amino acid
<220> FEATURE:
<221> NAME/KEY: misc_feature
<222> LOCATION: (985)..(985)
<223> OTHER INFORMATION: Xaa can be any naturally occurring amino acid
<220> FEATURE:
<221> NAME/KEY: misc_feature
<222> LOCATION: (989)..(989)
<223> OTHER INFORMATION: Xaa can be any naturally occurring amino acid
<220> FEATURE:
<221> NAME/KEY: misc_feature
<222> LOCATION: (991)..(991)
<223> OTHER INFORMATION: Xaa can be any naturally occurring amino acid
<220> FEATURE:
<221> NAME/KEY: misc_feature
<222> LOCATION: (993)..(993)
<223> OTHER INFORMATION: Xaa can be any naturally occurring amino acid
<220> FEATURE:
<221> NAME/KEY: misc_feature
<222> LOCATION: (996)..(1001)
<223> OTHER INFORMATION: Xaa can be any naturally occurring amino acid
<220> FEATURE:
<221> NAME/KEY: misc_feature
<222> LOCATION: (1003)..(1004)
<223> OTHER INFORMATION: Xaa can be any naturally occurring amino acid
<220> FEATURE:
<221> NAME/KEY: misc_feature
<222> LOCATION: (1006)..(1009)
<223> OTHER INFORMATION: Xaa can be any naturally occurring amino acid
<220> FEATURE:
<221> NAME/KEY: MISC_FEATURE
<222> LOCATION: (1011)..(1011)
<223> OTHER INFORMATION: The amino acid(s) can either be present or
      absent
<220> FEATURE:
<221> NAME/KEY: misc_feature
<222> LOCATION: (1013)..(1020)
<223> OTHER INFORMATION: Xaa can be any naturally occurring amino acid
<220> FEATURE:
<221> NAME/KEY: misc_feature
<222> LOCATION: (1022)..(1022)
<223> OTHER INFORMATION: Xaa can be any naturally occurring amino acid
<220> FEATURE:
<221> NAME/KEY: misc_feature
<222> LOCATION: (1024)..(1024)
<223> OTHER INFORMATION: Xaa can be any naturally occurring amino acid
<220> FEATURE:
<221> NAME/KEY: misc_feature
<222> LOCATION: (1027)..(1027)
<223> OTHER INFORMATION: Xaa can be any naturally occurring amino acid
<220> FEATURE:
<221> NAME/KEY: misc_feature
<222> LOCATION: (1029)..(1029)
<223> OTHER INFORMATION: Xaa can be any naturally occurring amino acid
<220> FEATURE:
<221> NAME/KEY: misc_feature
<222> LOCATION: (1031)..(1032)
<223> OTHER INFORMATION: Xaa can be any naturally occurring amino acid
<220> FEATURE:
<221> NAME/KEY: misc_feature
<222> LOCATION: (1034)..(1037)
<223> OTHER INFORMATION: Xaa can be any naturally occurring amino acid
<220> FEATURE:
<221> NAME/KEY: misc_feature
<222> LOCATION: (1039)..(1041)
<223> OTHER INFORMATION: Xaa can be any naturally occurring amino acid
<220> FEATURE:
<221> NAME/KEY: misc_feature
<222> LOCATION: (1043)..(1045)
<223> OTHER INFORMATION: Xaa can be any naturally occurring amino acid
<220> FEATURE:
<221> NAME/KEY: misc_feature
<222> LOCATION: (1047)..(1047)
<223> OTHER INFORMATION: Xaa can be any naturally occurring amino acid
<220> FEATURE:
<221> NAME/KEY: misc_feature
```

```
<222> LOCATION: (1049)..(1060)
<223> OTHER INFORMATION: Xaa can be any naturally occurring amino acid
<220> FEATURE:
<221> NAME/KEY: misc_feature
<222> LOCATION: (1062)..(1066)
<223> OTHER INFORMATION: Xaa can be any naturally occurring amino acid
<220> FEATURE:
<221> NAME/KEY: misc_feature
<222> LOCATION: (1068)..(1068)
<223> OTHER INFORMATION: Xaa can be any naturally occurring amino acid
<220> FEATURE:
<221> NAME/KEY: misc_feature
<222> LOCATION: (1070)..(1070)
<223> OTHER INFORMATION: Xaa can be any naturally occurring amino acid
<220> FEATURE:
<221> NAME/KEY: misc_feature
<222> LOCATION: (1073)..(1073)
<223> OTHER INFORMATION: Xaa can be any naturally occurring amino acid
<220> FEATURE:
<221> NAME/KEY: misc_feature
<222> LOCATION: (1075)..(1081)
<223> OTHER INFORMATION: Xaa can be any naturally occurring amino acid
<220> FEATURE:
<221> NAME/KEY: misc_feature
<222> LOCATION: (1083)..(1085)
<223> OTHER INFORMATION: Xaa can be any naturally occurring amino acid
<220> FEATURE:
<221> NAME/KEY: misc_feature
<222> LOCATION: (1087)..(1087)
<223> OTHER INFORMATION: Xaa can be any naturally occurring amino acid
<220> FEATURE:
<221> NAME/KEY: misc_feature
<222> LOCATION: (1090)..(1099)
<223> OTHER INFORMATION: Xaa can be any naturally occurring amino acid
<220> FEATURE:
<221> NAME/KEY: MISC_FEATURE
<222> LOCATION: (1100)..(1100)
<223> OTHER INFORMATION: The amino acid(s) can either be present or
      absent.  Xaa can be any naturally occurring amino acid
<220> FEATURE:
<221> NAME/KEY: misc_feature
<222> LOCATION: (1101)..(1101)
<223> OTHER INFORMATION: Xaa can be any naturally occurring amino acid
<220> FEATURE:
<221> NAME/KEY: MISC_FEATURE
<222> LOCATION: (1102)..(1122)
<223> OTHER INFORMATION: The amino acid(s) can either be present or
      absent.  Xaa can be any naturally occurring amino acid
<220> FEATURE:
<221> NAME/KEY: MISC_FEATURE
<222> LOCATION: (1123)..(1133)
<223> OTHER INFORMATION: The amino acid(s) can either be present or
      absent
<220> FEATURE:
<221> NAME/KEY: MISC_FEATURE
<222> LOCATION: (1134)..(1258)
<223> OTHER INFORMATION: The amino acid(s) can either be present or
      absent.  Xaa can be any naturally occurring amino acid
<220> FEATURE:
<221> NAME/KEY: MISC_FEATURE
<222> LOCATION: (1259)..(1378)
<223> OTHER INFORMATION: The amino acid(s) can either be present or
      absent

<400> SEQUENCE: 11

Met Ala Pro Gly His Gly Ser Gly Thr Asp Gly Arg Thr Leu Ala Arg
1               5                   10                  15

Arg Pro Arg Gly Ser Ser Arg Arg Pro Ser Val Leu Arg Ala Ala Gly
                20                  25                  30

Asn Gln Leu Val Thr Arg Asp Gly Arg Pro Arg His Thr Gly Xaa Leu
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
```

```
                65                  70                  75                  80
Xaa Arg Xaa Xaa Xaa Xaa Xaa Xaa Xaa Thr Xaa Arg Xaa Xaa Xaa
                    85                  90                  95
Xaa Xaa Arg Xaa Xaa Xaa Xaa Xaa Ala Xaa Xaa Xaa Xaa
                100                 105                 110
Xaa Xaa Ala Ala Ser Ala Leu Leu Xaa Xaa Pro Xaa Xaa Xaa
                115                 120                 125
Xaa Xaa Xaa Xaa Xaa Xaa Xaa Ala Xaa Gly Xaa Asp Trp Xaa Xaa
            130                 135                 140
Xaa Xaa Xaa Xaa Gly Gly Xaa Xaa Val Thr Xaa Xaa Leu Xaa Glu Xaa
145                 150                 155                 160
Leu Pro Xaa Val Xaa Asp Ala Pro Thr Leu Xaa Xaa Asp Gly Xaa Xaa
                165                 170                 175
Xaa Gly Xaa Ala Thr Glu Ser Ala Asp Gly Xaa Xaa Leu Xaa Xaa Xaa
                180                 185                 190
Thr Xaa Asp Xaa Xaa Val Xaa Ser Ala Xaa Xaa Val Xaa Xaa Gly Trp
            195                 200                 205
Xaa Ser Xaa Xaa Xaa Xaa Xaa Xaa Xaa Xaa Xaa Xaa Xaa Xaa
    210                 215                 220
Xaa Xaa Xaa Xaa Xaa Xaa Xaa Xaa Xaa Xaa Leu Xaa Xaa Xaa
225                 230                 235                 240
Ala Xaa Xaa Xaa Xaa Xaa Xaa Xaa Xaa Xaa Gly Xaa Xaa Xaa
                245                 250                 255
Xaa Xaa Glu Xaa Xaa Tyr Asp Phe Gly Asp Xaa Ala Val Xaa Leu Ala
            260                 265                 270
Xaa Ile Gly Gly Ile Arg Gly Glu Xaa Thr Gly Xaa Xaa Tyr Leu Xaa
        275                 280                 285
Xaa Xaa Xaa Gly Xaa Xaa Pro Thr Val Xaa Leu Leu His Gly Arg His
            290                 295                 300
Xaa Ser Cys Thr Val Pro Thr Gly Xaa Xaa Xaa Xaa Xaa Asn Pro Xaa
305                 310                 315                 320
Arg Trp Pro Cys Xaa Xaa Xaa Gln Xaa Asn Xaa Xaa Ser Tyr Xaa Gly
                325                 330                 335
Tyr Glu Xaa Thr Xaa Xaa Xaa Leu Ala Xaa Xaa Gly Tyr Xaa Val Xaa
            340                 345                 350
Ser Ile Xaa Ala Asn Ala Xaa Asn Xaa Asn Asp Asn Gln Leu Ala Xaa
        355                 360                 365
Asp Tyr Gly Ala Xaa Ala Arg Gly Xaa Leu Xaa Leu Asp Thr Leu Xaa
    370                 375                 380
Met Leu Xaa Xaa Ala Xaa Ala Gly Xaa Xaa Val Xaa Xaa Xaa Asp Xaa
385                 390                 395                 400
Xaa Xaa Xaa Xaa Xaa Xaa Xaa Xaa Xaa Xaa Xaa Xaa Xaa Xaa Xaa
                405                 410                 415
Xaa Xaa Ala Xaa Xaa Xaa Xaa Xaa Xaa Xaa Xaa Xaa Xaa Xaa
            420                 425                 430
Xaa Xaa Xaa Xaa Thr Xaa Ala Xaa Leu Xaa Gly Xaa Phe Asp Leu Xaa
            435                 440                 445
Xaa Val Gly Xaa Met Gly His Ser Arg Gly Gly Glu Gly Xaa Xaa Ser
    450                 455                 460
Ala Xaa Xaa Leu Asn Gln Xaa Leu Ala Xaa Pro Xaa Gly Ile Xaa Xaa
465                 470                 475                 480
Val Leu Pro Leu Ala Pro Val Asp Phe Gly Arg Xaa Thr Xaa Xaa Asp
                485                 490                 495
```

-continued

```
Xaa Xaa Xaa Xaa Val Xaa Leu Pro Tyr Cys Asp Gly Asp Val Ser Asn
            500                 505                 510

Gln Gln Gly Gln His Xaa Xaa Asp Asp Ser Arg Xaa Ala Xaa Xaa Asp
            515                 520                 525

Asp Xaa Xaa Arg Ser Xaa Xaa Trp Xaa Met Gly Ala Xaa His Asn Phe
            530                 535                 540

Phe Asn Xaa Val Trp Thr Pro Gly Xaa Tyr Pro Xaa Xaa Thr Xaa Asp
545                 550                 555                 560

Asp Trp Xaa Xaa Xaa Xaa Xaa Xaa Xaa Cys Xaa Pro Leu Xaa Xaa
            565                 570                 575

Xaa Xaa Xaa Arg Xaa Xaa Xaa Xaa Gln Tyr Xaa Val Gly Val Xaa
            580                 585                 590

Xaa Met Xaa Xaa Xaa Phe Arg Leu Thr Xaa Gly Gly Glu Xaa Xaa Phe
            595                 600                 605

Xaa Xaa Xaa Phe Asp Gly Ser Xaa Xaa Pro Xaa Xaa Xaa Xaa Xaa
            610                 615                 620

Xaa Ala Xaa Xaa Xaa Xaa Ala Xaa Xaa Pro Xaa Xaa Xaa Xaa Xaa
625                 630                 635                 640

Xaa Xaa Xaa Xaa Phe Xaa Xaa Xaa Xaa Xaa Xaa Arg Xaa Xaa Gly
            645                 650                 655

Xaa Ala Xaa Xaa Xaa Val Cys Xaa Xaa Xaa Xaa Xaa Xaa Xaa Xaa
            660                 665                 670

Xaa Xaa Xaa Xaa Pro Xaa Xaa Xaa Xaa Xaa Xaa Arg Xaa Xaa Xaa
            675                 680                 685

Xaa Xaa Pro His Trp Thr Pro Xaa Xaa Phe Xaa Xaa Asn Val Pro Xaa
            690                 695                 700

Xaa Pro Xaa Xaa Xaa Xaa Xaa Trp Xaa Gly Ala Ser Xaa Xaa Xaa Xaa
705                 710                 715                 720

Xaa Xaa Xaa Xaa Xaa Gly Xaa Xaa Xaa Val Xaa Xaa Pro Xaa Xaa Xaa
            725                 730                 735

Arg Asp Xaa Ser Xaa Xaa Xaa Xaa Leu Thr Xaa Lys Xaa Ala Pro Xaa
            740                 745                 750

Xaa Xaa Val Xaa Xaa Gly Thr Asp Xaa Xaa Xaa Thr Val Xaa Asp Gly
            755                 760                 765

Xaa Gly Xaa Xaa Xaa Xaa Xaa Xaa Ser Xaa Xaa Asn Xaa Xaa Ala
            770                 775                 780

Val Xaa Arg Xaa Pro Xaa Xaa Xaa Xaa Thr Leu Asn Lys Xaa Val
785                 790                 795                 800

Leu Gln Gln Xaa Xaa Pro Xaa Ser Xaa Xaa Xaa Gly Ser Ile Asp
            805                 810                 815

Xaa Xaa Asp Val Arg Glu Val Arg Xaa Xaa Xaa Xaa Gly Ala Asp
            820                 825                 830

Gly Thr Xaa Xaa Gly Gly Xaa Xaa Leu Ser Asp Leu Ala Phe Xaa Xaa
            835                 840                 845

Xaa Xaa Xaa Xaa Xaa Val Xaa Xaa Xaa Xaa Xaa Xaa Thr Val Asn
            850                 855                 860

Xaa Ala Xaa Thr Xaa Xaa Glu Glu Gly Xaa Xaa Xaa Xaa Ala Xaa
865                 870                 875                 880

Xaa Ala Xaa Xaa Leu Xaa Xaa Xaa Xaa Xaa Xaa Val Xaa Xaa Xaa
            885                 890                 895

Xaa Xaa Xaa Xaa Gly Xaa Xaa Xaa Xaa Xaa Xaa Xaa Xaa Xaa Ala
            900                 905                 910
```

```
Ala Xaa Xaa Val Xaa Phe Xaa Pro Gly Xaa Xaa Cys Xaa Xaa Xaa Xaa
            915             920             925

Val Xaa Xaa Xaa Gly Xaa Xaa Xaa Xaa Ala Xaa Xaa Xaa Xaa
    930             935             940

Xaa Xaa Xaa Xaa Xaa Xaa Xaa Xaa Xaa Xaa Xaa Xaa Gly Ala Xaa
945             950             955             960

Xaa Phe Xaa Xaa Xaa Xaa Val Arg Glu Asp Asp Xaa Xaa Thr Xaa Xaa
            965             970             975

Xaa Xaa Xaa Xaa Xaa Xaa Val Gly Xaa Gln Gly Asp Xaa Cys Xaa Glu
        980             985             990

Xaa Ala Ala Xaa Xaa Xaa Xaa Xaa Leu Xaa Xaa Ser Xaa Xaa Xaa
        995             1000            1005

Xaa Ala Pro Gly Xaa Xaa Xaa Xaa Xaa Xaa Xaa Gly Xaa Arg
    1010            1015            1020

Xaa Gly Glu Xaa Val Xaa Phe Xaa Xaa Gly Xaa Xaa Xaa Xaa Gly
    1025            1030            1035

Xaa Xaa Xaa Ala Xaa Xaa Xaa Gly Xaa Ala Xaa Xaa Xaa Xaa Xaa
    1040            1045            1050

Xaa Xaa Xaa Xaa Xaa Xaa Xaa Gly Xaa Xaa Xaa Xaa Xaa Ala Xaa
    1055            1060            1065

Gly Xaa Gly Ser Xaa Arg Xaa Xaa Xaa Xaa Xaa Xaa Val Xaa
    1070            1075            1080

Xaa Xaa Thr Xaa Thr Thr Xaa Xaa Xaa Xaa Xaa Xaa Xaa Xaa
    1085            1090            1095

Xaa Xaa Xaa Xaa Xaa Xaa Thr Xaa Xaa Ala Xaa Val Xaa Gly Xaa
    1100            1105            1110

Xaa Thr Xaa Gly Thr Val Thr Phe Val Val Ser Gly Ser Gly Ser
    1115            1120            1125

Gly Ala Ala Asp Ala Ala Xaa Xaa Xaa Xaa Xaa Leu Gly Xaa Xaa
    1130            1135            1140

Xaa Val Xaa Asp Gly Xaa Ala Xaa Leu Xaa Xaa Xaa Xaa Gly Xaa
    1145            1150            1155

Xaa Xaa Gly Xaa Xaa Xaa Xaa Xaa Ala Xaa Phe Xaa Xaa Thr Xaa
    1160            1165            1170

Xaa Ala Xaa Xaa Ser Xaa Ser Xaa Xaa Val Xaa Xaa Xaa Xaa Xaa
    1175            1180            1185

Xaa Xaa Xaa Thr Xaa Xaa Xaa Xaa Xaa Xaa Xaa Xaa Xaa Xaa
    1190            1195            1200

Xaa Xaa Gly Xaa Xaa Xaa Xaa Gly Xaa Xaa Xaa Xaa Xaa Xaa Xaa
    1205            1210            1215

Xaa Xaa Xaa Xaa Xaa Xaa Xaa Xaa Xaa Xaa Xaa Xaa Xaa Xaa Xaa
    1220            1225            1230

Xaa Xaa Xaa Xaa Xaa Xaa Xaa Xaa Gly Xaa Xaa Xaa Xaa Xaa Xaa
    1235            1240            1245

Xaa Xaa Xaa Xaa Xaa Xaa Xaa Xaa Xaa Xaa Ala Ser Tyr Ala Gly
    1250            1255            1260

Ser Arg Thr Leu Asp Thr Ser Ser Ala Arg Ala Ser Leu Thr Val
    1265            1270            1275

Leu Lys Ala Ala Pro Lys Val Thr Leu Ser Ala Pro Ala Thr Ala
    1280            1285            1290

Arg Lys Gly Ala Thr Val Thr Val Thr Val Lys Val Val Gly Val
    1295            1300            1305

Lys Gly Gly Val Arg Pro Thr Gly Lys Ala Val Val Lys Leu Gly
```

```
                    1310                1315                1320
Gly Lys Ala Val Lys Thr Val Ser Val Pro Ser Ser Gly Val Val
    1325                1330                1335

Lys Val Lys Val Arg Leu Ala Ser Ala Gly Thr Ala Lys Val Thr
1340                1345                1350

Ala Ala Tyr Gln Gly Ser Ala Tyr Tyr Thr Ala Ala Ser Ala Ala
    1355                1360                1365

Ala Lys Val Lys Val Lys Val Val Thr Lys
    1370                1375
```

<210> SEQ ID NO 12
<211> LENGTH: 5
<212> TYPE: PRT
<213> ORGANISM: Agromyces sp.

<400> SEQUENCE: 12

```
Ala Ala Thr Glu Asp
1               5
```

<210> SEQ ID NO 13
<211> LENGTH: 11
<212> TYPE: PRT
<213> ORGANISM: Agromyces sp.

<400> SEQUENCE: 13

```
Val Pro Glu His Gly Val Ile Ala Ser Gly Asp
1               5                   10
```

<210> SEQ ID NO 14
<211> LENGTH: 4
<212> TYPE: PRT
<213> ORGANISM: Artificial Sequence
<220> FEATURE:
<223> OTHER INFORMATION: Factor Xa

<400> SEQUENCE: 14

```
Ile Glu Gly Arg
1
```

<210> SEQ ID NO 15
<211> LENGTH: 6
<212> TYPE: PRT
<213> ORGANISM: Artificial Sequence
<220> FEATURE:
<223> OTHER INFORMATION: ProTEV

<400> SEQUENCE: 15

```
Glu Asn Leu Tyr Phe Gln
1               5
```

<210> SEQ ID NO 16
<211> LENGTH: 3468
<212> TYPE: DNA
<213> ORGANISM: Agromyces sp.
<220> FEATURE:
<221> NAME/KEY: CDS
<222> LOCATION: (1)..(3468)

<400> SEQUENCE: 16

```
atg aaa cgc atg aaa tcg ctg gct gcg gcg ctc acc gtc gct ggg gcc     48
Met Lys Arg Met Lys Ser Leu Ala Ala Ala Leu Thr Val Ala Gly Ala
1               5                   10                  15 atg ctg gcc gca cct gtg gca acg gca ctg ggc gct gct cct gct gct     96
Met Leu Ala Ala Pro Val Ala Thr Ala Leu Gly Ala Ala Pro Ala Ala
```

```
                     20                  25                  30
aac gcc gtc ccg gaa cac ggc gtg atc gcg tcc ggt gat gac tgg acc        144
Asn Ala Val Pro Glu His Gly Val Ile Ala Ser Gly Asp Asp Trp Thr
             35                  40                  45 att gag acc gct cct ggc ggc tac ctg gtc acc tac cag ctg gcc gag        192
Ile Glu Thr Ala Pro Gly Gly Tyr Leu Val Thr Tyr Gln Leu Ala Glu
 50                  55                  60 cca ctc cct atc gtt tcc gac gca ccg acc ctg ctc att gat ggc gag        240
Pro Leu Pro Ile Val Ser Asp Ala Pro Thr Leu Leu Ile Asp Gly Glu
 65                  70                  75                  80 cca gcg ggt tac gca acc gaa tcc gca gac ggc cgc tcc ctg tct ctc        288
Pro Ala Gly Tyr Ala Thr Glu Ser Ala Asp Gly Arg Ser Leu Ser Leu
                     85                  90                  95 ttc acc tct gat cca gac gtc gct tcc gcc cgt gaa gtt gag aag ggc        336
Phe Thr Ser Asp Pro Asp Val Ala Ser Ala Arg Glu Val Glu Lys Gly
            100                 105                 110 tgg gct tcc tct gag ggt gac aaa gca gct gaa tct cca gtg gcc gag        384
Trp Ala Ser Ser Glu Gly Asp Lys Ala Ala Glu Ser Pro Val Ala Glu
            115                 120                 125 tgg tcc acc gaa cag cct aac gat gag ctt ttg gaa cag ctt ggc cgc        432
Trp Ser Thr Glu Gln Pro Asn Asp Glu Leu Leu Glu Gln Leu Gly Arg
130                 135                 140 ttg gca cct atg gag aac ctg tac ttc cag ggt gca gca acc gaa gat        480
Leu Ala Pro Met Glu Asn Leu Tyr Phe Gln Gly Ala Ala Thr Glu Asp
145                 150                 155                 160 ccg ggc gac cca ggt gca tac gca gtg acc gaa gct gag tac gat ttc        528
Pro Gly Asp Pro Gly Ala Tyr Ala Val Thr Glu Ala Glu Tyr Asp Phe
                165                 170                 175 ggc gac cgt gct gtc gca ctc gca ggt atc ggc ggt att cgt ggc gag        576
Gly Asp Arg Ala Val Ala Leu Ala Gly Ile Gly Gly Ile Arg Gly Glu
                180                 185                 190 atg acc ggc aag ctt tac ttg acc gac gca cct ggt gaa cgt cct acc        624
Met Thr Gly Lys Leu Tyr Leu Thr Asp Ala Pro Gly Glu Arg Pro Thr
            195                 200                 205 gtc atc ctg ctc cac ggt cgt cac tcc tct tgc tcc acc ggc acc gct        672
Val Ile Leu Leu His Gly Arg His Ser Ser Cys Ser Thr Gly Thr Ala
            210                 215                 220 aac cca ctt cgc tgg cct tgt ggc ccg aac cag gtt aac gtg cgt tcc        720
Asn Pro Leu Arg Trp Pro Cys Gly Pro Asn Gln Val Asn Val Arg Ser
225                 230                 235                 240 tac cag ggt tac gag ggc acc gca cgt gct ctc gca tct cac ggc tac        768
Tyr Gln Gly Tyr Glu Gly Thr Ala Arg Ala Leu Ala Ser His Gly Tyr
                245                 250                 255 aac gtt gca tcc att gca gct aac gct gtg aac tcc aac gac aac cag        816
Asn Val Ala Ser Ile Ala Ala Asn Ala Val Asn Ser Asn Asp Asn Gln
                260                 265                 270 ctg gca ctc gat tac ggc gcg aag gca cgc ggt cag ctt atc ttg gat        864
Leu Ala Leu Asp Tyr Gly Ala Lys Ala Arg Gly Gln Leu Ile Leu Asp
            275                 280                 285 acc ctg acc atg ctc ggc aaa gct tct gcc ggt gaa ccg gtg gtc ctt        912
Thr Leu Thr Met Leu Gly Lys Ala Ser Ala Gly Glu Pro Val Val Leu
            290                 295                 300 gat gac att tcc tgg cca gat gct gac ggc aac gtt acc acc acc acc        960
Asp Asp Ile Ser Trp Pro Asp Ala Asp Gly Asn Val Thr Thr Thr Thr
305                 310                 315                 320 cgc tcc ttg gat gac gcg ctg gtg ctc gca acc acc cgt gct gac tct       1008
Arg Ser Leu Asp Asp Ala Leu Val Leu Ala Thr Thr Arg Ala Asp Ser
                325                 330                 335 cca gca gca cct ggc ggt gtg acc gca gct tcc ctt cag ggc cgc ttc       1056
Pro Ala Ala Pro Gly Gly Val Thr Ala Ala Ser Leu Gln Gly Arg Phe
```

```
                Pro Ala Ala Pro Gly Gly Val Thr Ala Ala Ser Leu Gln Gly Arg Phe
                                340                 345                 350 gat ttg gac cgt gtc ggc atc atg ggt cac tct cgc ggc ggt gaa ggt        1104
Asp Leu Asp Arg Val Gly Ile Met Gly His Ser Arg Gly Gly Glu Gly
            355                 360                 365 gct acc tct gca gtg acc ctt aac cag ggc ttg gct gat cca ttc ggt        1152
Ala Thr Ser Ala Val Thr Leu Asn Gln Gly Leu Ala Asp Pro Phe Gly
370                 375                 380 att gtc gca gtt ctt ccg ttg gct cca gtt gac ttc ggc cgt atg acc        1200
Ile Val Ala Val Leu Pro Leu Ala Pro Val Asp Phe Gly Arg Met Thr
385                 390                 395                 400 gtg gcc gat acc ccg atg gcg gtc ttc ctg cca tac tgc gat ggc gac        1248
Val Ala Asp Thr Pro Met Ala Val Phe Leu Pro Tyr Cys Asp Gly Asp
            405                 410                 415 gtc tct aac cag cag ggt cag cac atg gtt gat gac tcc cgc cac gca        1296
Val Ser Asn Gln Gln Gly Gln His Met Val Asp Asp Ser Arg His Ala
                420                 425                 430 ttc gtc gat gac gtt atg cgt tct gcc gtc tgg atc atg ggc gcg aac        1344
Phe Val Asp Asp Val Met Arg Ser Ala Val Trp Ile Met Gly Ala Asn
            435                 440                 445 cac aac ttc ttc aac acc gtt tgg acc cca ggt ctg tac cct tac gct        1392
His Asn Phe Phe Asn Thr Val Trp Thr Pro Gly Leu Tyr Pro Tyr Ala
    450                 455                 460 acc tct gat gac tgg aac cgc aac gac cag acc tct acc tgt tcc acc        1440
Thr Ser Asp Asp Trp Asn Arg Asn Asp Gln Thr Ser Thr Cys Ser Thr
465                 470                 475                 480 gca cac gag tcc cgt ctg acc cca gca cag cag tac caa gtg ggc gtc        1488
Ala His Glu Ser Arg Leu Thr Pro Ala Gln Gln Tyr Gln Val Gly Val
            485                 490                 495 tcc tac atg acc ggt ttc ttc cgc ctc acc atg ggc ggt gaa acc cag        1536
Ser Tyr Met Thr Gly Phe Phe Arg Leu Thr Met Gly Gly Glu Thr Gln
                500                 505                 510 ttc cag cct atg ttc gac ggc tcc gtc acc ccg acc acc acc gca acc        1584
Phe Gln Pro Met Phe Asp Gly Ser Val Thr Pro Thr Thr Thr Ala Thr
            515                 520                 525 ggt ttc gca gat gtt cgt gtg atg gcc tct cag cca gcg tcc gca acc        1632
Gly Phe Ala Asp Val Arg Val Met Ala Ser Gln Pro Ala Ser Ala Thr
530                 535                 540 acc gtt atc gca gat ttc gag gac cgc tcc acc ctg att cgt acc tct        1680
Thr Val Ile Ala Asp Phe Glu Asp Arg Ser Thr Leu Ile Arg Thr Ser
545                 550                 555                 560 ggc aac gct tcc gcc cag gtt tgc gcg aac gca gaa acc gca acc tct        1728
Gly Asn Ala Ser Ala Gln Val Cys Ala Asn Ala Glu Thr Ala Thr Ser
            565                 570                 575 atc gct cct tcc gtg ccg tac tgt acc gtg cgt cca gtc ggc acc gca        1776
Ile Ala Pro Ser Val Pro Tyr Cys Thr Val Arg Pro Val Gly Thr Ala
                580                 585                 590 cgt gtg ccg cac tgg acc cca gtc cgc ttc ggt ctg aac gtt cca gct        1824
Arg Val Pro His Trp Thr Pro Val Arg Phe Gly Leu Asn Val Pro Ala
            595                 600                 605 tac cct gtt acc cgt gtg ctc tgg acc ggc tcc acc tct acc ccg gca        1872
Tyr Pro Val Thr Arg Val Leu Trp Thr Gly Ser Thr Ser Thr Pro Ala
    610                 615                 620 gca cca tcc acc ggt gtg ctt cac gtc gca gtt ccg gaa ggc tct cgc        1920
Ala Pro Ser Thr Gly Val Leu His Val Ala Val Pro Glu Gly Ser Arg
625                 630                 635                 640 gac gtc tcc ggt cac acc cag ttg acc gtt aag gca gct cca gat atc        1968
Asp Val Ser Gly His Thr Gln Leu Thr Val Lys Ala Ala Pro Asp Ile
            645                 650                 655
```

| | | |
|---|---|---|
| tct gtg gac tcc ggc acc gat ttc acc atc acc gtc att gat ggt gct<br>Ser Val Asp Ser Gly Thr Asp Phe Thr Ile Thr Val Ile Asp Gly Ala<br>660                         665                       670 | | 2016 |
| ggc aac tcc ttc tct acc cct gct tcc gcc gtc aac ccg ctt gca gtt<br>Gly Asn Ser Phe Ser Thr Pro Ala Ser Ala Val Asn Pro Leu Ala Val<br>675                         680                       685 | | 2064 |
| aac cgc atg cca ggc ggc acc cac gct acc ttg aac aaa atc gtg ctt<br>Asn Arg Met Pro Gly Gly Thr His Ala Thr Leu Asn Lys Ile Val Leu<br>690                         695                       700 | | 2112 |
| cag cag ttg acc gtc ccg acc tct gag atg acc ggc att gat ctg acc<br>Gln Gln Leu Thr Val Pro Thr Ser Glu Met Thr Gly Ile Asp Leu Thr<br>705                         710                       715                       720 | | 2160 |
| gac gtc cgc gaa gtt cgt ttc gca gcg ggt gtg ggt gca gat ggc acc<br>Asp Val Arg Glu Val Arg Phe Ala Ala Gly Val Gly Ala Asp Gly Thr<br>                      725                       730                       735 | | 2208 |
| ggt gct ggc ggt ctg tac ctc tcc gac ctc gct ttc gat acc cct acc<br>Gly Ala Gly Gly Leu Tyr Leu Ser Asp Leu Ala Phe Asp Thr Pro Thr<br>                    740                       745                       750 | | 2256 |
| ttc gca cct gca gtt gtg ggc acc cgt acc acc gtt aac atc gcc tct<br>Phe Ala Pro Ala Val Val Gly Thr Arg Thr Thr Val Asn Ile Ala Ser<br>                  755                       760                       765 | | 2304 |
| acc ttc gtg gaa gag ggt gat tcc acc gac acc gca cag gtg gca gtc<br>Thr Phe Val Glu Glu Gly Asp Ser Thr Asp Thr Ala Gln Val Ala Val<br>      770                       775                       780 | | 2352 |
| tcc ctg gac cgt gaa gca gag cgt gaa gtg acc gct tgg gtc tct ttc<br>Ser Leu Asp Arg Glu Ala Glu Arg Glu Val Thr Ala Trp Val Ser Phe<br>785                         790                       795                       800 | | 2400 |
| gtt cca gtg tcc ggt cct gtc gca gct gca gtg cag gat gtc acc ttc<br>Val Pro Val Ser Gly Pro Val Ala Ala Ala Val Gln Asp Val Thr Phe<br>                    805                       810                       815 | | 2448 |
| gca cca ggc gag acc tgc cgt gtc gtt gaa gtc cca gtt acc ggt aac<br>Ala Pro Gly Glu Thr Cys Arg Val Val Glu Val Pro Val Thr Gly Asn<br>                  820                       825                       830 | | 2496 |
| acc gca cct tct gct acc gca tcc acc gca atc acc gtg tcc gca acc<br>Thr Ala Pro Ser Ala Thr Ala Ser Thr Ala Ile Thr Val Ser Ala Thr<br>                835                       840                       845 | | 2544 |
| aac acc gcg aac gca gtc atg ggt gct gac gca ttc ggc acc ctg gtg<br>Asn Thr Ala Asn Ala Val Met Gly Ala Asp Ala Phe Gly Thr Leu Val<br>850                         855                       860 | | 2592 |
| gtg cgt gag gat gac ggc gtg acc ggt cca gca gtc gaa ctc cca cct<br>Val Arg Glu Asp Asp Gly Val Thr Gly Pro Ala Val Glu Leu Pro Pro<br>865                         870                       875                       880 | | 2640 |
| gtg ggc gtc cag ggt gac gca tgc gca gag ctt gca gca gct cag gag<br>Val Gly Val Gln Gly Asp Ala Cys Ala Glu Leu Ala Ala Ala Gln Glu<br>                  885                       890                       895 | | 2688 |
| cct ggc gaa ttg acc gtt tct gca gat gag gtg gca ccg ggc ggt tcc<br>Pro Gly Glu Leu Thr Val Ser Ala Asp Glu Val Ala Pro Gly Gly Ser<br>                    900                       905                       910 | | 2736 |
| gtt gaa ctg acc gca gca ggt ttc cgt gtt ggt gaa tcc gtg cgt ttc<br>Val Glu Leu Thr Ala Ala Gly Phe Arg Val Gly Glu Ser Val Arg Phe<br>                915                       920                       925 | | 2784 |
| acc ttc ggc gat gac gag ctg ggt gct gtc ctc gct gac gcc gaa ggc<br>Thr Phe Gly Asp Asp Glu Leu Gly Ala Val Leu Ala Asp Ala Glu Gly<br>      930                       935                       940 | | 2832 |
| gtt gcc acc gtt acc gtg gat gtc cca gaa gag tcc gct ctc ggt gca<br>Val Ala Thr Val Thr Val Asp Val Pro Glu Glu Ser Ala Leu Gly Ala<br>945                         950                       955                       960 | | 2880 |
| cgt acc gca tct gca ttc ggt gca ggc tcc gca cgt gtc cag acc gca<br>Arg Thr Ala Ser Ala Phe Gly Ala Gly Ser Ala Arg Val Gln Thr Ala<br>                  965                       970                       975 | | 2928 |

```
atg gtt gat gtg ctt gct cct acc gcc acc acc ttg acc gtg gac gaa      2976
Met Val Asp Val Leu Ala Pro Thr Ala Thr Thr Leu Thr Val Asp Glu
            980                 985                 990 ggc tcc acc ctg gtc gag ggt gat gaa ctc acc ttc gtt gct gag gtg      3024
Gly Ser Thr Leu Val Glu Gly Asp Glu Leu Thr Phe Val Ala Glu Val
            995                 1000                1005 acc ggt gca gaa acc gca ggc acc gtc acc ttc gtt tcc ggt tct          3069
Thr Gly Ala Glu Thr Ala Gly Thr Val Thr Phe Val Ser Gly Ser
        1010                1015                1020 ggc tcc ggt gca gct gac gca gca gca gct ggc gag gtt ctg ggc          3114
Gly Ser Gly Ala Ala Asp Ala Ala Ala Ala Gly Glu Val Leu Gly
        1025                1030                1035 acc gca gat gtt gtg gac ggc gtg gct acc ctt acc ttg ggc gat          3159
Thr Ala Asp Val Val Asp Gly Val Ala Thr Leu Thr Leu Gly Asp
        1040                1045                1050 ggt ctc gct gaa ggt gcc tac tcc gtc gtt gcc gcg ttc gct cgc          3204
Gly Leu Ala Glu Gly Ala Tyr Ser Val Val Ala Ala Phe Ala Arg
        1055                1060                1065 acc gac atc gct tct gcc tcc tct tcc gat cca gtg gag ttc gaa          3249
Thr Asp Ile Ala Ser Ala Ser Ser Ser Asp Pro Val Glu Phe Glu
        1070                1075                1080 att tcc gca gct gcc acc aag ccg cca gtg gtc aac cct ccg ggc          3294
Ile Ser Ala Ala Ala Thr Lys Pro Pro Val Val Asn Pro Pro Gly
        1085                1090                1095 acc ggc acc cca ggc ggc ggc gac tcc ggc acc gca tct tcc tct          3339
Thr Gly Thr Pro Gly Gly Gly Asp Ser Gly Thr Ala Ser Ser Ser
        1100                1105                1110 gat ggc cct ctg gct cac acc ggt ttc gat ggc ctc ggt tgg gcc          3384
Asp Gly Pro Leu Ala His Thr Gly Phe Asp Gly Leu Gly Trp Ala
        1115                1120                1125 ctt ttg gcg gca ctg gcg ctc ttc gca gtt ggc gct acc gtt gtc          3429
Leu Leu Ala Ala Leu Ala Leu Phe Ala Val Gly Ala Thr Val Val
        1130                1135                1140 gtg gct cgt cgt cag acc cgt tct acc cca gag tcc taa                  3468
Val Ala Arg Arg Gln Thr Arg Ser Thr Pro Glu Ser
        1145                1150                1155

<210> SEQ ID NO 17
<211> LENGTH: 1155
<212> TYPE: PRT
<213> ORGANISM: Agromyces sp.

<400> SEQUENCE: 17

Met Lys Arg Met Lys Ser Leu Ala Ala Ala Leu Thr Val Ala Gly Ala
1               5                   10                  15

Met Leu Ala Ala Pro Val Ala Thr Ala Leu Gly Ala Ala Pro Ala Ala
            20                  25                  30

Asn Ala Val Pro Glu His Gly Val Ile Ala Ser Gly Asp Asp Trp Thr
        35                  40                  45

Ile Glu Thr Ala Pro Gly Gly Tyr Leu Val Thr Tyr Gln Leu Ala Glu
    50                  55                  60

Pro Leu Pro Ile Val Ser Asp Ala Pro Thr Leu Leu Ile Asp Gly Glu
65                  70                  75                  80

Pro Ala Gly Tyr Ala Thr Glu Ser Ala Asp Gly Arg Ser Leu Ser Leu
                85                  90                  95

Phe Thr Ser Asp Pro Asp Val Ala Ser Ala Arg Glu Val Glu Lys Gly
            100                 105                 110

Trp Ala Ser Ser Glu Gly Asp Lys Ala Ala Glu Ser Pro Val Ala Glu
```

```
            115                 120                 125
Trp Ser Thr Glu Gln Pro Asn Asp Glu Leu Leu Glu Gln Leu Gly Arg
    130                 135                 140

Leu Ala Pro Met Glu Asn Leu Tyr Phe Gln Gly Ala Ala Thr Glu Asp
145                 150                 155                 160

Pro Gly Asp Pro Gly Ala Tyr Ala Val Thr Glu Ala Glu Tyr Asp Phe
                165                 170                 175

Gly Asp Arg Ala Val Ala Leu Ala Gly Ile Gly Ile Arg Gly Glu
            180                 185                 190

Met Thr Gly Lys Leu Tyr Leu Thr Asp Ala Pro Gly Glu Arg Pro Thr
                195                 200                 205

Val Ile Leu Leu His Gly Arg His Ser Ser Cys Ser Thr Gly Thr Ala
            210                 215                 220

Asn Pro Leu Arg Trp Pro Cys Gly Pro Asn Gln Val Asn Val Arg Ser
225                 230                 235                 240

Tyr Gln Gly Tyr Glu Gly Thr Ala Arg Ala Leu Ala Ser His Gly Tyr
                245                 250                 255

Asn Val Ala Ser Ile Ala Ala Asn Ala Val Asn Ser Asn Asp Asn Gln
            260                 265                 270

Leu Ala Leu Asp Tyr Gly Ala Lys Ala Arg Gly Gln Leu Ile Leu Asp
            275                 280                 285

Thr Leu Thr Met Leu Gly Lys Ala Ser Ala Gly Glu Pro Val Val Leu
    290                 295                 300

Asp Asp Ile Ser Trp Pro Asp Ala Asp Gly Asn Val Thr Thr Thr Thr
305                 310                 315                 320

Arg Ser Leu Asp Asp Ala Leu Val Leu Ala Thr Thr Arg Ala Asp Ser
                325                 330                 335

Pro Ala Ala Pro Gly Gly Val Thr Ala Ala Ser Leu Gln Gly Arg Phe
                340                 345                 350

Asp Leu Asp Arg Val Gly Ile Met Gly His Ser Arg Gly Gly Glu Gly
                355                 360                 365

Ala Thr Ser Ala Val Thr Leu Asn Gln Gly Leu Ala Asp Pro Phe Gly
    370                 375                 380

Ile Val Ala Val Leu Pro Leu Ala Pro Val Asp Phe Gly Arg Met Thr
385                 390                 395                 400

Val Ala Asp Thr Pro Met Ala Val Phe Leu Pro Tyr Cys Asp Gly Asp
                405                 410                 415

Val Ser Asn Gln Gln Gly Gln His Met Val Asp Asp Ser Arg His Ala
                420                 425                 430

Phe Val Asp Asp Val Met Arg Ser Ala Val Trp Ile Met Gly Ala Asn
            435                 440                 445

His Asn Phe Phe Asn Thr Val Trp Thr Pro Gly Leu Tyr Pro Tyr Ala
    450                 455                 460

Thr Ser Asp Asp Trp Asn Arg Asn Asp Gln Thr Ser Thr Cys Ser Thr
465                 470                 475                 480

Ala His Glu Ser Arg Leu Thr Pro Ala Gln Gln Tyr Gln Val Gly Val
                485                 490                 495

Ser Tyr Met Thr Gly Phe Phe Arg Leu Thr Met Gly Gly Glu Thr Gln
            500                 505                 510

Phe Gln Pro Met Phe Asp Gly Ser Val Thr Pro Thr Thr Thr Ala Thr
                515                 520                 525

Gly Phe Ala Asp Val Arg Val Met Ala Ser Gln Pro Ala Ser Ala Thr
            530                 535                 540
```

```
Thr Val Ile Ala Asp Phe Glu Asp Arg Ser Thr Leu Ile Arg Thr Ser
545                 550                 555                 560

Gly Asn Ala Ser Ala Gln Val Cys Ala Asn Ala Glu Thr Ala Thr Ser
            565                 570                 575

Ile Ala Pro Ser Val Pro Tyr Cys Thr Val Arg Pro Val Gly Thr Ala
            580                 585                 590

Arg Val Pro His Trp Thr Pro Val Arg Phe Gly Leu Asn Val Pro Ala
            595                 600                 605

Tyr Pro Val Thr Arg Val Leu Trp Thr Gly Ser Thr Ser Thr Pro Ala
            610                 615                 620

Ala Pro Ser Thr Gly Val Leu His Val Ala Val Pro Glu Gly Ser Arg
625                 630                 635                 640

Asp Val Ser Gly His Thr Gln Leu Thr Val Lys Ala Ala Pro Asp Ile
                645                 650                 655

Ser Val Asp Ser Gly Thr Asp Phe Thr Ile Thr Val Ile Asp Gly Ala
                660                 665                 670

Gly Asn Ser Phe Ser Thr Pro Ala Ser Ala Val Asn Pro Leu Ala Val
            675                 680                 685

Asn Arg Met Pro Gly Gly Thr His Ala Thr Leu Asn Lys Ile Val Leu
690                 695                 700

Gln Gln Leu Thr Val Pro Thr Ser Glu Met Thr Gly Ile Asp Leu Thr
705                 710                 715                 720

Asp Val Arg Glu Val Arg Phe Ala Ala Gly Val Gly Ala Asp Gly Thr
                725                 730                 735

Gly Ala Gly Gly Leu Tyr Leu Ser Asp Leu Ala Phe Asp Thr Pro Thr
            740                 745                 750

Phe Ala Pro Ala Val Val Gly Thr Arg Thr Thr Val Asn Ile Ala Ser
            755                 760                 765

Thr Phe Val Glu Glu Gly Asp Ser Thr Asp Thr Ala Gln Val Ala Val
    770                 775                 780

Ser Leu Asp Arg Glu Ala Glu Arg Glu Val Thr Ala Trp Val Ser Phe
785                 790                 795                 800

Val Pro Val Ser Gly Pro Val Ala Ala Val Gln Asp Val Thr Phe
            805                 810                 815

Ala Pro Gly Glu Thr Cys Arg Val Val Glu Val Pro Val Thr Gly Asn
            820                 825                 830

Thr Ala Pro Ser Ala Thr Ala Ser Thr Ala Ile Thr Val Ser Ala Thr
            835                 840                 845

Asn Thr Ala Asn Ala Val Met Gly Ala Asp Ala Phe Gly Thr Leu Val
850                 855                 860

Val Arg Glu Asp Asp Gly Val Thr Gly Pro Ala Val Glu Leu Pro Pro
865                 870                 875                 880

Val Gly Val Gln Gly Asp Ala Cys Ala Glu Leu Ala Ala Gln Glu
            885                 890                 895

Pro Gly Glu Leu Thr Val Ser Ala Asp Glu Val Ala Pro Gly Gly Ser
            900                 905                 910

Val Glu Leu Thr Ala Ala Gly Phe Arg Val Gly Glu Ser Val Arg Phe
            915                 920                 925

Thr Phe Gly Asp Asp Glu Leu Gly Ala Val Leu Ala Asp Ala Glu Gly
            930                 935                 940

Val Ala Thr Val Thr Val Asp Val Pro Glu Glu Ser Ala Leu Gly Ala
945                 950                 955                 960
```

-continued

```
Arg Thr Ala Ser Ala Phe Gly Ala Gly Ser Ala Arg Val Gln Thr Ala
            965                 970                 975
Met Val Asp Val Leu Ala Pro Thr Ala Thr Thr Leu Thr Val Asp Glu
        980                 985                 990
Gly Ser Thr Leu Val Glu Gly Asp Glu Leu Thr Phe Val Ala Glu Val
        995                 1000                1005
Thr Gly Ala Glu Thr Ala Gly Thr Val Thr Phe Val Ser Gly Ser
    1010                1015                1020
Gly Ser Gly Ala Ala Asp Ala Ala Ala Ala Gly Glu Val Leu Gly
    1025                1030                1035
Thr Ala Asp Val Val Asp Gly Val Ala Thr Leu Thr Leu Gly Asp
    1040                1045                1050
Gly Leu Ala Glu Gly Ala Tyr Ser Val Val Ala Ala Phe Ala Arg
    1055                1060                1065
Thr Asp Ile Ala Ser Ala Ser Ser Ser Asp Pro Val Glu Phe Glu
    1070                1075                1080
Ile Ser Ala Ala Ala Thr Lys Pro Pro Val Val Asn Pro Pro Gly
    1085                1090                1095
Thr Gly Thr Pro Gly Gly Gly Asp Ser Gly Thr Ala Ser Ser Ser
    1100                1105                1110
Asp Gly Pro Leu Ala His Thr Gly Phe Asp Gly Leu Gly Trp Ala
    1115                1120                1125
Leu Leu Ala Ala Leu Ala Leu Phe Ala Val Gly Ala Thr Val Val
    1130                1135                1140
Val Ala Arg Arg Gln Thr Arg Ser Thr Pro Glu Ser
    1145                1150                1155

<210> SEQ ID NO 18
<211> LENGTH: 4052
<212> TYPE: DNA
<213> ORGANISM: Agromyces sp.

<400> SEQUENCE: 18
ggtacccaaa ttcctgtgaa gtagctgatt tagtactttt cggaggtgtc tattcttacc      60
aaatcgtcaa gttgtgggta gagtcacctg aatattaatt gcaccgcacg ggtgatatat     120
gcttatttgc tcaagtagtt cgaggttaag tgtattttag gtgaacaaat ttcagcttcg     180
ggtagaagac tttcgatgcg cttcagagct tctattggga aatctgacac cacttgatta     240
aatagcctac ccccgaattg ggggattggt catttttgc tgtgaaggta gttttgatgc      300
atatgacctg cgtttataaa gaaatgtaaa cgtgatcaga tcgatataaa agaaacagtt     360
tgtactcagg tttgaagcat tttctccgat tcgcctggca aaaatctcaa ttgtcgctta     420 cagttttct caacgacagg ctgctaagct gctagttcgg tggcctagtg agtggcgttt      480
acttggataa aagtaatccc atgtcgtgat cagccatttt gggttgtttc catagcaatc     540
caaaggtttc gtctttcgat acctattcaa ggagccttat gaaacgcatg aaatcgctgg     600
ctgcggcgct caccgtcgct ggggccatgc tggccgcacc tgtggcaacg gcactgggcg     660
ctgctcctgc tgctaacgcc gtcccggaac acggcgtgat cgcgtccggt gatgactgga     720
ccattgagac cgctcctggc ggctacctgg tcacctacca gctggccgag ccactcccta     780
tcgtttccga cgcaccgacc ctgctcattg atggcgagcc agcgggttac gcaaccgaat     840
ccgcagacgg ccgctcctg tctctcttca cctctgatcc agacgtcgct tccgcccgtg      900
aagttgagaa gggctgggct tcctctgagg gtgacaaagc agctgaatct ccagtggccg     960
```

-continued

```
agtggtccac cgaacagcct aacgatgagc ttttggaaca gcttggccgc ttggcaccta   1020
tggagaacct gtacttccag ggtgcagcaa ccgaagatcc gggcgaccca ggtgcatacg   1080
cagtgaccga agctgagtac gatttcggcg accgtgctgt cgcactcgca ggtatcggcg   1140
gtattcgtgg cgagatgacc ggcaagcttt acttgaccga cgcacctggt gaacgtccta   1200
ccgtcatcct gctccacggt cgtcactcct cttgctccac cggcaccgct aacccacttc   1260
gctggccttg tgcccgaac caggttaacg tgcgttccta ccagggttac gagggcaccg   1320
cacgtgctct cgcatctcac ggctacaacg ttgcatccat tgcagctaac gctgtgaact   1380
ccaacgacaa ccagctggca ctcgattacg gcgcgaaggc acgcggtcag cttatcttgg   1440
ataccctgac catgctcggc aaagcttctg ccggtgaacc ggtggtcctt gatgacattt   1500
cctggccaga tgctgacggc aacgttacca ccaccaccg ctccttggat gacgcgctgg   1560
tgctcgcaac cacccgtgct gactctccag cagcacctgg cggtgtgacc gcagcttccc   1620
ttcagggccg cttcgatttg gaccgtgtcg gcatcatggg tcactctcgc ggcggtgaag   1680
gtgctacctc tgcagtgacc cttaaccagg gcttggctga tccattcggt attgtcgcag   1740
ttcttccgtt ggctccagtt gacttcggcc gtatgaccgt ggccgatacc ccgatggcgg   1800
tcttcctgcc atactgcgat ggcgacgtct ctaaccagca gggtcagcac atggttgatg   1860
actcccgcca cgcattcgtc gatgacgtta tgcgttctgc cgtctggatc atgggcgcga   1920
accacaactt cttcaacacc gtttggaccc caggtctgta cccttacgct acctctgatg   1980
actggaaccg caacgaccag acctctacct gttccaccgc acacgagtcc cgtctgaccc   2040
cagcacagca gtaccaagtg ggcgtctcct acatgaccgg tttcttccgc ctcaccatgg   2100
gcggtgaaac ccagttccag cctatgttcg acggctccgt caccccgacc accaccgcaa   2160
ccggtttcgc agatgttcgt gtgatggcct ctcagccagc gtccgcaacc accgttatcg   2220
cagatttcga ggaccgctcc accctgattc gtacctctgg caacgcttcc gcccaggttt   2280
gcgcgaacgc agaaaccgca acctctatcg ctccttccgt gccgtactgt accgtgcgtc   2340
cagtcggcac cgcacgtgtg ccgcactgga ccccagtccg cttcggtctg aacgttccag   2400
cttaccctgt tacccgtgtg ctctggaccg gctccacctc tacccccggca gcaccatcca   2460
ccggtgtgct tcacgtcgca gttccggaag gctctcgcga cgtctccggt cacacccagt   2520
tgaccgttaa ggcagctcca gatatctctg tggactccgg caccgatttc accatcaccg   2580
tcattgatgg tgctggcaac tccttctcta cccctgcttc cgccgtcaac ccgcttgcag   2640
ttaaccgcat gccaggcggc acccacgcta ccttgaacaa aatcgtgctt cagcagttga   2700
ccgtcccgac ctctgagatg accggcattg atctgaccga cgtccgcgaa gttcgtttcg   2760
cagcgggtgt gggtgcagat ggcaccggtg ctggcggtct gtacctctcc gacctcgctt   2820
tcgataccc taccttcgca cctgcagttg tgggcacccg taccaccgtt aacatcgcct   2880
ctaccttcgt ggaagagggt gattccaccg acaccgcaca ggtggcagtc tccctggacc   2940
gtgaagcaga gcgtgaagtg accgcttggg tctctttcgt tccagtgtcc ggtcctgtcg   3000
cagctgcagt gcaggatgtc accttcgcac caggcgagac ctgccgtgtc gttgaagtcc   3060
cagttaccgg taacaccgca ccttctgcta ccgcatccac cgcaatcacc gtgtccgcaa   3120
ccaacaccgc gaacgcagtc atgggtgctg acgcattcgg caccctggtg gtgcgtgagg   3180
atgacggcgt gaccggtcca gcagtcgaac tcccacctgt gggcgtccag ggtgacgcat   3240
gcgcagagct tgcagcagct caggagcctg gcgaattgac cgtttctgca gatgaggtgg   3300
caccgggcgg ttccgttgaa ctgaccgcag caggtttccg tgttggtgaa tccgtgcgtt   3360
```

```
tcaccttcgg cgatgacgag ctgggtgctg tcctcgctga cgccgaaggc gttgccaccg    3420
ttaccgtgga tgtcccagaa gagtccgctc tcggtgcacg taccgcatct gcattcggtg    3480
caggctccgc acgtgtccag accgcaatgg ttgatgtgct tgctcctacc gccaccacct    3540
tgaccgtgga cgaaggctcc accctggtcg agggtgatga actcaccttc gttgctgagg    3600
tgaccggtgc agaaaccgca ggcaccgtca ccttcgtttc cggttctggc tccggtgcag    3660
ctgacgcagc agcagctggc gaggttctgg caccgcagat gttgtggac ggcgtggcta    3720 cccttacctt gggcgatggt ctcgctgaag gtgcctactc cgtcgttgcc gcgttcgctc    3780
gcaccgacat cgcttctgcc tcctcttccg atccagtgga gttcgaaatt ccgcagctg    3840 ccaccaagcc gccagtggtc aaccctccgg gcaccggcac ccaggcggc ggcgactccg    3900 gcaccgcatc ttcctctgat ggccctctgg ctcacaccgg tttcgatggc ctcggttggg    3960
cccttttggc ggcactggcg ctcttcgcag ttggcgctac cgttgtcgtg gctcgtcgtc    4020
agacccgttc taccccagag tcctaaggat cc                                  4052

<210> SEQ ID NO 19
<211> LENGTH: 3393
<212> TYPE: DNA
<213> ORGANISM: Agromyces sp.
<220> FEATURE:
<221> NAME/KEY: CDS
<222> LOCATION: (1)..(3393)

<400> SEQUENCE: 19 ctg ggt gct gct ccg gct gca aat gct gtg ccg gaa cat ggc gtt atc     48
Leu Gly Ala Ala Pro Ala Ala Asn Ala Val Pro Glu His Gly Val Ile
1               5                   10                  15 gct tcg ggt gac gac tgg acg att gaa acc gct ccg ggt ggc tat ctg    96
Ala Ser Gly Asp Asp Trp Thr Ile Glu Thr Ala Pro Gly Gly Tyr Leu
                20                  25                  30 gtg acc tac cag ctg gca gaa ccg ctg ccg att gtt tct gac gcg ccg    144
Val Thr Tyr Gln Leu Ala Glu Pro Leu Pro Ile Val Ser Asp Ala Pro
            35                  40                  45 acc ctg ctg atc gat ggc gaa ccg gct ggt tat gcg acc gaa agt gcg    192
Thr Leu Leu Ile Asp Gly Glu Pro Ala Gly Tyr Ala Thr Glu Ser Ala
        50                  55                  60 gat ggt cgt tca ctg tcg ctg ttt acc agc gat ccg gac gtt gca agc    240
Asp Gly Arg Ser Leu Ser Leu Phe Thr Ser Asp Pro Asp Val Ala Ser
65                  70                  75                  80 gca cgc gaa gtc gaa aaa ggc tgg gcc agc tct gaa ggt gac aaa gcg    288
Ala Arg Glu Val Glu Lys Gly Trp Ala Ser Ser Glu Gly Asp Lys Ala
                85                  90                  95 gcc gaa tct ccg gtg gca gaa tgg agt acc gaa cag ccg aat gat gaa    336
Ala Glu Ser Pro Val Ala Glu Trp Ser Thr Glu Gln Pro Asn Asp Glu
            100                 105                 110 ctg ctg gaa caa ctg ggc cgt ctg gcg ccg atg gaa aac ctg tat ttc    384
Leu Leu Glu Gln Leu Gly Arg Leu Ala Pro Met Glu Asn Leu Tyr Phe
        115                 120                 125 cag ggt gca gct acc gaa gat ccg ggc gac ccg ggt gct tat gca gtg    432
Gln Gly Ala Ala Thr Glu Asp Pro Gly Asp Pro Gly Ala Tyr Ala Val
    130                 135                 140 acc gaa gcc gaa tac gat ttt ggc gac cgt gcc gtt gca ctg gct ggt    480
Thr Glu Ala Glu Tyr Asp Phe Gly Asp Arg Ala Val Ala Leu Ala Gly
145                 150                 155                 160 att ggc ggt atc cgc ggc gaa atg acc ggt aaa ctg tac ctg acg gat    528
Ile Gly Gly Ile Arg Gly Glu Met Thr Gly Lys Leu Tyr Leu Thr Asp
                165                 170                 175
```

```
gca ccg ggt gaa cgt ccg acc gtg att ctg ctg cat ggt cgt cac agt      576
Ala Pro Gly Glu Arg Pro Thr Val Ile Leu Leu His Gly Arg His Ser
            180                 185                 190 tcc tgc tcc acg ggc acc gca aat ccg ctg cgt tgg ccg tgt ggt ccg      624
Ser Cys Ser Thr Gly Thr Ala Asn Pro Leu Arg Trp Pro Cys Gly Pro
        195                 200                 205 aat cag gtc aac gtg cgt tca tat caa ggt tac gaa ggc acc gca cgt      672
Asn Gln Val Asn Val Arg Ser Tyr Gln Gly Tyr Glu Gly Thr Ala Arg
    210                 215                 220 gca ctg gca tcg cat ggt tat aat gtc gcg agc atc gcg gcc aac gcc      720
Ala Leu Ala Ser His Gly Tyr Asn Val Ala Ser Ile Ala Ala Asn Ala
225                 230                 235                 240 gtg aac tct aat gac aac cag ctg gcg ctg gat tac ggc gct aaa gcg      768
Val Asn Ser Asn Asp Asn Gln Leu Ala Leu Asp Tyr Gly Ala Lys Ala
                245                 250                 255 cgc ggt caa ctg att ctg gat acg ctg acc atg ctg ggc aaa gcc tct      816
Arg Gly Gln Leu Ile Leu Asp Thr Leu Thr Met Leu Gly Lys Ala Ser
            260                 265                 270 gca ggt gaa ccg gtg gtt ctg gat gac atc agt tgg ccg gat gcg gac      864
Ala Gly Glu Pro Val Val Leu Asp Asp Ile Ser Trp Pro Asp Ala Asp
        275                 280                 285 ggc aat gtg acc acg acc acg cgt agc ctg gat gac gct ctg gtt ctg      912
Gly Asn Val Thr Thr Thr Thr Arg Ser Leu Asp Asp Ala Leu Val Leu
    290                 295                 300 gca acc acg cgt gca gat tcc ccg gca gct ccg ggc ggt gtg acc gcg      960
Ala Thr Thr Arg Ala Asp Ser Pro Ala Ala Pro Gly Gly Val Thr Ala
305                 310                 315                 320 gcc tca ctg cag ggc cgt ttc gat ctg gac cgc gtt ggc att atg ggt     1008
Ala Ser Leu Gln Gly Arg Phe Asp Leu Asp Arg Val Gly Ile Met Gly
                325                 330                 335 cac tct cgt ggc ggt gaa ggt gcc acc agt gca gtg acg ctg aac cag     1056
His Ser Arg Gly Gly Glu Gly Ala Thr Ser Ala Val Thr Leu Asn Gln
            340                 345                 350 ggc ctg gcc gat ccg ttt ggt atc gtt gca gtc ctg ccg ctg gca ccg     1104
Gly Leu Ala Asp Pro Phe Gly Ile Val Ala Val Leu Pro Leu Ala Pro
        355                 360                 365 gtc gac ttc ggt cgc atg acc gtg gca gat acg ccg atg gct gtt ttt     1152
Val Asp Phe Gly Arg Met Thr Val Ala Asp Thr Pro Met Ala Val Phe
    370                 375                 380 ctg ccg tat tgc gat ggc gac gtt tcg aat cag cag ggt cag cat atg     1200
Leu Pro Tyr Cys Asp Gly Asp Val Ser Asn Gln Gln Gly Gln His Met
385                 390                 395                 400 gtc gat gac agc cgt cac gcg ttt gtt gat gac gtc atg cgc tct gca     1248
Val Asp Asp Ser Arg His Ala Phe Val Asp Asp Val Met Arg Ser Ala
                405                 410                 415 gtg tgg att atg ggc gct aat cat aac ttt ttc aac acg gtt tgg acc     1296
Val Trp Ile Met Gly Ala Asn His Asn Phe Phe Asn Thr Val Trp Thr
            420                 425                 430 ccg ggt ctg tat ccg tac gcc acc agc gat gac tgg aat cgt aac gat     1344
Pro Gly Leu Tyr Pro Tyr Ala Thr Ser Asp Asp Trp Asn Arg Asn Asp
        435                 440                 445 cag acg tct acc tgt agt acc gca cac gaa tcg cgt ctg acg ccg gca     1392
Gln Thr Ser Thr Cys Ser Thr Ala His Glu Ser Arg Leu Thr Pro Ala
    450                 455                 460 cag caa tat caa gtg ggc gtt agc tac atg acc ggt ttc ttc cgt ctg     1440
Gln Gln Tyr Gln Val Gly Val Ser Tyr Met Thr Gly Phe Phe Arg Leu
465                 470                 475                 480 acc atg ggc ggt gaa acg cag ttt caa ccg atg ttc gac ggc tct gtg     1488
Thr Met Gly Gly Glu Thr Gln Phe Gln Pro Met Phe Asp Gly Ser Val
```

-continued

|     |     |     |     |     | 485 |     |     |     | 490 |     |     |     |     | 495 |     |      |
|-----|-----|-----|-----|-----|-----|-----|-----|-----|-----|-----|-----|-----|-----|-----|-----|------|
| acc | ccg | acc | acg | acc | gca | acg | ggt | ttc | gct | gat | gtc | cgt | gtg | atg | gca | 1536 |
| Thr | Pro | Thr | Thr | Thr | Ala | Thr | Gly | Phe | Ala | Asp | Val | Arg | Val | Met | Ala |      |
|     |     |     | 500 |     |     |     |     | 505 |     |     |     |     | 510 |     |     |      |

| tcg | cag | ccg | gct | agc | gca | acg | acc | gtt | att | gcg | gat | ttt | gaa | gac | cgt | 1584 |
|-----|-----|-----|-----|-----|-----|-----|-----|-----|-----|-----|-----|-----|-----|-----|-----|------|
| Ser | Gln | Pro | Ala | Ser | Ala | Thr | Thr | Val | Ile | Ala | Asp | Phe | Glu | Asp | Arg |      |
|     |     | 515 |     |     |     |     | 520 |     |     |     |     | 525 |     |     |     |      |

| agt | acc | ctg | atc | cgc | acg | tct | ggc | aat | gcc | agt | gca | caa | gtg | tgc | gct | 1632 |
|-----|-----|-----|-----|-----|-----|-----|-----|-----|-----|-----|-----|-----|-----|-----|-----|------|
| Ser | Thr | Leu | Ile | Arg | Thr | Ser | Gly | Asn | Ala | Ser | Ala | Gln | Val | Cys | Ala |      |
|     | 530 |     |     |     |     | 535 |     |     |     |     | 540 |     |     |     |     |      |

| aac | gcg | gaa | acg | gcg | acc | agc | att | gcc | ccg | tca | gtt | ccg | tat | tgt | acc | 1680 |
|-----|-----|-----|-----|-----|-----|-----|-----|-----|-----|-----|-----|-----|-----|-----|-----|------|
| Asn | Ala | Glu | Thr | Ala | Thr | Ser | Ile | Ala | Pro | Ser | Val | Pro | Tyr | Cys | Thr |      |
| 545 |     |     |     |     | 550 |     |     |     |     | 555 |     |     |     |     | 560 |      |

| gtg | cgt | ccg | gtt | ggc | acg | gca | cgc | gtg | ccg | cat | tgg | acc | ccg | gtt | cgt | 1728 |
|-----|-----|-----|-----|-----|-----|-----|-----|-----|-----|-----|-----|-----|-----|-----|-----|------|
| Val | Arg | Pro | Val | Gly | Thr | Ala | Arg | Val | Pro | His | Trp | Thr | Pro | Val | Arg |      |
|     |     |     |     | 565 |     |     |     |     | 570 |     |     |     |     | 575 |     |      |

| ttt | ggt | ctg | aac | gtc | ccg | gca | tac | ccg | gtc | acc | cgt | gtg | ctg | tgg | acg | 1776 |
|-----|-----|-----|-----|-----|-----|-----|-----|-----|-----|-----|-----|-----|-----|-----|-----|------|
| Phe | Gly | Leu | Asn | Val | Pro | Ala | Tyr | Pro | Val | Thr | Arg | Val | Leu | Trp | Thr |      |
|     |     |     | 580 |     |     |     |     | 585 |     |     |     |     | 590 |     |     |      |

| ggc | agc | acg | tct | acc | ccg | gca | gct | ccg | agc | acc | ggt | gtg | ctg | cat | gtt | 1824 |
|-----|-----|-----|-----|-----|-----|-----|-----|-----|-----|-----|-----|-----|-----|-----|-----|------|
| Gly | Ser | Thr | Ser | Thr | Pro | Ala | Ala | Pro | Ser | Thr | Gly | Val | Leu | His | Val |      |
|     |     | 595 |     |     |     |     | 600 |     |     |     |     | 605 |     |     |     |      |

| gcg | gtc | ccg | gaa | ggc | tcg | cgt | gat | gtt | agc | ggt | cac | acg | cag | ctg | acc | 1872 |
|-----|-----|-----|-----|-----|-----|-----|-----|-----|-----|-----|-----|-----|-----|-----|-----|------|
| Ala | Val | Pro | Glu | Gly | Ser | Arg | Asp | Val | Ser | Gly | His | Thr | Gln | Leu | Thr |      |
|     | 610 |     |     |     |     | 615 |     |     |     |     | 620 |     |     |     |     |      |

| gtc | aaa | gcg | gcc | ccg | gat | atc | tcc | gtg | gac | tca | ggc | acc | gat | ttt | acg | 1920 |
|-----|-----|-----|-----|-----|-----|-----|-----|-----|-----|-----|-----|-----|-----|-----|-----|------|
| Val | Lys | Ala | Ala | Pro | Asp | Ile | Ser | Val | Asp | Ser | Gly | Thr | Asp | Phe | Thr |      |
| 625 |     |     |     |     | 630 |     |     |     |     | 635 |     |     |     |     | 640 |      |

| att | acc | gtt | atc | gat | ggt | gcg | ggc | aat | agt | ttc | tcc | acc | ccg | gca | tcg | 1968 |
|-----|-----|-----|-----|-----|-----|-----|-----|-----|-----|-----|-----|-----|-----|-----|-----|------|
| Ile | Thr | Val | Ile | Asp | Gly | Ala | Gly | Asn | Ser | Phe | Ser | Thr | Pro | Ala | Ser |      |
|     |     |     |     | 645 |     |     |     |     | 650 |     |     |     |     | 655 |     |      |

| gca | gtt | aat | ccg | ctg | gca | gtc | aac | cgt | atg | ccg | ggc | ggt | acg | cac | gca | 2016 |
|-----|-----|-----|-----|-----|-----|-----|-----|-----|-----|-----|-----|-----|-----|-----|-----|------|
| Ala | Val | Asn | Pro | Leu | Ala | Val | Asn | Arg | Met | Pro | Gly | Gly | Thr | His | Ala |      |
|     |     |     | 660 |     |     |     |     | 665 |     |     |     |     | 670 |     |     |      |

| acc | ctg | aac | aaa | att | gtg | ctg | cag | caa | ctg | acg | gtt | ccg | acc | tct | gaa | 2064 |
|-----|-----|-----|-----|-----|-----|-----|-----|-----|-----|-----|-----|-----|-----|-----|-----|------|
| Thr | Leu | Asn | Lys | Ile | Val | Leu | Gln | Gln | Leu | Thr | Val | Pro | Thr | Ser | Glu |      |
|     |     | 675 |     |     |     |     | 680 |     |     |     |     | 685 |     |     |     |      |

| atg | acc | ggt | atc | gat | ctg | acg | gac | gtt | cgt | gaa | gtc | cgt | ttc | gca | gct | 2112 |
|-----|-----|-----|-----|-----|-----|-----|-----|-----|-----|-----|-----|-----|-----|-----|-----|------|
| Met | Thr | Gly | Ile | Asp | Leu | Thr | Asp | Val | Arg | Glu | Val | Arg | Phe | Ala | Ala |      |
|     | 690 |     |     |     |     | 695 |     |     |     |     | 700 |     |     |     |     |      |

| ggt | gtg | ggt | gca | gat | ggc | acc | ggt | gcc | ggc | ggt | ctg | tat | ctg | agc | gac | 2160 |
|-----|-----|-----|-----|-----|-----|-----|-----|-----|-----|-----|-----|-----|-----|-----|-----|------|
| Gly | Val | Gly | Ala | Asp | Gly | Thr | Gly | Ala | Gly | Gly | Leu | Tyr | Leu | Ser | Asp |      |
| 705 |     |     |     |     | 710 |     |     |     |     | 715 |     |     |     |     | 720 |      |

| ctg | gcg | ttt | gat | acg | ccg | acc | ttc | gct | ccg | gca | gtc | gtg | ggc | acc | cgt | 2208 |
|-----|-----|-----|-----|-----|-----|-----|-----|-----|-----|-----|-----|-----|-----|-----|-----|------|
| Leu | Ala | Phe | Asp | Thr | Pro | Thr | Phe | Ala | Pro | Ala | Val | Val | Gly | Thr | Arg |      |
|     |     |     |     | 725 |     |     |     |     | 730 |     |     |     |     | 735 |     |      |

| acg | acc | gtc | aat | att | gcc | tcc | acg | ttt | gtg | gaa | gaa | ggt | gat | agc | acg | 2256 |
|-----|-----|-----|-----|-----|-----|-----|-----|-----|-----|-----|-----|-----|-----|-----|-----|------|
| Thr | Thr | Val | Asn | Ile | Ala | Ser | Thr | Phe | Val | Glu | Glu | Gly | Asp | Ser | Thr |      |
|     |     |     | 740 |     |     |     |     | 745 |     |     |     |     | 750 |     |     |      |

| gac | acc | gct | cag | gtg | gcg | gtt | agc | ctg | gat | cgt | gaa | gcg | gaa | cgc | gaa | 2304 |
|-----|-----|-----|-----|-----|-----|-----|-----|-----|-----|-----|-----|-----|-----|-----|-----|------|
| Asp | Thr | Ala | Gln | Val | Ala | Val | Ser | Leu | Asp | Arg | Glu | Ala | Glu | Arg | Glu |      |
|     |     | 755 |     |     |     |     | 760 |     |     |     |     | 765 |     |     |     |      |

| gtg | acc | gcc | tgg | gtt | tcc | ttc | gtc | ccg | gtg | tca | ggt | ccg | gtg | gca | gca | 2352 |
|-----|-----|-----|-----|-----|-----|-----|-----|-----|-----|-----|-----|-----|-----|-----|-----|------|
| Val | Thr | Ala | Trp | Val | Ser | Phe | Val | Pro | Val | Ser | Gly | Pro | Val | Ala | Ala |      |
|     | 770 |     |     |     |     | 775 |     |     |     |     | 780 |     |     |     |     |      |

| gca | gtg | cag | gat | gtt | acc | ttt | gca | ccg | ggc | gaa | acg | tgc | cgt | gtt | gtc | 2400 |
|-----|-----|-----|-----|-----|-----|-----|-----|-----|-----|-----|-----|-----|-----|-----|-----|------|
| Ala | Val | Gln | Asp | Val | Thr | Phe | Ala | Pro | Gly | Glu | Thr | Cys | Arg | Val | Val |      |
| 785 |     |     |     |     | 790 |     |     |     |     | 795 |     |     |     |     | 800 |      |

| gaa | gtt | ccg | gtc | acg | ggt | aac | acc | gca | ccg | tct | gca | acg | gca | agt | acc | 2448 |
|-----|-----|-----|-----|-----|-----|-----|-----|-----|-----|-----|-----|-----|-----|-----|-----|------|

-continued

```
                Glu Val Pro Val Thr Gly Asn Thr Ala Pro Ser Ala Thr Ala Ser Thr
                                805                 810                 815 gca atc acc gtg agc gct acg aat acc gct aac gcg gtt atg ggc gcc              2496
Ala Ile Thr Val Ser Ala Thr Asn Thr Ala Asn Ala Val Met Gly Ala
            820                 825                 830 gat gca ttt ggc acc ctg gtg gtg cgt gaa gat gac ggt gtg acg ggt              2544
Asp Ala Phe Gly Thr Leu Val Val Arg Glu Asp Asp Gly Val Thr Gly
            835                 840                 845 ccg gca gtt gaa ctg ccg ccg gtg ggc gtt cag ggt gat gct tgt gcg              2592
Pro Ala Val Glu Leu Pro Pro Val Gly Val Gln Gly Asp Ala Cys Ala
    850                 855                 860 gaa ctg gct gcg gcc caa gaa ccg ggt gaa ctg acc gtc tcg gca gat              2640
Glu Leu Ala Ala Ala Gln Glu Pro Gly Glu Leu Thr Val Ser Ala Asp
865                 870                 875                 880 gaa gtg gct ccg ggc ggt agc gtg gaa ctg acc gca gct ggc ttc cgt              2688
Glu Val Ala Pro Gly Gly Ser Val Glu Leu Thr Ala Ala Gly Phe Arg
                885                 890                 895 gtc ggt gaa agt gtg cgc ttt acc ttc ggc gat gac gaa ctg ggt gcc              2736
Val Gly Glu Ser Val Arg Phe Thr Phe Gly Asp Asp Glu Leu Gly Ala
            900                 905                 910 gtt ctg gcc gac gca gaa ggc gtc gca acg gtc acc gtg gat gtt ccg              2784
Val Leu Ala Asp Ala Glu Gly Val Ala Thr Val Thr Val Asp Val Pro
            915                 920                 925 gaa gaa tcc gca ctg ggt gca cgt acc gct tcc gca ttt ggt gct ggc              2832
Glu Glu Ser Ala Leu Gly Ala Arg Thr Ala Ser Ala Phe Gly Ala Gly
930                 935                 940 tca gca cgt gtg cag acc gca atg gtc gat gtg ctg gca ccg acc gca              2880
Ser Ala Arg Val Gln Thr Ala Met Val Asp Val Leu Ala Pro Thr Ala
945                 950                 955                 960 acg acc ctg acg gtg gac gaa ggc agc acc ctg gtt gaa ggt gat gaa              2928
Thr Thr Leu Thr Val Asp Glu Gly Ser Thr Leu Val Glu Gly Asp Glu
                965                 970                 975 ctg acg ttc gtc gcc gaa gtg acc ggt gct gaa acg gcc ggt acg gtt              2976
Leu Thr Phe Val Ala Glu Val Thr Gly Ala Glu Thr Ala Gly Thr Val
            980                 985                 990 acc ttt gtc tca ggt tcg ggc agc  ggt gca gca gat gca  gct gca gcc            3024
Thr Phe Val Ser Gly Ser Gly Ser  Gly Ala Ala Asp Ala  Ala Ala Ala
            995                 1000                1005 ggc gaa gtg ctg ggc acc gca  gat gtc gtg gac ggt  gtt gca acg                3069
Gly Glu Val Leu Gly Thr Ala  Asp Val Val Asp Gly  Val Ala Thr
    1010                1015                1020 ctg acc ctg ggt gat ggt ctg  gca gaa ggt gca tac  agt gtt gtc                3114
Leu Thr Leu Gly Asp Gly Leu  Ala Glu Gly Ala Tyr  Ser Val Val
    1025                1030                1035 gca gct ttc gcg cgc acc gac  att gcc tcc gca tca  tcg agc gat                3159
Ala Ala Phe Ala Arg Thr Asp  Ile Ala Ser Ala Ser  Ser Ser Asp
    1040                1045                1050 ccg gtg gaa ttt gaa atc tca  gcg gcc gca acc aaa  ccg ccg gtg                3204
Pro Val Glu Phe Glu Ile Ser  Ala Ala Ala Thr Lys  Pro Pro Val
    1055                1060                1065 gtt aat ccg ccg ggc acg ggc  acc ccg ggc ggc ggc  gac agc ggc                3249
Val Asn Pro Pro Gly Thr Gly  Thr Pro Gly Gly Gly  Asp Ser Gly
    1070                1075                1080 acc gca tct agt tcc gat ggt  ccg ctg gca cat acg  ggt ttc gat                3294
Thr Ala Ser Ser Ser Asp Gly  Pro Leu Ala His Thr  Gly Phe Asp
    1085                1090                1095 ggt ctg ggt tgg gca ctg ctg  gct gca ctg gct ctg  ttt gct gtc                3339
Gly Leu Gly Trp Ala Leu Leu  Ala Ala Leu Ala Leu  Phe Ala Val
    1100                1105                1110
```

```
ggt gct acg gtt gtt gtc gcc cgc cgc cag acc cgc agt acc ccg    3384
Gly Ala Thr Val Val Val Ala Arg Arg Gln Thr Arg Ser Thr Pro
1115                1120                1125 gaa tca taa                                                     3393
Glu Ser
    1130
```

<210> SEQ ID NO 20
<211> LENGTH: 1130
<212> TYPE: PRT
<213> ORGANISM: Agromyces sp.

<400> SEQUENCE: 20

```
Leu Gly Ala Ala Pro Ala Ala Asn Ala Val Pro Glu His Gly Val Ile
1               5                   10                  15

Ala Ser Gly Asp Asp Trp Thr Ile Glu Thr Ala Pro Gly Gly Tyr Leu
            20                  25                  30

Val Thr Tyr Gln Leu Ala Glu Pro Leu Pro Ile Val Ser Asp Ala Pro
        35                  40                  45

Thr Leu Leu Ile Asp Gly Glu Pro Ala Gly Tyr Ala Thr Glu Ser Ala
    50                  55                  60

Asp Gly Arg Ser Leu Ser Leu Phe Thr Ser Asp Pro Asp Val Ala Ser
65                  70                  75                  80

Ala Arg Glu Val Glu Lys Gly Trp Ala Ser Ser Glu Gly Asp Lys Ala
                85                  90                  95

Ala Glu Ser Pro Val Ala Glu Trp Ser Thr Glu Gln Pro Asn Asp Glu
            100                 105                 110

Leu Leu Glu Gln Leu Gly Arg Leu Ala Pro Met Glu Asn Leu Tyr Phe
        115                 120                 125

Gln Gly Ala Ala Thr Glu Asp Pro Gly Asp Pro Gly Ala Tyr Ala Val
    130                 135                 140

Thr Glu Ala Glu Tyr Asp Phe Gly Asp Arg Ala Val Ala Leu Ala Gly
145                 150                 155                 160

Ile Gly Gly Ile Arg Gly Glu Met Thr Gly Lys Leu Tyr Leu Thr Asp
                165                 170                 175

Ala Pro Gly Glu Arg Pro Thr Val Ile Leu Leu His Gly Arg His Ser
            180                 185                 190

Ser Cys Ser Thr Gly Thr Ala Asn Pro Leu Arg Trp Pro Cys Gly Pro
        195                 200                 205

Asn Gln Val Asn Val Arg Ser Tyr Gln Gly Tyr Glu Gly Thr Ala Arg
    210                 215                 220

Ala Leu Ala Ser His Gly Tyr Asn Val Ala Ser Ile Ala Ala Asn Ala
225                 230                 235                 240

Val Asn Ser Asn Asp Asn Gln Leu Ala Leu Asp Tyr Gly Ala Lys Ala
                245                 250                 255

Arg Gly Gln Leu Ile Leu Asp Thr Leu Thr Met Leu Gly Lys Ala Ser
            260                 265                 270

Ala Gly Glu Pro Val Val Leu Asp Asp Ile Ser Trp Pro Asp Ala Asp
        275                 280                 285

Gly Asn Val Thr Thr Thr Thr Arg Ser Leu Asp Ala Leu Val Leu
    290                 295                 300

Ala Thr Thr Arg Ala Asp Ser Pro Ala Ala Pro Gly Val Thr Ala
305                 310                 315                 320

Ala Ser Leu Gln Gly Arg Phe Asp Leu Asp Arg Val Gly Ile Met Gly
                325                 330                 335
```

-continued

```
His Ser Arg Gly Gly Glu Gly Ala Thr Ser Ala Val Thr Leu Asn Gln
            340                 345                 350

Gly Leu Ala Asp Pro Phe Gly Ile Val Ala Val Leu Pro Leu Ala Pro
        355                 360                 365

Val Asp Phe Gly Arg Met Thr Val Ala Asp Thr Pro Met Ala Val Phe
    370                 375                 380

Leu Pro Tyr Cys Asp Gly Asp Val Ser Asn Gln Gln Gly Gln His Met
385                 390                 395                 400

Val Asp Asp Ser Arg His Ala Phe Val Asp Val Met Arg Ser Ala
                405                 410                 415

Val Trp Ile Met Gly Ala Asn His Asn Phe Asn Thr Val Trp Thr
                420                 425                 430

Pro Gly Leu Tyr Pro Tyr Ala Thr Ser Asp Asp Trp Asn Arg Asn Asp
        435                 440                 445

Gln Thr Ser Thr Cys Ser Thr Ala His Glu Ser Arg Leu Thr Pro Ala
        450                 455                 460

Gln Gln Tyr Gln Val Gly Val Ser Tyr Met Thr Gly Phe Phe Arg Leu
465                 470                 475                 480

Thr Met Gly Gly Glu Thr Gln Phe Gln Pro Met Phe Asp Gly Ser Val
                485                 490                 495

Thr Pro Thr Thr Thr Ala Thr Gly Phe Ala Asp Val Arg Val Met Ala
                500                 505                 510

Ser Gln Pro Ala Ser Ala Thr Val Ile Ala Asp Phe Glu Asp Arg
        515                 520                 525

Ser Thr Leu Ile Arg Thr Ser Gly Asn Ala Ser Ala Gln Val Cys Ala
530                 535                 540

Asn Ala Glu Thr Ala Thr Ser Ile Ala Pro Ser Val Pro Tyr Cys Thr
545                 550                 555                 560

Val Arg Pro Val Gly Thr Ala Arg Val Pro His Trp Thr Pro Val Arg
                565                 570                 575

Phe Gly Leu Asn Val Pro Ala Tyr Pro Val Thr Arg Val Leu Trp Thr
                580                 585                 590

Gly Ser Thr Ser Thr Pro Ala Ala Pro Ser Thr Gly Val Leu His Val
            595                 600                 605

Ala Val Pro Glu Gly Ser Arg Asp Val Ser Gly His Thr Gln Leu Thr
    610                 615                 620

Val Lys Ala Ala Pro Asp Ile Ser Val Asp Ser Gly Thr Asp Phe Thr
625                 630                 635                 640

Ile Thr Val Ile Asp Gly Ala Gly Asn Ser Phe Ser Thr Pro Ala Ser
                645                 650                 655

Ala Val Asn Pro Leu Ala Val Asn Arg Met Pro Gly Gly Thr His Ala
                660                 665                 670

Thr Leu Asn Lys Ile Val Leu Gln Gln Leu Thr Val Pro Thr Ser Glu
        675                 680                 685

Met Thr Gly Ile Asp Leu Thr Asp Val Arg Glu Val Arg Phe Ala Ala
        690                 695                 700

Gly Val Gly Ala Asp Gly Thr Gly Ala Gly Gly Leu Tyr Leu Ser Asp
705                 710                 715                 720

Leu Ala Phe Asp Thr Pro Thr Phe Ala Pro Ala Val Val Gly Thr Arg
                725                 730                 735

Thr Thr Val Asn Ile Ala Ser Thr Phe Val Glu Glu Gly Asp Ser Thr
                740                 745                 750

Asp Thr Ala Gln Val Ala Val Ser Leu Asp Arg Glu Ala Glu Arg Glu
```

```
                755                 760                 765
Val Thr Ala Trp Val Ser Phe Val Pro Val Ser Gly Pro Val Ala Ala
770                 775                 780

Ala Val Gln Asp Val Thr Phe Ala Pro Gly Glu Thr Cys Arg Val Val
785                 790                 795                 800

Glu Val Pro Val Thr Gly Asn Thr Ala Pro Ser Ala Thr Ala Ser Thr
                805                 810                 815

Ala Ile Thr Val Ser Ala Thr Asn Thr Ala Asn Ala Val Met Gly Ala
                820                 825                 830

Asp Ala Phe Gly Thr Leu Val Val Arg Glu Asp Gly Val Thr Gly
            835                 840                 845

Pro Ala Val Glu Leu Pro Pro Val Gly Val Gln Gly Asp Ala Cys Ala
850                 855                 860

Glu Leu Ala Ala Ala Gln Glu Pro Gly Glu Leu Thr Val Ser Ala Asp
865                 870                 875                 880

Glu Val Ala Pro Gly Gly Ser Val Glu Leu Thr Ala Ala Gly Phe Arg
                885                 890                 895

Val Gly Glu Ser Val Arg Phe Thr Phe Gly Asp Asp Glu Leu Gly Ala
                900                 905                 910

Val Leu Ala Asp Ala Glu Gly Val Ala Thr Val Thr Val Asp Val Pro
            915                 920                 925

Glu Glu Ser Ala Leu Gly Ala Arg Thr Ala Ser Ala Phe Gly Ala Gly
930                 935                 940

Ser Ala Arg Val Gln Thr Ala Met Val Asp Val Leu Ala Pro Thr Ala
945                 950                 955                 960

Thr Thr Leu Thr Val Asp Gly Ser Thr Leu Val Glu Gly Asp Glu
                965                 970                 975

Leu Thr Phe Val Ala Glu Val Thr Gly Ala Glu Thr Ala Gly Thr Val
                980                 985                 990

Thr Phe Val Ser Gly Ser Gly Ser  Gly Ala Ala Asp Ala  Ala Ala Ala
            995                 1000                1005

Gly Glu  Val Leu Gly Thr Ala  Asp Val Val Asp Gly  Val Ala Thr
        1010                1015                1020

Leu Thr  Leu Gly Asp Gly Leu  Ala Glu Gly Ala Tyr  Ser Val Val
        1025                1030                1035

Ala Ala  Phe Ala Arg Thr Asp  Ile Ala Ser Ala Ser  Ser Ser Asp
        1040                1045                1050

Pro Val  Glu Phe Glu Ile Ser  Ala Ala Ala Thr Lys  Pro Pro Val
        1055                1060                1065

Val Asn  Pro Pro Gly Thr Gly  Thr Pro Gly Gly Gly  Asp Ser Gly
        1070                1075                1080

Thr Ala  Ser Ser Ser Asp Gly  Pro Leu Ala His Thr  Gly Phe Asp
        1085                1090                1095

Gly Leu  Gly Trp Ala Leu Leu  Ala Ala Leu Ala Leu  Phe Ala Val
        1100                1105                1110

Gly Ala  Thr Val Val Val Ala  Arg Arg Gln Thr Arg  Ser Thr Pro
        1115                1120                1125

Glu Ser
        1130

<210> SEQ ID NO 21
<211> LENGTH: 24
<212> TYPE: DNA
<213> ORGANISM: Artificial Sequence
```

```
<220> FEATURE:
<223> OTHER INFORMATION: primer

<400> SEQUENCE: 21
taggtaatct ctgcttaaaa gcac                                              24

<210> SEQ ID NO 22
<211> LENGTH: 23
<212> TYPE: DNA
<213> ORGANISM: Artificial Sequence
<220> FEATURE:
<223> OTHER INFORMATION: primer

<400> SEQUENCE: 22
cctaccttcg ataccaccac tac                                               23

<210> SEQ ID NO 23
<211> LENGTH: 40
<212> TYPE: DNA
<213> ORGANISM: Artificial Sequence
<220> FEATURE:
<223> OTHER INFORMATION: primer

<400> SEQUENCE: 23
ggtatcgaag gtaggctggg tgctgctccg gctgcaaatg                             40

<210> SEQ ID NO 24
<211> LENGTH: 40
<212> TYPE: DNA
<213> ORGANISM: Artificial Sequence
<220> FEATURE:
<223> OTHER INFORMATION: primer

<400> SEQUENCE: 24
agcagagatt acctattatg attccggggt actgcgggtc                             40

<210> SEQ ID NO 25
<211> LENGTH: 2931
<212> TYPE: DNA
<213> ORGANISM: Leifsonia xyli
<220> FEATURE:
<221> NAME/KEY: CDS
<222> LOCATION: (1)..(2931)

<400> SEQUENCE: 25 ctg acc acg gct ccg gcg gca ctg gcg gca ccg gca ccg gac ccg gtt        48
Leu Thr Thr Ala Pro Ala Ala Leu Ala Ala Pro Ala Pro Asp Pro Val
1               5                   10                  15 gtt gcg tct ggc tcg gat tgg gct gtt acg acc tca ccg ggc ggt tat        96
Val Ala Ser Gly Ser Asp Trp Ala Val Thr Thr Ser Pro Gly Gly Tyr
            20                  25                  30 ctg gtt acc ctg gac ctg gat gaa ccg ctg ccg atg gtc gat gac gca       144
Leu Val Thr Leu Asp Leu Asp Glu Pro Leu Pro Met Val Asp Asp Ala
        35                  40                  45 ccg acc ctg gtg gtt gat ggt gaa ccg att ggc ctg gct acg gaa tcc       192
Pro Thr Leu Val Val Asp Gly Glu Pro Ile Gly Leu Ala Thr Glu Ser
    50                  55                  60 gca gac ggt ctg acc ctg ggc gtc gtg acc acc gat ccg gca gtg gct       240
Ala Asp Gly Leu Thr Leu Gly Val Val Thr Thr Asp Pro Ala Val Ala
65                  70                  75                  80 tca gcg agc tct gtt acc aaa ggt tgg agt tcc ggc gca gat gac aaa       288
Ser Ala Ser Ser Val Thr Lys Gly Trp Ser Ser Gly Ala Asp Asp Lys
                85                  90                  95 gca gca gaa acg ccg gaa gca ccg gca acc ccg gcg gtg ccg gaa aat       336
```

|  |  |  |  |  |  |  |  |  |  |  |  |  |
|---|---|---|---|---|---|---|---|---|---|---|---|---|
| Ala | Ala | Glu | Thr<br>100 | Pro | Glu | Ala | Pro<br>105 | Ala | Thr | Pro | Ala<br>110 | Val | Pro | Glu | Asn |

```
acc acg ctg acc gaa cag ctg aaa tct ttt gcc caa ctg gaa aac ctg     384
Thr Thr Leu Thr Glu Gln Leu Lys Ser Phe Ala Gln Leu Glu Asn Leu
            115                 120                 125 tat ttc cag ggt gtg gca gtt gaa gac ccg gct gat ctg ggc agt tat     432
Tyr Phe Gln Gly Val Ala Val Glu Asp Pro Ala Asp Leu Gly Ser Tyr
        130                 135                 140 acc gtg acg gaa gcc gaa tac gac ttt ggt gat caa gca gtt ccg ctg     480
Thr Val Thr Glu Ala Glu Tyr Asp Phe Gly Asp Gln Ala Val Pro Leu
145                 150                 155                 160 gca gct att ggc ggt atc cgt ggt gaa ctg acc ggc aaa atg tac ctg     528
Ala Ala Ile Gly Gly Ile Arg Gly Glu Leu Thr Gly Lys Met Tyr Leu
                165                 170                 175 acg aat gcc acc ggt gca cgt ccg acc gtt gtc ctg ctg cat ggt cgt     576
Thr Asn Ala Thr Gly Ala Arg Pro Thr Val Val Leu Leu His Gly Arg
            180                 185                 190 cac acc agt tgc tcc ggc acg ggt gca aat ccg ctg cgt tgg ccg tgt     624
His Thr Ser Cys Ser Gly Thr Gly Ala Asn Pro Leu Arg Trp Pro Cys
        195                 200                 205 ggt ccg acc cag atg aac att cgc tcc tat ctg ggt tac gaa ggc acc     672
Gly Pro Thr Gln Met Asn Ile Arg Ser Tyr Leu Gly Tyr Glu Gly Thr
    210                 215                 220 gct cgt gca ctg gca tcg cgc ggc tat aat gtt ctg agc atc gcg gcc     720
Ala Arg Ala Leu Ala Ser Arg Gly Tyr Asn Val Leu Ser Ile Ala Ala
225                 230                 235                 240 aac gca gtc aac agt aat gac aac cag ctg gcg ctg gat tac ggt gca     768
Asn Ala Val Asn Ser Asn Asp Asn Gln Leu Ala Leu Asp Tyr Gly Ala
                245                 250                 255 caa gct cgt ggc cgc ctg gtg ctg gat acg ctg ggt atg ctg gcg aaa     816
Gln Ala Arg Gly Arg Leu Val Leu Asp Thr Leu Gly Met Leu Ala Lys
            260                 265                 270 gcc acc gca ggc gat gct gtg gcg tat gat gac atc acc acg gcg acc     864
Ala Thr Ala Gly Asp Ala Val Ala Tyr Asp Asp Ile Thr Thr Ala Thr
        275                 280                 285 gat acg gtt ccg agc acc acg acc acg cgt acc ctg gac gaa gca ctg     912
Asp Thr Val Pro Ser Thr Thr Thr Thr Arg Thr Leu Asp Glu Ala Leu
    290                 295                 300 ctg cgt gca acc acg cgt gct gat cag ccg gca gct gca tcc ggt att     960
Leu Arg Ala Thr Thr Arg Ala Asp Gln Pro Ala Ala Ala Ser Gly Ile
305                 310                 315                 320 acc gca gca tca ctg aaa ggc cgt ttt gat ctg ggc cat gtt ggt atc    1008
Thr Ala Ala Ser Leu Lys Gly Arg Phe Asp Leu Gly His Val Gly Ile
                325                 330                 335 atg ggt cac tct cgc ggc ggt gaa ggc gtg gtt agc gct gcg acc ctg    1056
Met Gly His Ser Arg Gly Gly Glu Gly Val Val Ser Ala Ala Thr Leu
            340                 345                 350 aat cag gcc ctg gca aaa ccg tat ggt att gaa tct gtc ctg ccg ctg    1104
Asn Gln Ala Leu Ala Lys Pro Tyr Gly Ile Glu Ser Val Leu Pro Leu
        355                 360                 365 gca ccg gtg gac ttt ggt cgc atg acg ctg ccg gat gtt ccg acc gcg    1152
Ala Pro Val Asp Phe Gly Arg Met Thr Leu Pro Asp Val Pro Thr Ala
    370                 375                 380 gtc ttc ctg ccg tac tgc gac ggt gat gtg agc aac cag caa ggc cag    1200
Val Phe Leu Pro Tyr Cys Asp Gly Asp Val Ser Asn Gln Gln Gly Gln
385                 390                 395                 400 cat ttt atc gat gac tct cgt cac gcc ttc gat gac gat gtt ctg cgc    1248
His Phe Ile Asp Asp Ser Arg His Ala Phe Asp Asp Asp Val Leu Arg
                405                 410                 415
```

-continued

| | | |
|---|---|---|
| agt gcg gtc tgg gtg atg ggt gcc aat cat aac ttt ttc aat acg gtg<br>Ser Ala Val Trp Val Met Gly Ala Asn His Asn Phe Phe Asn Thr Val<br>420                               425                      430 | | 1296 |
| tgg acc ccg ggt ctg tat ccg gca gca acc ggt gac gat tgg cgt acc<br>Trp Thr Pro Gly Leu Tyr Pro Ala Ala Thr Gly Asp Asp Trp Arg Thr<br>          435                     440                      445 | | 1344 |
| acg gat acc acg tcg acc tgt gcg acc acg aac ccg acg cgt atg acc<br>Thr Asp Thr Thr Ser Thr Cys Ala Thr Thr Asn Pro Thr Arg Met Thr<br>450                               455                      460 | | 1392 |
| gct gca cag caa tat cag gtt ggt gtc agc tac atg acc ggc ttt ttc<br>Ala Ala Gln Gln Tyr Gln Val Gly Val Ser Tyr Met Thr Gly Phe Phe<br>465                             470                     475                  480 | | 1440 |
| cgt ctg acc atg ggc ggt gaa acg cgc ttt caa tct ctg ttc gat ggc<br>Arg Leu Thr Met Gly Gly Glu Thr Arg Phe Gln Ser Leu Phe Asp Gly<br>                     485                     490                     495 | | 1488 |
| agt gtg aaa ccg tcc acg gcc tca acc gct tac gcg gat gtt cgt acg<br>Ser Val Lys Pro Ser Thr Ala Ser Thr Ala Tyr Ala Asp Val Arg Thr<br>                500                     505                     510 | | 1536 |
| atg gcg acc cag ccg gcc tcg aaa acc agc ctg gtg aat gat ttt acc<br>Met Ala Thr Gln Pro Ala Ser Lys Thr Ser Leu Val Asn Asp Phe Thr<br>               515                     520                     525 | | 1584 |
| gaa acg tca tcg ctg gtg cgt gtt agc ggc ggt gca acc gca gca gtg<br>Glu Thr Ser Ser Leu Val Arg Val Ser Gly Gly Ala Thr Ala Ala Val<br>530                               535                      540 | | 1632 |
| tgc acg aac ctg acc ggt cgt acg gtt ccg cag tcc ctg ccg ttt tgt<br>Cys Thr Asn Leu Thr Gly Arg Thr Val Pro Gln Ser Leu Pro Phe Cys<br>545                               550                     555                  560 | | 1680 |
| gcc acc acg aaa gcc tca gca caa gtt ccg cat tgg acc ccg ggc tcg<br>Ala Thr Thr Lys Ala Ser Ala Gln Val Pro His Trp Thr Pro Gly Ser<br>                     565                     570                     575 | | 1728 |
| ttc gca ccg aac gtc ccg gaa ttt ccg gtg acc cgt ttc ctg tgg acg<br>Phe Ala Pro Asn Val Pro Glu Phe Pro Val Thr Arg Phe Leu Trp Thr<br>                        580                     585                     590 | | 1776 |
| ggt gca tcc acc acc gat ccg gct gtg ccg tca acg ggt gaa ctg cgt<br>Gly Ala Ser Thr Thr Asp Pro Ala Val Pro Ser Thr Gly Glu Leu Arg<br>595                               600                     605 | | 1824 |
| gtc acc gtg ccg gca aaa gac cgt gat gcc tct cgc cac agt cag ctg<br>Val Thr Val Pro Ala Lys Asp Arg Asp Ala Ser Arg His Ser Gln Leu<br>          610                     615                     620 | | 1872 |
| acc ctg aaa acg gca ccg gat gaa gct gtt caa acc ggt acg gac ttt<br>Thr Leu Lys Thr Ala Pro Asp Glu Ala Val Gln Thr Gly Thr Asp Phe<br>625                               630                     635                  640 | | 1920 |
| cgt att acg gtc gtg gat ggc gca ggt aaa acc ttc gct acc acg gct<br>Arg Ile Thr Val Val Asp Gly Ala Gly Lys Thr Phe Ala Thr Thr Ala<br>                       645                     650                     655 | | 1968 |
| tct gcg gtt aat ccg ctg gca gtc aac cgt atg ccg ggc ggc acc aat<br>Ser Ala Val Asn Pro Leu Ala Val Asn Arg Met Pro Gly Gly Thr Asn<br>                   660                     665                     670 | | 2016 |
| acc acg ctg aac aaa gtt gtc ctg cag caa ctg acc att ccg acc agc<br>Thr Thr Leu Asn Lys Val Val Leu Gln Gln Leu Thr Ile Pro Thr Ser<br>               675                     680                     685 | | 2064 |
| acg att acc ggt atc gac ctg acg gat gtc cgt gaa gtg cgc ctg acc<br>Thr Ile Thr Gly Ile Asp Leu Thr Asp Val Arg Glu Val Arg Leu Thr<br>          690                     695                     700 | | 2112 |
| gct gcg atc ggt gca gat ggc acg ggc acc ggc ggt gtg tat ctg tcg<br>Ala Ala Ile Gly Ala Asp Gly Thr Gly Thr Gly Gly Val Tyr Leu Ser<br>705                               710                     715                  720 | | 2160 |
| gac ctg gcc ttt gat acc ccg agc gtg ggt acg gcc gtt gca cag acc<br>Asp Leu Ala Phe Asp Thr Pro Ser Val Gly Thr Ala Val Ala Gln Thr<br>                     725                     730                     735 | | 2208 |

```
cgt acc acg gtt aat gtc gcg ccg acc acg gtt gaa gaa ggc gac ggt    2256
Arg Thr Thr Val Asn Val Ala Pro Thr Thr Val Glu Glu Gly Asp Gly
            740                 745                 750 ccg ggc acc gct gat gtg gca gtt tat ctg aac cgc gcc gaa aaa agc    2304
Pro Gly Thr Ala Asp Val Ala Val Tyr Leu Asn Arg Ala Glu Lys Ser
            755                 760                 765 gcc gtg acg gca tac gtc tcc gtg att ggc tca gca acc gca gca gtc    2352
Ala Val Thr Ala Tyr Val Ser Val Ile Gly Ser Ala Thr Ala Ala Val
        770                 775                 780 ggt atc ggt atg gaa aaa gtg gct ttc gcg ccg ggt gaa acc tgc aaa    2400
Gly Ile Gly Met Glu Lys Val Ala Phe Ala Pro Gly Glu Thr Cys Lys
785                 790                 795                 800 gcc gtt acc gtc ccg acg ctg ggt aat acg gca acc agc gct gca ccg    2448
Ala Val Thr Val Pro Thr Leu Gly Asn Thr Ala Thr Ser Ala Ala Pro
            805                 810                 815 agc tct gca ttt aaa gtg tcg gtt acc aat agc acg aac gcg gtg atg    2496
Ser Ser Ala Phe Lys Val Ser Val Thr Asn Ser Thr Asn Ala Val Met
            820                 825                 830 ggc gcc tca gca ttc gct aac ctg acg gtt cgc gaa gac gat ggt gtc    2544
Gly Ala Ser Ala Phe Ala Asn Leu Thr Val Arg Glu Asp Asp Gly Val
            835                 840                 845 acc ggt gca gca ccg gca ctg gca ccg gtg ggt gca cag ggt gat gtt    2592
Thr Gly Ala Ala Pro Ala Leu Ala Pro Val Gly Ala Gln Gly Asp Val
850                 855                 860 tgt acc gaa ctg gct gca gca acc acg ccg gtc ccg ctg gaa acc tct    2640
Cys Thr Glu Leu Ala Ala Ala Thr Thr Pro Val Pro Leu Glu Thr Ser
865                 870                 875                 880 gca gaa gat gtg gcc ccg ggc ggt agt ttt acc ctg cgt gca acg ggt    2688
Ala Glu Asp Val Ala Pro Gly Gly Ser Phe Thr Leu Arg Ala Thr Gly
            885                 890                 895 tat cgc gca ggt gaa acc gtg gca ttc cgt tac ggt gct acc gac ctg    2736
Tyr Arg Ala Gly Glu Thr Val Ala Phe Arg Tyr Gly Ala Thr Asp Leu
            900                 905                 910 ggc acg cag gtt gca gct acc gat ggt acg gca agc gtg gtt gtc acc    2784
Gly Thr Gln Val Ala Ala Thr Asp Gly Thr Ala Ser Val Val Val Thr
            915                 920                 925 gtg ccg gaa gac gca gat ctg ggt ccg gca gaa gct acc gca tca ggt    2832
Val Pro Glu Asp Ala Asp Leu Gly Pro Ala Glu Ala Thr Ala Ser Gly
930                 935                 940 tcg ggc agc ggt cgt gca gca acc gtc tct gtg agt gtt ctg gca ccg    2880
Ser Gly Ser Gly Arg Ala Ala Thr Val Ser Val Ser Val Leu Ala Pro
945                 950                 955                 960 acc gaa acc acc gtt acc gtc acc ccg gca aaa ccg acc gca ggc caa    2928
Thr Glu Thr Thr Val Thr Val Thr Pro Ala Lys Pro Thr Ala Gly Gln
            965                 970                 975 taa                                                                2931

<210> SEQ ID NO 26
<211> LENGTH: 976
<212> TYPE: PRT
<213> ORGANISM: Leifsonia xyli

<400> SEQUENCE: 26

Leu Thr Thr Ala Pro Ala Ala Leu Ala Ala Pro Ala Pro Asp Pro Val
1               5                   10                  15

Val Ala Ser Gly Ser Asp Trp Ala Val Thr Thr Ser Pro Gly Gly Tyr
            20                  25                  30

Leu Val Thr Leu Asp Leu Asp Glu Pro Leu Pro Met Val Asp Asp Ala
        35                  40                  45
```

-continued

Pro Thr Leu Val Val Asp Gly Glu Pro Ile Gly Leu Ala Thr Glu Ser
    50                  55                  60

Ala Asp Gly Leu Thr Leu Gly Val Val Thr Thr Asp Pro Ala Val Ala
65                  70                  75                  80

Ser Ala Ser Ser Val Thr Lys Gly Trp Ser Ser Gly Ala Asp Asp Lys
                85                  90                  95

Ala Ala Glu Thr Pro Glu Ala Pro Ala Thr Pro Ala Val Pro Glu Asn
            100                 105                 110

Thr Thr Leu Thr Glu Gln Leu Lys Ser Phe Ala Gln Leu Glu Asn Leu
            115                 120                 125

Tyr Phe Gln Gly Val Ala Val Glu Asp Pro Ala Asp Leu Gly Ser Tyr
        130                 135                 140

Thr Val Thr Glu Ala Glu Tyr Asp Phe Gly Asp Gln Ala Val Pro Leu
145                 150                 155                 160

Ala Ala Ile Gly Gly Ile Arg Gly Glu Leu Thr Gly Lys Met Tyr Leu
                165                 170                 175

Thr Asn Ala Thr Gly Ala Arg Pro Thr Val Val Leu Leu His Gly Arg
            180                 185                 190

His Thr Ser Cys Ser Gly Thr Gly Ala Asn Pro Leu Arg Trp Pro Cys
        195                 200                 205

Gly Pro Thr Gln Met Asn Ile Arg Ser Tyr Leu Gly Tyr Glu Gly Thr
    210                 215                 220

Ala Arg Ala Leu Ala Ser Arg Gly Tyr Asn Val Leu Ser Ile Ala Ala
225                 230                 235                 240

Asn Ala Val Asn Ser Asn Asp Asn Gln Leu Ala Leu Asp Tyr Gly Ala
                245                 250                 255

Gln Ala Arg Gly Arg Leu Val Leu Asp Thr Leu Gly Met Leu Ala Lys
            260                 265                 270

Ala Thr Ala Gly Asp Ala Val Ala Tyr Asp Asp Ile Thr Thr Ala Thr
        275                 280                 285

Asp Thr Val Pro Ser Thr Thr Thr Arg Thr Leu Asp Glu Ala Leu
    290                 295                 300

Leu Arg Ala Thr Thr Arg Ala Asp Gln Pro Ala Ala Ser Gly Ile
305                 310                 315                 320

Thr Ala Ala Ser Leu Lys Gly Arg Phe Asp Leu Gly His Val Gly Ile
                325                 330                 335

Met Gly His Ser Arg Gly Gly Glu Gly Val Val Ser Ala Ala Thr Leu
            340                 345                 350

Asn Gln Ala Leu Ala Lys Pro Tyr Gly Ile Glu Ser Val Leu Pro Leu
        355                 360                 365

Ala Pro Val Asp Phe Gly Arg Met Thr Leu Pro Asp Val Pro Thr Ala
    370                 375                 380

Val Phe Leu Pro Tyr Cys Asp Gly Asp Val Ser Asn Gln Gln Gly Gln
385                 390                 395                 400

His Phe Ile Asp Asp Ser Arg His Ala Phe Asp Asp Val Leu Arg
                405                 410                 415

Ser Ala Val Trp Val Met Gly Ala Asn His Asn Phe Phe Asn Thr Val
            420                 425                 430

Trp Thr Pro Gly Leu Tyr Pro Ala Ala Thr Gly Asp Asp Trp Arg Thr
        435                 440                 445

Thr Asp Thr Thr Ser Thr Cys Ala Thr Thr Asn Pro Thr Arg Met Thr
    450                 455                 460

```
Ala Ala Gln Gln Tyr Gln Val Gly Val Ser Tyr Met Thr Gly Phe Phe
465                 470                 475                 480

Arg Leu Thr Met Gly Gly Glu Thr Arg Phe Gln Ser Leu Phe Asp Gly
                485                 490                 495

Ser Val Lys Pro Ser Thr Ala Ser Thr Ala Tyr Ala Asp Val Arg Thr
            500                 505                 510

Met Ala Thr Gln Pro Ala Ser Lys Thr Ser Leu Val Asn Asp Phe Thr
        515                 520                 525

Glu Thr Ser Ser Leu Val Arg Val Ser Gly Ala Thr Ala Ala Val
    530                 535                 540

Cys Thr Asn Leu Thr Gly Arg Thr Val Pro Gln Ser Leu Pro Phe Cys
545                 550                 555                 560

Ala Thr Thr Lys Ala Ser Ala Gln Val Pro His Trp Thr Pro Gly Ser
                565                 570                 575

Phe Ala Pro Asn Val Pro Glu Phe Pro Val Thr Arg Phe Leu Trp Thr
            580                 585                 590

Gly Ala Ser Thr Thr Asp Pro Ala Val Pro Ser Thr Gly Glu Leu Arg
        595                 600                 605

Val Thr Val Pro Ala Lys Asp Arg Asp Ala Ser Arg His Ser Gln Leu
    610                 615                 620

Thr Leu Lys Thr Ala Pro Asp Glu Ala Val Gln Thr Gly Thr Asp Phe
625                 630                 635                 640

Arg Ile Thr Val Val Asp Gly Ala Gly Lys Thr Phe Ala Thr Thr Ala
                645                 650                 655

Ser Ala Val Asn Pro Leu Ala Val Asn Arg Met Pro Gly Gly Thr Asn
            660                 665                 670

Thr Thr Leu Asn Lys Val Val Leu Gln Gln Leu Thr Ile Pro Thr Ser
        675                 680                 685

Thr Ile Thr Gly Ile Asp Leu Thr Asp Val Arg Glu Val Arg Leu Thr
    690                 695                 700

Ala Ala Ile Gly Ala Asp Gly Thr Gly Thr Gly Gly Val Tyr Leu Ser
705                 710                 715                 720

Asp Leu Ala Phe Asp Thr Pro Ser Val Gly Thr Ala Val Ala Gln Thr
                725                 730                 735

Arg Thr Thr Val Asn Val Ala Pro Thr Thr Val Glu Glu Gly Asp Gly
            740                 745                 750

Pro Gly Thr Ala Asp Val Ala Val Tyr Leu Asn Arg Ala Glu Lys Ser
        755                 760                 765

Ala Val Thr Ala Tyr Val Ser Val Ile Gly Ser Ala Thr Ala Ala Val
    770                 775                 780

Gly Ile Gly Met Glu Lys Val Ala Phe Ala Pro Gly Glu Thr Cys Lys
785                 790                 795                 800

Ala Val Thr Val Pro Thr Leu Gly Asn Thr Ala Thr Ser Ala Ala Pro
                805                 810                 815

Ser Ser Ala Phe Lys Val Ser Val Thr Asn Ser Thr Asn Ala Val Met
            820                 825                 830

Gly Ala Ser Ala Phe Ala Asn Leu Thr Val Arg Glu Asp Asp Gly Val
        835                 840                 845

Thr Gly Ala Ala Pro Ala Leu Ala Pro Val Gly Ala Gln Gly Asp Val
    850                 855                 860

Cys Thr Glu Leu Ala Ala Ala Thr Thr Pro Val Pro Leu Glu Thr Ser
865                 870                 875                 880

Ala Glu Asp Val Ala Pro Gly Gly Ser Phe Thr Leu Arg Ala Thr Gly
```

```
                        885                 890                 895
Tyr Arg Ala Gly Glu Thr Val Ala Phe Arg Tyr Gly Ala Thr Asp Leu
                    900                 905                 910

Gly Thr Gln Val Ala Ala Thr Asp Gly Thr Ala Ser Val Val Thr
                915                 920                 925

Val Pro Glu Asp Ala Asp Leu Gly Pro Ala Glu Ala Thr Ala Ser Gly
            930                 935                 940

Ser Gly Ser Gly Arg Ala Ala Thr Val Ser Val Ser Val Leu Ala Pro
945                 950                 955                 960

Thr Glu Thr Thr Val Thr Val Thr Pro Ala Lys Pro Thr Ala Gly Gln
                965                 970                 975

<210> SEQ ID NO 27
<211> LENGTH: 39
<212> TYPE: DNA
<213> ORGANISM: Artificial Sequence
<220> FEATURE:
<223> OTHER INFORMATION: primer

<400> SEQUENCE: 27
ggtatcgaag gtaggctgac cacggctccg gcggcactg                            39

<210> SEQ ID NO 28
<211> LENGTH: 38
<212> TYPE: DNA
<213> ORGANISM: Artificial Sequence
<220> FEATURE:
<223> OTHER INFORMATION: primer

<400> SEQUENCE: 28
agcagagatt acctattatt ggcctgcggt cggttttg                             38

<210> SEQ ID NO 29
<211> LENGTH: 3333
<212> TYPE: DNA
<213> ORGANISM: Microbacterium testaceum
<220> FEATURE:
<221> NAME/KEY: CDS
<222> LOCATION: (1)..(3333)

<400> SEQUENCE: 29 ctg agt tgt gct ccg gcg gct gtt gcg gct ccg ggc gat ggc acg gtt      48
Leu Ser Cys Ala Pro Ala Ala Val Ala Ala Pro Gly Asp Gly Thr Val
1               5                   10                  15 gct tct ggc gat gat tgg tcg gtt acg acg gct ccg ggc ggt tat att      96
Ala Ser Gly Asp Asp Trp Ser Val Thr Thr Ala Pro Gly Gly Tyr Ile
            20                  25                  30 gtt acc gtc gaa ctg agc gaa ccg ctg ccg atc gtc gca gat gca ccg     144
Val Thr Val Glu Leu Ser Glu Pro Leu Pro Ile Val Ala Asp Ala Pro
        35                  40                  45 acc ctg gtg gtt gac ggt gtt acc ctg ggc ctg gcg acg gaa agt gcc     192
Thr Leu Val Val Asp Gly Val Thr Leu Gly Leu Ala Thr Glu Ser Ala
    50                  55                  60 gat ggt cgt tca ctg tcg gtc gtg acc gcc gat ccg aaa gtg gct tcc     240
Asp Gly Arg Ser Leu Ser Val Val Thr Ala Asp Pro Lys Val Ala Ser
65                  70                  75                  80 gca cgt gac gtt gaa aaa ggt tgg gcg tcc ggc gat gaa gaa aaa gca     288
Ala Arg Asp Val Glu Lys Gly Trp Ala Ser Gly Asp Glu Glu Lys Ala
                85                  90                  95 ccg gaa tca acc ggc gct gaa att gtg gat gaa ccg gcc aat gac gaa     336
Pro Glu Ser Thr Gly Ala Glu Ile Val Asp Glu Pro Ala Asn Asp Glu
            100                 105                 110
```

| | | |
|---|---|---|
| ctg atc cgt cag ctg agc cgt ctg gca ccg gca gaa aac ctg tat ttt<br>Leu Ile Arg Gln Leu Ser Arg Leu Ala Pro Ala Glu Asn Leu Tyr Phe<br>115              120              125 | 384 | |
| caa ggt gca gca gtg gat gaa ccg tct acc ccg ggt gct ttt gcg gtt<br>Gln Gly Ala Ala Val Asp Glu Pro Ser Thr Pro Gly Ala Phe Ala Val<br>130              135              140 | 432 | |
| acg gaa gcg gaa tac gat ttc ggt gac cgt gca gtg gaa ctg gct ggc<br>Thr Glu Ala Glu Tyr Asp Phe Gly Asp Arg Ala Val Glu Leu Ala Gly<br>145              150              155              160 | 480 | |
| att ggc ggt atc cgc ggt gaa atg acc ggc aaa atg tat ctg acg gat<br>Ile Gly Gly Ile Arg Gly Glu Met Thr Gly Lys Met Tyr Leu Thr Asp<br>165              170              175 | 528 | |
| gca ccg ggt gaa cgt ccg acc gtt att ctg ctg cat ggt cgt cac ggc<br>Ala Pro Gly Glu Arg Pro Thr Val Ile Leu Leu His Gly Arg His Gly<br>180              185              190 | 576 | |
| tcc tgc gca acg ggc acc agc aat ccg ctg cgt tgg ccg tgt ggc ccg<br>Ser Cys Ala Thr Gly Thr Ser Asn Pro Leu Arg Trp Pro Cys Gly Pro<br>195              200              205 | 624 | |
| aat cag gtg aac gtt cgt agc tat caa ggt tac gaa ggc acc ggt cgt<br>Asn Gln Val Asn Val Arg Ser Tyr Gln Gly Tyr Glu Gly Thr Gly Arg<br>210              215              220 | 672 | |
| gca ctg gca tcg cat ggt tat aat gtg ctg agc att gca gct aac gcg<br>Ala Leu Ala Ser His Gly Tyr Asn Val Leu Ser Ile Ala Ala Asn Ala<br>225              230              235              240 | 720 | |
| gtt aac tct aat gat aac cag ctg gcc ctg gac tac ggt gct aaa gcg<br>Val Asn Ser Asn Asp Asn Gln Leu Ala Leu Asp Tyr Gly Ala Lys Ala<br>245              250              255 | 768 | |
| cgt ggc caa ctg gtg ctg gat acc ctg gcc atg ctg gaa agt gcc aac<br>Arg Gly Gln Leu Val Leu Asp Thr Leu Ala Met Leu Glu Ser Ala Asn<br>260              265              270 | 816 | |
| gca ggt gat gca gtt tcc ttt gat gac atc tca tgg gct gac gca gaa<br>Ala Gly Asp Ala Val Ser Phe Asp Asp Ile Ser Trp Ala Asp Ala Glu<br>275              280              285 | 864 | |
| ggt gca acc acg acc gtg acc cgt tca ctg gat gac gca ctg cgt tac<br>Gly Ala Thr Thr Thr Val Thr Arg Ser Leu Asp Asp Ala Leu Arg Tyr<br>290              295              300 | 912 | |
| gca acg acc cgt acc gat atg ccg gca ccg ggt gcc ggt gtg acg gca<br>Ala Thr Thr Arg Thr Asp Met Pro Ala Pro Gly Ala Gly Val Thr Ala<br>305              310              315              320 | 960 | |
| gcc tcg ctg cag ggt cgt ttc gat ctg gac acc gtt ggt ctg atg ggc<br>Ala Ser Leu Gln Gly Arg Phe Asp Leu Asp Thr Val Gly Leu Met Gly<br>325              330              335 | 1008 | |
| cat tcc cgc ggc ggt gaa ggc gtt gtc tca gca gct acc ctg aat cag<br>His Ser Arg Gly Gly Glu Gly Val Val Ser Ala Ala Thr Leu Asn Gln<br>340              345              350 | 1056 | |
| ggt ctg gcc gat ccg tat ggt att gtc agc gtg ctg ccg ctg gca ccg<br>Gly Leu Ala Asp Pro Tyr Gly Ile Val Ser Val Leu Pro Leu Ala Pro<br>355              360              365 | 1104 | |
| gtg gat ttt ggt cgt atg acc ctg ccg gac gtg ccg ctg ggc gtt ttc<br>Val Asp Phe Gly Arg Met Thr Leu Pro Asp Val Pro Leu Gly Val Phe<br>370              375              380 | 1152 | |
| ctg ccg tac tgc gat ggt gac gtt tcc aat cag caa ggc cag cat atg<br>Leu Pro Tyr Cys Asp Gly Asp Val Ser Asn Gln Gln Gly Gln His Met<br>385              390              395              400 | 1200 | |
| gtc gat gac tca cgt cac gcg ttt ggt gat gac gtg ctg cgt tcg gca<br>Val Asp Asp Ser Arg His Ala Phe Gly Asp Asp Val Leu Arg Ser Ala<br>405              410              415 | 1248 | |
| gtt tgg gtc atg ggt gcc aat cac aac ttt ttc aac acc gtt tgg acg<br>Val Trp Val Met Gly Ala Asn His Asn Phe Phe Asn Thr Val Trp Thr | 1296 | |

-continued

```
              420                 425                 430
ccg ggt ctg tat ccg tac agc acc tct gat gac tgg aat cgt aac gat      1344
Pro Gly Leu Tyr Pro Tyr Ser Thr Ser Asp Asp Trp Asn Arg Asn Asp
            435                 440                 445 acg acc agc tct tgt tca acc cgt gac agt tcc cgt ctg acg gca gca      1392
Thr Thr Ser Ser Cys Ser Thr Arg Asp Ser Ser Arg Leu Thr Ala Ala
450                 455                 460 cag caa tat caa gtg ggt gtt tcg tac atg acc ggc ttt ttc cgc ctg      1440
Gln Gln Tyr Gln Val Gly Val Ser Tyr Met Thr Gly Phe Phe Arg Leu
465                 470                 475                 480 acc atg ggc ggt gaa acg cag ttt caa ccg ctg ttc gat ggc tcg gca      1488
Thr Met Gly Gly Glu Thr Gln Phe Gln Pro Leu Phe Asp Gly Ser Ala
                485                 490                 495 acc ccg agc acg gca gct acc ttt gca gac gtg cgt att atg gct          1536
Thr Pro Ser Thr Ala Ala Thr Thr Phe Ala Asp Val Arg Ile Met Ala
            500                 505                 510 tct cag ccg caa agt gca acg acc ctg gtc acc gat ttc gca acg gca      1584
Ser Gln Pro Gln Ser Ala Thr Thr Leu Val Thr Asp Phe Ala Thr Ala
            515                 520                 525 ggt ccg ctg gtg cgt acg acc ggc agt gca tcc gtc gct gtg tgc gct      1632
Gly Pro Leu Val Arg Thr Thr Gly Ser Ala Ser Val Ala Val Cys Ala
530                 535                 540 aac gcg gaa acc gcc tca tcg atc tca ccg tcg gtt ccg tat tgt acc      1680
Asn Ala Glu Thr Ala Ser Ser Ile Ser Pro Ser Val Pro Tyr Cys Thr
545                 550                 555                 560 ccg cgt gat gtc ggt acg agt cgc gtg ccg cat tgg acc ccg gtc cgt      1728
Pro Arg Asp Val Gly Thr Ser Arg Val Pro His Trp Thr Pro Val Arg
                565                 570                 575 ttt ggc ctg aat gtg ccg gcg tac ccg gtc tcc cag ttc gtg tgg aac      1776
Phe Gly Leu Asn Val Pro Ala Tyr Pro Val Ser Gln Phe Val Trp Asn
            580                 585                 590 ggt agc gca tct gca ccg gct acc ccg tct acg ggt gaa ctg cgt gtg      1824
Gly Ser Ala Ser Ala Pro Ala Thr Pro Ser Thr Gly Glu Leu Arg Val
            595                 600                 605 agt att ccg gca gca cag cgt gat gtc agc cag cgt gcg caa ctg acc      1872
Ser Ile Pro Ala Ala Gln Arg Asp Val Ser Gln Arg Ala Gln Leu Thr
610                 615                 620 gtg aaa gca gct ccg gtg ctg tct gtt acg acc ggc acc gat ttt acg      1920
Val Lys Ala Ala Pro Val Leu Ser Val Thr Thr Gly Thr Asp Phe Thr
625                 630                 635                 640 att acc gtg gtt gac ggt gca ggt gca acc ttc tcc gtt ccg gca agc      1968
Ile Thr Val Val Asp Gly Ala Gly Ala Thr Phe Ser Val Pro Ala Ser
                645                 650                 655 tct atc aat ccg ctg gca gtc aac cgt ctg ccg ggc ggc acc cac gcg      2016
Ser Ile Asn Pro Leu Ala Val Asn Arg Leu Pro Gly Gly Thr His Ala
            660                 665                 670 acg ctg aat aaa att gtg ctg cag caa ctg acc atc ccg acg tct gaa      2064
Thr Leu Asn Lys Ile Val Leu Gln Gln Leu Thr Ile Pro Thr Ser Glu
            675                 680                 685 atg acc ggt atc gat ctg acg gac gtc cgt gaa gtg cgc ttt acc gca      2112
Met Thr Gly Ile Asp Leu Thr Asp Val Arg Glu Val Arg Phe Thr Ala
            690                 695                 700 ggc gtg ggt gct gat ggc acg ggt gca ggc ggt gtt ttt ctg tcg gat      2160
Gly Val Gly Ala Asp Gly Thr Gly Ala Gly Gly Val Phe Leu Ser Asp
705                 710                 715                 720 ctg gca ttc gac acc ccg agc ctg ggc acg acc gtc gtg cag acg cgt      2208
Leu Ala Phe Asp Thr Pro Ser Leu Gly Thr Thr Val Val Gln Thr Arg
                725                 730                 735 acg acc gtg aac att gcg acg acc cgc atc gaa gaa ggt gat gca ccg      2256
```

-continued

```
                Thr Thr Val Asn Ile Ala Thr Thr Arg Ile Glu Glu Gly Asp Ala Pro
                            740                 745                 750 ggc acg gca acc att gca gca tat ctg gac gca ccg gct acc gaa ccg         2304
Gly Thr Ala Thr Ile Ala Ala Tyr Leu Asp Ala Pro Ala Thr Glu Pro
            755                 760                 765 gtg acg ggt tac gtt tct ctg gtc gca gct ggt cct gtt agt gca gca         2352
Val Thr Gly Tyr Val Ser Leu Val Ala Ala Gly Pro Val Ser Ala Ala
770                 775                 780 gtg cag gca gtt acc ttt gct ccg ggt gaa tcg tgc cgt gca atc agc         2400
Val Gln Ala Val Thr Phe Ala Pro Gly Glu Ser Cys Arg Ala Ile Ser
785                 790                 795                 800 gtc ccg acc gtg ggt gat gac gtt ccg tct gca gtc ggt gca acc ggt         2448
Val Pro Thr Val Gly Asp Asp Val Pro Ser Ala Val Gly Ala Thr Gly
            805                 810                 815 tat acc gtt agt gtc acg aat acc cag aac gcg gtg atg ggt gca gct         2496
Tyr Thr Val Ser Val Thr Asn Thr Gln Asn Ala Val Met Gly Ala Ala
            820                 825                 830 gcg ttt ggc caa ctg gtt gtc cgc gaa gat gac ggt gtt acc agc ccg         2544
Ala Phe Gly Gln Leu Val Val Arg Glu Asp Asp Gly Val Thr Ser Pro
            835                 840                 845 ggc gtc gaa ctg ccg ccg gtg ggt gtt cag ggt gat gca tgt gcc gaa         2592
Gly Val Glu Leu Pro Pro Val Gly Val Gln Gly Asp Ala Cys Ala Glu
850                 855                 860 ctg gcc gca tcg ttc gaa ccg acc gaa ctg gct gca agc acg ctg gaa         2640
Leu Ala Ala Ser Phe Glu Pro Thr Glu Leu Ala Ala Ser Thr Leu Glu
865                 870                 875                 880 gca gca ccg ggt gat gaa gtg acg ttt acc ggc agc ggt ttc cgt gtg         2688
Ala Ala Pro Gly Asp Glu Val Thr Phe Thr Gly Ser Gly Phe Arg Val
                885                 890                 895 ggc gaa gaa gtt gaa ttt gcc ctg ggt gat gca gtt gct ggc acc gca         2736
Gly Glu Glu Val Glu Phe Ala Leu Gly Asp Ala Val Ala Gly Thr Ala
            900                 905                 910 att gca gat cgt gac ggt gtc gca gtg ttc acg ctg gca ctg gct gat         2784
Ile Ala Asp Arg Asp Gly Val Ala Val Phe Thr Leu Ala Leu Ala Asp
            915                 920                 925 gac gca gat ctg ggt gca cag gtg gtt cgt gca acc ggt gct ggt agc         2832
Asp Ala Asp Leu Gly Ala Gln Val Val Arg Ala Thr Gly Ala Gly Ser
930                 935                 940 gca cgt gtt caa gtc acg acc ctg gca gtg ctg gca ccg acc gct acg         2880
Ala Arg Val Gln Val Thr Thr Leu Ala Val Leu Ala Pro Thr Ala Thr
945                 950                 955                 960 acc ctg gca ctg gca ccg ggt agt tcc ctg gtt gcg ggc ggt ccg ctg         2928
Thr Leu Ala Leu Ala Pro Gly Ser Ser Leu Val Ala Gly Gly Pro Leu
                965                 970                 975 acc ttt gtt gcg acc gtc agt ggt gcc gaa acc gat ggc acg gtg acc         2976
Thr Phe Val Ala Thr Val Ser Gly Ala Glu Thr Asp Gly Thr Val Thr
            980                 985                 990 ttc acg gac ggc acc gaa ctg ggc  acg gcc gaa gtc gtg  gat ggc gtt       3024
Phe Thr Asp Gly Thr Glu Leu Gly  Thr Ala Glu Val Val  Asp Gly Val
            995                 1000                1005 gca acc ctg acg ctg cgt gaa  ggt ctg gct gca ggc  acc tat gca           3069
Ala Thr Leu Thr Leu Arg Glu  Gly Leu Ala Ala Gly  Thr Tyr Ala
            1010                1015                1020 gtg gca gca gaa ttt gcc cgt  acg gat gtt gca agt  gct tcc cgc           3114
Val Ala Ala Glu Phe Ala Arg  Thr Asp Val Ala Ser  Ala Ser Arg
            1025                1030                1035 tca gac gaa ctg gaa gtt acc  atc gct gca gca ccg  gtc gca ggc           3159
Ser Asp Glu Leu Glu Val Thr  Ile Ala Ala Ala Pro  Val Ala Gly
            1040                1045                1050
```

| | | | | | | | | | | | | | | |
|---|---|---|---|---|---|---|---|---|---|---|---|---|---|---|
| ggt | ccg | ggc | tct | gat | ggc | acc | ggt | agt | ggt | gca | acg | ggc | ggt | acg |
| Gly | Pro | Gly | Ser | Asp | Gly | Thr | Gly | Ser | Gly | Ala | Thr | Gly | Gly | Thr |
| | 1055 | | | | 1060 | | | | | 1065 | | | | |

3204

| acc | ccg | gat | tgg | ctg | gca | gtg | acc | ggt | gct | gac | ggt | ttc | ggc | tgg |
|---|---|---|---|---|---|---|---|---|---|---|---|---|---|---|
| Thr | Pro | Asp | Trp | Leu | Ala | Val | Thr | Gly | Ala | Asp | Gly | Phe | Gly | Trp |
| | 1070 | | | | 1075 | | | | | 1080 | | | | |

3249

| atg | ctg | ctg | gca | gct | gcg | ggc | ctg | ctg | ggt | acg | ggt | ggt | gct | ctg |
|---|---|---|---|---|---|---|---|---|---|---|---|---|---|---|
| Met | Leu | Leu | Ala | Ala | Ala | Gly | Leu | Leu | Gly | Thr | Gly | Gly | Ala | Leu |
| | 1085 | | | | 1090 | | | | | 1095 | | | | |

3294

| ctg | tat | gtg | cgt | cgt | cgt | cgt | gct | cgc | gtt | gat | gct | tga | | |
|---|---|---|---|---|---|---|---|---|---|---|---|---|---|---|
| Leu | Tyr | Val | Arg | Arg | Arg | Arg | Ala | Arg | Val | Asp | Ala | | | |
| | 1100 | | | | 1105 | | | | | 1110 | | | | |

3333

<210> SEQ ID NO 30
<211> LENGTH: 1110
<212> TYPE: PRT
<213> ORGANISM: Microbacterium testaceum

<400> SEQUENCE: 30

Leu Ser Cys Ala Pro Ala Ala Val Ala Ala Pro Gly Asp Gly Thr Val
1               5                   10                  15

Ala Ser Gly Asp Asp Trp Ser Val Thr Thr Ala Pro Gly Gly Tyr Ile
            20                  25                  30

Val Thr Val Glu Leu Ser Glu Pro Leu Pro Ile Val Ala Asp Ala Pro
        35                  40                  45

Thr Leu Val Val Asp Gly Val Thr Leu Gly Leu Ala Thr Glu Ser Ala
    50                  55                  60

Asp Gly Arg Ser Leu Ser Val Val Thr Ala Asp Pro Lys Val Ala Ser
65                  70                  75                  80

Ala Arg Asp Val Glu Lys Gly Trp Ala Ser Gly Asp Glu Lys Ala
                85                  90                  95

Pro Glu Ser Thr Gly Ala Glu Ile Val Asp Glu Pro Ala Asn Asp Glu
            100                 105                 110

Leu Ile Arg Gln Leu Ser Arg Leu Ala Pro Ala Glu Asn Leu Tyr Phe
        115                 120                 125

Gln Gly Ala Ala Val Asp Glu Pro Ser Thr Pro Gly Ala Phe Ala Val
    130                 135                 140

Thr Glu Ala Glu Tyr Asp Phe Gly Asp Arg Ala Val Glu Leu Ala Gly
145                 150                 155                 160

Ile Gly Gly Ile Arg Gly Glu Met Thr Gly Lys Met Tyr Leu Thr Asp
                165                 170                 175

Ala Pro Gly Glu Arg Pro Thr Val Ile Leu Leu His Gly Arg His Gly
            180                 185                 190

Ser Cys Ala Thr Gly Thr Ser Asn Pro Leu Arg Trp Pro Cys Gly Pro
        195                 200                 205

Asn Gln Val Asn Val Arg Ser Tyr Gln Gly Tyr Glu Gly Thr Gly Arg
    210                 215                 220

Ala Leu Ala Ser His Gly Tyr Asn Val Leu Ser Ile Ala Ala Asn Ala
225                 230                 235                 240

Val Asn Ser Asn Asp Asn Gln Leu Ala Leu Asp Tyr Gly Ala Lys Ala
                245                 250                 255

Arg Gly Gln Leu Val Leu Asp Thr Leu Ala Met Leu Glu Ser Ala Asn
            260                 265                 270

Ala Gly Asp Ala Val Ser Phe Asp Asp Ile Ser Trp Ala Asp Ala Glu
        275                 280                 285

Gly Ala Thr Thr Thr Val Thr Arg Ser Leu Asp Asp Ala Leu Arg Tyr 290                 295                 300
Ala Thr Thr Arg Thr Asp Met Pro Ala Pro Gly Ala Gly Val Thr Ala
305                 310                 315                 320

Ala Ser Leu Gln Gly Arg Phe Asp Leu Asp Thr Val Gly Leu Met Gly
                325                 330                 335

His Ser Arg Gly Gly Glu Gly Val Val Ser Ala Ala Thr Leu Asn Gln
                340                 345                 350

Gly Leu Ala Asp Pro Tyr Gly Ile Val Ser Val Leu Pro Leu Ala Pro
                355                 360                 365

Val Asp Phe Gly Arg Met Thr Leu Pro Asp Val Pro Leu Gly Val Phe
370                 375                 380

Leu Pro Tyr Cys Asp Gly Asp Val Ser Asn Gln Gln Gly Gln His Met
385                 390                 395                 400

Val Asp Asp Ser Arg His Ala Phe Gly Asp Val Leu Arg Ser Ala
                405                 410                 415

Val Trp Val Met Gly Ala Asn His Asn Phe Asn Thr Val Trp Thr
                420                 425                 430

Pro Gly Leu Tyr Pro Tyr Ser Thr Ser Asp Asp Trp Asn Arg Asn Asp
                435                 440                 445

Thr Thr Ser Ser Cys Ser Thr Arg Asp Ser Ser Arg Leu Thr Ala Ala
                450                 455                 460

Gln Gln Tyr Gln Val Gly Val Ser Tyr Met Thr Gly Phe Phe Arg Leu
465                 470                 475                 480

Thr Met Gly Gly Glu Thr Gln Phe Gln Pro Leu Phe Asp Gly Ser Ala
                485                 490                 495

Thr Pro Ser Thr Ala Ala Thr Thr Phe Ala Asp Val Arg Ile Met Ala
                500                 505                 510

Ser Gln Pro Gln Ser Ala Thr Thr Leu Val Thr Asp Phe Ala Thr Ala
                515                 520                 525

Gly Pro Leu Val Arg Thr Thr Gly Ser Ala Ser Val Ala Val Cys Ala
530                 535                 540

Asn Ala Glu Thr Ala Ser Ser Ile Ser Pro Ser Val Pro Tyr Cys Thr
545                 550                 555                 560

Pro Arg Asp Val Gly Thr Ser Arg Val Pro His Trp Thr Pro Val Arg
                565                 570                 575

Phe Gly Leu Asn Val Pro Ala Tyr Pro Val Ser Gln Phe Val Trp Asn
                580                 585                 590

Gly Ser Ala Ser Ala Pro Ala Thr Pro Ser Thr Gly Glu Leu Arg Val
                595                 600                 605

Ser Ile Pro Ala Ala Gln Arg Asp Val Ser Gln Arg Ala Gln Leu Thr
610                 615                 620

Val Lys Ala Ala Pro Val Leu Ser Val Thr Thr Gly Thr Asp Phe Thr
625                 630                 635                 640

Ile Thr Val Val Asp Gly Ala Gly Ala Thr Phe Ser Val Pro Ala Ser
                645                 650                 655

Ser Ile Asn Pro Leu Ala Val Asn Arg Leu Pro Gly Gly Thr His Ala
                660                 665                 670

Thr Leu Asn Lys Ile Val Leu Gln Gln Leu Thr Ile Pro Thr Ser Glu
                675                 680                 685

Met Thr Gly Ile Asp Leu Thr Asp Val Arg Glu Val Arg Phe Thr Ala
                690                 695                 700

Gly Val Gly Ala Asp Gly Thr Gly Ala Gly Val Phe Leu Ser Asp
705                 710                 715                 720

Leu Ala Phe Asp Thr Pro Ser Leu Gly Thr Val Gln Thr Arg
                725                 730                 735

Thr Thr Val Asn Ile Ala Thr Thr Arg Ile Glu Glu Gly Asp Ala Pro
            740                 745                 750

Gly Thr Ala Thr Ile Ala Ala Tyr Leu Asp Ala Pro Ala Thr Glu Pro
            755                 760                 765

Val Thr Gly Tyr Val Ser Leu Val Ala Ala Gly Pro Val Ser Ala Ala
        770                 775                 780

Val Gln Ala Val Thr Phe Ala Pro Gly Glu Ser Cys Arg Ala Ile Ser
785                 790                 795                 800

Val Pro Thr Val Gly Asp Asp Val Pro Ser Ala Val Gly Ala Thr Gly
                805                 810                 815

Tyr Thr Val Ser Val Thr Asn Thr Gln Asn Ala Val Met Gly Ala Ala
                820                 825                 830

Ala Phe Gly Gln Leu Val Val Arg Glu Asp Asp Gly Val Thr Ser Pro
            835                 840                 845

Gly Val Glu Leu Pro Pro Val Gly Val Gln Gly Asp Ala Cys Ala Glu
        850                 855                 860

Leu Ala Ala Ser Phe Glu Pro Thr Glu Leu Ala Ala Ser Thr Leu Glu
865                 870                 875                 880

Ala Ala Pro Gly Asp Glu Val Thr Phe Thr Gly Ser Gly Phe Arg Val
                885                 890                 895

Gly Glu Glu Val Glu Phe Ala Leu Gly Asp Ala Val Ala Gly Thr Ala
                900                 905                 910

Ile Ala Asp Arg Asp Gly Val Ala Val Phe Thr Leu Ala Leu Ala Asp
            915                 920                 925

Asp Ala Asp Leu Gly Ala Gln Val Val Arg Ala Thr Gly Ala Gly Ser
    930                 935                 940

Ala Arg Val Gln Val Thr Thr Leu Ala Val Leu Ala Pro Thr Ala Thr
945                 950                 955                 960

Thr Leu Ala Leu Ala Pro Gly Ser Ser Leu Val Ala Gly Gly Pro Leu
            965                 970                 975

Thr Phe Val Ala Thr Val Ser Gly Ala Glu Thr Asp Gly Thr Val Thr
            980                 985                 990

Phe Thr Asp Gly Thr Glu Leu Gly Thr Ala Glu Val Val Asp Gly Val
        995                 1000                1005

Ala Thr Leu Thr Leu Arg Glu Gly Leu Ala Ala Gly Thr Tyr Ala
    1010                1015                1020

Val Ala Ala Glu Phe Ala Arg Thr Asp Val Ala Ser Ala Ser Arg
    1025                1030                1035

Ser Asp Glu Leu Glu Val Thr Ile Ala Ala Ala Pro Val Ala Gly
    1040                1045                1050

Gly Pro Gly Ser Asp Gly Thr Gly Ser Gly Ala Thr Gly Gly Thr
    1055                1060                1065

Thr Pro Asp Trp Leu Ala Val Thr Gly Ala Asp Gly Phe Gly Trp
    1070                1075                1080

Met Leu Leu Ala Ala Ala Gly Leu Leu Gly Thr Gly Gly Ala Leu
    1085                1090                1095

Leu Tyr Val Arg Arg Arg Ala Arg Val Asp Ala
    1100                1105                1110

<210> SEQ ID NO 31
<211> LENGTH: 40

```
<212> TYPE: DNA
<213> ORGANISM: Artificial Sequence
<220> FEATURE:
<223> OTHER INFORMATION: primer

<400> SEQUENCE: 31
ggtatcgaag gtaggctgag ttgtgctccg gcggctgttg                              40

<210> SEQ ID NO 32
<211> LENGTH: 38
<212> TYPE: DNA
<213> ORGANISM: Artificial Sequence
<220> FEATURE:
<223> OTHER INFORMATION: primer

<400> SEQUENCE: 32
agcagagatt acctatcaag catcaacgcg agcacgac                                38
```